United States Patent
Adcock et al.

(10) Patent No.: US 8,343,966 B2
(45) Date of Patent: Jan. 1, 2013

(54) ORGANIC COMPOUNDS

(75) Inventors: Claire Adcock, Horsham (GB); Urs Baettig, Horsham (GB); Peter Hunt, Horsham (GB); Catherine Leblanc, Horsham (GB); Maude Nadine Pierrette Pipet, Horsham (GB); Robert Alexander Pulz, Basel (CH); Katrin Spiegel, Horsham (GB); Nikolaus Johannes Stiefl, Basel (CH)

(73) Assignee: Novartis AG, Basel (CH)

( * ) Notice: Subject to any disclaimer, the term of this patent is extended or adjusted under 35 U.S.C. 154(b) by 701 days.

(21) Appl. No.: 12/319,234

(22) Filed: Jan. 2, 2009

(65) Prior Publication Data

US 2009/0215776 A1 Aug. 27, 2009

(30) Foreign Application Priority Data

Jan. 11, 2008 (EP) .................................... 08150187
Nov. 3, 2008 (EP) .................................... 08168207

(51) Int. Cl.
| | | |
|---|---|---|
| A61K 31/5355 | (2006.01) | |
| A61K 31/536 | (2006.01) | |
| A61K 31/496 | (2006.01) | |
| A61K 31/506 | (2006.01) | |
| A61K 31/4453 | (2006.01) | |
| A61K 31/444 | (2006.01) | |
| A61K 31/4402 | (2006.01) | |
| A61K 31/443 | (2006.01) | |
| A61K 31/4439 | (2006.01) | |
| C07D 401/14 | (2006.01) | |
| C07D 405/14 | (2006.01) | |
| C07D 413/14 | (2006.01) | |
| C07D 211/04 | (2006.01) | |
| C07D 211/48 | (2006.01) | |
| C07D 211/62 | (2006.01) | |
| C07D 213/53 | (2006.01) | |

(52) U.S. Cl. ............... 514/230.5; 514/235.5; 514/236.5; 514/253.01; 514/253.13; 514/256; 514/318; 514/333; 514/334; 544/124; 544/131; 544/333; 544/364; 546/148; 546/194; 546/255; 546/256

(58) Field of Classification Search .................... None
See application file for complete search history.

(56) References Cited

U.S. PATENT DOCUMENTS

| | | | |
|---|---|---|---|
| 2,909,529 | A | 10/1959 | Thesing |
| 3,829,426 | A | 8/1974 | Schroder et al. |

FOREIGN PATENT DOCUMENTS

| | | |
|---|---|---|
| WO | WO 2004/013135 | 2/2004 |
| WO | WO 2004/058762 | 7/2004 |
| WO | WO 2006/026135 | 3/2006 |
| WO | WO 2007/124288 | 11/2007 |
| WO | WO 2007/124544 | 11/2007 |
| WO | WO 2007/124545 | 11/2007 |
| WO | WO 2007/124546 | 11/2007 |
| WO | WO 2008/114157 | 9/2008 |
| WO | WO 2008/122378 | * 10/2008 |
| WO | WO 2008/132505 | 11/2008 |

OTHER PUBLICATIONS

Farhannullah et al. J. Org. Chem. 2003, 68, pp. 2983-2985.*
Farhanullah Na et al "Synthesis of Aminonicotinonitriles and Diaminopyridines through Base-Catalyzed Ring Transformation of 2H-Pyran-2-ones" J Org Chem 68:2983-2985 (2003).
Iwamoto Ken-ichi et al "Ring Transformation of Fused Pyridazines. VI. Construction of 3-(2-Pyridyl)Indole Skeleton by Means of N—N Bond Cleavage Reaction of Fused Pyridazines with Ynamines" Heterocycles 45 (8):1551-1557 (1997).
Kobayashi Goro et al "Synthesis of Alpha-Pyridone Derivatives with Pyridinium Ylide" Database CAPLUS, Accession No. 551643 (1971) XP-002532248.
Paluchowska Maria H et al "Modification of the Structure of 4,6-Disubstituted 2-(4-Alkyl-1-piperazinyl) pyridines: Synthesis and Their 5-HT2A Receptor Activity" Arch Pharm Pharm Med Chem 2:104-110 (2003).
Shibata Katsuyoshi et al "Synthesis of 4,6-Disubstituted 2-Methylpyridines and their 3-Carboxamides" J Heterocyclic Chem 30:277-181 (Jan.-Feb. 1993).
Goel Atul et al "Substituent-Dictated Concise Synthesis of 4,6-Disubstituted N-Alkyl-2-pyridones and 2-Aminopyridines" Synlett 13:2027-2030 (2005).
Zelechonok Yu B et at "Homolytical alkylation of aromatic bases by 1,4-dioxane and its macrocyclic analogs" Database CAPLUS Accession No. 492964 (1988) XP-002531695.

* cited by examiner

Primary Examiner — Joseph K. McKane
Assistant Examiner — Alicia L Otton
(74) Attorney, Agent, or Firm — John B. Alexander

(57) ABSTRACT

Compounds of formula I

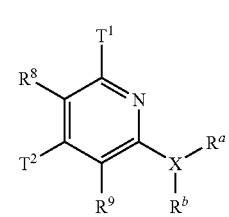

I in free or salt or solvate form, where $T^1$, $T^2$, $X$, $R^a$, $R^b$, $R^8$ and $R^9$ have the meanings as indicated in the specification, are useful for treating inflammatory or obstructive airways, pulmonary hypertension, pulmonary fibrosis, liver fibrosis, muscle diseases and systemic skeletal disorders. Pharmaceutical compositions that contain the compounds and processes for preparing the compounds are also described.

2 Claims, No Drawings

ORGANIC COMPOUNDS

This application claims benefit of priority under 35 U.S.C. 119(a)-(d) or 365(b) to European Patent Application No. 08150187.6, filed 11 Jan. 2008, and European Patent Application No. 08168207.2, filed 3 Nov. 2008.

This invention relates to organic compounds and their use as pharmaceuticals, in particular for the treatment of inflammatory or obstructive airways diseases, pulmonary hypertension, pulmonary fibrosis, liver fibrosis, cancer, muscle diseases such as muscle atrophies and muscle dystrophies, and systemic skeletal disorders such as osteoporosis.

In one aspect, the present invention provides a compound of formula I in free or salt or solvate form, where $T^1$ is a 4- to 14-membered heterocyclic group or $C_4$-$C_{15}$-cycloalkenyl, each optionally substituted by one, two or three substituents each independently selected from $R^1$, O—$R^1$, $C_3$-$C_5$-cycloalkyl, $C_1$-$C_8$-alkylthio, halo, halo-$C_1$-$C_8$-alkyl, amino, $C_1$-$C_8$-alkylamino, di($C_1$-$C_8$-alkyl)amino, cyano, oxo, hydroxy, carboxy and nitro;

$T^2$ is a 4- to 14-membered heterocyclic group optionally substituted by one, two or three substituents each independently selected from $R^1$, $R^2$, $R^5$, O—$R^1$, $C_1$-$C_8$-alkoxycarbonyl, $C_1$-$C_8$-alkylthio, halo, halo-$C_1$-$C_8$-alkyl, amino, $C_1$-$C_8$-alkylamino, di($C_1$-$C_8$-alkyl)amino, cyano, oxo, hydroxy, carboxy and nitro;

X is selected from $CR^c$, N, O and S, provided that when X is O or S, $R^a$ is absent;

$R^a$ and $R^b$ are each independently selected from
  hydrogen; OH; $NHR^{10}$;
  $C_1$-$C_8$-alkyl optionally substituted at one, two or three positions by $R^4$;
  $C_3$-$C_{10}$-cycloalkyl optionally substituted at one or two positions by hydroxy, amino, $C_1$-$C_8$-alkyl, $C_1$-$C_8$-alkoxy, halo, cyano, oxo, carboxy or nitro; and
  $C_6$-$C_{15}$-aryl optionally substituted at one, two or three positions by halo, hydroxy, amino, cyano, oxo, carboxy, nitro or $R^5$; or
  $R^a$ and $R^b$ together with X form a 3-, 4-, 5- or 6-membered cyclic group, optionally substituted by OH, halo, $NR^6R^7$ or $R^1$;

$R^c$ is selected from H, OH, $C_1$-$C_8$-alkyl and $NHR^{10}$;

$R^1$ is $C_1$-$C_8$-alkyl, $C_2$-$C_8$-alkenyl, $C_3$-$C_8$-cycloalkyl or $C_2$-$C_8$-alkynyl, each optionally substituted by one, two or three substituents each independently selected from hydroxy, cyano, amino, halo, $R^5$, —C(=O)—$R^5$, $C_1$-$C_8$-alkylamino, di($C_1$-$C_8$-alkyl)amino, $C_1$-$C_8$-alkanoylamino, $C_1$-$C_8$-alkoxy, —C(=O)$NR^6R^7$, —NH(C=O)—$C_1$-$C_8$-alkyl and —$SO_2NR^6R^7$;

$R^2$ is $C_6$-$C_{15}$-aryl or $C_4$-$C_{15}$-cycloalkenyl, each optionally substituted by one, two or three substituents each independently selected from halo, hydroxy, $R^1$, $R^5$, $C_1$-$C_8$-alkylthio, cyano, C(=O)H, nitro, —O—$C_6$-$C_{15}$-aryl, halo-$C_1$-$C_8$-alkyl, —$NR^6R^7$, —$C_1$-$C_8$-alkyl-$NR^6R^7$, —$C_1$-$C_8$-alkyl-$R^5$, —O—$R^1$ optionally substituted by $NR^6R^7$, —O—$R^5$, —C(=O)—$R^5$, —C(=O)$NR^6R^7$, —C(=O)—O—$R^1$, —O—C(=O)—$R^1$, —$SO_2$—$NH_2$, —$SO_2$—$R^1$, —NH—$SO_2$—$C_1$-$C_8$-alkyl, —C(=O)—NH—$R^1$, —C(=O)—NH—$R^5$, —$SO_2$—$C_6$-$C_{15}$-aryl, —$SO_2$—$R^5$ and —$SO_2NR^6R^7$;

$R^4$ is hydroxy, $C_1$-$C_8$-alkoxy, $C_1$-$C_8$-alkylthio, halo, halo-$C_1$-$C_8$-alkyl, cyano, carboxy, nitro, —N(H)—C(=NH)—$NH_2$, —N(H)—$SO_2$—$R^2$, —$R^2$, —C(=O)—$R^2$, —C(=O)—$R^5$, —O—$R^2$, —O—$R^5$, —N(H)—$R^5$, —N(H)—$R^2$, —$NR^6R^7$, —C(=O)—$R^1$, —C(=O)—$NH_2$, —$SO_2$—$R^5$, —C(=O)—O—$R^1$, —C(=O)—O—$R^2$, —C(=O)—O—$R^5$, —$SO_2$—$R^2$ or —C(=O)—N(H)—$C_1$-$C_8$-alkyl-C(=O)—N(H)—$R^2$;

or $R^4$ is a 4- to 14-membered heterocyclic group, that group being optionally substituted by one, two or three substituents each independently selected from hydroxy, halo, oxo, cyano, —$NR^6R^7$, carboxy, nitro, —N(H)$R^1$, —N(H)—$SO_2$—$C_1$-$C_8$-alkyl, —N(H)—C(=O)—$C_1$-$C_4$-alkyl-$R^2$, —C(=O)—$NH_2$, —C(=O)—$NR^6R^7$, —C(=O)—N(H)—$C_1$-$C_8$-alkyl-$R^6$, —C(=O)—$R^2$, —C(=O)—$R^5$, $C_1$-$C_8$-alkoxy, $C_1$-$C_8$-alkylthio, $C_3$-$C_{10}$-cycloalkyl, —C(=O)—$R^1$, halo-$C_1$-$C_8$-alkyl, —$R^2$, —$C_1$-$C_8$-alkyl-$R^2$, —$R^5$, —$SO_2$—$C_1$-$C_8$-alkyl, —$SO_2$—$R^2$, —$SO_2$—$R^5$, —$SO_2NR^6R^7$ and $C_1$-$C_8$-alkyl optionally substituted by hydroxy;

or $R^4$ is $C_6$-$C_{15}$-aryl optionally substituted by one, two or three substituents each independently selected from hydroxy, $C_1$-$C_8$-alkoxy, —O—$C_6$-$C_{15}$-aryl and $C_1$-$C_8$-alkyl optionally substituted by hydroxy;

or $R^4$ is $C_3$-$C_{10}$-cycloalkyl substituted by one, two or three substituents each independently selected from hydroxy, —$NR^6R^7$, halo, cyano, carboxy, nitro and $C_1$-$C_8$-alkyl;

$R^5$ is a 4- to 14-membered heterocyclic group optionally substituted by one, two or three substituents each independently selected from oxo, halo, —$NR^6R^7$, cyano, hydroxy, carboxy, nitro, —$R^1$, $C_1$-$C_8$-alkoxy, $C_1$-$C_8$-alkylthio, halo-$C_1$-$C_8$-alkyl, —C(=O)—$NH_2$, —$SO_2$—$NH_2$, an ether group containing 2 to 8 carbon atoms and one, two or three oxygen linking atoms, and a 4- to 10-membered heterocyclic group containing one or more heteroatoms independently selected from N, O and S, optionally substituted by one or more $C_1$-$C_6$ alkyl groups;

$R^6$ and $R^7$ are each independently hydrogen, —$R^1$, $C_6$-$C_{15}$-aryl, —$C_1$-$C_8$-alkyl-$C_6$-$C_{15}$-aryl, $R^5$ or —$C_1$-$C_8$-alkyl-$R^5$; or $R^6$ and $R^7$ together with the nitrogen atom to which they are attached form a 4- to 10-membered heterocyclic ring optionally containing one or more further heteroatoms independently selected from N, O and S, wherein the heterocyclic ring is optionally substituted by one or more $C_1$-$C_6$ alkyl groups;

$R^8$ and $R^9$ are each independently H, halo, OH, $R^1$, O—$R^1$ or CN; and $R^{10}$ is H, $R^1$, $R^2$, $R^5$, —$SO_2$—$R^1$, —C(=O)—$C_1$-$C_4$-alkyl-$R^2$, —C(=O)—$NR^6R^7$, —C(=O)—$R^2$, —C(=O)—$R^5$, —C(=O)—$R^1$, —$C_1$-$C_8$-alkyl-$R^2$, —$SO_2$—$R^1$, —$SO_2$—$R^2$, —$SO_2$—$R^5$ or —$SO_2NR^6R^7$.

The skilled person will appreciate that certain combinations of substituents or variables as defined above may result in unstable compounds. Chemically unstable compounds are not intended to be within the scope of protection being sought. For example, when X is O or N, then $R^b$ and $R^c$ are typically not OH or $NHR^{10}$. Similarly, when X is $CR^c$, then $R^a$, $R^b$ and $R^c$ are typically not all OH or $NHR^{10}$.

Terms used in the specification have the following meanings:

"Optionally substituted at one, two or three positions" as used herein means the group referred to can be substituted at one or two or three positions by any one or any combination of the radicals listed thereafter. Thus, where two or more substituents are present, these may be the same or different.

"Halo" or "halogen" as used herein denotes a element belonging to group 17 (formerly group VII) of the Periodic Table of Elements, which may be, for example, fluorine, chlorine, bromine or iodine.

"$C_1$-$C_8$-alkyl" as used herein denotes straight chain or branched alkyl that contains one to eight carbon atoms.

"$C_2$-$C_8$-alkenyl" as used herein denotes straight chain or branched hydrocarbon chains that contain two to eight carbon atoms and one or more carbon-carbon double bonds.

"$C_2$-$C_8$-alkynyl" as used herein denotes straight chain or branched hydrocarbon chains that contain two to eight carbon atoms and one or more carbon-carbon triple bonds.

"$C_6$-$C_{15}$-aryl" as used herein denotes an aromatic group having 6- to 15-ring carbon atoms. Examples of $C_6$-$C_{15}$-aryl groups include but are not limited to phenyl, phenylene, benzenetriyl, indanyl, naphthyl, naphthylene, naphthalenetriyl and anthrylene, "4- to 14-membered heterocyclic group" as used herein denotes a 4- to 14-membered heterocyclic ring containing at least one ring heteroatom selected from the group consisting of nitrogen, oxygen and sulphur, which may be saturated, partially saturated or unsaturated. Examples of 4- to 14-membered heterocyclic groups include but are not limited to furan, azetidine, pyrrole, pyrrolidine, pyrazole, imidazole, triazole, isotriazole, tetrazole, thiadiazole, isothiazole, oxadiazole, pyridine, piperidine, oxazole, isoxazole, pyrazine, pyridazine, pyrimidine, piperazine, pyrrolidinone, morpholine, triazine, oxazine, tetrahydrofuran, tetrahydrothiophene, tetrahydrothiopyran, tetrahydropyran, 1,4-dioxane, 1,4-oxathiane, indazole, quinoline, indole, thiazole, isoquinoline, tetrahydroisoquinoline, benzothiophene, benzoxazole, benzisoxazole, benzothiazole, benzoisothiazole, benzofuran, dihydrobenzofuran, dihydrobenzoxazine, benzodioxole, benzimidazole, tetrahydronaphthyridine, pyrrolopyridine, tetrahydrocarbazole, benzotriazole and tetrahydrothiopyranoindole. The 4- to 14-membered heterocyclic group can be unsubstituted or substituted.

"N-heterocyclic group" as used herein denotes a heterocyclic group wherein at least one of the ring atoms is a nitrogen atom. The N-heterocyclic group can be unsubstituted or substituted.

"$C_3$-$C_{10}$-cycloalkyl" denotes a fully saturated carbocyclic ring having 3 to 10 ring carbon atoms, for example a monocyclic group such as a cyclopropyl, cyclobutyl, cyclopentyl or cyclohexyl, cycloheptyl, cyclooctyl, cyclononyl or cyclodecyl, or a bicyclic group such as bicycloheptyl or bicyclooctyl. $C_4$-$C_{15}$-Cycloalkenyl is a partially unsaturated carbocylic, mono-, bi- or tricyclic ring with at least one double bond, such as cyclobutenyl, cyclopentenyl, e.g. cyclopenten-2- or -3-yl, cyclohexenyl, e.g. cyclohexen-2- or -3-yl, cycloheptenyl, e.g. cyclohepten-2-, -3- or -4-yl, cyclooctenyl, cyclononenyl or cyclodecenyl, or a bicyclic group such as bicycloheptenyl or bicyclooctenyl, and can be unsubstituted or substituted.

"Halo-$C_1$-$C_8$-alkyl" as used herein denotes $C_1$-$C_8$-alkyl as hereinbefore defined substituted by one or more halogen atoms, preferably one, two or three halogen atoms.

"$C_1$-$C_8$-alkylamino" and "di($C_1$-$C_8$-alkyl)amino" as used herein denote amino substituted respectively by one or two $C_1$-$C_8$-alkyl groups as hereinbefore defined, which may be the same or different.

"$C_1$-$C_8$-alkylthio" as used herein denotes straight chain or branched alkylthio having 1 to 8 carbon atoms.

"$C_1$-$C_8$-alkoxy" as used herein denotes straight chain or branched alkoxy that contains 1 to 8 carbon atoms.

"$C_1$-$C_8$-alkoxycarbonyl" as used herein denotes $C_1$-$C_8$-alkoxy as hereinbefore defined attached through the oxygen atom to a carbonyl group.

In the above definitions where the number of carbon atoms or ring members are specified, these may be varied in certain embodiments. For example, an embodiment may define alkyl as being $C_1$-$C_4$-alkyl. In such cases where a different number of carbon atoms or ring members is specified, the above definitions should be amended accordingly.

Where variables are defined with reference to other variables, e.g. $R^2$ is $C_6$-$C_{15}$ aryl optionally substituted by $R^1$ or $R^5$, this means that the $R^2$ group is optionally substituted by one or more substituents each independently selected from the definition of $R^1$ and/or $R^5$. Where a compound includes more than one substituent selected from the definition of a particular variable (e.g. $R^1$), each substituent may be the same or different.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

In an embodiment of the invention as defined anywhere herein, $T^1$ is a 4- to 14-membered heterocyclic group or $C_4$-$C_{15}$-cycloalkenyl, each optionally substituted at one or two positions by $R^1$, O—$R^1$, OH or halo. Optionally, $T^1$ is a 4- to 14-membered heterocyclic group optionally substituted as defined herein. Suitably, $T^1$ is a 5- or 6-membered heterocyclic group optionally substituted at one or two positions by $R^1$, O—$R^1$, OH or halo. The heterocyclic group typically contains at least one heteroatom selected from O and N.

$T^1$ is suitably a 5- or 6-membered N-heterocyclic group optionally substituted at one position by $C_1$-$C_8$-alkyl (e.g. $C_1$-$C_4$-alkyl, but preferably methyl). For example $T^1$ is unsubstituted pyridinyl, especially pyridin-2-yl, or pyridyl substituted by $C_1$-$C_4$-alkyl (especially methyl), for example 6-methyl-pyridin-2-yl.

In an embodiment of the invention as defined anywhere herein, $T^2$ is a 4- to 14-membered heterocyclic group optionally substituted at one or two positions by $R^1$, O—$R^1$, halo, $R^2$ or $R^5$. Suitably, $T^2$ is a 5- or 6-membered N-heterocyclic group optionally substituted at one or two positions by $R^1$, O—$R^1$, halo, $R^2$ or $R^5$.

$T^2$ is suitably a 5- or 6-membered N-heterocyclic group optionally substituted at one position by $C_1$-$C_4$-alkoxy (especially methoxy); halo; $C_6$-$C_{15}$-aryl (especially phenyl) optionally substituted by halo, $C_1$-$C_4$-alkoxy (especially methoxy), $R^5$, $C_1$-$C_4$-alkyl-$R^5$ or —C(=O)—$R^5$; or a 4- to 14-membered heterocyclic group optionally substituted at one position by $C_1$-$C_4$-alkoxy or $C_1$-$C_4$-alkyl. For example $T^2$ may be unsubstituted pyridinyl, especially unsubstituted pyridin-3-yl, or $T^2$ may be pyridinyl substituted by methoxy or by phenyl substituted at one position by $C_1$-$C_4$-alkoxy or $R^5$.

Optionally, when X is $CR^c$, one of $R^a$ and $R^c$ is OH or $NHR^{10}$;

In an embodiment of the invention as defined anywhere herein, X is O or N. Suitably, X is N.

$R^a$ is suitably hydrogen.

$R^b$ is suitably H or $C_1$-$C_4$-alkyl optionally substituted at one position by $R^4$, and wherein $R^4$ is especially either (i) indolyl optionally substituted at one position by halo, hydroxy, $C_1$-$C_8$-alkyl, $C_1$-$C_8$-alkoxy or cyano, or (ii) phenyl optionally substituted at one position by hydroxy, halo, $C_1$-$C_8$-alkyl or $C_1$-$C_8$-alkoxy.

Alternatively $R^b$ is suitably $C_3$-$C_{10}$-cycloalkyl, especially $C_3$-$C_5$-cycloalkyl i.e. cyclopropyl, cyclobutyl or cyclopentyl.

In certain embodiments, $R^b$ is other than hydrogen.

In further embodiments of the invention, X may be $CR^c$, wherein $R^c$ is selected from OH and $NHR^{10}$. Where $R^c$ is selected from OH and $NHR^{10}$, $R^a$ and $R^b$ may be selected from H; $C_1$-$C_8$-alkyl optionally substituted at one, two or three positions by $R^4$; $C_3$-$C_{10}$-cycloalkyl optionally substituted at one or two positions by hydroxy, amino, $C_1$-$C_8$-alkyl, $C_1$-$C_8$-alkoxy, halo, cyano, oxo, carboxy or nitro; and $C_6$-$C_{15}$-aryl optionally substituted at one, two or three positions by halo, hydroxy, amino, cyano, oxo, carboxy, nitro or $R^5$. Optionally, $R^a$ and $R^b$ are both other than H when X is $CR^c$ and $R^c$ is OH or $NHR^{10}$.

In embodiments of the invention as defined anywhere herein, $R^8$ is H, halo, OH or Me and $R^9$ is hydrogen. Optionally, $R^8$ and $R^9$ are both hydrogen.

$R^1$ is suitably $C_1$-$C_4$-alkyl optionally substituted at one position by hydroxy or halo.

$R^2$ is suitably $C_6$-$C_{15}$-aryl, optionally substituted at one, two or three positions by halo, hydroxy, $R^1$, $R^5$, $C_1$-$C_8$-alkylthio, cyano, C(=O)H, nitro, —O—$C_6$-$C_{15}$-aryl, halo-$C_1$-$C_8$-alkyl, —$NR^6R^7$, —$C_1$-$C_8$-alkyl-$NR^6R^7$, —O—$C_1$-$C_8$-alkyl-$NR^6R^7$, —$C_1$-$C_8$-alkyl-$R^5$, —O—$R^1$ optionally substituted at one position by $NR^6R^7$, —O—$R^5$, —C(=O)—$R^5$, —C(=O)—$NH_2$, —C(=O)$NR^6R^7$, —C(=O)—O—$R^1$, —O—C(=O)—$R^1$, —$SO_2$—$NH_2$, —$SO_2$—$R^1$, —NH—$SO_2$—$C_1$-$C_8$-alkyl, —C(=O)—NH—$R^1$, —C(=O)—NH—$R^5$, —$SO_2$—$C_6$-$C_{15}$-aryl, —$SO_2$—$R^5$ or —$SO_2NR^6R^7$. Optionally, $R^2$ is $C_6$-$C_{10}$-aryl, especially phenyl, optionally substituted at one or two positions by halo, —$R^1$, O—$R^1$, CHO, $R^5$, —$C_1$-$C_4$-alkyl-$R^5$, —C(=O)—$R^5$, —$SO_2$—$NH_2$, —$SO_2$—$C_1$-$C_4$-alkyl, —NH—$SO_2$—$C_1$-$C_4$-alkyl, —C(=O)—NH—$R^1$, —C(=O)—NH—$R^5$ or $C_1$-$C_4$-alkyl optionally substituted at one position by di($C_1$-$C_4$-alkyl)amino.

$R^4$ is suitably a 4- to 10-membered heterocyclic group (especially indolyl) optionally substituted at one position by hydroxy, halo, cyano, $C_1$-$C_4$-alkyl or $C_1$-$C_4$-alkoxy.

Alternatively, $R^4$ may be phenyl optionally substituted at one or two positions by hydroxy, halo, $C_1$-$C_4$-alkyl or $C_1$-$C_4$-alkoxy.

As a further alternative, $R^4$ may be a $C_3$-$C_6$-cycloalkyl substituted at one, two or three positions by hydroxy, —$NR^6R^7$, halo or $C_1$-$C_8$-alkyl;

$R^5$ is suitably a 4- to 10-membered heterocyclic group (especially a 5- or 6-membered heterocyclic group) optionally substituted at one or two positions by $C_1$-$C_4$-alkyl, an ether group containing 2 to 6 carbon atoms and one oxygen atom, or $NR^6R^7$. For example $R^5$ may be morpholinyl, pyrazolyl, pyrrolidinyl, piperazinyl, piperidinyl or tetrahydropyranyl.

Suitable compounds of formula I include compounds in free or salt or solvate form wherein $T^1$ is a 4- to 14-membered heterocyclic group optionally substituted at one or two positions by halo, O—$R^1$ or $R^1$;

$T^2$ is a 4- to 14-membered N-heterocyclic group optionally substituted at one or two positions by $R^1$, $R^2$, $R^5$, halo, $C_1$-$C_8$-alkoxy, $C_1$-$C_8$-alkoxycarbonyl or cyano;

X is $CR^c$, O or N, provided that when X is O, $R^a$ is absent;

$R^a$ and $R^b$ are each independently selected from hydrogen;

$C_1$-$C_8$-alkyl optionally substituted at one or two positions by $R^4$; and $C_3$-$C_{10}$-cycloalkyl; or $R^a$ and $R^b$ together with X form a 3-, 4-, 5- or 6-membered cyclic group, optionally substituted by OH, halo, $NR^6R^7$ or $R^1$;

$R^c$ is $C_1$-$C_8$-alkyl, OH or $NHR^{10}$;

$R^1$ is $C_1$-$C_8$-alkyl or $C_3$-$C_6$-cycloalkyl;

$R^2$ is $C_6$-$C_{10}$-aryl, especially phenyl, optionally substituted at one or two positions by halo, —CHO, —$R^1$, $OR^1$, $R^5$, —$C_1$-$C_4$-alkyl-$R^5$, —C(=O)—$R^5$, —$SO_2$—$NH_2$, —$SO_2$—$C_1$-$C_4$-alkyl, —NH—$SO_2$—$C_1$-$C_4$-alkyl, —C(=O)—NH—$R^1$, —C(=O)—NH—$R^5$ or $C_1$-$C_4$-alkyl optionally substituted at one position by di($C_1$-$C_4$-alkyl)amino;

$R^4$ is hydroxy, —C(=O)—$R^5$ or —$SO_2$—$R^2$;

or $R^4$ is a 4- to 14-membered heterocyclic group, that group being optionally substituted at one or two positions by hydroxy, halo, cyano, amino, carboxy, —N(H)—$SO_2$—$C_1$-$C_8$-alkyl, $C_1$-$C_8$-alkoxy, $C_3$-$C_{10}$-cycloalkyl, —C(=O)—$R^1$, $R^2$, —$SO_2$—$C_1$-$C_8$-alkyl, $R^5$ or by $C_1$-$C_8$-alkyl optionally substituted at one position by hydroxy;

or $R^4$ is $C_6$-$C_{15}$-aryl optionally substituted at one or two positions by hydroxy, $C_1$-$C_8$-alkoxy, —O—$C_6$-$C_{15}$-aryl or by $C_1$-$C_8$-alkyl optionally substituted at one position by hydroxy;

or $R^4$ is $C_3$-$C_{10}$-cycloalkyl substituted at one, two or three positions by hydroxy, —$NR^6R^7$, halo or $C_1$-$C_8$-alkyl;

$R^5$ is a 4- to 14-membered heterocyclic group optionally substituted at one or two positions by $C_1$-$C_4$-alkyl, an ether group containing 2 to 6 carbon atoms and one oxygen atom, or $NR^6R^7$;

$R^6$ and $R^7$ are each independently hydrogen or —$R^1$;

$R^8$ is H, halo, OH or Me; and $R^9$ is hydrogen.

Especially suitable compounds of formula I include compounds in free or salt or solvate form wherein $T^1$ is a 5- or 6-membered heterocyclic group optionally substituted at one position by halo, O—$R^1$ or $R^1$;

$T^2$ is a 5- or 6-membered N-heterocyclic group optionally substituted at one or two positions by $R^1$, $R^2$, $R^5$, halo, $C_1$-$C_4$-alkoxy, $C_1$-$C_4$-alkoxycarbonyl or cyano;

X is $CR^c$ or N;

$R^a$ is hydrogen or $C_1$-$C_4$-alkyl;

$R^b$ is hydrogen; $C_1$-$C_4$-alkyl optionally substituted at one or two positions by $R^4$; or $C_3$-$C_6$-cycloalkyl;

$R^c$ is OH;

$R^1$ is $C_1$-$C_4$-alkyl or $C_3$-$C_5$-cycloalkyl;

$R^2$ is phenyl optionally substituted at one position by halo, CHO, $R^1$, —$OR^1$, $R^5$, $C_1$-$C_4$-alkyl-$R^5$, —C(=O)—$R^5$, —$SO_2$—$NH_2$, —$SO_2$—$R^1$, —NH—$SO_2$—$C_1$-$C_4$-alkyl, —C(=O)—NH—$R^1$, —C(=O)—NH—$R^5$ or by $C_1$-$C_4$-alkyl optionally substituted at one position by di($C_1$-$C_4$-alkyl)amino;

$R^4$ is hydroxyl;

or $R^4$ is a 4- to 14-membered heterocyclic group, that group being optionally substituted at one or two positions by hydroxy, halo, cyano, amino, carboxy, —N(H)—$SO_2$—$C_1$-$C_8$-alkyl, $C_1$-$C_8$-alkoxy, $C_3$-$C_{10}$-cycloalkyl, —C(=O)—$R^1$, $R^2$, —$SO_2$—$C_1$-$C_8$-alkyl, $R^5$ or by $C_1$-$C_8$-alkyl optionally substituted at one position by hydroxy;

or $R^4$ is phenyl optionally substituted at one or two positions by hydroxy, $C_1$-$C_8$-alkoxy, —O—$C_6$-$C_{15}$-aryl or by $C_1$-$C_8$-alkyl optionally substituted at one position by hydroxy;

or $R^4$ is $C_3$-$C_6$-cycloalkyl substituted at one, two or three positions by hydroxy, —$NR^6R^7$, halo or $C_1$-$C_8$-alkyl;

$R^5$ is a 4- to 14-membered heterocyclic group optionally substituted at one or two positions by $C_1$-$C_4$-alkyl, an ether group containing 2 to 6 carbon atoms and one oxygen atom, or $NR^6R^7$;

$R^6$ and $R^7$ are each independently hydrogen or —$R^1$; and $R^8$ and $R^9$ are both hydrogen.

According to formula I, the above-described embodiments and/or suitable features of the invention may be incorporated independently, collectively or in any combination. Thus, the term "an embodiment of the invention as defined anywhere herein" should be taken to mean "an embodiment of the invention as defined anywhere herein in any embodiment or aspect" and it should be clear to the skilled person that specific features of different embodiments or aspects can be combined within the scope of the invention as defined herein.

Compounds of formula I that contain a basic centre are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid, hydroiodic acid, nitric acid, sulfuric acid, phosphoric acid; and organic acids, for example aliphatic monocarboxylic acids such as formic acid, acetic acid, trifluoroacetic acid, propionic acid and butyric acid, caprylic acid, dichloroacetic acid, hippuric acid, aliphatic hydroxy acids such as lactic acid, citric acid, tartaric acid or malic acid, gluconic acid, mandelic acid, dicarboxylic acids such as maleic acid or succinic acid, adipic acid, aspartic acid, fumaric acid, glutamic acid, malonic acid, sebacic acid, aromatic carboxylic acids such as benzoic acid, p-chloro-benzoic acid, nicotinic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid, ethanesulfonic acid, ethane-1,2-disulfonic acid, 2-hydroxy-ethanesulfonic acid, (+) camphor-10-sulfonic acid, naphthalene-2-sulfonic acid, naphthalene-1,5-disulfonic acid or p-toluenesulfonic acid. These salts may be prepared from compounds of formula I by known salt-forming procedures. Pharmaceutically acceptable solvates are generally hydrates.

Compounds of formula I which contain acidic, e.g. carboxyl groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine, arginine, benethamine, benzathine, diethanolamine, 4-(2-hydroxyethyl)morpholine, 1-(2-hydroxyethyl) pyrrolidine, N-methyl glucamine, piperazine, triethanolamine or tromethamine. These salts may be prepared from compounds of formula I by known salt-forming procedures. Compounds of formula I that contain acidic, e.g. carboxyl groups may also exist as zwitterions with the quaternary ammonium centre.

Compounds of formula I in free form may be converted into salt form, and vice versa, in a conventional manner. The compounds in free or salt form can be obtained in the form of hydrates or solvates containing a solvent used for crystallisation. Compounds of formula I can be recovered from reaction mixtures and purified in a conventional manner. Isomers, such as enantiomers, may be obtained in a conventional manner, e.g. by fractional crystallisation or asymmetric synthesis from correspondingly asymmetrically substituted, e.g. optically active, starting materials.

Many compounds of the invention contain at least one asymmetric carbon atom and thus they exist in individual optically active isomeric forms or as mixtures thereof, e.g. as racemic mixtures. In cases where additional asymmetric centres exist the present invention also embraces both individual optically active isomers as well as mixtures, e.g. diastereomeric mixtures, thereof.

The invention includes all such forms, in particular the pure isomeric forms. The different isomeric forms may be separated or resolved one from the other by conventional methods, or any given isomer may be obtained by conventional synthetic methods or; by stereospecific or asymmetric syntheses. Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

The invention includes all pharmaceutically acceptable isotopically-labelled compounds of formula I wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen e.g. $^{2}H$ and $^{3}H$, carbon e.g. $^{11}C$, $^{13}C$ and $^{14}C$, chlorine e.g. $^{36}Cl$, fluorine e.g. $^{18}F$, iodine e.g. $^{123}I$ and $^{125}I$, nitrogen e.g. $^{13}N$ and $^{15}N$, oxygen e.g. $^{15}O$, $^{17}O$ and $^{18}O$, and sulfur e.g. $^{35}S$.

Certain isotopically-labelled compounds of formula I, for example those incorporating a radioactive isotope, are useful in drug and/or substrate tissue distribution studies. The radioactive isotopes tritium ($^{3}H$) and carbon-14 ($^{14}C$) are particularly useful for this purpose in view of their ease of incorporation and ready means of detection. Substitution with heavier isotopes such as deuterium ($^{2}H$) may afford certain therapeutic advantages that result from greater metabolic stability, for example increased in vivo half-life or reduced dosage requirements, and hence may be preferred in some circumstances. Substitution with positron emitting isotopes, such as $^{11}C$, $^{18}F$, $^{15}O$, and $^{13}N$ can be useful in Positron Emission Topography (PET) studies for examining substrate receptor occupancy.

Isotopically-labelled compounds of formula I can generally be prepared by conventional techniques known to those skilled in the art or by processes analogous to those described in the accompanying examples using an appropriate isotopically-labelled reagent in place of the non-labelled reagent previously used.

Pharmaceutically acceptable solvates in accordance with the invention include those wherein the solvent of crystallisation may be isotopically substituted e.g. $D_2O$, $d_6$-acetone or $d_6$-DMSO.

Specific especially preferred compounds of the invention are those described hereinafter in the Examples.

The invention also provides a process for the preparation of compounds of formula I which comprises:

(i) Reacting compounds (1) and (2) to form intermediate (3)

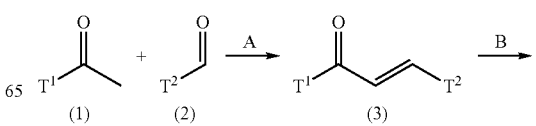

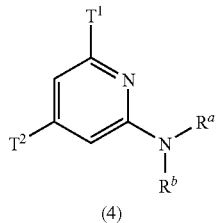

(4)

which is then cyclised to prepare a compound (4), a compound of Formula I wherein X is N and wherein $T^1$, $T^2$, $R^a$ and $R^b$ are as defined above; and (ii) recovering the product in free or salt or solvate form.

Step A of the reaction is conveniently carried out in an organic solvent, for example THF, optionally in the presence of an organic or inorganic base, for example DBU or potassium carbonate.

Step B of the reaction is conveniently carried out in an organic solvent, for example ethanol, to which a cyclising agent such as α-(benzotriazol-1-yl)acetonitrile is added. Amine is typically added to the reaction mixture. Suitable reaction temperatures are elevated temperatures, e.g. from 100° C. to 160° C., preferably by microwaving at about 120° C.

Compounds of formula (1) and (2) are known or may be prepared by known procedures.

The general scheme shown above may be modified as appropriate using known procedures or based on the specific examples described in detail herein. In addition, the compound (4) may be further derivitised using known techniques, such as palladium catalysed cross coupling reactions.

Compounds of formula I in pharmaceutically acceptable salt, hereinafter referred to alternatively as "agents of the invention", are useful as pharmaceuticals. Accordingly the invention also provides a compound of formula I in pharmaceutically acceptable salt for use as a pharmaceutical. The agents of the invention act as activin-like kinase ("ALK")-5 inhibitors. At least many agents of the invention also act as ALK-4 inhibitors too.

TGF-β1 is the prototypic member of a family of cytokines including the TGF-βs, activins, inhibins, bone morphogenetic proteins and Mullerian-inhibiting substance, that signal through a family of single transmembrane serine/threonine kinase receptors. These receptors can be divided into two classes, the type I or activin like kinase (ALK) receptors and type II receptors. The ALK receptors are distinguished from the type II receptors in that the ALK receptors (a) lack the serine/threonine rich intracellular tail, (b) possess serine/threonine kinase domains that are very homologous between type I receptors, and (c) share a common sequence motif called the GS domain, consisting of a region rich in glycine and serine residues. The GS domain is at the amino terminal end of the intracellular kinase domain and is critical for activation by the type II receptor. Several studies have shown that TGF-β signalling requires both the ALK and type II receptors. Specifically, the type II receptor phosphorylates the GS domain of the type I receptor for TGF-β, ALK5, in the presence of TGF-β. The ALK5, in turn, phosphorylates the cytoplasmic proteins Smad2 and Smad3 at two carboxy terminal serines. The phosphorylated Smad proteins translocate into the nucleus and activate genes that contribute to the production of extracellular matrix. Therefore, preferred compounds of this invention are selective in that they inhibit the type I receptor.

Activins transduce signals in a manner similar to TGF-β. Activins bind to serine/thereonine kinase, the activin type II receptor (ActRIIB), and the activated type II receptor hyperphosphorylates serine/threonine residues in the GS region of the ALK4. The activated ALK4 in turn phosphorylates Smad2 and Smad3. The consequent formation of a hetero-Smad complex with Smad4 results in the activin-induced regulation of gene transcription.

Activation of the TGF-β1 axis and expansion of extracellular matrix are early and persistent contributors to the development and progression of chronic renal disease and vascular disease. Border W. A., et al, *N. Engl. J. Med.*, 1994; 331(19), 1286-92. Further, TGF-β1 plays a role in the formation of fibronectin and plasminogen activator inhibitor-1, components of sclerotic deposits, through the action of Smad3 phosphorylation by the TGF-β1 receptor ALK5. Zhang Y., et al, *Nature*, 1998; 394(6696), 909-13; Usui T., et al, *Invest. Opthalmol. Vis. Sci.*, 1998; 39(11), 1981-9.

Progressive fibrosis in the kidney and cardiovascular system is a major cause of suffering and death and an important contributor to the cost of health care. TGF-β1 has been implicated in many renal fibrotic disorders. Border W. A., et al, *N. Engl. J. Med.*, 1994; 331(19), 1286-92. TGF-β1 is elevated in acute and chronic glomerulonephritis Yoshioka K., et al, *Lab. Invest.*, 1993; 68(2), 154-63, diabetic nephropathy Yamamoto, T., et al, 1993, *PNAS* 90, 1814-1818, allograft rejection, HIV nephropathy and angiotensin-induced nephropathy Border W. A., et al, *N. Engl. 5 J. Med.*, 1994; 331(19), 1286-92. In these diseases the levels of TGF-β1 expression coincide with the production of extracellular matrix. Three lines of evidence suggest a causal relationship between TGF-β1 and the production of matrix. First, normal glomeruli, mesangial cells and non-renal cells can be induced to produce extracellular-matrix protein and inhibit protease activity by exogenous TGF-β1 in vitro. Second, neutralizing antibodies against TGF-β1 can prevent the accumulation of extracellular matrix in nephritic rats. Third, TGF-β1 transgenic mice or in vivo transfection of the TGF-β1 gene into normal rat kidneys resulted in the rapid development of glomerulosclerosis. Kopp J. B., et al, *Lab. Invest.*, 1996; 74(6), 991 1003. Thus, inhibition of TGF-β1 activity is indicated as a therapeutic intervention in chronic renal disease.

TGF-β1 and its receptors are increased in injured blood vessels and are indicated in neointima formation following balloon angioplasty Saltis J., et al, *Clin. Exp. Pharmacol. Physiol.*, 1996; 23(3), 193-200. In addition TGF-β1 is a potent stimulator of smooth muscle cell ("SMC") migration in vitro and migration of SMC in the arterial wall is a contributing factor in the pathogenesis of atherosclerosis and restenosis. Moreover, in multivariate analysis of the endothelial cell products against total cholesterol, TGF-β receptor ALK5 correlated with total cholesterol (P<0.001) Blann A. D., et al, *Atherosclerosis*, 1996; 120(1-2), 221-6. Furthermore, SMC derived from human atherosclerotic lesions have an increased ALK5/TGF-β type II receptor ratio. Because TGF-β1 is over-expressed in fibroproliferative vascular lesions, receptor-I variant cells would be allowed to grow in a slow, but uncontrolled fashion, while overproducing extracellular matrix components McCaffrey T. A., et al, *Jr., J. Clin.; Invest.*, 1995; 96(6), 2667-75. TGF-β1 was immunolocalized to non-foamy macrophages in atherosclerotic lesions where active matrix synthesis occurs, suggesting that non-foamy macrophages may participate in modulating matrix gene expression in atherosclerotic remodelling via a TGF-β-dependent mechanism. Therefore, inhibiting the action of TGF-β1 on ALK5 is also indicated in atherosclerosis and restenosis.

Liver fibrosis is the result of unbalanced wound healing response to chronic liver injury trigged by a number of agents, such as hepatitis B and hepatitis C virus, alcohol or drugs, and autoimmune diseases. Ultimately, liver fibrosis could lead to life-threatening cirrhosis and liver cancer (see review article by Gressner et al (2006) *J. Cell. Mol. Med.* 2006, 10(1): 76-99).

Several cellular signaling pathways are known to be altered upon chronic liver injury. TGFβ signaling, its receptors and associated Smad-signaling proteins are well documented to be present in cell types involved in fibrogenesis. The circulating levels of TGFβ have been found to be elevated in a number of animal models of fibrotic diseases including liver fibrosis. Transgenic mice with overexpression of TGFβ1 develop fibrosis in multiple organs including liver, kidney, lungs and heart. It is apparent that an elevated TGFβ signaling is involved in all types of fibrotic diseases including liver fibrosis. This notion has been further validated in several studies using TGFβ inhibitors in fibrosis models. TGFβ mediates it signal by binding to two ser/thr kinase receptors, TGFβRII and ALK5. Expressing a dominant negative TGF-βRII showed beneficial effects in a rat model of dimethylnitrosamine induced liver fibrosis (see Qi et al (1999) *Proc. Natl. Acad. Sci.* 96: 2345-9 and Nakamura et al (2000) *Hepatology* 32: 247-55). Inhibiting TGFβ expression using an antisense approach also reduced liver fibrosis induced by bile duct ligation (see Arias et al (2003) BMC *Gastroenterol.* 3: 29). Recently, a small molecule inhibitor of ALK5, GW6604, when given therapeutically to rat, had significant effect in the treatment of dimethylnitrosamine induced liver fibrosis. It is quite remarkable that GW6604 prevented 40% of the death rate and inhibited extracellular matrix deposition by 60%, a key measurement for fibrosis. Importantly, no obvious side effects were noted during the 3 weeks treatment with GW6604 (see De Gouville et al (2005) *Br. J. Pharmacol.* 145: 166-77). Taken together these studies suggest that inhibiting TGFβ signaling could be an effective treatment for liver fibrotic diseases.

TGF-β1 is also indicated in wound repair. Neutralizing antibodies to TGF-β1 have been used in a number of models to illustrate that inhibition of TGF-β1 signalling is beneficial in restoring function after injury by limiting excessive scar formation during the healing process. For example, neutralizing antibodies to TGF-β1 and TGF-β2 reduced scar formation and improved the cytoarchitecture of the neodermis by reducing the number of monocytes and macrophages as well as decreasing dermal fibronectin and collagen deposition in rats Shah M., *J. Cell. Sci.*, 1995, 108, 985-1002. Moreover, TGF-β antibodies also improve healing of corneal wounds in rabbits Moller-Pedersen T., *Curr. Eye Res.*, 1998, 17, 736-747, and accelerate wound healing of gastric ulcers in the rat, Ernst H., *Gut,* 1996, 39, 172-175. These data strongly suggest that limiting the activity of TGF-β would be beneficial in many tissues and suggest that any disease with chronic elevation of TGF-β would benefit by inhibiting Smad2 and Smad3 signalling pathways.

TGF-β is also implicated in peritoneal adhesions Sand G. M., et al, *Wound Repair Regeneration,* 1999 November-December, 7(6), 504-510. Therefore, inhibitors of ALK5 would be beneficial in preventing peritoneal and sub-dermal fibrotic adhesions following surgical procedures.

TGF-β is also implicated in photoaging of the skin (see Fisher et al, Mechanisms of photoaging and chronological skin ageing, *Archives of Dermatology,* 138(11):1462-1470, 2002 November and Schwartz E. Sapadin A N. Kligman L H. "Ultraviolet B radiation increases steady state mRNA levels for cytokines and integrins in hairless mouse skin-modulation by 25 topical tretinoin", *Archives of Dermatological Research,* 290(3):137-144, 1998 March).

TGF-β signalling is also implicated in the development of pulmonary disorders, in particular pulmonary hypertension and pulmonary fibrosis (see Morrell N W et al, Altered growth responses of pulmonary artery smooth muscle cells from patients with primary pulmonary hypertension to transforming growth factor-beta(1) and bone morphogenetic proteins *Circulation.* 2001 Aug. 14; 104(7):790-5 and Bhatt N et al, Promising pharmacologic innovations in treating pulmonary fibrosis, *Curr Opin Pharmacol.* 2006 Apr. 28).

TGF-β1 levels are increased in animal models of pulmonary hypertension (Mata-Greenwood E et al, Alterations in TGF-beta1 expression in lambs with increased pulmonary blood flow and pulmonary hypertension, *Am. J. Physiol. Lung Cell Mol. Physiol.* 2003 July; 285(1):L209-21). Other studies have suggested that pulmonary endothelial cell-derived TGF-β1 can stimulate the growth of pulmonary vascular smooth muscle cells which may underlie the enhanced muscularisation observed in the pulmonary vasculature of individuals with pulmonary hypertension (Sakao S et al, Apoptosis of pulmonary microvascular endothelial cells stimulates vascular smooth muscle cell growth, *Am. J. Physiol. Lung Cell Mol. Physiol.* 2006 Apr. 14). Therefore, inhibiting the action of TGF-β1 on ALK5 is indicated as a therapeutic intervention in pulmonary hypertension.

Additionally, dys-regulated TGF-β signalling has also been implicated in the development of idiopathic pulmonary fibrosis. Activation of ALK5 results in Smad3-activation and downstream modulation of the expression of genes involved in the fibrotic process such as plasminogen activator inhibitor-1, pro-collagen 3A1, and connective tissue growth factor. The levels of TGF-β1 and its downstream pro-fibrotic mediators have been demonstrated to be up-regulated in bronchoalveolar lavage taken from patients with idiopathic pulmonary fibrosis (Hiwatari N et al, Significance of elevated procollagen-III-peptide and transforming growth factor-beta levels of bronchoalveolar lavage fluids from idiopathic pulmonary fibrosis patients, *Tohoku J. Exp. Med.* 1997 February; 181(2): 285-95) and in animal models of idiopathic pulmonary fibrosis (Westergren-Thorsson G et al, Altered expression of small proteoglycans, collagen, and transforming growth factor-beta 1 in developing bleomycin-induced pulmonary fibrosis in rats, *J. Clin. Invest.* 1993 August; 92(2): 632-7).

Transient over-expression of active TGF-β1 in murine lungs, using adenoviral vector-mediated gene transfer, resulted in progressive pulmonary fibrosis in wild-type mice, whereas no fibrosis was seen in the lungs of Smad3 knockout mice up to 28 days following TGF-β1 challenge (Khalil N et al, Differential expression of transforming growth factor-beta type I and II receptors by pulmonary cells in bleomycin-induced lung injury: correlation with repair and fibrosis, *Exp. Lung. Res.* 2002 April-May; 28(3):233-50. Thus, inhibition of TGF-β1 activation of ALK5 is also indicated for pulmonary fibrosis.

TGF-beta 1 may also be implicated in tumors and hence the agents of the invention may be useful in the treatment of cancer, including prostate cancer, breast cancer, gastric cancer, angiogenesis, metastasis, tumors, e.g. in the treatment and/or prevention of tumor progression.

Activin signaling and overexpression of activin is linked to pathological disorders that involve extracellular matrix accumulation and fibrosis (e.g., Matsuse, T. et al., *Am. J. Respir Cell Mol. Biol.* 13:17-24 (1995); Inoue, S. et al., *Biochem. Biophys. Res. Comn.* 205:441-448 (1994); Matsuse, T. et al., *Am. J. Pathol.* 148:707-713 (1996); De Bleser et al., *Hepa-* tology 26:905-912 (1997); Pawlowski, J. E., et al., *J. Clin. Invest.* 100:639-648 (1997); Sugiyama, M. et al., *Gastroenterology* 114:550-558 (1998); Munz, B. et al., EMBO J. 18:5205-5215 (1999)), inflammatory responses (e.g., Rosendahl, A. et al., *Am. J. Respir. Cell Mol. Biol.* 25:60-68 (2001), cachexia or wasting (Matzuk7 M. M. et al., *Proc. Natl. Acad. Sci. USA* 91:8817-8821 (1994); Coerver, K. A. et al., *Mol. Endocrinol.* 10:531 543 (1996); Cipriano, S. C. et al., *Endocrinology* 141:2319-2327 (2000)), diseases or pathological responses in the central nervous system (e.g., Logan, A. et al., *Eur. J. Neurosci.* 11:2367-2374 (1999); Logan, A. et al., *Exp. Neurol.* 159:504-510 (1999); Masliah, E. et al., *Neurochem. Int.* 39:393-400 (2001); De Groot, C. J. A. et al., *J. Neuropathol. Exp. Neural.* 58:174-187 (1999); John, G. R. et al., *Nat. Med.* 8:1115-1121 (2002)) and hypertension (e.g., Dahly, A. J. et al., *Am. J. Physiol. Regul. Integr Comp. Physiol.* 283: R757-767 (2002)). Studies have shown that TGF-β and activin can act synergistically to induce extracellular matrix production (e.g., Sugiyama, M. et al., *Gastroertology* 114; 550-558 (1998)).

It follows, therefore, that inhibition of ALK5 and/or ALK4 phosphorylation of Smad2 and Smad3 by the compounds of the present invention can be useful to treat and prevent disorders that involve these signaling pathways.

Activin signalling is also implicated in the development of pulmonary disorders, in particular pulmonary hypertension and pulmonary fibrosis. For example, the expression of activin A in lung samples from patients with interstitial pulmonary fibrosis demonstrated strong expression of activin A on metaplastic epithelium, hyperplastic smooth muscle cells, desquamated cells, and alveolar macrophages. Pulmonary arteries from patients with primary or secondary pulmonary hypertension showed abundant immunoreactive activin A on smooth muscle cells. These findings suggest a potential role for this growth factor, activin A, in the pathogenesis of pulmonary tissue remodeling associated with interstitial pulmonary fibrosis and pulmonary hypertension (Matsuse T et al, Expression of immunoreactive activin A protein in remodeling lesions associated with interstitial pulmonary fibrosis, *Am. J. Pathol.* 1996 March; 148(3):707-13). An increase in fibroblasts and associated connective tissue is a feature of pulmonary fibrosis and pulmonary hypertension. Activin A has been demonstrated to modulate human lung fibroblast (HFL1) activity, particularly with respect to proliferation and its differentiation into myofibroblast, thus activin A has potential effects on proliferation of lung fibroblast and its differentiation into myofibroblast, and may contribute to structural remodeling observed in pulmonary fibrosis and hypertension (Ohga E et al, Effects of activin A on proliferation and differentiation of human lung fibroblasts, *Biochem. Biophys. Res. Commun.* 1996 Nov. 12; 228(2):391-6). The induction of pulmonary fibrosis mediated by bleomycin challenge in rats results in the up-regulated expression of activin A in macrophages infiltrated in the lung, and was detected in fibroblasts accumulated in the fibrotic area. Administration of follistatin, an antagonist of activin signalling to bleomycin-treated rats significantly reduced the number of macrophages and neutrophils in bronchoalveolar lavage and reduced the protein content. Follistatin markedly reduced the number of infiltrating cells, ameliorated the destruction of lung architecture, and attenuated lung fibrosis (Aoki F et al, Attenuation of bleomycin-induced pulmonary fibrosis by follistatin, *Am. J. Respir. Crit. Care Med.* 2005 Sep. 15; 172(6):713-20).

Therefore, inhibiting activin signalling via ALK4 inhibition may also be beneficial for the treatment of pulmonary fibrosis and pulmonary hypertension.

It has been demonstrated recently that reduction in TGF-β signalling, through its effector Smad3, enhances the mechanical properties and mineral concentration of the bone matrix, as well as the bone mass, enabling the bone to better resist fracture. These results suggest that reduction of TGF-β signalling could be considered as a therapeutic target to treat bone disorders. (Balooch G, et al. *Proc. Natl. Acad. Sci. USA.* 2005 Dec. 27; 102(52):18813-8). Thus, inhibition of TGF-β1 activation of ALK5 is also indicated for increasing mineral density strength and content of bone and may be utilized to treat a wide variety of conditions, including for example, osteopenia, osteoporosis, fractures and other disorders in which low bone mineral density are a hallmark of the disease.

Having regard to their inhibition of ALK-5 and/or ALK-4 receptors, agents of the invention are useful in the treatment of conditions mediated by the ALK-5 and/or ALK-4 receptors. Treatment in accordance with the invention may be symptomatic or prophylactic.

Therefore according to a further aspect, the invention provides the use of a compound defined in the first aspect in the preparation of a medicament for treating or preventing a disease or condition mediated by ALK-5 inhibition or ALK-4 inhibition.

Diseases or condition mediated by ALK-5 inhibition or ALK-4 inhibition include glomerulo-nephritis, diabetic nephropathy, lupus nephritis, hypertension-induced nephropathy, renal interstitial fibrosis, renal fibrosis resulting from complications of drug exposure, HIV-associated nephropathy, transplant necropathy, liver fibrosis due to all etiologies, hepatic dysfunction attributable to infections, alcohol-induced hepatitis, disorders of the biliary tree, pulmonary fibrosis, pulmonary hypertension, acute lung injury, adult respiratory distress syndrome, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, vascular stenosis, restenosis, atherosclerosis, ocular scarring, corneal scarring, proliferative vitreoretinopathy, excessive or hypertrophic scar or keloid formation in the dermis occurring during wound healing resulting from trauma or surgical wounds, peritoneal and sub dermal adhesion, scleroderma, fibrosclerosis, progressive systemic sclerosis, dermatomyositis, polymyositis, arthritis, ulcers, impaired neurological function, male erectile dysfunction, Alzheimer's disease, Raynaud's syndrome, fibrotic cancers, tumor metastasis growth, radiation-induced fibrosis, thrombosis, and bone conditions such as osteopenia and osteoporosis, which are associated with increased calcium depletion or resorption or in which stimulation of bone formation and calcium fixation in the bone is desirable.

Diseases or conditions mediated by ALK-5 inhibition in particular include chronic renal disease, acute renal disease, wound healing, arthritis, osteoporosis, kidney disease, congestive heart failure, inflammatory or obstructive airways diseases, pulmonary hypertension, ulcers (including diabetic ulcers, chronic ulcers, gastric ulcers, and duodenal ulcers), ocular disorders, corneal wounds, diabetic nephropathy, impaired neurological function, Alzheimer's disease, atherosclerosis, peritoneal and sub-dermal adhesion, any disease wherein fibrosis is a major component, including, but not limited to kidney fibrosis, lung fibrosis and liver fibrosis, for example, hepatitis B virus (HBV), hepatitis C virus (HCV), alcohol-induced hepatitis, haemochromatosis, primary biliary cirrhosis, restenosis, retroperitoneal fibrosis, mesenteric fibrosis, endometriosis, keloids, cancer, abnormal bone function, inflammatory disorders, scarring and photaging of the skin.

Inflammatory or obstructive airways diseases to which the present invention is applicable include asthma of whatever type or genesis including both intrinsic (non-allergic) asthma and extrinsic (allergic) asthma. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant from any previously administered symptomatic asthma therapy.

Other inflammatory or obstructive airways diseases and conditions to which the present invention is applicable include adult/acute respiratory distress syndrome (ARDS), chronic obstructive pulmonary or airways disease (COPD or COAD), including chronic bronchitis, or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Preferably the disease or condition mediated by ALK-5 inhibition or ALK-4 inhibition is pulmonary hypertension, pulmonary fibrosis, liver fibrosis or osteoporosis.

Pulmonary hypertension to be treated in accordance with the invention includes primary pulmonary hypertension (PPH); secondary pulmonary hypertension (SPH); familial PPH; sporadic PPH; precapillary pulmonary hypertension; pulmonary arterial hypertension (PAH); pulmonary artery hypertension; idiopathic pulmonary hypertension; thrombotic pulmonary arteriopathy (TPA); plexogenic pulmonary arteriopathy; functional classes I to IV pulmonary hypertension; and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vascular disease, congenital heart disease, HIV virus infection, drugs and toxins such as fenfluramines, congenital heart disease, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus, schistosomiasis, sarcoidosis or pulmonary capillary hemangiomatosis.

Pulmonary hypertension to be treated in accordance with the invention is most particularly pulmonary hypertension associated with disorders of the respiratory system and/or hypoxemia, including chronic obstructive pulmonary disease, interstitial lung disease, sleep-disordered breathing, alveolar hypoventilation disorders, chronic exposure to high altitude, neonatal lung disease and alveolar-capillary dysplasia, but especially chronic obstructive pulmonary disease.

Lung fibrosis includes idiopathic pulmonary fibrosis in particular.

Compounds of the present may also be used to treat muscle diseases including muscular atrophies (e.g. disuse), muscular dystrophies (e.g. Duchenne's Muscle Dystrophy, Becker's Muscle Dystrophy, Limb-Girdle Muscle Dystrophy, Facioscapulohumeral Dystrophy), sarcopenia and cachexia. Treatment of muscular diseases such as muscle atrophies and dystrophies is a largely unmet medical need. There are only few compounds approved for the use in assorted muscle disorders, mainly in the area of cancer-induced and HIV muscle wasting or cachexia, and a few more drugs are used off-label for these indications. In addition, most of these drugs only address the weight loss and do not specifically affect muscular growth and function. There is therefore a need for effective therapies to treat functional impairments associated with muscle diseases related to cachexia (e.g. in cancer, HIV and COPD), disuse atrophy, sarcopenia and dystrophy.

Myostatin, a member of the transforming growth factor β (TGFβ) family, is a key negative regulator of skeletal muscle mass. In double-muscle cattle and in a human body with skeletal muscle hypertrophy, different mutations in the myostatin gene were detected (McPherron et al (1997) *Nature* 387:83-90; Schuelke et al (2004) *N. Engl. J. Med.* 350:2682-2688). The important role of myostatin for skeletal muscle growth and disorders was confirmed in a wide variety of in vivo and in vitro studies. For example, muscle-specific overexpression of myostatin in mice causes loss of muscle mass (Reisz-Porszasz et al (2003) AJP-*Endo.* 285:876-888), whereas myostatin null mice have increased skeletal muscle mass and reduced body fat (Lin et al (2002) *Biochem. Biophys. Res. Comm.* 291: 701-706). In accordance systemic administration of myostatin induces cachexia (Zimmers et al (2002) *Science* 296:1486-1488), whereas inhibition of myostatin by, for example, the myostatin neutralizing antibody JA16 increases muscle mass and strength in wildtype and dystrophic mdx mice (Bogdanovich et al (2002) *Nature* 420: 418-421.2002; Wagner et al (2002)*Ann. Neurol.* 52: 832-836; Wolfman et al (2003) *Proc. Natl. Acad. Sci.* 100(26): 15842-15846). In addition, elevated myostatin levels have been observed in both experimental and clinical muscle atrophies such as in patients with Human Immunodeficiency Virus (HIV), cancer or liver cirrhosis as well as in sarcopenia of old age and under glucocorticoid-treatment (Ma et al (2003) *Am. J. Physiol. Endocrinol. Metab.* 285: E363-371; Gonzales-Cadavid et al (1998) *Proc. Natl. Acad. Sci.* 95: 14938-14943; see also Reisz-Porszasz et al (2003) AJP-*Endo.* 285:876-888 and Jespersen et al (2006) *Scand. J. Med. Sci. Sports.* 16: 74-82). These findings show the high potential of myostatin inhibitors as treatments for muscular atrophies and dystrophies.

The mode of action of myostatin is still under investigation. It is relatively well established that myostatin signals through Smad2/3 (Lee S. J. (2004) *Ann. Rev. Dev. Biol.* 20: 61-86). Moreover, mature myostatin has been shown to act via activin type IIb and activin receptor like kinase (ALK) receptors in adipocytes (Rebbarpragada et al (2003) *Mol. Cell. Biol.* 23: 7230-7242). However, respective findings in skeletal muscle cells are not described. Myostatin is believed to inhibit differentiation and cause atrophy via ALK signaling. Moreover, inhibition of ALK signaling promotes skMC differentiation and causes skMC hypertrophy.

Osteoporosis is a systemic skeletal disorder characterized by low bone mass and micro-architectural deterioration of bone tissue, with a consequent increase in bone fragility and susceptibility to fracture. The osteoporotic syndrome is multi faceted, encompassing primary disorders such as postmenopausal or age-related osteoporosis, and secondary conditions that accompany disease states or medications. The mechanical properties and composition of bone matrix, along with bone mass and architecture, are critical determinants of a bone's ability to resist fracture.

Thus in a further aspect the invention includes a method for preventing or treating bone conditions which are associated with increased calcium depletion or resorption or in which stimulation of bone formation and calcium fixation in the bone is desirable in which an effective amount of a compound of formula I as defined above, or a pharmaceutically-acceptable and -cleavable ester, or acid addition salt thereof is administered to a patient in need of such treatment.

In a yet further aspect the invention includes a pharmaceutical composition for preventing or treating bone conditions which are associated with increased calcium depletion or resorption or in which stimulation of bone formation and calcium fixation in the bone is desirable comprising a compound of formula I as defined above, or a pharmaceutically-acceptable and -cleavable ester, or acid addition salt thereof, in admixture with a pharmaceutically acceptable excipient, diluent or carrier.

The compounds of the Examples herein below generally have $IC_{50}$ values below 2 μM, and mostly below 1 μM. For instance, specific $IC_{50}$ values for certain of the exemplified compounds are shown in the table below:

| Ex. | $IC_{50}$ (μM) |
|---|---|
| 1.1 | 0.016 |
| 1.2 | 0.019 |
| 1.3 | 0.023 |
| 1.6 | 0.029 |
| 1.10 | 0.057 |
| 1.15 | 0.190 |
| 1.23 | 0.214 |
| 2.1 | 0.017 |
| 2.2 | 0.030 |
| 2.12 | 0.209 |
| 2.17 | 0.236 |
| 2.23 | 0.016 |
| 2.24 | 0.014 |
| 2.26 | 0.012 |
| 2.28 | 0.052 |
| 2.30 | 0.008 |
| 2.31 | 0.004 |
| 2.62 | 0.235 |
| 2.69 | 0.028 |
| 2.70 | 0.089 |
| 2.71 | 0.074 |
| 2.72 | 0.042 |
| 2.80 | 0.039 |
| 2.81 | 0.028 |
| 2.82 | 0.036 |
| 2.83 | 0.059 |
| 2.84 | 0.020 |
| 2.85 | 0.074 |
| 2.86 | 0.092 |
| 2.87 | 0.139 |
| 2.88 | 0.022 |
| 2.89 | 0.017 |
| 2.90 | 0.071 |
| 2.91 | 0.032 |
| 2.92 | 0.035 |
| 2.95 | 0.209 |
| 2.100 | 0.011 |
| 2.102 | 0.014 |
| 2.104 | 0.013 |
| 2.106 | 0.009 |
| 2.107 | 0.013 |
| 2.111 | 0.154 |
| 2.114 | 0.042 |
| 2.116 | 0.048 |
| 2.119 | 0.064 |
| 2.120 | 0.022 |
| 2.125 | 0.038 |
| 2.133 | 0.357 |
| 2.134 | 0.022 |
| 2.158 | 0.035 |
| 2.159 | 0.024 |
| 2.172 | 0.010 |
| 2.179 | 0.005 |

The kinase activity of ALK5 is assessed by measuring radiolabelled phosphate [33P] incorporation in to the generic substrate, casein. The kinase domain of human ALK5 (amino acids 200-503) is fused to an N-terminal histidine tag. The kinase activity of ALK5 is rendered constitutive via point mutation at amino acid 204 (threonine to aspartate modification, ALK5 T204D) and the kinase construct is engineered to be expressed from a baculovirus expression construct in insect cells. The purified, recombinantly-expressed histidine-tagged ALK5 T204D protein is dissolved at 5.4 mg/ml in 50 mM Tris-HCl pH 8.0, 150 mM NaCl, 5 mM DTT. ALK5 T204D is dissolved to 2.5 μg/ml in assay buffer (Assay buffer: 20 mM Tris-HCl pH 7.4, 10 mM $MgCl_2$, 2 mM $MnCl_2$) on the day of use.

Test compounds and reference compounds are dissolved in assay buffer without DTT containing 5% (v/v) DMSO. Stock solutions of test and reference compounds are diluted in assay buffer with DTT (1.25 mM) containing 4.5% (v/v) DMSO. 10 μl of test or reference compound are added to the appropriate wells of 96 well U-bottomed plate. Total enzyme activity is determined by measuring ALK5 T204D activity in the absence of ALK5 kinase inhibitor reference compounds. Non-specific binding (NSB) is determined by measuring the activity of ALK5 T204D in the presence of ALK5 kinase inhibitor reference compounds. 10 μl of dephosphorylated casein stock solution (dephosphorylated casein is dissolved in $ddH_2O$ at 20 mg/ml) is added per well (200 μg/well final assay concentration). 20 μl of ALK5 T204D (2.5 μg/ml solution) is added per well (50 ng/well final assay concentration). The plates are left to incubate at room temperature for 10 minutes.

10 μl of ATP mix is added to the well to initiate the reaction (0.66 nM [$^{33}P$]ATP/1 μM unlabelled ATP/well final assay concentration). The ATP mix is prepared as follows, unlabelled ATP (3 mM) is dissolved in $ddH_2O$ and pH adjusted to 7.4. The stock concentration of [$^{33}P$]ATP is 10 μCi/μl. The appropriate volume of [$^{33}P$]ATP is added to unlabelled ATP solution such that the final assay concentration per well is 0.1 μCi. Following addition of the ATP mix, the plates are incubated at room temperature for 50 minutes. The kinase reaction is terminated by the addition of 50 μL Stop Buffer (20 mM Tris-HCl pH 7.4, 10 mM EDTA).

75 μl/well from the reaction plate is transferred to a Multiscreen-IP plate (MultiScreen-IP plates are prepared by added 50 μL of 70% (v/v) ethanol per well and incubated for 5 minutes at room temperature. The ethanol is removed by aspiration via a MultiScreen HTS Vacuum Manifold unit (Millipore, Cat no: MSVMHT500). The plates are washed twice by adding 200 μl/well ddH$_2$O). The MultiScreen-IP plate is incubated at room temperature for 30 minutes to allowing binding of casein to the plate. The MultiScreen-IP plates are washed three times by adding 200 μl/well 100 mM phosphoric acid solution and the gasket is carefully removed from the back of the MultiScreen-IP plate and the plate dried in the oven for 30 minutes. The MultiScreen-IP plate is backsealed, 50 μL of Microscint™20 is added, then the plates are topsealed and radiolabelled casein detected and quantified on a TopCount™ plate-reader using the $^{33}$P scintillation protocol.

The agents of the invention are also useful as co-therapeutic agents for use in combination with other drug substances such as anti-inflammatory, bronchodilatory, antihistamine, decongestant or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with one or more other drug substances in a fixed pharmaceutical composition or it may be administered separately, before, simultaneously with or after the other drug substance(s).

Such anti-inflammatory drugs include steroids, in particular glucocorticosteroids such as budesonide, beclamethasone, fluticasone, ciclesonide or mometasone, or steroids described in WO 02/88167, WO 02/12266, WO 02/100879 or WO 02/00679 (especially those of Examples 3, 11, 14, 17, 19, 26, 34, 37, 39, 51, 60, 67, 72, 73, 90, 99 and 101), and non-steroidal steroid agonists such as those described in WO 00/00531, WO 02/10143, WO 03/82280, WO 03/82787, WO 03/104195 and WO 04/05229; LTB4 antagonists such as BIIL 284, CP-195543, DPC11870, LTB4 ethanolamide, LY 293111, LY 255283, CGS025019C, CP-195543, ONO-4057, SB 209247 and SC-53228, and those described in U.S. Pat. No. 5,451,700 and WO 04/108720; LTD4 antagonists such as montelukast, pranlukast, zafirlukast, accolate, SR2640, Wy-48, 252, ICI 198615, MK-571, LY-171883, Ro 24-5913 and L-648051; dopamine receptor agonists such as cabergoline, bromocriptine, ropinirole and 4-hydroxy-7-[2-[[2-[[3-(2-phenyl-ethoxy)-propyl]-sulfonyl]ethyl]amino]ethyl]-2(3H)-benzothiazolone and pharmaceutically acceptable salts thereof (the hydrochloride being Viozan®-AstraZeneca); PDE4 inhibitors such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo) and GRC 3886 (Oglemilast, Glenmark), and those described in WO 92/19594, WO 93/19749, WO 93/19750, WO 93/19751, WO 98/18796, WO 99/16766, WO 01/13953, WO 03/39544, WO 03/104204, WO 03/104205, WO 04/00814, WO 04/00839 and WO 04/05258 (Merck), WO 04/18450, WO 04/18451, WO 04/18457, WO 04/18465, WO 04/18431, WO 04/18449, WO 04/18450, WO 04/18451, WO 04/18457, WO 04/18465, WO 04/019944, WO 04/19945, WO 04/45607, WO 04/37805, WO 04/63197, WO 04/103998, WO 04/111044, WO 05/12252, WO 05/12253, WO 05/13995, WO 05/30212, WO 05/30725, WO 05/87744, WO 05/87745, WO 05/87749 and WO 05/90345; A2a agonists such as those described in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/86408, WO 04/39762, WO 04/39766, WO 04/45618 and WO 04/46083; and A2b antagonists such as those described in WO 02/42298 and WO 03/42214.

Such bronchodilatory drugs include beta-2 adrenoceptor agonists. Suitable beta-2 adrenoceptor agonists include albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula I of WO 00/75114, which document is incorporated herein by reference, preferably compounds of the Examples thereof, especially a compound of formula

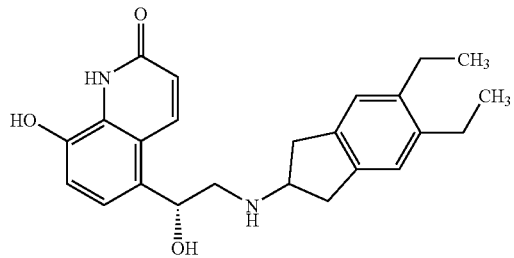 [SMILES: CCc1cc2c(cc1CC)CC(NC[C@H](O)c1ccc(O)c3[nH]c(=O)ccc13)C2]

and pharmaceutically acceptable salts thereof, as well as compounds (in free or salt or solvate form) of formula I of WO 04/16601, and also compounds of EP 147719, EP 1440966, EP 1460064, EP 1477167, EP 1574501, JP 05025045, JP 2005/87357, US 2002/0055651, US 2004/0242622, US 2004/0229904, US 2005/0133417, US 2005/5159448, US 2005/5159448, US 2005/171147, US 2005/182091, US 2005/182092, US 2005/209227, US 2005/256115, US 2005/277632, US 2005/272769, US 2005/239778, US 2005/215542, US 2005/215590, US 2006/19991, US 2006/58530, WO 93/18007, WO 99/64035, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, WO 04/087142, WO 04/89892, WO 04/108675, WO 04/108676, WO 05/33121, WO 05/40103, WO 05/44787, WO 05/58867, WO 05/65650, WO 05/66140, WO 05/70908, WO 05/74924, WO 05/77361, WO 05/90288, WO 05/92860, WO 05/92887, WO 05/90287, WO 05/95328, WO 05/102350, WO 06/56471, WO 06/74897 or WO 06/8173.

Such bronchodilatory drugs also include other anticholinergic or antimuscarinic agents, in particular formoterol, carmoterol, ipratropium bromide, oxitropium bromide, tiotropium salts, glycopyrrolate, CHF 4226 (Chiesi) and SVT-40776, and also those described in EP 424021, U.S. Pat. No. 3,714,357, U.S. Pat. No. 5,171,744, US 2005/171147, US 2005/182091, WO 01/04118, WO 02/00652, WO 02/51841, WO 02/53564, WO 03/00840, WO 03/33495, WO 03/53966, WO 03/87094, WO 04/18422, WO 04/05285, WO 04/96800, WO 05/77361 and WO 06/48225.

Suitable dual anti-inflammatory and bronchodilatory drugs include dual beta-2 adrenoceptor agonist/muscarinic antagonists such as those disclosed in US 2004/0167167, US 2004/0242622, US 2005/182092, WO 04/74246 and WO 04/74812.

Suitable antihistaminic/anti-allergic drug substances include acetaminophen, activastine, astemizole, azelastin, bamipin, cetirizine hydrochloride, cexchloropheniramine, chlorophenoxamine, clemastine fumarate, desloratidine, dimenhydrinate, dimetinden, diphenhydramine, doxylamine, ebastine, emedastin, epinastine, fexofenadine hydrochloride, ketotifen, levocabastin, loratidine, meclizine, mizolastine, pheniramine, promethazine and tefenadine, as well as those disclosed in JP 2004107299, WO 03/099807 and WO 04/026841 (including any pharmacologically acceptable acid addition salts thereof which may exist).

According to a further embodiment of the invention, the agents of the invention may be employed as adjunct or adjuvant to other therapy, e.g. a therapy using a bone resorption inhibitor, for example as in osteoporosis therapy, in particular a therapy employing calcium, a ealeitonin or an analogue or derivative thereof, e.g. salmon, eel or human calcitonin, a steroid hormone, e.g. an estrogen, a partial estrogen agonist or estrogen-gestagen combination, a SERM (Selective Estrogen Receptor Modulator) e.g. raloxifene, lasofoxifene, TSE-424, FC1271, Tibolone (Livial A), vitamin D or an analog thereof or PTH, a PTH fragment or a PTH derivative e.g. PTH (1-84), PTH (1-34), PTH (1-36), PTH (1-38), PTH (1-31) NH2 or PTS 893.

In accordance with the foregoing, the present invention also provides a method for the treatment of an obstructive or inflammatory airways disease which comprises administering to a subject, particularly a human subject, in need thereof a compound of formula I, or a pharmaceutically acceptable salt or solvate thereof, as hereinbefore described. In another aspect, the invention provides a compound of formula I, or a pharmaceutically acceptable salt or solvate thereof, as hereinbefore described for use in the preparation of a medicament for the treatment of an obstructive or inflammatory airways disease.

The agents of the invention may be administered by any appropriate route, e.g. orally, for example in the form of a tablet or capsule; parenterally, for example intravenously; topically to the skin, for example in the treatment of psoriasis; intranasally, for example in the treatment of hay fever; or, preferably, by inhalation, particularly in the treatment of obstructive or inflammatory airways diseases. In particular, the agents of the invention may be delivered as an inhalable formulation for the treatment of COPD and asthma.

In a further aspect, the invention also provides a pharmaceutical composition comprising a compound of formula I in free form or in the form of a pharmaceutically acceptable salt or solvate thereof, optionally together with a pharmaceutically acceptable diluent or carrier therefor. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

Where the inhalable form of the active ingredient is an aerosol composition, the inhalation device may be an aerosol vial provided with a valve adapted to deliver a metered dose, such as 10 to 100 µl, e.g. 25 to 50 µl, of the composition, i.e. a device known as a metered dose inhaler. Suitable such aerosol vials and procedures for containing within them aerosol compositions under pressure are well known to those skilled in the art of inhalation therapy. For example, an aerosol composition may be administered from a coated can, for example as described in EP-A-0642992. Where the inhalable form of the active ingredient is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 ml, commonly 1 to 10 ml, of the dispersion; or a hand-held nebulizer, sometimes referred to as a soft mist or soft spray inhaler, for example an electronically controlled device such as an AERx (Aradigm, US) or Aerodose (Aerogen), or a mechanical device such as a RESPIMAT (Boehringer Ingelheim) nebulizer which allows much smaller nebulized volumes, e.g. 10 to 100 µl, than conventional nebulizers. Where the inhalable form of the active ingredient is the finely divided particulate form, the inhalation device may be, for example, a dry powder inhalation device adapted to deliver dry powder from a capsule or blister containing a dry powder comprising a dosage unit of (A) and/or (B) or a multidose dry powder inhalation (MDPI) device adapted to deliver, for example, 3-25 mg of dry powder comprising a dosage unit of (A) and/or (B) per actuation. The dry powder composition preferably contains a diluent or carrier, such as lactose, and a compound that helps to protect against product performance deterioration due to moisture e.g. magnesium stearate. Suitable such dry powder inhalation devices include devices disclosed in U.S. Pat. No. 3,991,761 (including the AEROLIZER™ device), WO 05/113042, WO 97/20589 (including the CERTIHALER™ device), WO 97/30743 (including the TWISTHALER™ device) and WO 05/37353 (including the GYROHALER™ device).

The invention also includes (A) a compound of formula I as hereinbefore described in free form, or a pharmaceutically acceptable salt or solvate thereof, in inhalable form; (B) an inhalable medicament comprising such a compound in inhalable form together with a pharmaceutically acceptable carrier in inhalable form; (C) a pharmaceutical product comprising such a compound in inhalable form in association with an inhalation device; and (D) an inhalation device containing such a compound in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.0001 to 30 mg/kg, typically 0.01 to 10 mg per patient, while for oral administration suitable daily doses are of the order of 0.01 to 100 mg/kg.

The invention is illustrated by the following Examples.

EXAMPLES

Compounds of the present invention include compounds of formula X

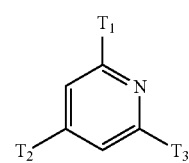

X where T[1], T[2] and T[3] are as shown in Table 1 and Table 2 below. The method of preparation being described hereinafter.

TABLE 1

| Ex. | T[1] | T[2] | T[3] | [M + H]+ |
|---|---|---|---|---|
| 1.1 | 2-methylfuran | 3-methylpyridine | N-methyltryptamine | 381 |
| 1.2 | 2-methylfuran | 3-methylpyridine | (1H-indol-4-yl)methyl-N-methylamine | 367 |
| 1.3 | 2,5-dimethylfuran | 3-methylpyridine | N-methyltryptamine | 395 |
| 1.4 | 2-methylpyridine | 5-methoxy-3-methylpyridine | N-methyltryptamine | 422 |
| 1.5 | 2-methylpyridine | 5-methoxy-3-methylpyridine | (1H-indol-4-yl)methyl-N-methylamine | 408 |
| 1.6 | 2-methylpyridine | 3-methylpyridine | 2-(1H-indol-4-yl)-N-methylethanamine | 392 |

TABLE 1-continued

| Ex. | T[1] | T[2] | T[3] | [M + H]+ |
|---|---|---|---|---|
| 1.7 | 2-methylpyridine | 3-methylpyridine | 4-(2-methylaminoethyl)phenol | 369 |
| 1.8 | 6-methyl-2-bromopyridine | 3-methylpyridine | N-methyltryptamine | 470 & 472 |
| 1.9 | 2-methylfuran | 3-methylpyridine | 4-(2-methylaminoethyl)phenol | 358 |
| 1.10 | 2-methylpyridine | 3-methylpyridine | N-methyltryptamine | 392 |
| 1.11 | 2-methylpyrrole | 3-methylpyridine | N-methyltryptamine | 380 |
| 1.12 | 2,5-dimethylpyrrole | 3-methylpyridine | N-methyltryptamine | 408 |

TABLE 1-continued

| Ex. | T¹ | T² | T³ | [M + H]⁺ |
|---|---|---|---|---|
| 1.13 | 2-methylpyridine | 3-methyl-5-iodopyridine | N-methyl-(1H-indol-4-yl)methylamine | 504 |
| 1.14 | 2-methylpyridine | 3-methyl-5-bromopyridine | N-methyl-2-(1H-indol-3-yl)ethylamine | 470 & 472 |
| 1.15 | 2-methylpyridine | 3-methylpyridine | N-methyl-(1H-indol-4-yl)methylamine | 378 |
| 1.16 | 2-methylpyridine | 3-methyl-5-bromopyridine | N-methyl-(1H-indol-4-yl)methylamine | 456/458 |
| 1.17 | 3-methylpyridine | 2-methylpyridine | N-methyl-2-(1H-indol-3-yl)ethylamine | 392 |
| 1.18 | 2-methylpyridine | 3-methyl-5-hydroxypyridine | N-methyl-2-(1H-indol-3-yl)ethylamine | 407 |
| 1.19 | 2-methylpyridine | 3-methyl-5-iodopyridine | N-methyl-2-(1H-indol-3-yl)ethylamine | 518 |
| 1.20 | 2-methylpyridine | 3-methylpyridine | N-methylbenzylamine | 339 |
| 1.21 | 2,6-dimethylpyridine with CH₃ linker | 3-methylpyridine | N-methyl-2-(1H-indol-3-yl)ethylamine | 460 |
| 1.22 | 6-methylpyridine with OCH₃ | 3-methylpyridine | N-methyl-2-(1H-indol-3-yl)ethylamine | 422 |
| 1.23 | 2-methylpyridine | 3-methyl-5-bromopyridine | N-methyl-(3-hydroxyphenyl)methylamine | 433/435 |
| 1.24 | 2-methylpyridine | 3-methyl-5-bromopyridine | N-ethyl-N-methylamine | 355/357 |
| 1.25 | 2-methylpyridine | 3-methyl-5-bromopyridine | N-methylbenzylamine | 417/419 |

TABLE 1-continued

| Ex. | T¹ | T² | T³ | [M + H]⁺ |
|---|---|---|---|---|
| 1.26 | 2-methylpyridine | 5-bromo-3-methylpyridine | cyclopropyl-NH- | 367/369 |
| 1.27 | 2,6-dimethylpyridine | 5-bromo-3-methylpyridine | CH₃-NH- | 355/357 |
| 1.28 | 2,6-dimethylpyridine | 5-bromo-3-methylpyridine | tert-butyl-NH- | 397/399 |
| 1.29 | 2-methylpyridine | 5-bromo-3-methylpyridine | CD₃-NH- | 344/346 |
| 1.30 | 2,5-dimethylfuran | 5-bromo-3-methylpyridine | cyclopropyl-NH- | 370/372 |
| 1.31 | 2-methylpyridine | 5-bromo-3-methylpyridine | -NH₂ | 327/329 |

TABLE 2

| Ex. | T¹ | T² | T³ | [M + H]⁺ |
|---|---|---|---|---|
| 2.1 | 2-methylpyridine | 5-methylpyridin-3-yl with 4-(4-methylpiperazine-1-carbonyl)phenyl | CH₃-NH- | 465 |
| 2.2 | 2-methylpyridine | 5-methylpyridin-3-yl with 4-(4-methylpiperazin-1-yl)phenyl | CH₃-NH- | 437 |
| 2.3 | 2-methylpyridine | 5-methylpyridin-3-yl with 1H-indol-4-yl | CH₃-NH- | 378 |

TABLE 2-continued
| Ex. | T¹ | T² | T³ | [M + H]⁺ |
|---|---|---|---|---|
| 2.4 | 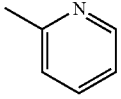 | 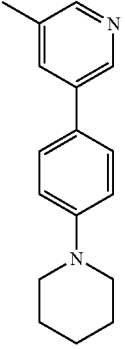 |  | 422 |
| 2.5 | 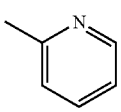 | 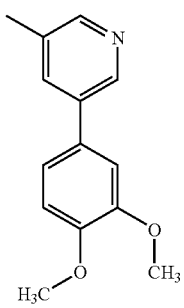 |  | 399 |
| 2.6 | 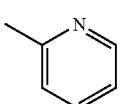 | 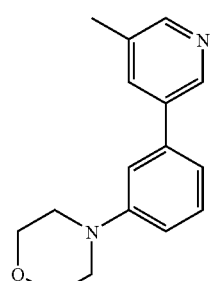 |  | 424 |
| 2.7 | 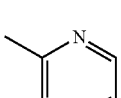 | 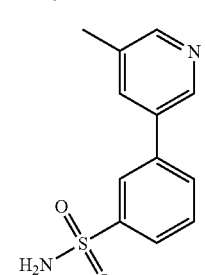 |  | 418 |
| 2.8 | 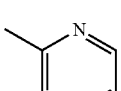 | 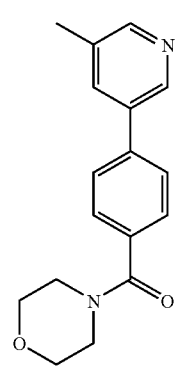 |  | 452 |

TABLE 2-continued

| Ex. | T¹ | T² | T³ | [M + H]⁺ |
|---|---|---|---|---|
| 2.9 | 2-methylpyridine | 5-methyl-3-(3-ethoxyphenyl)pyridine | NHCH₃ | 383 |
| 2.10 | 2-methylpyridine | 5-methyl-3-(3-(methylsulfonyl)phenyl)pyridine | NHCH₃ | 417 |
| 2.11 | 2-methylpyridine | 5-methyl-3-(3-(methylsulfonamido)phenyl)pyridine | NHCH₃ | 432 |
| 2.12 | 2-methylpyridine | 5-methyl-3-(3-(pyrrolidin-1-yl)phenyl)pyridine | NHCH₃ | 408 |
| 2.13 | 2-methylpyridine | 5-methyl-3-(4-(morpholinomethyl)phenyl)pyridine | NHCH₃ | 438 |

TABLE 2-continued
| Ex. | T¹ | T² | T³ | [M + H]⁺ |
|---|---|---|---|---|
| 2.14 | 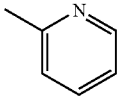 | 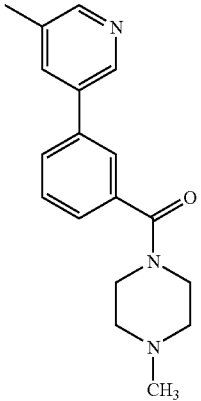 |  | 465 |
| 2.15 | 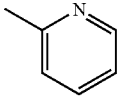 | 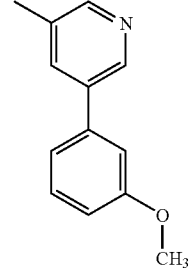 |  | 369 |
| 2.16 | 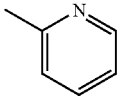 | 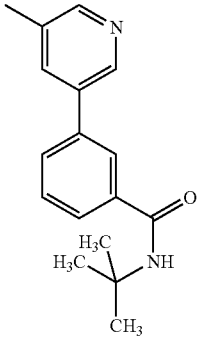 |  | 438 |
| 2.17 | 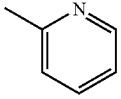 | 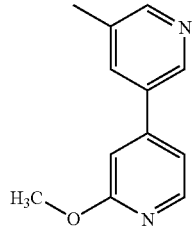 |  | 370 |
| 2.18 | 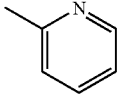 | 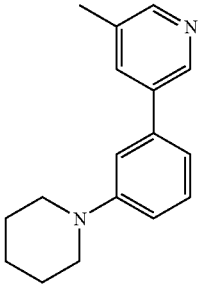 |  | 422 |

TABLE 2-continued
| Ex. | T¹ | T² | T³ | [M + H]⁺ |
|---|---|---|---|---|
| 2.19 | 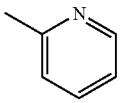 | 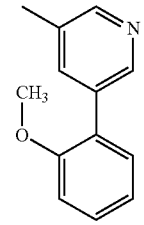 |  | 369 |
| 2.20 | 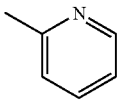 | 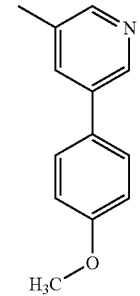 |  | 369 |
| 2.21 | 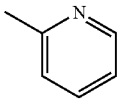 | 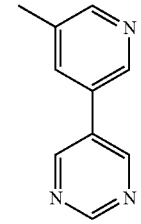 |  | 341 |
| 2.22 | 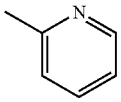 | 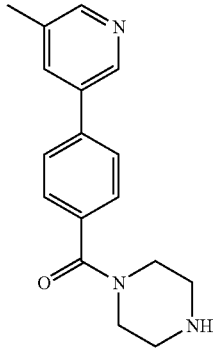 |  | 451 |
| 2.23 | 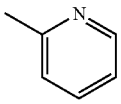 | 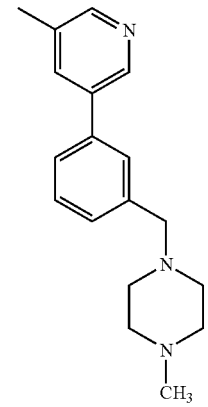 |  | 451 |

TABLE 2-continued
| Ex. | T¹ | T² | T³ | [M + H]⁺ |
|---|---|---|---|---|
| 2.24 | 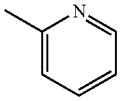 | 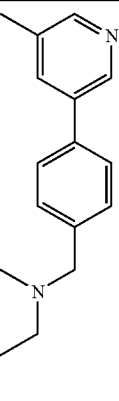 |  | 479 |
| 2.25 | 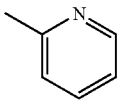 | 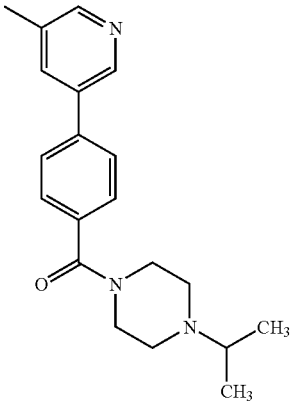 |  | 493 |
| 2.26 | 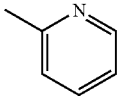 | 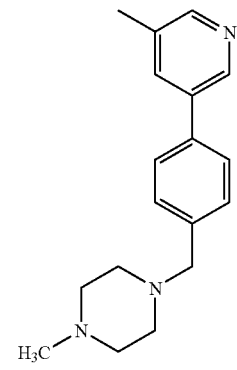 |  | 451 |
| 2.27 | 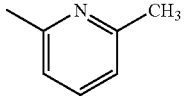 | 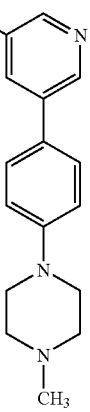 |  | 451 |

TABLE 2-continued
| Ex. | T¹ | T² | T³ | [M + H]⁺ |
|---|---|---|---|---|
| 2.28 |  | 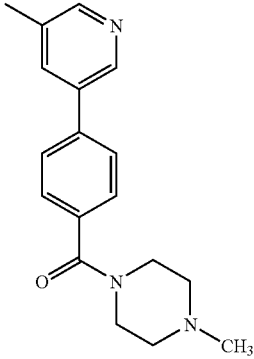 |  | 479 |
| 2.29 | 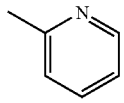 | 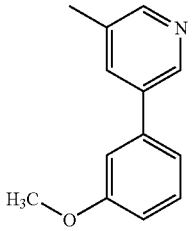 | 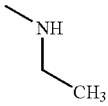 | 383 |
| 2.30 | 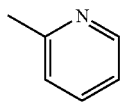 | 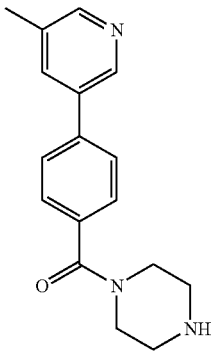 | 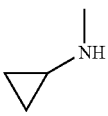 | 477 |
| 2.31 | 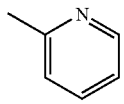 | 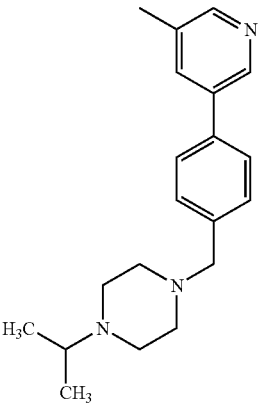 | 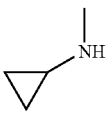 | 505 |
| 2.32 | 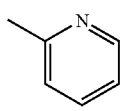 | 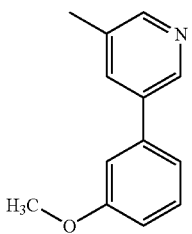 | 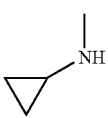 | 395 |

TABLE 2-continued
| Ex. | T¹ | T² | T³ | [M + H]⁺ |
|---|---|---|---|---|
| 2.33 | 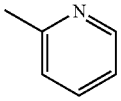 | 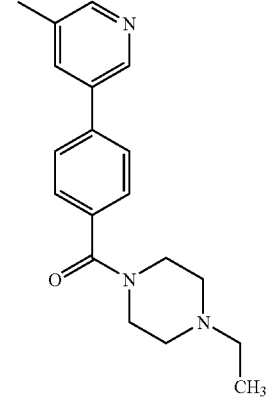 | 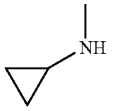 | 505 |
| 2.34 | 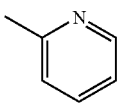 | 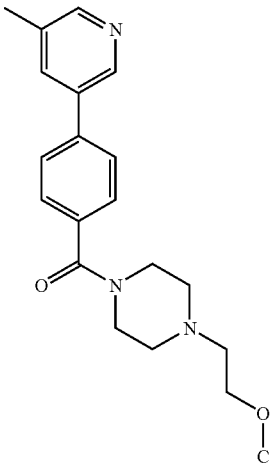 | 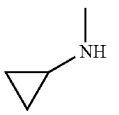 | 535 |
| 2.35 | 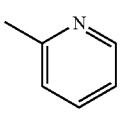 | 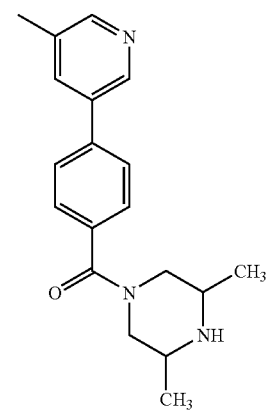 | 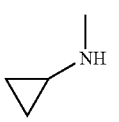 | 505 |

TABLE 2-continued
| Ex. | T¹ | T² | T³ | [M + H]⁺ |
|---|---|---|---|---|
| 2.36 | 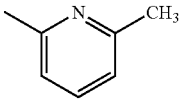 | 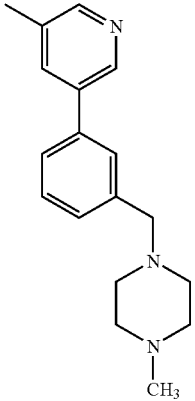 | 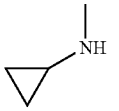 | 491 |
| 2.37 | 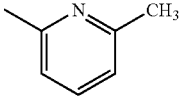 | 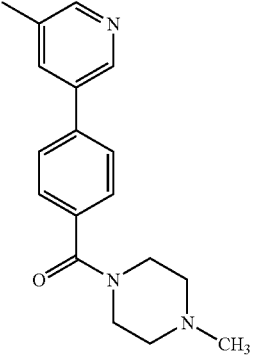 | 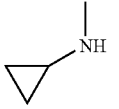 | 505 |
| 2.38 | 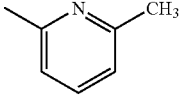 | 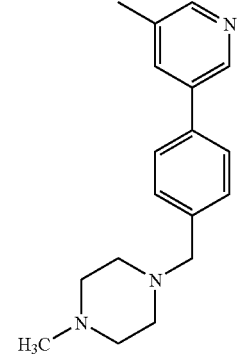 | 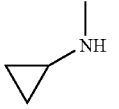 | 491 |
| 2.39 | 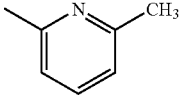 | 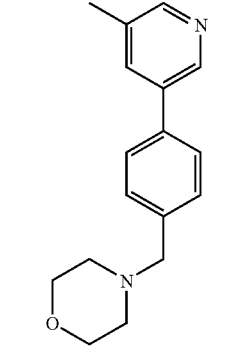 | 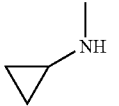 | 478 |

TABLE 2-continued

| Ex. | T¹ | T² | T³ | [M + H]⁺ |
|---|---|---|---|---|
| 2.40 | 2,6-dimethylpyridin-3-yl | 4-(4-methylpiperazin-1-yl)phenyl-substituted 5-methylpyridin-3-yl | benzylamino (NHCH₂Ph) | 527 |
| 2.41 | 2,6-dimethylpyridin-3-yl | 4-(4-methylpiperazine-1-carbonyl)phenyl-substituted 5-methylpyridin-3-yl | benzylamino | 555 |
| 2.42 | 2,6-dimethylpyridin-3-yl | 5-(3-methoxyphenyl)-3-methylpyridin-3-yl | benzylamino | 459 |
| 2.43 | 2-methylpyridin-3-yl | 5-(3-methoxyphenyl)-3-methylpyridin-3-yl | benzylamino | 445 |

TABLE 2-continued

| Ex. | T¹ | T² | T³ | [M + H]⁺ |
|---|---|---|---|---|
| 2.44 | 2-methylpyridine | 5-methyl-3-(4-(4-methylpiperazine-1-carbonyl)phenyl)pyridine | (1H-indol-4-yl)-N-methylmethanamine | 580 |
| 2.45 | 2-methylpyridine | 3-(3-methoxyphenyl)-5-methylpyridine | 3-((methylamino)methyl)phenol | 461 |
| 2.46 | 2-methylpyridine | 3-(4-(4-isopropylpiperazine-1-carbonyl)phenyl)-5-methylpyridine | N-methylpropan-2-amine | 521 |
| 2.47 | 2-methylpyridine | 5-methyl-3-(4-(piperazine-1-carbonyl)phenyl)pyridine | N-methylpropan-2-amine | 479 |

TABLE 2-continued

| Ex. | T¹ | T² | T³ | [M + H]⁺ |
|---|---|---|---|---|
| 2.48 | 2-methylpyridine | 5-methyl-3-pyridyl-phenyl-C(O)-piperazine(NH) | tert-butyl(methyl)amine | 493 |
| 2.49 | 2-methylpyridine | 5-methyl-3-pyridyl-phenyl-C(O)-N-methylpiperazine | tert-butyl(methyl)amine | 507 |
| 2.50 | 2-methylpyridine | 5-methyl-3-pyridyl-phenyl-C(O)-piperazine(NH) | —NH₂ | 437 |
| 2.51 | 2-methylpyridine | 5-methyl-3-pyridyl-(3-methoxyphenyl) | —NH₂ | 355 |

TABLE 2-continued

| Ex. | T¹ | T² | T³ | [M + H]⁺ |
|---|---|---|---|---|
| 2.52 | 2-methylpyridine | 5-methylpyridin-3-yl-phenyl-C(O)-(4-methylpiperazin-1-yl) | —NH₂ | 451 |
| 2.53 | 2-methylpyridine | 5-methyl-3-(1H-pyrazol-4-yl)pyridine | N-methyl-2-(1H-indol-3-yl)ethylamine | 458 |
| 2.54 | 2-methylpyridine | 5-methylpyridin-3-yl-phenyl-C(O)-(4-isopropylpiperazin-1-yl) | N-methylcyclopropylamine | 519 |
| 2.55 | 2-methylpyridine | 5-methylpyridin-3-yl-phenyl-C(O)-(3-(dimethylamino)pyrrolidin-1-yl) | N-methylcyclopropylamine | 505 |

TABLE 2-continued

| Ex. | T¹ | T² | T³ | [M + H]⁺ |
|---|---|---|---|---|
| 2.56 | 2-methylpyridine | 5-methyl-3-[4-(4-cyclopropylpiperazine-1-carbonyl)phenyl]pyridine | cyclopropyl-NH-CH₃ | 517 |
| 2.57 | 2-methylpyridine | 5-methyl-3-[4-(pyrrolidin-1-ylmethyl)phenyl]pyridine | cyclopropyl-NH-CH₃ | 448 |
| 2.58 | 2-methylpyridine | 5-methyl-3-{4-[(3R)-3-(dimethylamino)pyrrolidine-1-carbonyl]phenyl}pyridine | cyclopropyl-NH-CH₃ | 505 |
| 2.59 | 2-methylpyridine | 5-methyl-3-{4-[(3S)-3-(dimethylamino)pyrrolidine-1-carbonyl]phenyl}pyridine | cyclopropyl-NH-CH₃ | 505 |

TABLE 2-continued

| Ex. | T¹ | T² | T³ | [M + H]⁺ |
|---|---|---|---|---|
| 2.60 | 2-methylpyridine | 5-methyl-3-[4-(3,4-dimethylpiperazine-1-carbonyl)phenyl]pyridine | cyclopropyl-NH-CH₃ | 505 |
| 2.61 | 2-methylpyridine | 5-methyl-3-(4-methyl-3,4-dihydro-2H-benzo[1,4]oxazin-6-yl)pyridine | cyclopropyl-NH-CH₃ | 436 |
| 2.62 | 2-methylpyridine | 5-methyl-3-[4-((3S)-3-dimethylaminopyrrolidin-1-ylmethyl)phenyl]pyridine | cyclopropyl-NH-CH₃ | 491 |
| 2.63 | 2-methylpyridine | 5-methyl-3-[4-((3R)-3-dimethylaminopyrrolidin-1-ylmethyl)phenyl]pyridine | cyclopropyl-NH-CH₃ | 491 |

TABLE 2-continued
| Ex. | T¹ | T² | T³ | [M + H]⁺ |
|---|---|---|---|---|
| 2.64 |  |  |  | 393 |
| 2.65 |  |  |  | 505 |
| 2.66 |  | 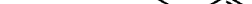 |  | 519 |
| 2.67 |  |  |  | 436 |

TABLE 2-continued
| Ex. | T¹ | T² | T³ | [M + H]⁺ |
|---|---|---|---|---|
| 2.68 | 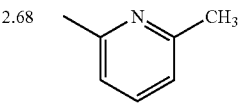 | 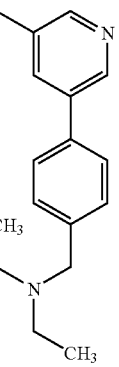 | 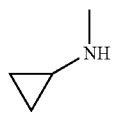 | 464 |
| 2.69 | 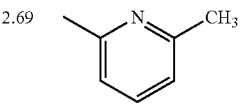 | 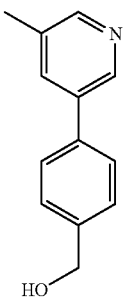 | 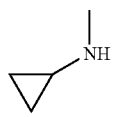 | 409 |
| 2.70 | 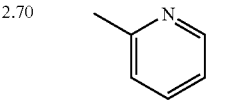 | 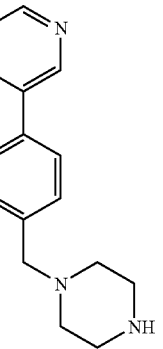 | 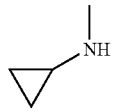 | 463 |
| 2.71 | 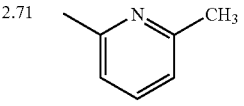 | 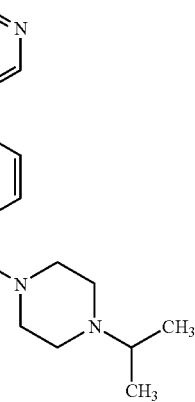 | —NH₂ | 479 |

TABLE 2-continued

| Ex. | T¹ | T² | T³ | [M + H]⁺ |
|---|---|---|---|---|
| 2.72 | 2-methylpyridine | 3-methyl-5-(4-((4-isopropylpiperazin-1-yl)methyl)phenyl)pyridine | —NH$_2$ | 465 |
| 2.73 | 2-methylpyridine | 3-methyl-5-(4-(4-isopropylpiperazine-1-carbonyl)phenyl)pyridine | tert-butyl(methyl)amine | 535 |
| 2.74 | 2-methylpyridine | 3-methyl-5-(4-(4-isopropylpiperazine-1-carbonyl)phenyl)pyridine | —NH$_2$ | 479 |

TABLE 2-continued
| Ex. | T¹ | T² | T³ | [M + H]⁺ |
|---|---|---|---|---|
| 2.75 | 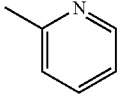 | 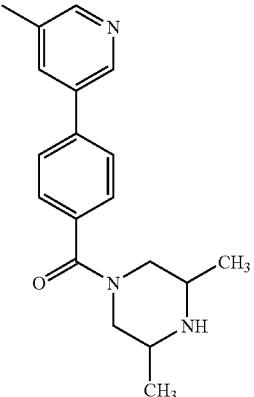 | 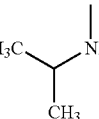 | 507 |
| 2.76 | 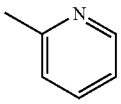 | 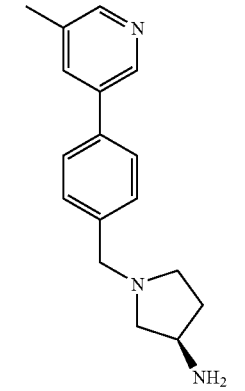 |  | 463 |
| 2.77 | 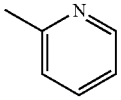 | 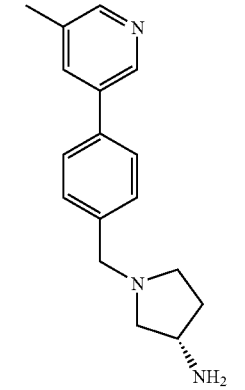 |  | 463 |
| 2.78 | 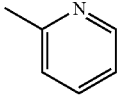 | 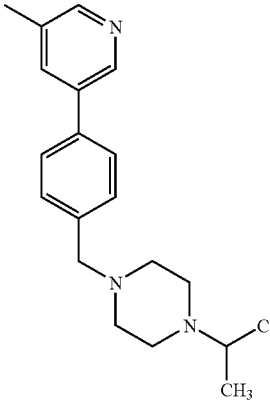 | 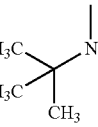 | 521 |

TABLE 2-continued
| Ex. | T¹ | T² | T³ | [M + H]⁺ |
|---|---|---|---|---|
| 2.79 | 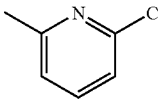 | 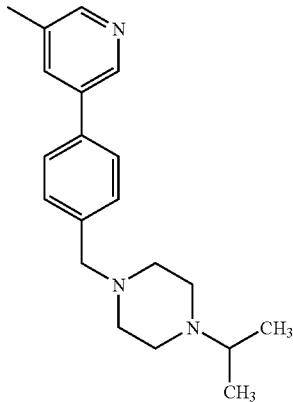 | 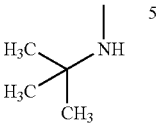 | 535 |
| 2.80 | 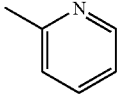 | 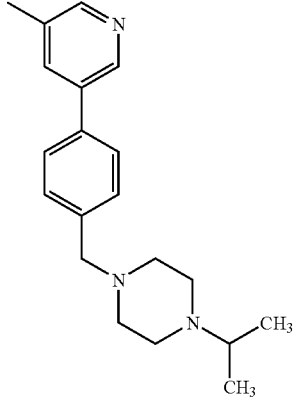 | 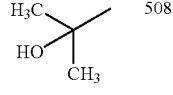 | 508 |
| 2.81 | 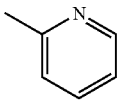 | 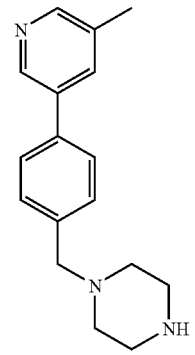 | 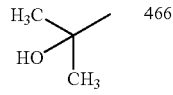 | 466 |
| 2.82 | 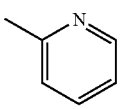 | 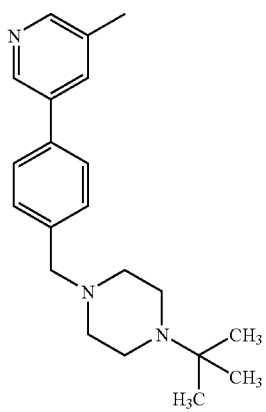 | 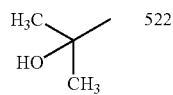 | 522 |

TABLE 2-continued
| Ex. | T¹ | T² | T³ | [M + H]⁺ |
|---|---|---|---|---|
| 2.83 | | | | 497 |
| 2.84 | | | | 442 |
| 2.85 | | | | 483 |
| 2.86 | | | | 372 |
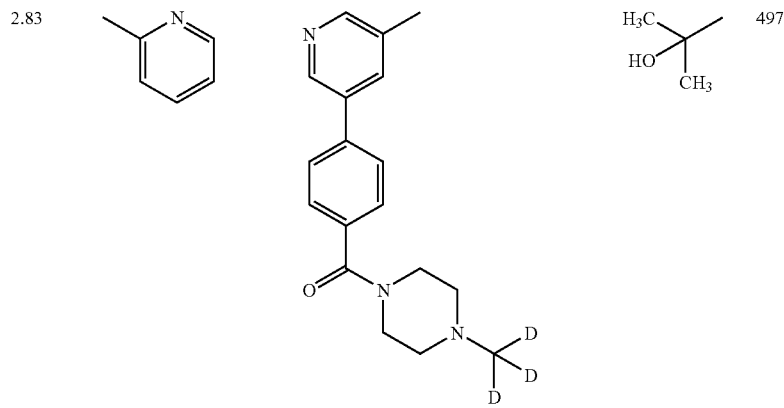
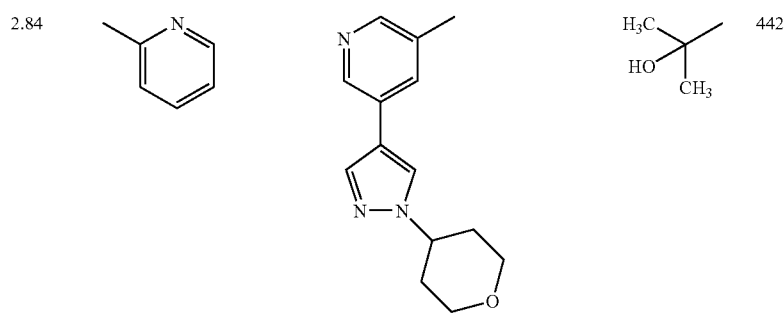
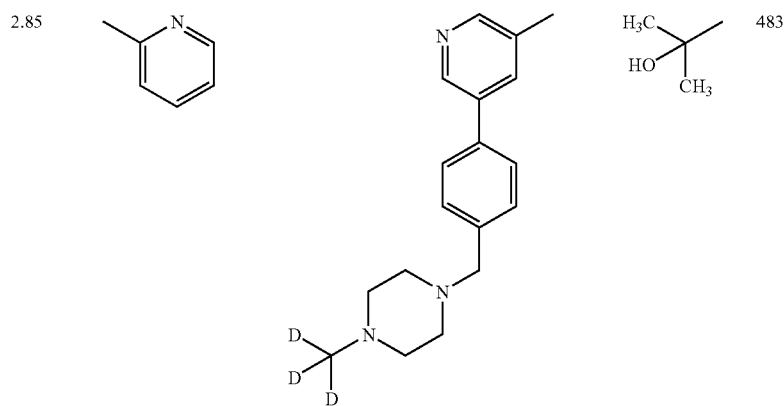
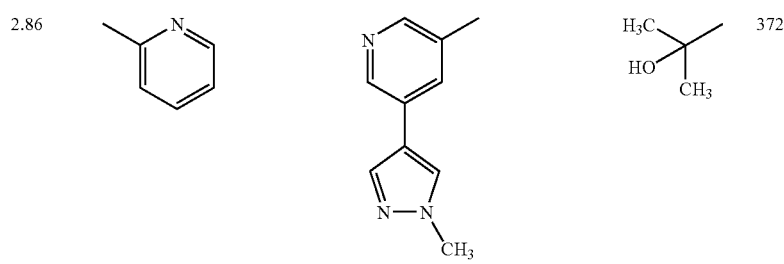

TABLE 2-continued
| Ex. | T¹ | T² | T³ | [M + H]⁺ |
|---|---|---|---|---|
| 2.87 | 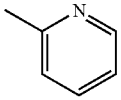 | 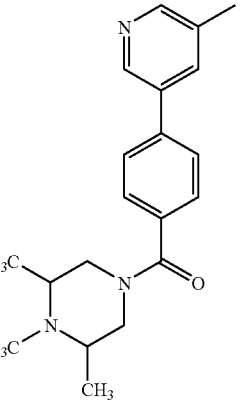 | 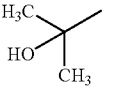 | 522 |
| 2.88 | 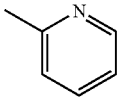 | 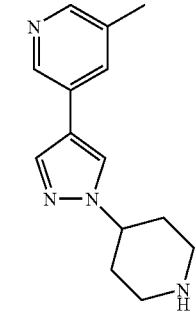 | 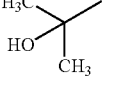 | 441 |
| 2.89 | 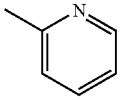 | 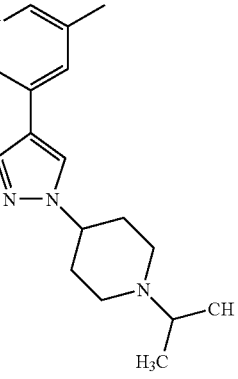 | 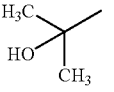 | 483 |
| 2.90 | 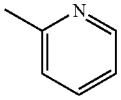 | 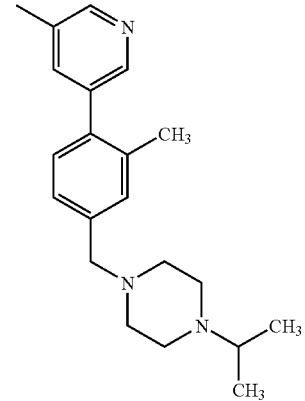 | 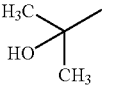 | 522 |

TABLE 2-continued
| Ex. | T¹ | T² | T³ | [M + H]⁺ |
|---|---|---|---|---|
| 2.91 | 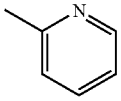 | 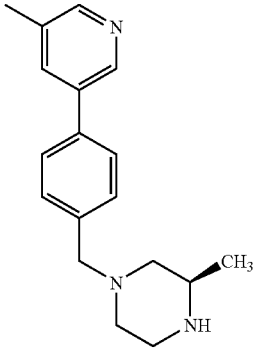 |  | 480 |
| 2.92 | 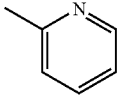 | 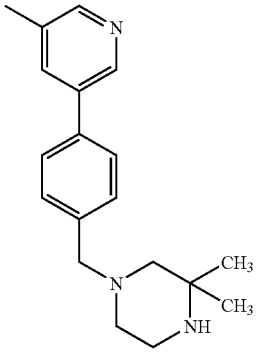 |  | 494 |
| 2.93 | 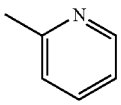 | 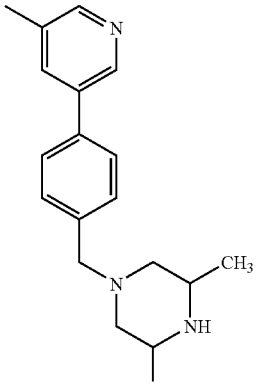 |  | |
| 2.94 | 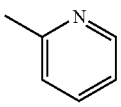 | 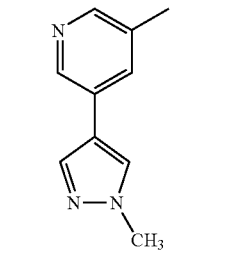 |  | 370 |

TABLE 2-continued
| Ex. | T¹ | T² | T³ | [M + H]⁺ |
|---|---|---|---|---|
| 2.95 | 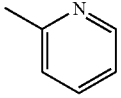 | 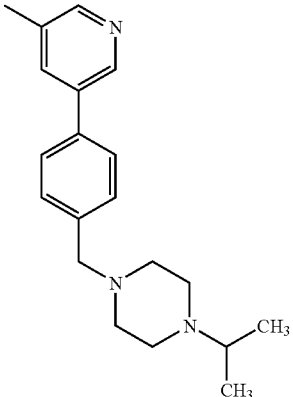 |  | 506 |
| 2.96 | 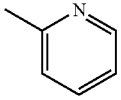 | 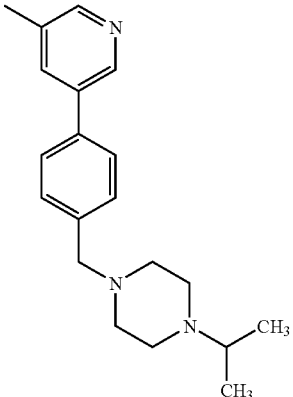 | 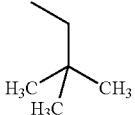 | 520 |
| 2.97 | 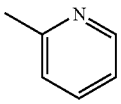 | 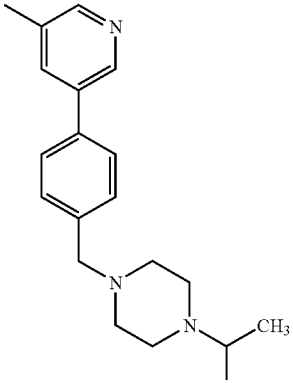 |  | 507 |
| 2.98 | 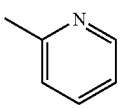 | 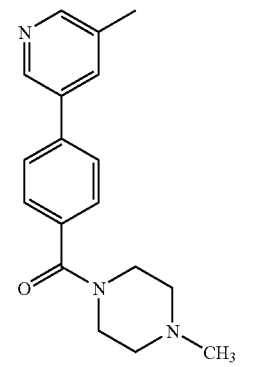 | 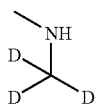 | 468 |

TABLE 2-continued
| Ex. | T¹ | T² | T³ | [M + H]⁺ |
|---|---|---|---|---|
| 2.99 | 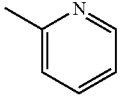 | 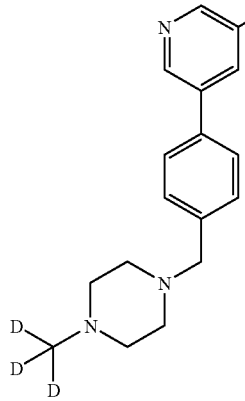 |  | 457 |
| 2.100 | 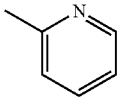 | 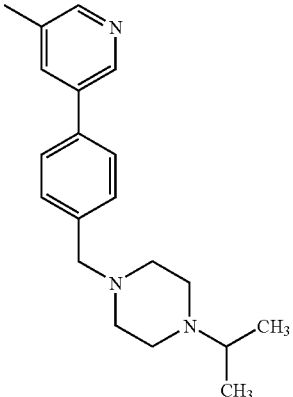 |  | 482 |
| 2.101 | 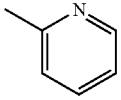 | 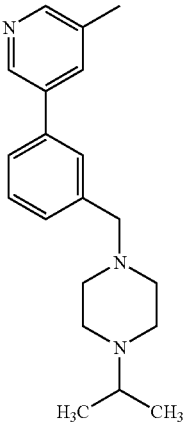 |  | 482 |
| 2.102 | 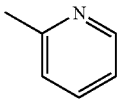 | 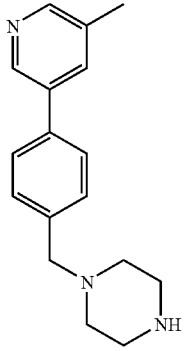 |  | 440 |

TABLE 2-continued
| Ex. | T¹ | T² | T³ | [M + H]⁺ |
|---|---|---|---|---|
| 2.103 | 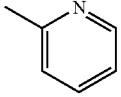 | 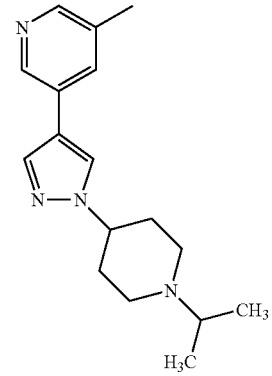 |  | 457 |
| 2.104 | 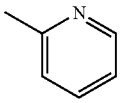 | 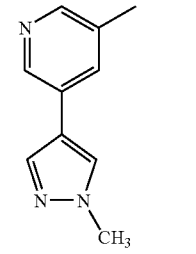 |  | 346 |
| 2.105 | 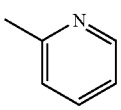 | 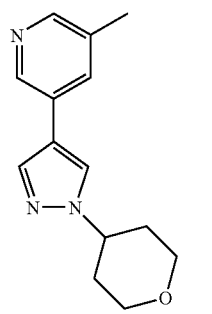 |  | 416 |
| 2.106 | 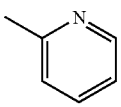 | 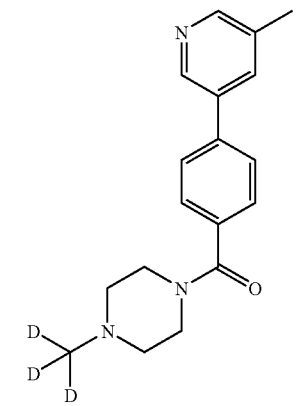 |  | 471 |

TABLE 2-continued

| Ex. | T¹ | T² | T³ | [M + H]⁺ |
|---|---|---|---|---|
| 2.107 | 2-methylpyridine | 5-methyl-3-(4-((4-tert-butylpiperazin-1-yl)methyl)phenyl)pyridine | N-methyl-CD₃ amine (NH-CD₃ with methyl) | 496 |
| 2.108 | 2-methylpyridine | 5-methyl-3-(4-(((S)-3-(dimethylamino)pyrrolidin-1-yl)methyl)phenyl)pyridine | NH-CD₃ with methyl | 468 |
| 2.109 | 2,6-dimethylpyridine | 5-methyl-3-(4-((4-isopropylpiperazine-1-carbonyl)phenyl)pyridine | —OH (methyl) | 494 |

TABLE 2-continued
| Ex. | T¹ | T² | T³ | [M + H]⁺ |
|---|---|---|---|---|
| 2.110 |  | 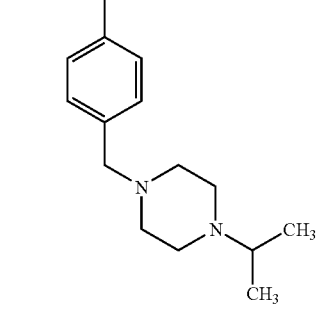 |  | 480 |
| 2.111 |  | 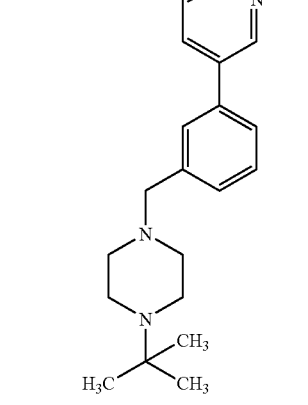 |  | 507 |
| 2.112 |  | 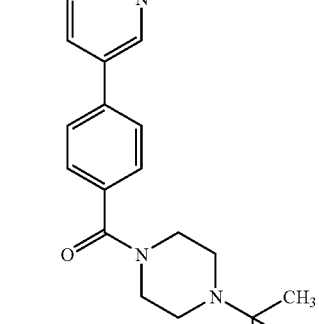 |  | 521 |

TABLE 2-continued
| Ex. | T¹ | T² | T³ | [M + H]⁺ |
|---|---|---|---|---|
| 2.113 | 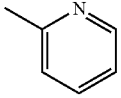 | 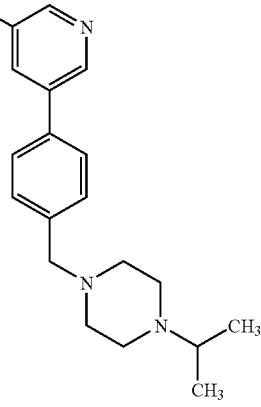 | 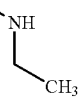 | 493 |
| 2.114 | 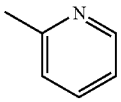 | 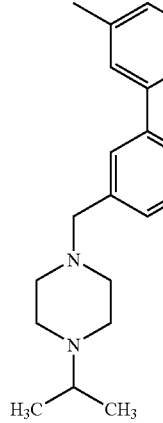 |  | 493 |
| 2.115 | 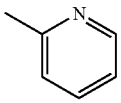 | 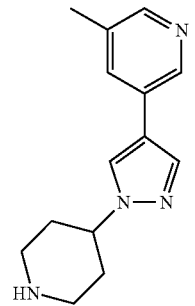 |  | 426 |
| 2.116 | 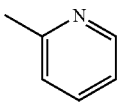 | 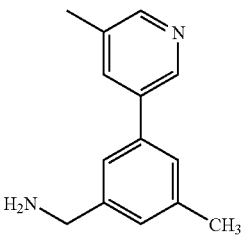 |  | 396 |

TABLE 2-continued
| Ex. | T¹ | T² | T³ | [M + H]⁺ |
|---|---|---|---|---|
| 2.117 | 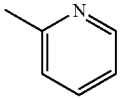 | 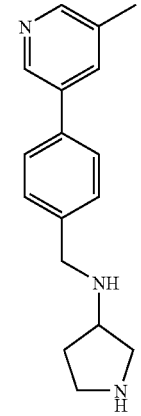 |  | 463 |
| 2.118 | 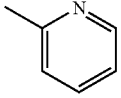 | 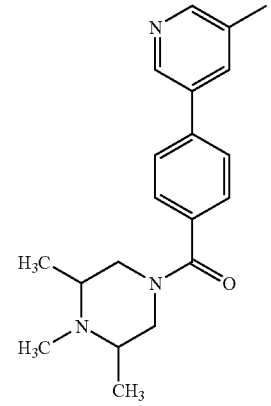 |  | 519 |
| 2.119 | 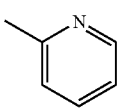 | 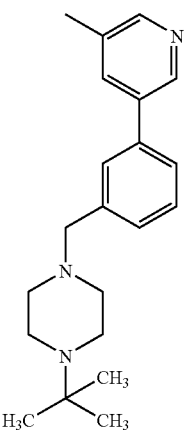 |  | 519 |

TABLE 2-continued

| Ex. | T¹ | T² | T³ | [M + H]⁺ |
|---|---|---|---|---|
| 2.120 | 2-methylpyridine | 5-methyl-3-pyridyl-phenyl-CH₂-piperazine-N-tBu | cyclopropyl-NH | 519 |
| 2.121 | 2-methylpyridine | 5-methyl-3-pyridyl-phenyl-C(O)-piperazine-N-tBu | cyclopropyl-NH | 533 |
| 2.122 | 2-methylpyridine | 5-methyl-3-pyridyl-phenyl-CH₂NH₂ | cyclopropyl-NH | 394 |
| 2.123 | 2-methylpyridine | 5-methyl-3-pyridyl-phenyl-CH₂-pyrrolidine-N(CH₃)₂ | cyclopropyl-NH | 477 |

TABLE 2-continued
| Ex. | T¹ | T² | T³ | [M + H]⁺ |
|---|---|---|---|---|
| 2.124 | 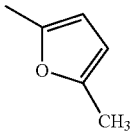 | 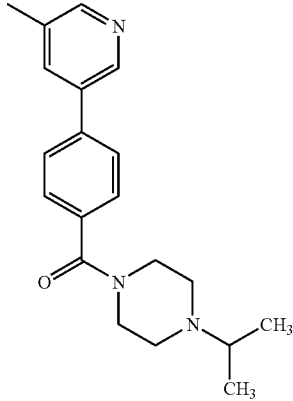 |  | 522 |
| 2.125 | 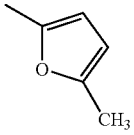 | 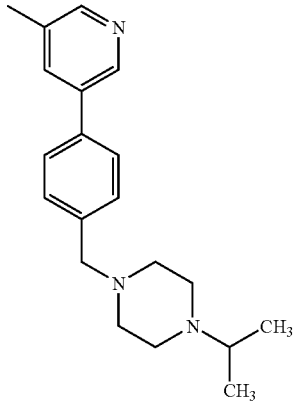 |  | 508 |
| 2.126 | 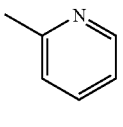 | 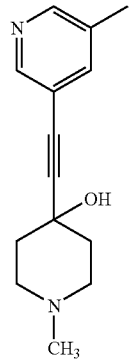 |  | 426 |
| 2.127 | 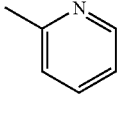 | 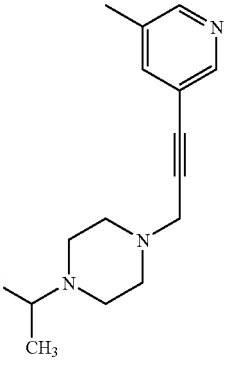 |  | 453 |

TABLE 2-continued
| Ex. | T¹ | T² | T³ | [M + H]⁺ |
|---|---|---|---|---|
| 2.128 | 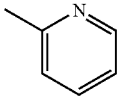 | 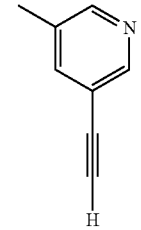 |  | 313 |
| 2.129 | 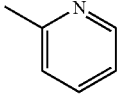 | 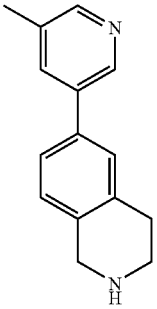 |  | 420 |
| 2.130 | 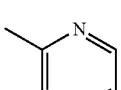 | 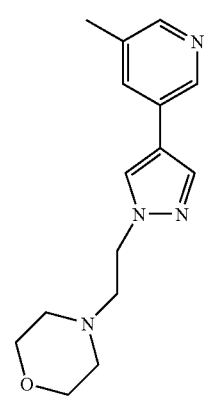 |  | 468 |
| 2.131 | 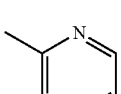 | 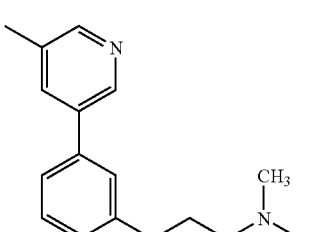 |  | 452 |

TABLE 2-continued
| Ex. | T¹ | T² | T³ | [M + H]⁺ |
|---|---|---|---|---|
| 2.132 | 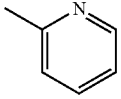 | 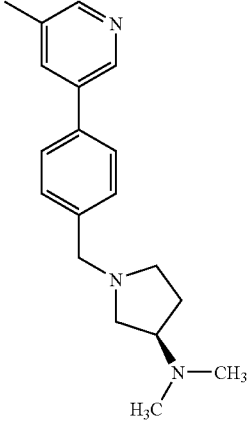 | 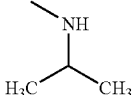 | 493 |
| 2.133 | 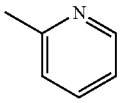 | 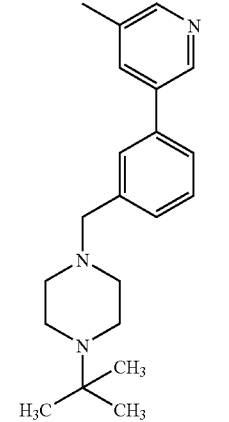 | 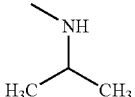 | 521 |
| 2.134 | 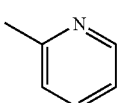 | 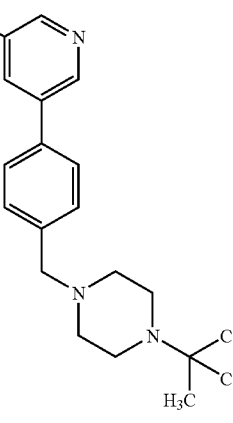 | 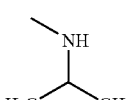 | 521 |

TABLE 2-continued
| Ex. | T¹ | T² | T³ | [M + H]⁺ |
|---|---|---|---|---|
| 2.135 | 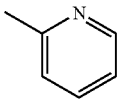 | 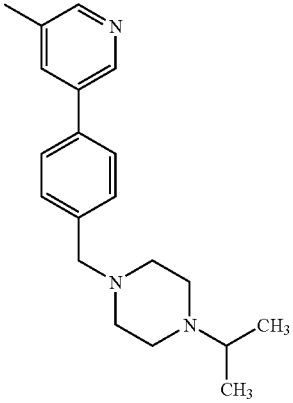 | 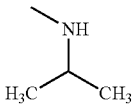 | 507 |
| 2.136 | 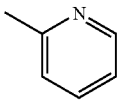 | 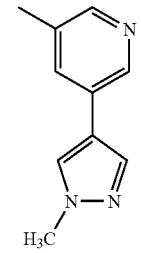 | 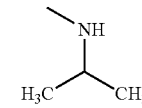 | 371 |
| 2.137 | 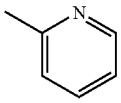 | 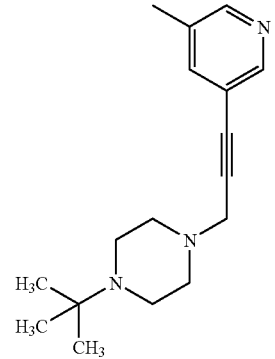 | 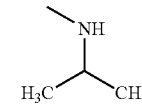 | 469 |
| 2.138 | 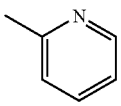 | 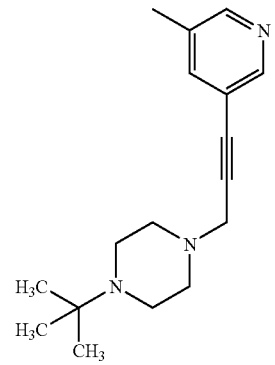 | 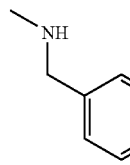 | 517 |

TABLE 2-continued
| Ex. | T¹ | T² | T³ | [M + H]⁺ |
|---|---|---|---|---|
| 2.139 | 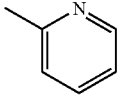 | 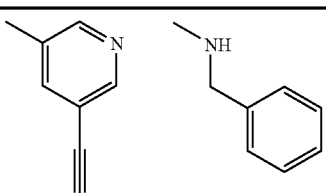 | 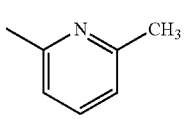 | 503 |
| 2.140 | 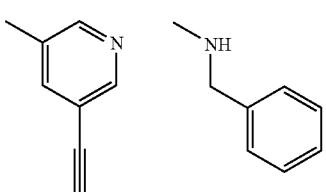 | 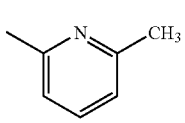 | 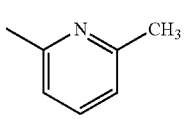 | 531 |
| 2.141 | 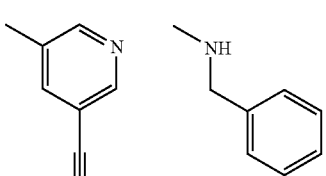 | 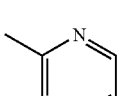 | 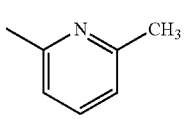 | 517 |
| 2.142 | 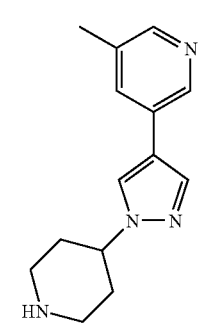 | 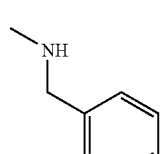 | 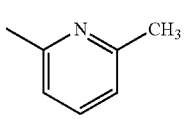 | 488 |

TABLE 2-continued

| Ex. | T¹ | T² | T³ | [M + H]⁺ |
|---|---|---|---|---|
| 2.143 | 2-methylpyridine | 5-methyl-3-(3-hydroxyphenyl)pyridine | N-methylbenzylamine | 431 |
| 2.144 | 2-methylpyridine | 5-methyl-3-[3-(2-dimethylaminoethoxy)phenyl]pyridine | N-methylbenzylamine | 502 |
| 2.145 | 1,3-dimethylpyrazole | 5-methyl-3-[1-(piperidin-4-yl)-1H-pyrazol-4-yl]pyridine | N-methylbenzylamine | 491 |
| 2.146 | 2-methylpyridine | 5-methyl-3-{3-[(4-tert-butylpiperazin-1-yl)methyl]phenyl}pyridine | N-methylcyclopentylamine | 547 |

TABLE 2-continued
| Ex. | T¹ | T² | T³ | [M + H]⁺ |
|---|---|---|---|---|
| 2.147 | 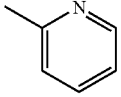 | 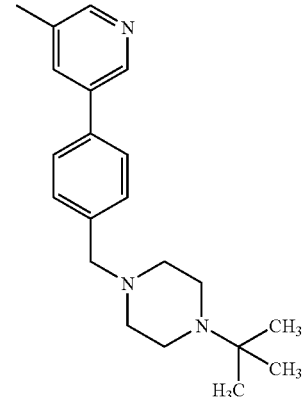 | 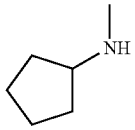 | 547 |
| 2.148 | 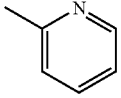 | 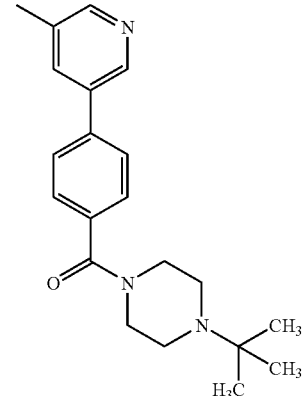 | 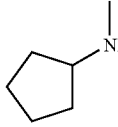 | 561 |
| 2.149 | 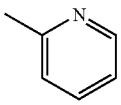 | 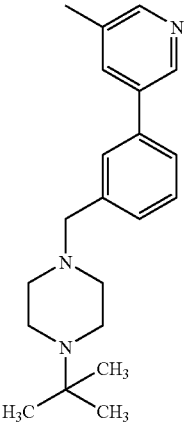 | 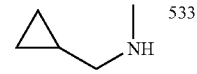 | 533 |

TABLE 2-continued
| Ex. | T¹ | T² | T³ | [M + H]⁺ |
|---|---|---|---|---|
| 2.150 | 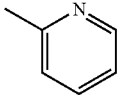 | 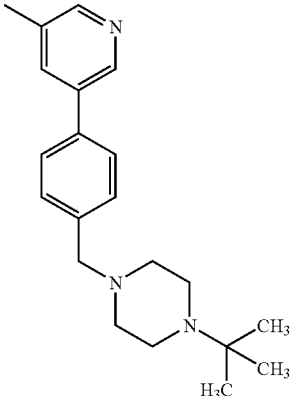 | 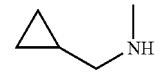 | 533 |
| 2.151 | 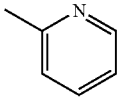 | 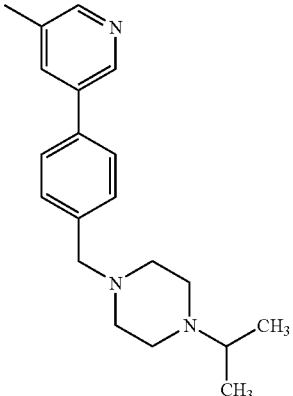 | 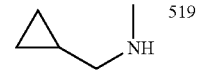 | 519 |
| 2.152 | 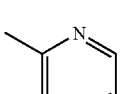 | 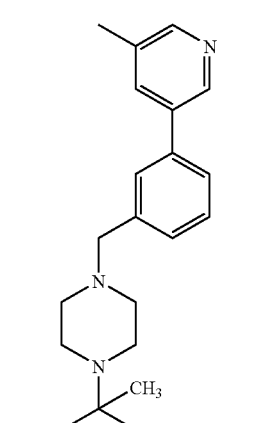 | 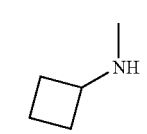 | 533 |

TABLE 2-continued
| Ex. | T¹ | T² | T³ | [M + H]⁺ |
|---|---|---|---|---|
| 2.153 | 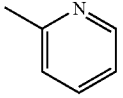 | 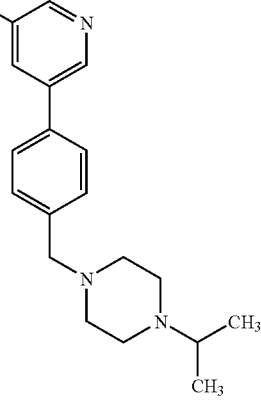 |  | 493 |
| 2.154 | 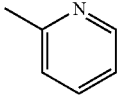 | 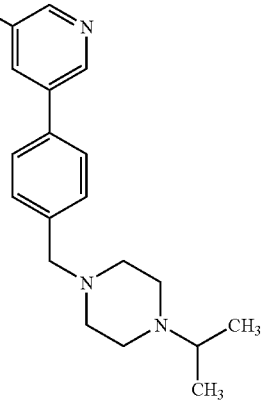 | 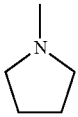 | 519 |
| 2.155 | 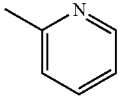 | 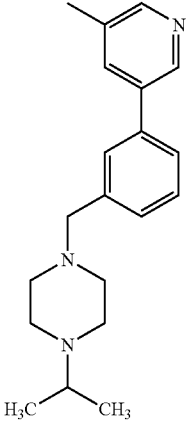 | —NH₂ | 465 |
| 2.156 | 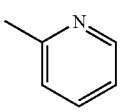 | 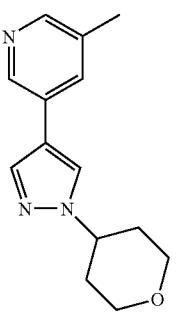 | —NH₂ | 399 |

TABLE 2-continued
| Ex. | T¹ | T² | T³ | [M + H]⁺ |
|---|---|---|---|---|
| 2.157 | 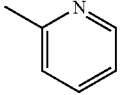 | 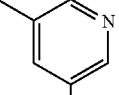 | —NH₂ | 368 |
| 2.158 | 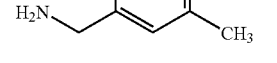 | 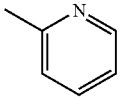 | —NH₂ | 479 |
| 2.159 | 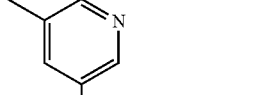 | 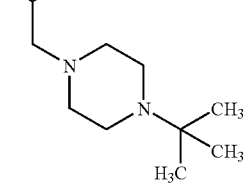 | —NH₂ | 423 |
| 2.160 | 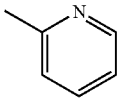 | 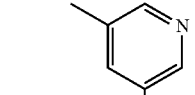 | —NH₂ | 398 |

US 8,343,966 B2
TABLE 2-continued
| Ex. | T¹ | T² | T³ | [M + H]⁺ |
|---|---|---|---|---|
| 2.161 | 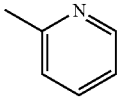 | 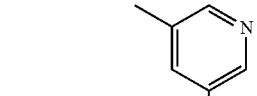 | —NH₂ | 440 |
| 2.162 | 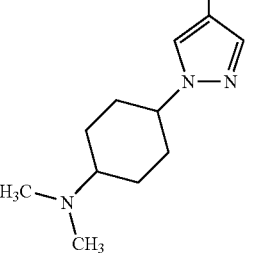 | 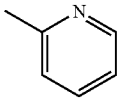 | —NH₂ | 428 |
| 2.163 | 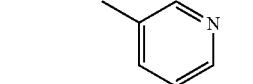 | 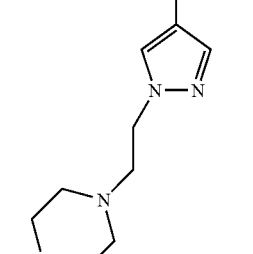 | —NH₂ | 329 |
| 2.164 | 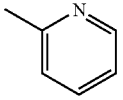 | 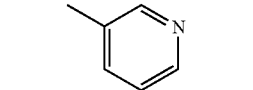 | —NH₂ | 451 |

TABLE 2-continued
| Ex. | T¹ | T² | T³ | [M + H]⁺ |
|---|---|---|---|---|
| 2.165 | 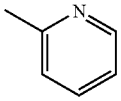 | 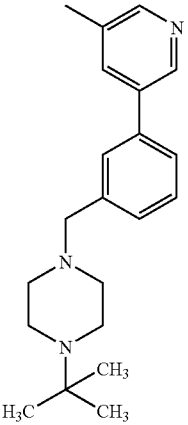 |  | 493 |
| 2.166 | 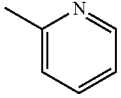 | 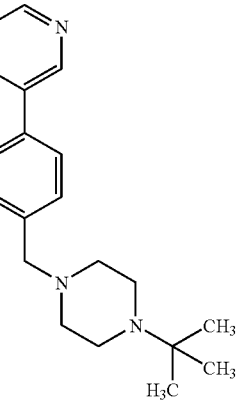 |  | 493 |
| 2.167 | 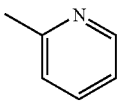 | 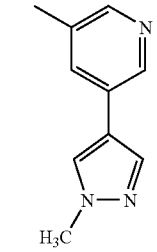 |  | 343 |
| 2.168 | 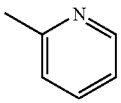 | 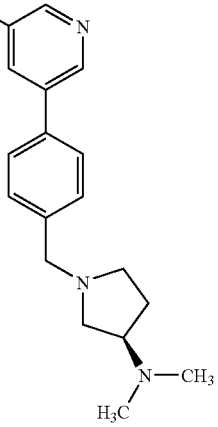 |  | 465 |

TABLE 2-continued
| Ex. | T¹ | T² | T³ | [M + H]⁺ |
|---|---|---|---|---|
| 2.169 | 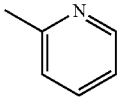 | 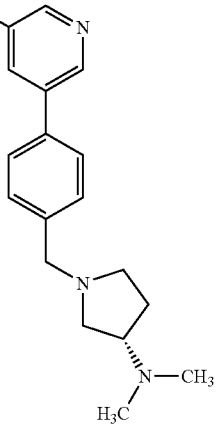 |  | 465 |
| 2.170 | 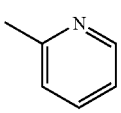 | 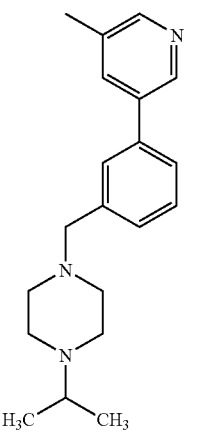 |  | 479 |
| 2.171 | 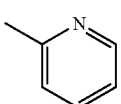 | 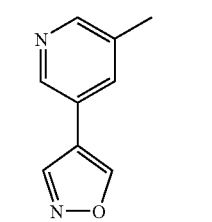 |  | 330 |
| 2.172 | 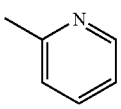 | 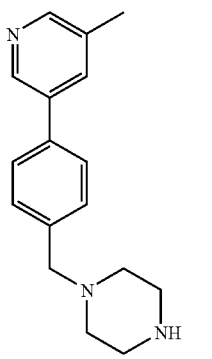 |  | 437 |

TABLE 2-continued
| Ex. | T¹ | T² | T³ | [M + H]⁺ |
|---|---|---|---|---|
| 2.173 | 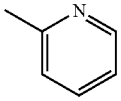 | 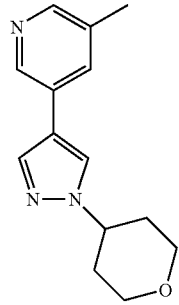 |  | 413 |
| 2.174 | 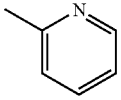 | 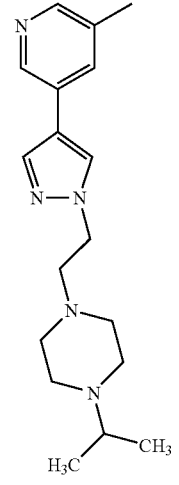 |  | 483 |
| 2.175 | 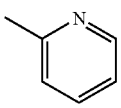 | 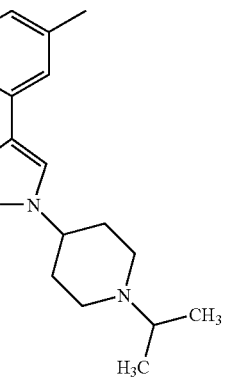 |  | 454 |
| 2.176 | 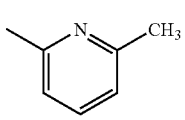 | 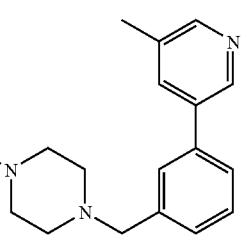 |  | 465 |

TABLE 2-continued
| Ex. | T¹ | T² | T³ | [M + H]⁺ |
|---|---|---|---|---|
| 2.177 | 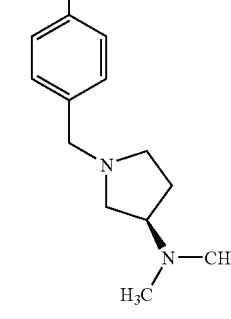 | 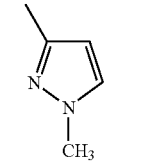 | 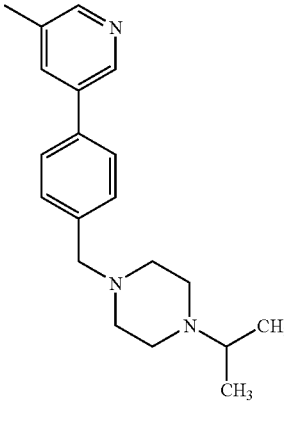 | 479 |
| 2.178 |  | 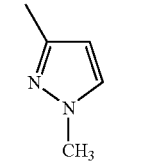 | 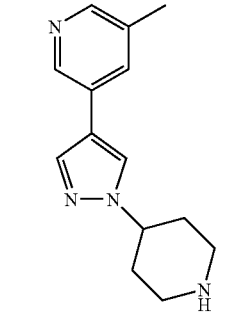 | 482 |
| 2.179 |  | 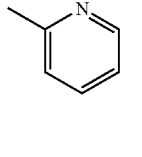 | 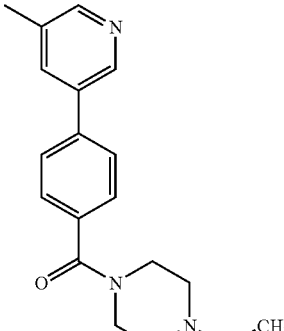 | 415 |
| 2.180 |  | | | 507 |

TABLE 2-continued
| Ex. | T¹ | T² | T³ | [M + H]⁺ |
|---|---|---|---|---|
| 2.181 | 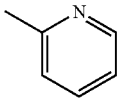 | 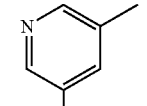 |  | 427 |
| 2.182 | 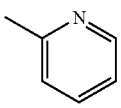 | 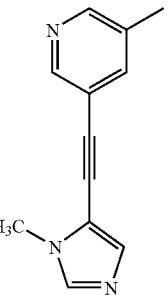 |  | 367 |
| 2.183 | 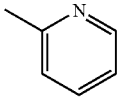 | 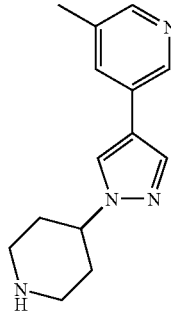 |  | 412 |
| 2.184 | 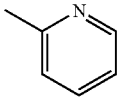 | 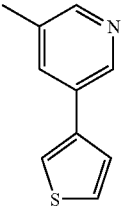 |  | 354 |
| 2.185 | 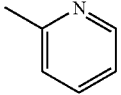 | 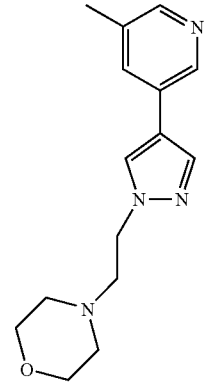 |  | 442 |

TABLE 2-continued

| Ex. | T¹ | T² | T³ | [M + H]⁺ |
|---|---|---|---|---|
| 2.186 | 2-methylpyridine | 5-methyl-3-(1-methylpyrazol-3-yl)pyridine | NHCH₃ | 343 |
| 2.187 | 2,6-dimethylpyridine | 5-methyl-3-[4-[(4-isopropylpiperazin-1-yl)methyl]phenyl]pyridine | NHCH₃ | 493 |
| 2.188 | 2,6-dimethylpyridine | 5-methyl-3-[1-(piperidin-4-yl)pyrazol-4-yl]pyridine | NHCH₃ | 426 |
| 2.189 | 2-methylpyridine | 5-methyl-3-[3-(2-pyrrolidin-1-ylethoxy)phenyl]pyridine | NHCH₃ | 453 |

General Conditions:

Mass spectra are run on an open access Waters 600/ZQ HPLC/Mass Spectrometer system using electrospray ionization. [M+H]⁺ refers to mono-isotopic molecular weights.

Unless otherwise stated, all starting materials are obtained from commercial suppliers and used without further purification.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

In addition various trade reagents and materials available from have been utilized. Such reagents and materials include: [include examples such as Isolute™ (available from Biotage)] and can be readily obtained from the suppliers indicated.

The following examples are intended to illustrate the invention and are not to be construed as being limitations thereon. Temperatures are given in degrees centrigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. If not defined, the terms have their generally accepted meanings.

The following abbreviations are used in the examples and throughout the specification: DCM is dichloromethane, DIPEA is N,N-diisopropylethylamine, DME is dimethylethylene glycol, DMF is dimethylformamide, DBU is 1,8-diazabicyclo[5.4.0]undec-7-ene, HATU is O-(7-azabenzotriazol-1-yl)-N,N,N',N'-tetramethyluronium hexafluorophosphate, HCl is hydrochloric acid, THF is tetrahydrofuran, MeCN is acetonitrile, CHCl$_3$ is chloroform, EtOAc is ethyl acetate, EtOH is ethanol, H$_2$O is water, HPLC is high performance liquid chromatography, MgSO$_4$ is magnesium sulfate, NMP is 1-methyl-2-pyrrolidone, Na$_2$CO$_3$ is sodium carbonate, NaHCO$_3$ is sodium hydrogencarbonate, NaBH(OAc)$_3$ is sodium triacetoxyborohydride, MeOH is methanol, NH$_3$ is ammonia, NEt$_3$ is triethylamine, Pd is palladium, PdCl$_2$(dppf).DCM is [1,1-Bis(diphenylphosphino)-ferrocene] dichloropalladium(II) complex with dichloromethane, SCX-2 is strong cation exchange, TFA is trifluoroacetic acid and RT is room temperature.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

Preparation of Final Compounds

Example 1.1

(6'-Furan-2-yl-[3,4']bipyridinyl-2'-yl)-[2-(1H-indol-3-yl)-ethyl]-amine (E)-1-Furan-2-yl-3-pyridin-3-yl-propenone (Intermediate A1) (1 eq, 0.302 mmol, 60 mg), α-(benzotriazol-1-yl)-acetonitrile (1 eq, 0.302 mmol, 47.6 mg) and tryptamine (1 eq, 0.302 mmol, 48.3 mg) are mixed together in EtOH (1 ml) and heated using microwave radiation at 120° C. for 2 hours. The reaction mixture is dissolved in DCM and washed with water. The organic solvent is reduced in vacuo and the residue is purified by reverse phase chromatography (Isolute™ C18, 0-40% acetonitrile in water –0.1% TFA). The appropriate fractions by HPLC are combined and concentrated in vacuo. The resulting residue is dissolved in MeOH and loaded onto a SCX-2 cartridge eluting with MeOH followed by 2M NH$_3$ in MeOH. The methanolic ammonia fractions are combined, concentrated in vacuo and dried under vacuum to afford the title compound; [M+H]$^+$ 381.

Examples 1.2 to 1.32

These compounds namely,
(6'-Furan-2-yl-[3,4']bipyridinyl-2'-yl)-(1H-indol-4-ylmethyl)-amine (Example 1.2),
[2-(1H-Indol-3-yl)-ethyl]-[6'-(5-methyl-furan-2-yl)-[3,4']bipyridinyl-2'-yl]-amine (Example 1.3),
[2-(1H-Indol-3-yl)-ethyl]-(5"-methoxy-[2,2';4',3"]terpyridin-6'-yl)-amine (Example 1.4),
(1H-Indol-4-ylmethyl)-(5"-methoxy-[2,2';4',3"]terpyridin-6'-yl)-amine (Example 1.5),
[2-(1H-Indol-4-yl)-ethyl]-[2,2';4',3"]terpyridin-6'-yl-amine (Example 1.6),
4-[2-([2,2';4',3"]Terpyridin-6'-ylamino)-ethyl]-phenol (Example 1.7),
(6-Bromo-[2,2';4',3"]terpyridin-6'-yl)-[2-(1H-indol-3-yl)-ethyl]-amine (Example 1.8),
4-[2-(6'-Furan-2-yl-[3,4']bipyridinyl-2'-ylamino)-ethyl]-phenol (Example 1.9),
[2-(1H-Indol-3-yl)-ethyl]-[2,2';4',3"]terpyridin-6'-yl-amine (Example 1.10),
[2-(1H-Indol-3-yl)-ethyl]-[6'-(1H-pyrrol-2-yl)-[3,4']bipyridinyl-2'-yl]-amine (Example 1.11),
[6'-(3,5-Dimethyl-1H-pyrrol-2-yl)-[3,4']bipyridinyl-2'-yl]-[2-(1H-indol-3-yl)-ethyl]-amine (Example 1.12),
(1H-Indol-4-ylmethyl)-(5"-iodo-[2,2';4',3"]terpyridin-6'-yl)-amine (Example 1.13),
(5"-Bromo-[2,2';4',3"]terpyridin-6'-yl)-[2-(1H-indol-3-yl)-ethyl]-amine (Example 1.14),
(1H-Indol-4-ylmethyl)-[2,2';4',3"]terpyridin-6'-yl-amine (Example 1.15),
(5"-Bromo-[2,2';4',3"]terpyridin-6'-yl)-(1H-indol-4-ylmethyl)-amine (Example 1.16),
[2-(1H-Indol-3-yl)-ethyl]-[2,4';2',3"]terpyridin-6'-yl-amine (Example 1.17),
3-{6-[2-(1H-Indol-3-yl)-ethylamino]-[2,2']bipyridinyl-4-yl}-phenol (Example 1.18),
[2-(1H-Indol-3-yl)-ethyl]-(5"-iodo-[2,2';4',3"]terpyridin-6'-yl)-amine (Example 1.19),
Benzyl-[2,2';4',3"]terpyridin-6'-yl-amine (Example 1.20),
[2-(1H-Indol-3-yl)-ethyl]-(6-methyl-[2,2';4',3"]terpyridin-6'-yl)-amine (Example 1.21),
[2-(1H-Indol-3-yl)-ethyl]-(6-methoxy-[2,2';4',3"]terpyridin-6'-yl)-amine (Example 1.22),
3-[(5"-Bromo-[2,2';4',3"]terpyridin-6'-ylamino)-methyl]-phenol (Example 1.23),
(5"-Bromo-[2,2';4',3"]terpyridin-6'-yl)-ethyl-amine (Example 1.24),
Benzyl-(5"-bromo-[2,2';4',3"]terpyridin-6'-yl)-amine (Example 1.25),
(5"-Bromo-[2,2';4',3"]terpyridin-6'-yl)-cyclopropyl-amine (Example 1.26)
(5"-Bromo-6-methyl-[2,2';4',3"]terpyridin-6'-yl)-methyl-amine (Example 1.27) and
(5"-Bromo-6-methyl-[2,2';4',3"]terpyridin-6'-yl)-tert-butyl-amine (Example 1.28)
(5"-Bromo-[2,2';4',3"]terpyridin-6'-yl)-methyl-d3-amine (Example 1.29)
[5-Bromo-6'-(5-methyl-furan-2-yl)-[3,4']bipyridinyl-2'-yl]-cyclopropyl-amine (Example 1.30)
are prepared analogously to (6'-Furan-2-yl-[3,4']bipyridinyl-2'-yl)-[2-(1H-indol-3-yl)-ethyl]-amine (Example 1.1) by replacing (E)-1-furan-2-yl-3-pyridin-3-yl-propenone (Intermediate A1) with the appropriate chalcone intermediate (preparations described hereinafter) and by replacing tryptamine with the appropriate amine.

Example 1.31

5"-Bromo-[2,2';4',3"]terpyridin-6'-ylamine (E)-3-(5-Bromo-pyridin-3-yl)-1-pyridin-2-yl-propenone (Intermediate A10) (1 eq, 6.92 mmol, 2 g), α-(benzotriazol-1-y)-acetonitrile (1 eq, 6.92 mmol, 1.09 g) and 2M ammonia (6 eq, 41.5 mmol, 20.8 mL) are mixed together in EtOH (20 ml) and heated using a Buchi mini autoclave at 120° C. overnight. The reaction mixture is dissolved in EtOAc and washed with water. The organic solvent is reduced in vacuo and the residue is purified by reverse phase chromatography (Isolute™ C18, 0-40% acetonitrile in water—0.1% TFA).

The appropriate fractions by HPLC are combined and concentrated in vacuo. The resulting residue is dissolved in MeOH and loaded onto a SCX-2 cartridge eluting with MeOH followed by 2M $NH_3$ in MeOH. The methanolic ammonia fractions are combined, concentrated in vacuo and dried under vacuum to afford the title compound; $[M+H]^+$ 327/329.

Example 2.1

[4-(6'-Methylamino-[2,2';4',3"]terpyridin-5"-yl)-phenyl]-(4-methyl-piperazin-1-yl)-methanone Step 1: (5"-Bromo-[2,2';4',3"]terpyridin-6'-yl)-methyl-amine (E)-3-(5-Bromo-pyridin-3-yl)-1-pyridin-2-yl-propenone (Intermediate A10) (1 eq, 7.26 mmol, 2.1 g), α-(benzotriazol-1-yl)-acetonitrile (1 eq, 7.26 mmol, 1.15 g) and 33% methylamine solution in EtOH (1.5 eq, 3.46 mmol, 1.36 ml) are mixed together in EtOH (30 ml) and heated using microwave radiation at 120° C. for 75 mins. The reaction mixture is dissolved in DCM and washed with water. The combined organic extracts are washed with brine, dried over $MgSO_4$ and concentrated in vacuo. The residue is purified by flash chromatography (0-50% EtOAc in iso-hexane) to afford the title compound; $[M+H]^+$ 342/344.

Step 2: [4-(6'-Methylamino-[2,2';4',3"]terpyridin-5"-yl)-phenyl]-(4-methyl-piperazin-1-yl)-methanone To a solution of (4-Methyl-piperazin-1-yl)-[4-(4,4,5,5-tetramethyl-[1,3,2]dioxaborolan-2-yl)-phenyl]-methanone (1.2 eq, 1.55 mmol, 0.511 g) and 2M $Na_2CO_3$ (2.0 eq, 2.58 mmol, 1.3 ml) in DME (10 ml) is added (5"-Bromo-[2,2';4',3"]terpyridin-6'-yl)-methyl-amine (1 eq, 1.29 mmol, 0.44 g) followed by [1,1'-Bis(diphenylphosphino)-ferrocene]dichloropalladium (II), complex with DCM (0.1 eq, 0.128 mmol, 0.094 g). The reaction mixture is heated using microwave radiation at 90° C. for 90 mins. The reaction mixture is dissolved in DCM and washed with water. The organic layer is washed with brine, dried over drying agent $MgSO_4$, filtered and the organic solvent is reduced in vacuo. The crude residue is purified by reverse phase column chromatography (Isolute™ C18, 0-20% acetonitrile in water—0.1% TFA). The appropriate fractions by HPLC are combined and concentrated in vacuo. The resulting residue is dissolved in MeOH and loaded onto a SCX-2 cartridge eluting with MeOH followed by 2M $NH_3$ in MeOH. The methanolic ammonia fractions are combined, concentrated in vacuo and dried under vacuum to afford the title compound; $[M+H]^+$ 465.

Examples 2.2 to 2.22

These compounds namely,
Methyl-{5"-[4-(4-methyl-piperazin-1-yl)-phenyl]-[2,2';4',3"]terpyridin-6'-yl}-amine (Example 2.2)
[5"-(1H-Indol-4-yl)-[2,2';4',3"]terpyridin-6'-yl]-methyl-amine (Example 2.3)
Methyl-[5"-(4-piperidin-1-yl-phenyl)-[2,2';4',3"]terpyridin-6'-yl]-amine (Example 2.4)
[5"-(3,4-Dimethoxy-phenyl)-[2,2';4',3"]terpyridin-6'-yl]-methyl-amine (Example 2.5)
Methyl-[5"-(3-morpholin-4-yl-phenyl)-[2,2';4',3"]terpyridin-6'-yl]-amine (Example 2.6)
3-(6'-Methylamino-[2,2';4',3"]terpyridin-5"-yl)-benzenesulfonamide (Example 2.7)
[4-(6'-Methylamino-[2,2';4',3"]terpyridin-5"-yl)-phenyl]-morpholin-4-yl-methanone (Example 2.8)
[5"-(3-Ethoxy-phenyl)-[2,2';4',3"]terpyridin-6'-yl]-methyl-amine (Example 2.9)
[5"-(3-Methanesulfonyl-phenyl)-[2,2';4',3"]terpyridin-6'-yl]-methyl-amine (Example 2.10)
N-[3-(6'-Methylamino-[2,2';4',3"]terpyridin-5"-yl)-phenyl]-methanesulfonamide (Example 2.11)
Methyl-[5"-(3-pyrrolidin-1-yl-phenyl)-[2,2';4',3"]terpyridin-6'-yl]-amine (Example 2.12)
Methyl-[5"-(4-morpholin-4-ylmethyl-phenyl)-[2,2';4',3"]terpyridin-6'-yl]-amine (Example 2.13)
[3-(6'-Methylamino-[2,2';4',3"]terpyridin-5"-yl)-phenyl]-(4-methyl-piperazin-1-yl)-methanone (Example 2.14)
[5"-(3-Methoxy-phenyl)-[2,2';4',3"]terpyridin-6'-yl]-methyl-amine (Example 2.15)
N-tert-Butyl-3-(6'-methylamino-[2,2';4',3"]terpyridin-5"-yl)-benzamide (Example 2.16)
(2'''-Methoxy-[2,2';4',3";5",4''']quaterpyridin-6'-yl)-methyl-amine (Example 2.17)
Methyl-[5"-(3-piperidin-1-yl-phenyl)-[2,2';4',3"]terpyridin-6'-yl]-amine (Example 2.18)
[5"-(2-Methoxy-phenyl)-[2,2';4',3"]terpyridin-6'-yl]-methyl-amine (Example 2.19)
5"-(4-Methoxy-phenyl)-[2,2';4',3"]terpyridin-6'-yl]-methyl-amine (Example 2.20)
Methyl-/(5"-pyrimidin-5-yl-[2,2';4',3"]terpyridin-6'-yl)-amine (Example 2.21) and
[4-(6'-Methylamino-[2,2';4',3"]terpyridin-5"-yl)-phenyl]-piperazin-1-yl-methanone (Example 2.22)
are prepared analogously to [4-(6'-Methylamino-[2,2';4',3"]terpyridin-5"-yl)-phenyl]-(4-methyl-piperazin-1-yl)-methanone (Example 2.1) by replacing (4-Methyl-piperazin-1-yl)-[4-(4,4,5,5-tetramethyl-[1,3,2]dioxaborolan-2-yl)-phenyl]-methanone (step 2) with the appropriate boronic acid.

Example 2.23

Methyl-{5"-[3-(4-methyl-piperazin-1-ylmethyl)-phenyl]-[2,2';4',3"]terpyridin-6'-yl}-amine To a solution of 3-((4-Methyl-piperazin-1-yl)methyl)-phenyl boronic acid (Intermediate B1) (1.2 eq, 0.704 mmol, 0.165 g) and 2M $Na_2CO_3$ (2.0 eq, 1.17 mmol, 0.6 ml) in DME (3 ml) is added (5"-Bromo-[2,2';4',3"]terpyridin-6'-yl)-methyl-amine (Example 2.1; step1) (1 eq, 0.586 mmol, 0.2 g) followed by [1,1'-Bis(diphenylphosphino)-ferrocene]dichloropalladium (II), complex with DCM (0.1 eq, 0.058 mmol, 0.043 g). The reaction mixture is heated using microwave radiation at 90° C. for 4 hours. The reaction mixture is dissolved in EtOAc and washed with water. The organic layer is washed with brine, dried over drying agent $MgSO_4$, filtered and the organic solvent is reduced in vacuo. The crude residue is purified by reverse phase column chromatography (Isolute™ C18, 0-20% acetonitrile in water—0.1% TFA). The appropriate fractions by HPLC are combined and concentrated in vacuo. The resulting residue is dissolved in MeOH and loaded onto a SCX-2 cartridge eluting with MeOH followed by 2 M $NH_3$ in MeOH. The methanolic ammonia fractions are combined, concentrated in vacuo and dried under vacuum to afford the title compound; $[M+H]^+$ 451.

Examples 2.24 to 2.26

These compounds namely,
{5"-[4-(4-Isopropyl-piperazin-1-ylmethyl)-phenyl]-[2,2';4',3"]terpyridin-6'-yl}-methyl-amine (Example 2.24)

4-Isopropyl-piperazin-1-yl)-[4-(6'-methylamino-[2,2';4',3"]
terpyridin-5"-yl)-phenyl]-methanone (Example 2.25) and
Methyl-{5"-[4-(4-methyl-piperazin-1-ylmethyl)-phenyl]-[2,
2';4',3"]terpyridin-6'-yl}-amine (Example 2.26)
are prepared analogously to Methyl-{5"-[3-(4-methyl-piperazin-1-ylmethyl)-phenyl]-[2,2';4',3"]terpyridin-6'-yl}-amine (Example 2.23) by replacing 3-(4-Methyl-piperazin-1-ylmethyl)-phenyl boronic acid with the appropriate boronic acid (preparations described hereinafter).

Examples 2.27 to 2.29

These compounds namely,
Methyl-{6-methyl-5"-[4,(4-methyl-piperazin-1-yl)-phenyl]-[2,2',4',3"]terpyridin-6'-yl}-amine (Example 2.27)
[4-(6-Methyl-6'-methylamino-[2,2';4',3"]terpyridin-5"-yl)-phenyl]-(4-methyl-piperazin-1-yl)-methanone (Example 2.28) and
Ethyl-[5"-(3-methoxy-phenyl)-[2,2';4',3"]terpyridin-6'-yl]-amine (Example 2.29)
are prepared analogously to [4-(6'-Methylamino-[2,2';4',3"]
terpyridin-5"-yl)-phenyl]-(4-methyl-piperazin-1-yl)-methanone (Example 2.1) by replacing (5"-Bromo-[2,2';4',3"]
terpyridin-6'-yl)-methyl-amine with appropriate intermediate (Example 1.24 or Example 1.27) and by replacing (4-Methyl-piperazin-1-yl)-[4-(4,4,5,5-tetramethyl-[1,3,2]dioxaborolan-2-yl)-phenyl]-methanone with the appropriate boronic acid.

Examples 2.30

[4-(6'-Cyclopropylamino-[2,2';4',3"]terpyridin-5"-yl)-phenyl]-piperazin-1-yl-methanone To a solution of piperazin-1-yl-[4-(4,4,5,5-tetramethyl-[1,3,2]dioxaborolan-2-yl)-phenyl]-methanone (1.2 eq, 0.163 mmol, 0.052 g) in dry DME (1 ml) under an inert atmosphere of argon is added 2M $Na_2CO_3$ (3 eq, 0.408 mmol, 0.2 ml) followed by (5"-Bromo-[2,2';4',3"]terpyridin-6'-yl)-cyclopropyl-amine (Example 1.26) (1 eq, 0.136 mmol, 0.050 g) and $PdCl_2$dppf (0.1 eq, 0.0136 mmol, 0.001 g). The reaction mixture is heated using microwave radiation at 90° C. for 2 hours 30. The reaction mixture is dissolved in DCM and washed with water. The organic layer is dried over drying agent $MgSO_4$, filtered and the organic solvent is reduced in vacuo. The crude residue is purified by reverse phase column chromatography (Isolute™ C18, 0-40% acetonitrile in water—0.1% TFA). The appropriate fractions by HPLC are combined and concentrated in vacuo. The resulting residue is dissolved in MeOH and loaded onto a SCX-2 cartridge eluting with MeOH and followed by 2M $NH_3$ in MeOH. The methanolic ammonia fractions are combined, concentrated in vacuo and dried under vacuum to afford the title compound; $[M+H]^+$ 477.

Examples 2.31

Cyclopropyl-{5"-[4-(4-isopropyl-piperazin-1-ylmethyl)-phenyl]-[2,2';4',3"]terpyridin-6'-yl}-amine To a solution of 4-((4-Isopropyl-piperazin-1-yl)methyl)-phenyl boronic acid (Intermediate B3) (3 eq, 0.408 mmol, 0.106 g) in dry DME (1 ml) under an inert atmosphere of argon is added 2M $Na_2CO_3$ (6 eq, 0.816 mmol, 0.8 ml) followed by (5"-Bromo-[2,2';4',3"]terpyridin-6'-yl)-cyclopropyl-amine (Example 1.26) (1 eq, 0.136 mmol, 50 mg) and PdCl2dppf (0.1 eq, 0.0136 mmol, 10 mg). The reaction mixture is heated using microwave radiation at 90° C. for 2 hours. The reaction mixture is dissolved in DCM and washed with water. The organic solvent is reduced in vacuo and the residue is purified by reverse phase column chromatography (Isolute™ C18, 0-40% acetonitrile in water—0.1% TFA). The appropriate fractions by HPLC are combined and concentrated in vacuo. The resulting residue is dissolved in MeOH and loaded onto a SCX-2 cartridge eluting with MeOH followed by 2M $NH_3$ in MeOH. The methanolic ammonia fractions are combined, concentrated in vacuo and dried under vacuum to afford the title compound; $[M+H]^+$ 505.

Examples 2.32 to 2.35

These compounds namely,
Cyclopropyl-[5"-(3-methoxy-phenyl)-[2,2';4',3"]terpyridin-6'-yl]-amine (Example 2.32)
[4-(6'-Cyclopropylamino-[2,2';4',3"]terpyridin-5"-yl)-phenyl]-(4-ethyl-piperazin-1-yl)-methanone (Example 2.33)
[4-(6'-Cyclopropylamino-[2,2';4',3"]terpyridin-5"-yl)-phenyl]-[4-(2-methoxy-ethyl)-piperazin-1-yl]-methanone (Example 2.34) and
[4-(6'-Cyclopropylamino-[2,2';4',3"]terpyridin-5"-yl)-phenyl]-(3,5-dimethyl-piperazin-1-yl)-methanone (Example 2.35)
are prepared analogously to Cyclopropyl-{5"-[4-(4-isopropyl-piperazin-1-ylmethyl)-phenyl]-[2,2';4',3"]terpyridin-6'-yl}-amine (Example 2.31) by replacing 4-(4-Isopropyl-piperazin-1-ylmethyl)-phenyl boronic acid with the appropriate boronic acid.

Example 2.36

Cyclopropyl-{6-methyl-5"-[3-(4-methyl-piperazin-1-ylmethyl)-phenyl]-[2,2';4',3"]terpyridin-6'-yl}-amine Step 1: (5"-Bromo-6-methyl-[2,2';4',3"]terpyridin-6'-yl)-cyclopropyl-amine (E)-3-(5-Bromo-pyridin-3-yl)-1-(6-methyl-pyridin-2-yl)-propenone (Intermediate A11) (1 eq, 1.81 mmol, 0.550 g), α-(benzotriazol-1-yl)-acetonitrile (1 eq, 1.81 mmol, 0.287 g) and cyclopropylamine (1.5 eq, 2.72 mmol, 0.155 g) are mixed together in EtOH (10 ml) and heated using microwave radiation at 120° C. for 4 hours. The reaction mixture is dissolved in EtOAc and washed with water. The combined organic extracts are washed with brine, dried over $MgSO_4$, filtered and concentrated in vacuo. The residue is purified by reverse phase column chromatography (Isolute™ C18, 0-30% acetonitrile in water—0.1% TFA). The appropriate fractions by HPLC are combined and concentrated in vacuo. The resulting residue is dissolved in MeOH and loaded onto a SCX-2 cartridge eluting with MeOH followed by 2M $NH_3$ in MeOH. The methanolic ammonia fractions are combined, concentrated in vacuo and dried under vacuum to afford the title compound; $[M+H]^+$ 381/383.

Step 2: Cyclopropyl-{6-methyl-5"-[3-(4-methyl-piperazin-1-ylmethyl)-phenyl]-[2,2';4',3"]terpyridin-6'-yl}-amine To a solution of 3-((4-Methyl-piperazin-1-yl)methyl)-phenyl boronic acid (Intermediate B1) (1.2 eq, 0.157 mmol, 0.037 g) and 2M $Na_2CO_3$ (2.0 eq, 0.262 mmol, 0.1 ml) in DME (1 ml) is added (5"-Bromo-6-methyl-[2,2';4',3"]terpyridin-6'-yl)-cyclopropyl-amine (Example 2.36; step1) (1 eq, 0.131 mmol, 0.05 g) followed by [1,1'-Bis(diphenylphosphino)-ferrocene]dichloropalladium (II), complex with DCM (0.1 eq, 0.013 mmol, 9.6 mg). The reaction mixture is heated using microwave radiation at 90° C. for 1 hour 30 mins. The reaction mixture is dissolved in EtOAc and washed with water. The organic layer is washed with brine, dried over drying agent MgSO$_4$, filtered and the organic solvent is reduced in vacuo. The crude residue is purified by reverse phase column chromatography (Isolute™ C18, 0-30% acetonitrile in water—0.1% TFA). The appropriate fractions by HPLC are combined and concentrated in vacuo. The resulting residue is dissolved in MeOH and loaded onto a SCX-2 cartridge eluting with MeOH followed by 2M NH$_3$ in MeOH. The methanolic ammonia fractions are combined, concentrated in vacuo and dried under vacuum to afford the title compound; [M+H]$^+$ 491.

Examples 2.37 to 2.39

These compounds namely,
[4-(6'-Cyclopropylamino-6-methyl-[2,2';4',3"]terpyridin-5"-yl)-phenyl]-(4-methyl-piperazin-1-yl)-methanone (Example 2.37)
Cyclopropyl-{6-methyl-5"-[4-(4-methyl-piperazin-1-ylmethyl)-phenyl]-[2,2';4',3"]terpyridin-6'-yl}-amine (Example 2.38) and
Cyclopropyl-[6-methyl-5"-(4-morpholin-4-ylmethyl-phenyl)-[2,2';4',3"]terpyridin-6'-yl]-amine (Example 2.39)
are prepared analogously to Cyclopropyl-{6-methyl-5"-[3-(4-methyl-piperazin-1-ylmethyl)-phenyl]-[2,2';4',3"]terpyridin-6'-yl}-amine (Example 2.36) by replacing 3-((4-Methyl-piperazin-1-yl)methyl)-phenyl boronic acid with the appropriate boronic acid.

Example 2.40

Benzyl-{6-methyl-5"-[4-(4-methyl-piperazin-1-yl)-phenyl]-[2,2';4',3"]terpyridin-6'-yl}-amine Step 1: Benzyl-(5"-bromo-6-methyl-[2,2';4',3"]terpyridin-6'-yl)-amine (E)-3-(5-Bromo-pyridin-3-yl)-1-(6-methyl-pyridin-2-yl)-propenone (Intermediate A11) (1 eq, 0.66 mmol, 0.200 g), α-(benzotriazol-1-yl)-acetonitrile (1 eq, 0.66 mmol, 0.095 g) and benzylamine (1.5 eq, 0.99 mmol, 0.106 g) are mixed together in EtOH (4 ml) and heated using microwave radiation at 120° C. for 2 hours. The reaction mixture is dissolved in DCM and washed with water. The combined organic extracts are washed with brine, dried over MgSO$_4$, filtered and concentrated in vacuo. The residue is purified by reverse phase column chromatography (Isolute™ C18, 0-50% acetonitrile in water—0.1% TFA). The appropriate fractions by HPLC are combined and concentrated in vacuo. The resulting residue is dissolved in MeOH and loaded onto a SCX-2 cartridge eluting with MeOH followed by 2M NH$_3$ in MeOH. The methanolic ammonia fractions are combined, concentrated in vacuo and dried under vacuum to afford the title compound; [M+H]$^+$ 431/433.

Step 2: Benzyl-{6-methyl-5"-[4-(4-methyl-piperazin-1-yl)-phenyl]-[2,2';4',3"]terpyridin-6'-yl}-amine To a solution of 1-Methyl-4[4-(4,4,5,5-tetramethyl-[1,3,2]-dioxaborolan-2-yl)-phenyl]-piperazine (1.2 eq, 0.083 mmol, 0.025 g) and 2M Na$_2$CO$_3$ (4.0 eq, 0.138 mmol, 0.1 ml) in DME (1 ml) is added Benzyl-(5"-bromo-6-methyl-[2,2';4', 3"]terpyridin-6'-yl)-amine (Example 2.40; step1) (1 eq, 0.069 mmol, 0.03 g) followed by [1,1'-Bis(diphenylphosphino)-ferrocene]dichloropalladium (II), complex with DCM (0.1 eq, 0.0069 mmol, 5 mg). The reaction mixture is heated using microwave radiation at 90° C. for 1 hour 15 mins. The reaction mixture is dissolved in DCM and washed with water. The organic layer is washed with brine, dried over drying agent MgSO$_4$, filtered and the organic solvent is reduced in vacuo. The crude residue is purified by reverse phase column chromatography (Isolute™ C18, 0-50% acetonitrile in water—0.1% TFA). The appropriate fractions by HPLC are combined and concentrated in vacuo. The resulting residue is dissolved in MeOH and loaded onto a SCX-2 cartridge eluting with MeOH followed by 2M NH$_3$ in MeOH. The methanolic ammonia fractions are combined, concentrated in vacuo and dried under vacuum to afford the title compound; [M+H]$^+$ 527.

Examples 2.41 to 2.43

These compounds namely,
[4-(6'-Benzylamino-6-methyl-[2,2';4',3"]terpyridin-5"-yl)-phenyl]-(4-methyl-piperazin-1-yl)-methanone (Example 2.41)
Benzyl-[5"-(3-methoxy-phenyl)-6-methyl-[2,2';4',3"]terpyridin-6'-yl]-amine (Example 2.42) and
Benzyl-[5"-(3-methoxy-phenyl)-[2,2';4',3"]terpyridin-6'-yl]-amine (Example 2.43)
are prepared analogously to Benzyl-{6-methyl-5"-[4-(4-methyl-piperazin-1-yl)-phenyl]-[2,2';4',3"]terpyridin-6'-yl})-amine (Example 2.40) by replacing 1-Methyl-4[4-(4,4,5,5-tetramethyl-[1,3,2]-dioxaborolan-2-yl)-phenyl]-piperazine with the appropriate boronic acid.

Examples 2.44 to 2.45

These compounds namely,
(4-{6'-[(1H-Indol-4-ylmethyl)-amino]-[2,2';4',3"]terpyridin-5"-yl}-phenyl)-(4-methyl-piperazin-1-yl)-methanone (Example 2.44) and
3-{[5"-(3-Methoxy-phenyl)-[2,2';4',3"]terpyridin-6'-ylamino]-methyl}-phenol (Example 2.45)
are prepared analogously to [4-(6'-Methylamino-[2,2';4',3"]terpyridin-5"-yl)-phenyl]-(4-methyl-piperazin-1-yl)-methanone (Example 2.1) by replacing (5"-Bromo-[2,2';4',3"]terpyridin-6'-yl)-methyl-amine with appropriate intermediate (Example 1.16 or Example 1.23) and by replacing (4-Methyl-piperazin-1-yl)-[4-(4,4,5,5-tetramethyl-[1,3,2]dioxaborolan-2-yl)-phenyl]-methanone with the appropriate boronic acid.

Examples 2.46

[4-(6'-Isopropylamino-[2,2';4',3"]terpyridin-5"-yl)-phenyl]-(4-isopropyl-piperazin-1-yl)-methanone Step 1: (5"-Bromo-[2,2';4',3"]terpyridin-6'-yl)-isopropyl-amine (E)-3-(5-Bromo-pyridin-3-yl)-1-pyridin-2-yl-propenone (Intermediate A10) (1 eq, 1.73 mmol, 0.500 g), α-(benzotriazol-1-y)-acetonitrile (1 eq, 1.73 mmol, 0.273 g) and isopropylamine (1.5 eq, 2.60 mmol, 0.22 ml) are mixed together in EtOH (5 ml) and heated using microwave radiation at 120° C. for 1.5 hours. The reaction mixture is dissolved in DCM and washed with water. The combined organic extracts are washed with brine, dried over MgSO$_4$ and concentrated in vacuo. The residue is purified by flash chromatography (0-20% EtOAc in iso-hexane) to afford the title compound; [M+H]+ 370/372.

Step 2: [4-(6'-Isopropylamino-[2,2';4',3"]terpyridin-5"-yl)-phenyl]-(4-isopropyl-piperazin-1-yl)-methanone To a solution of (4-Isopropyl-piperazin-1-yl)-[4-(4,4,5,5-tetramethyl-[1,3,2]dioxaborolan-2-yl)-phenyl]-methanone (Intermediate B4) (1.2 eq, 0.162 mmol, 58 mg) and 2M $Na_2CO_3$ (2.0 eq, 0.262 mmol, 0.13 ml) in DME (1 ml) are added (5"-Bromo-[2,2';4',3"]terpyridin-6'-yl)-isopropyl-amine (Ex. 2.46; step1) (1 eq, 0.131 mmol, 50 mg) and [1,1'-Bis(diphenylphosphino)-ferrocene]dichloropalladium (II), complex with DCM (0.1 eq, 0.0131 mmol, 9.6 mg). The reaction mixture is heated using microwave radiation at 90° C. for 3 hours. The reaction mixture is dissolved in DCM and washed with water. The organic layer is washed with brine, dried over drying agent $MgSO_4$, filtered and the organic solvent is reduced in vacuo. The residue is purified by reverse phase chromatography (Isolute™ C18, 0-20% acetonitrile in water—0.1% TFA). The appropriate fractions by HPLC are combined and concentrated in vacuo. The resulting residue is dissolved in MeOH and loaded onto a SCX-2 cartridge eluting with MeOH and 2M $NH_3$ in MeOH. The methanolic ammonia fractions are combined, concentrated in vacuo and dried under vacuum to afford the title compound; [M+H]+ 521.

Example 2.47

[4-(6'-Methylamino-[2,2';4',3"]terpyridin-5"-yl)-phenyl]-piperazin-1-yl-methanone This compound is prepared analogously to [4-(6'-Isopropylamino-[2,2';4',3"]terpyridin-5"-yl)-phenyl]-(4-isopropyl-piperazin-1-yl)-methanone (Example 2.46) by replacing (4-Isopropyl-piperazin-1-yl)-[4-(4,4,5,5-tetramethyl-[1,3,2] dioxaborolan-2-yl)-phenyl]-methanone (Intermediate B4) with the appropriate boronic acid.

Example 2.48

[4-(6'-tert-Butylamino-[2,2';4',3"]terpyridin-5"-yl)-phenyl]-piperazin-1-yl-methanone Step 1: (5"-Bromo-[2,2';4',3"]terpyridin-6'-yl)-tert-butyl-amine (E)-3-(5-Bromo-pyridin-3-yl)-1-pyridin-2-yl-propenone (Intermediate A10) (1 eq, 3.46 mmol, 1 g), α-(benzotriazol-1-yl)-acetonitrile (1 eq, 3.46 mmol, 1 g) and tert-butylamine (1 eq, 3.46 mmol, 0.275 ml) are mixed together in EtOH (10 ml) and heated using microwave radiation at 120° C. for 4 hours. The reaction mixture is dissolved in DCM and washed with water. The organic solvent is reduced in vacuo and the residue is purified by flash chromatography (0-30% EtOAc in iso-hexane) to afford the title compound; [M+H]+ 383/385.

Step 2: [4-(6'-tert-Butylamino-[2,2';4',3"]terpyridin-5"-yl)-phenyl]-piperazin-1-yl-methanone To a solution of piperazin-1-yl-[4-(4,4,5,5-tetramethyl-[1,3,2]dioxaborolan-2-yl)-phenyl]-methanone (1.2 eq, 0.25 mmol, 0.079 g) and 2M $Na_2CO_3$ (3 eq, 0.624 mmol, 0.3 ml) in dry DME (1.5 ml) are added (5"-Bromo-[2,2';4',3"]terpyridin-6'-yl)-tert-butyl-amine (Ex. 2.48; step 1) (1 eq, 0.208 mmol, 80 mg) and $PdCl_2dppf$ (0.1 eq, 0.0208 mmol, 15 mg). The reaction mixture is heated using microwave radiation at 90° C. for 1 hour. The reaction mixture is dissolved in DCM and washed with water. The organic solvent is reduced in vacuo and the residue is purified by reverse phase column chromatography (Isolute™ C18, 0-40% acetonitrile in water—0.1% TFA). The appropriate fractions by HPLC are combined and concentrated in vacuo. The resulting residue is dissolved in MeOH and loaded onto a SCX-2 cartridge eluting with MeOH followed by 2M $NH_3$ in MeOH. The methanolic ammonia fractions are combined, concentrated in vacuo and dried under vacuum to afford the title compound; [M+H]+ 493.

Example 2.49

[4-(6'-tert-Butylamino-[2,2';4',3"]terpyridin-5"-yl)-phenyl]-(4-methyl-piperazin-1-yl)-methanone The title compound is prepared analogously to [4-(6'-tert-Butylamino-[2,2';4',3"]terpyridin-5"-yl)-phenyl]-piperazin-1-yl-methanone (Example 2.48) by replacing piperazin-1-yl-[4-(4,4,5,5-tetramethyl-[1,3,2]dioxaborolan-2-yl)-phenyl]-methanone with the appropriate boronic acid.

Example 2.50

4-(6'-Amino-[2,2';4',3"]terpyridin-5"-yl)-phenyl]-piperazin-1-yl-methanone

A solution of [4-(6'-tert-Butylamino-[2,2';4',3"]terpyridin-5"-yl)-phenyl]-piperazin-1-yl-methanone (Example 2.48) (1 eq, 0.097 mmol, 0.048 g) in TFA (3 ml) is heated at 75° C. for 6 hours. The reaction mixture is allowed to cool to room temperature and reduced in vacuo to afford a mixture of the title compound and 2,2,2-Trifluoro-N-{5"-[4-(piperazine-1-carbonyl)-phenyl]-[2,2';4',3"]terpyridin-6'-yl}-acetamide. The mixture is dissolved in dioxane (1.5 ml) and $K_3PO_4$ (1.27 M, 10 eq, 0.97 mmol, 0.75 ml) is added. The reaction mixture is heated at 50° C. for 1 hour 30 mins. The reaction mixture is dissolved in EtOAc and washed with water. The organic solvent is reduced in vacuo and the residue dried under vacuum to afford the title compound; [M+H]+ 437.

Example 2.51

5"-(3-Methoxy-phenyl)-[2,2';4',3"]terpyridin-6'-ylamine

Step 1: Tert-Butyl-[5"-(3-methoxy-phenyl)-[2,2';4',3"]terpyridin-6'-yl]-amine

To a solution of 3-Methoxy boronic acid (1.2 eq, 0.252 mmol, 32 mg) and 2M $Na_2CO_3$ (1 eq, 0.21 mmol, 0.1 ml) in dry DME (1 ml) under an inert atmosphere of argon are added (5"-Bromo-[2,2';4',3"]terpyridin-6'-yl)-tert-butyl-amine (Example 2.48; Step 1) (1 eq, 0.21 mmol, 80 mg) and $PdCl_2dppf$ (0.1 eq, 0.021 mmol, 15 mg). The reaction mixture is heated using microwave radiation at 90° C. for 2 hours 30 mins. The reaction mixture is dissolved in DCM and washed with water. The organic solvent is reduced in vacuo and the residue is purified by reverse phase chromatography (Isolute™ C18, 0-40% acetonitrile in water—0.1% TFA). The appropriate fractions by HPLC are combined and concentrated in vacuo. The resulting residue is dissolved in MeOH and loaded onto a SCX-2 cartridge eluting with MeOH and 2M NH₃ in MeOH. The methanolic ammonia fractions are combined, concentrated in vacuo and dried under vacuum to afford the title compound; [M+H]⁺ 411.

Step 2: 5"-(3-Methoxy-phenyl)-[2,2';4',3"]terpyridin-6'-ylamine

Tert-Butyl-[5"-(3-methoxy-phenyl)-[2,2';4',3"]terpyridin-6'-yl]-amine (1 eq, 0.073 mmol, 0.030 g) is dissolved in TFA (6 ml)/DCM (1 ml) and the reaction mixture is heated at 70° C. for 5 hours. The reaction mixture is cooled down and reduced in vacuo. The resulting residue is dissolved in MeOH and loaded onto a SCX-2 cartridge eluting with MeOH followed by 2M NH₃ in MeOH. The methanolic ammonia fractions are combined, concentrated in vacuo and dried under vacuum to afford the title compound; [M+H]⁺ 355.

Example 2.52

[4-(6'-Amino-[2,2';4',3"]terpyridin-5"-yl)-phenyl]-(4-methyl-piperazin-1-yl)-methanone The title compound is prepared analogously to 4-(6'-Amino-[2,2';4',3"]terpyridin-5"-yl)-phenyl]-piperazin-1-yl-methanone (Example 2.50) by replacing Example 2.48 with Example 2.49.

Example 2.53

[2-(1H-Indol-3-yl)-ethyl]-[5"-(1H-pyrazol-4-yl)-[2,2';4',3"]terpyridin-6'-yl]-amine 4-(4,4,5,5-Tetramethyl-[1,3,2]dioxaborolan-2-yl)-pyrazole-1-carboxylic acid tert-butyl ester (1.1 eq, 0.12 mmol, 34 mg) is stirred in NMP (1 ml) and 2M Na₂CO₃ (2 eq, 0.21 mmol, 0.106 ml) for 15 minutes, under an inert atmosphere of argon. (5"-Bromo-[2,2';4',3"]terpyridin-6'-yl)-[2-(1H-indol-3-yl)-ethyl]-amine (Example 1.14) (1 eq, 0.11 mmol, 50 mg) and 1,4-bis(diphenylphosphino)butane-palladium(II) chloride (0.2 eq, 0.021 mmol, 12 mg) are added and the reaction mixture is flushed with argon and heated using microwave radiation at 100° C. for 2 hours. The reaction mixture is extracted into EtOAc washing with water. The organic phase is washed with brine, dried over MgSO₄, filtered and concentrated in vacuo. The crude residue is purified by reverse phase column chromatography (Isolute™ C18, 0-50% acetonitrile in water—0.1% TFA) and the appropriate fractions are combined and concentrated in vacuo. The resulting residue is dissolved in MeOH and loaded onto a SCX-2 cartridge eluting with MeOH followed by 2M NH₃ in MeOH. The methanolic ammonia fractions are concentrated in vacuo and dried under vacuum to afford the title compound; [M+H]⁺ 458.

Examples 2.54 to 2.61

These compounds namely,
[4-(6'-Cyclopropylamino-[2,2';4',3"]terpyridin-5"-yl)-phenyl]-(4-isopropyl-piperazin-1-yl)-methanone (Example 2.54)
[4-(6'-Cyclopropylamino-[2,2';4',3"]terpyridin-5"-yl)-phenyl]-(3-dimethylamino-pyrrolidin-1-yl)-methanone (Example 2.55)
[4-(6'-Cyclopropylamino-[2,2';4',3"]terpyridin-5"-yl)-phenyl]-(4-cyclopropyl-piperazin-1-yl)-methanone (Example 2.56)
Cyclopropyl-[5"-(4-pyrrolidin-1-ylmethyl-phenyl)-[2,2';4',3"]terpyridin-6'-yl]-amine (Example 2.57)
[4-(6'-Cyclopropylamino-[2,2';4',3"]terpyridin-5"-yl)-phenyl]-((R)-3-dimethylamino-pyrrolidin-1-yl)-methanone (Example 2.58)
[4-(6'-Cyclopropylamino-[2,2';4',3"]terpyridin-5"-yl)-phenyl]-((S)-3-dimethylamino-pyrrolidin-1-yl)-methanone (Example 2.59)
[4-(6'-Cyclopropylamino-[2,2';4',3"]terpyridin-5"-yl)-phenyl]-(3,4-dimethyl-piperazin-1-yl)-methanone (Example 2.60) and
Cyclopropyl-[5"-(4-methyl-3,4-dihydro-2H-benzo[1,4]oxazin-6-yl)-[2,2';4',3"]terpyridin-6'-yl]-amine (Example 2.61)
are prepared analogously to (Example 2.30) by replacing piperazin-1-yl-[4-(4,4,5,5-tetramethyl-[1,3,2]dioxaborolan-2-yl)-phenyl]-methanone with the appropriate boronate ester.

Examples 2.62 to 2.65

These compounds namely,
Cyclopropyl-{5"-[4-((R)-3-dimethylamino-pyrrolidin-1-ylmethyl)-phenyl]-[2,2';4',3"]terpyridin-6'-yl}-amine (Example 2.62)
Cyclopropyl-{5"-[4-((S)-3-dimethylamino-pyrrolidin-1-ylmethyl)-phenyl]-[2,2';4',3"]terpyridin-6'-yl}-amine (Example 2.63)
4-(6'-Cyclopropylamino-[2,2';4',3"]terpyridin-5"-yl)-benzaldehyde (Example 2.64) and
Cyclopropyl-{5"-[3-(4-isopropyl-piperazin-1-ylmethyl)-phenyl]-[2,2';4',3"]terpyridin-6'-yl}-amine (Example 2.65)
are prepared analogously to Cyclopropyl-{5"-[4-(4-isopropyl-piperazin-1-ylmethyl)-phenyl]-[2,2';4',3"]terpyridin-6'-yl}-amine (Example 2.31) by replacing 4-(4-isopropyl-piperazin-1-ylmethyl)-phenyl boronic acid with the appropriate boronic acid.

Examples 2.66 to 2.70

These compounds namely,
Cyclopropyl-{5"-[4-(4-isopropyl-piperazin-1-ylmethyl)-phenyl]-6-methyl-[2,2';4',3"]terpyridin-6'-yl}-amine (Example 2.66)
Cyclopropyl-[5"-(4-dimethylaminomethyl-phenyl)-6-methyl-[2,2';4',3"]terpyridin-6'-yl]-amine (Example 2.67)
Cyclopropyl-[5"-(4-diethylaminomethyl-phenyl)-6-methyl-[2,2';4',3"]terpyridin-6'-yl]-amine (Example 2.68)
[4-(6'-Cyclopropylamino-6-methyl-[2,2';4',3"]terpyridin-5"-yl)-phenyl]-methanol (Example 2.69) and
Cyclopropyl-[5"-(4-piperazin-1-ylmethyl-phenyl)-[2,2';4',3"]terpyridin-6'-yl]-amine (Example 2.70)
are prepared analogously to Cyclopropyl-(6-methyl-5"-[3-(4-methyl-piperazin-1-ylmethyl)-phenyl]-[2,2';4',3"]terpyridin-6'-yl)-amine (Example 2.36) by replacing 3-((4-Methyl-piperazin-1-yl)methyl)-phenyl boronic acid with the appropriate boronic acid.

Examples 2.71 to 2.72

These compounds namely,
5"-[4-(4-Isopropyl-piperazin-1-ylmethyl)-phenyl]-6-methyl-[2,2';4',3"]terpyridin-6'-ylamine (Example 2.71) and
5"-[4-(4-Isopropyl-piperazin-1-ylmethyl)-phenyl]-[2,2';4',3"]terpyridin-6'-ylamine (Example 2.72)
are prepared analogously to 5"-(3-Methoxy-phenyl)-[2,2';4',3"]terpyridin-6'-ylamine (Example 2.51) by replacing (5"-Bromo-[2,2';4',3"]terpyridin-6'-yl)-tert-butyl-amine (Example 2.48; Step 1) with the appropriate starting compound (the methods of preparation described herein) and by replacing 3-Methoxy boronic acid with the appropriate boronic acid or boronate ester.

Example 2.73

[4-(6'-tert-Butylamino-[2,2';4',3"]terpyridin-5"-yl)-phenyl]-(4-isopropyl-piperazin-1-yl)-methanone This compound is prepared from (5"-Bromo-[2,2';4',3"]terpyridin-6'-yl)-tert-butyl-amine (Example 2.48; Step 1) analogously to Methyl-{5"-[3-(4-methyl-piperazin-1-ylmethyl)-phenyl]-[2,2';4',3"]terpyridin-6'-yl}-amine (Example 2.23) with the appropriate boronic acid.

Example 2.74

[4-(6'-Amino-[2,2';4',3"]terpyridin-5"-yl)-phenyl]-(4-isopropyl-piperazin-1-yl)-methanone This compound is prepared from [4-(6'-tert-Butylamino-[2,2';4',3"]terpyridin-5"-yl)-phenyl]-(4-isopropyl-piperazin-1-yl)-methanone (Example 2.73) analogously to 4-(6'-Amino-[2,2';4',3"]terpyridin-5"-yl)-phenyl]-piperazin-1-yl-methanone (Example 2.50).

Example 2.75

(3,5-Dimethyl-piperazin-1-yl)-[4-(6'-isopropylamino-[2,2';4',3"]terpyridin-5"-yl)-phenyl]-methanone This compound is prepared from (5"-Bromo-[2,2';4',3"]terpyridin-6'-yl)-isopropyl-amine (Example 2.46; Step 1) analogously to 5"-(3-Methoxy-phenyl)-[2,2';4',3"]terpyridin-6'-ylamine (Example 2.51) with the appropriate boronate ester. The deprotection is carried out under milder conditions; TFA/DCM, 10 mins at room temperature and the compound is purified by reverse phase column chromatography (Isolute™ C18, acetonitrile in water—0.1% TFA).

Example 2.76

{5"-[4-((R)-3-Amino-pyrrolidin-1-ylmethyl)-phenyl]-[2,2';4',3"]terpyridin-6'-yl}-cyclopropyl-amine Step 1:{(R)-1-[4-(6'-Cyclopropylamino-[2,2';4',3"]terpyridin-5"-yl)-benzyl]-pyrrolidin-3-yl}-carbamic acid tert-butyl ester A solution of 4-(6'-cyclopropylamino-[2,2';4',3"]terpyridin-5"-yl)-benzaldehyde (Example 2.64)(1 eq, 0.204 mmol, 80 mg) in DCM (3 ml) is treated with (R)-pyrrolidin-3-yl-carbamic acid tert-butyl ester (2.2 eq, 0.448 mmol, 83.2 mg) followed by AcOH (1.2 eq, 0.245 mmol, 0.14 ml) and sodium triacetoxyborohydride (3.1 eq, 0.632 mmol, 134 mg). The reaction mixture is stirred at room temperature overnight and then extracted with DCM. The organic portion is washed with water, dried (MgSO$_4$) and concentrated in vacuo to afford the title compound which is used in the next step without further purification; [M+H]$^+$ 563.

Step 2: {5"-[4-((R)-3-Amino-pyrrolidin-1-ylmethyl)-phenyl]-[2,2';4',3"]terpyridin-6'-yl}-cyclopropyl-amine A solution of {(R)-1-[4-(6'-cyclopropylamino-[2,2';4',3"]terpyridin-5"-yl)-benzyl]-pyrrolidin-3-yl}-carbamic acid tert-butyl ester (step 1) (1 eq, 0.204 mmol, 115 mg) in DCM/TFA (1 ml of a 3:1 mixture) is stirred at room temperature for 30 mins. The solvent is reduced in vacuo and the residue is purified by preparative HPLC (C18, 0-100% acetonitrile in water—0.1% TFA). The appropriate fractions by HPLC are combined and concentrated in vacuo. The resulting residue is dissolved in MeOH and loaded onto a SCX-2 cartridge eluting with MeOH and 2M NH$_3$ in MeOH. The methanolic ammonia fractions are combined, concentrated in vacuo and dried under vacuum to afford the title compound; [M+H]$^+$ 463.

Example 2.77

{5"-[4-((S)-3-Amino-pyrrolidin-1-ylmethyl)-phenyl]-[2,2';4',3"]terpyridin-6'-yl}-cyclopropyl-amine This compound is prepared analogously to {5"-[4-((R)-3-Amino-pyrrolidin-1-ylmethyl)-phenyl]-[2,2';4',3"]terpyridin-6'-yl}-cyclopropyl-amine (Example 2.76) by replacing (R)-pyrrolidin-3-yl-carbamic acid tert-butyl ester with (S)-pyrrolidin-3-yl-carbamic acid tert-butyl ester. [M+H]$^+$ 463.

Example 2.78 tert-Butyl-{5"-[4-(4-isopropyl-piperazin-1-ylmethyl)-phenyl]-[2,2';4',3"]terpyridin-6'-yl}-amine This compound is prepared from (5"-Bromo-[2,2';4',3"]terpyridin-6'-yl)-tert-butyl-amine (Example 2.48; Step 1) analogously to Methyl-{5"-[3-(4-methyl-piperazin-1-ylmethyl)-phenyl]-[2,2';4',3"]terpyridin-6'-yl}-amine (Example 2.23) with the appropriate boronic acid.

Example 2.79 tert-Butyl-{5"-[4-(4-isopropyl-piperazin-1-ylmethyl)-phenyl]-6-methyl-[2,2';4',3"]terpyridin-6'-yl}-amine This compound is prepared from (5"-Bromo-6-methyl-[2,2';4',3"]terpyridin-6'-yl)-tert-butyl-amine (Example 1.28) analogously to Methyl-{5"-[3-(4-methyl-piperazin-1-ylmethyl)-phenyl]-[2,2';4',3"]terpyridin-6'-yl}-amine (Example 2.23) with the appropriate boronic acid.

Example 2.80

2-(5"-[4-(4-Isopropyl-piperazin-1-ylmethyl)-phenyl]-[2,2';4',3"]terpyridin-6'-yl)-propan-2-ol Step 1: (E)-1-(5-Bromo-pyridin-3-yl)-4-hydroxy-4-methyl-pent-1-en-3-one A solution of sodium hydroxide (1.1 eq, 29.6 mmol, 29.6 ml) in MeOH (100 ml) under an inert atmosphere of nitrogen is cooled at 0° C. and treated with 5-bromo-pyridine-3-carbaldehyde (1 eq, 26.9 mmol, 5 g). After 1 h at 0° C., 3-hydroxy-3-methyl-butan-2-one (1 eq, 26.9 mmol, 2.75 g) is added and the reaction mixture is stirred at room temperature for 3 hours. The reaction mixture is dissolved in EtOAc and washed with water. The combined organic extracts are washed with brine, dried over MgSO$_4$ and concentrated in vacuo. The residue is purified by flash chromatography (0-50% EtOAc in iso-hexane) to afford the title compound; [M+H]$^+$ 270/272.

Step 2: 2-(5"-Bromo-[2,2';4',3"]terpyridin-6'-yl)-propan-2-ol (E,Z)-P,P-diphenyl-N-(1-(pyridin-2-yl)ethylidene)phosphinic amide (Intermediate C1) (1 eq, 6.24 mmol, 2 g) in DMF (1 ml) under an inert atmosphere of nitrogen is treated with potassium-tert-butoxide (1 eq, 6.87 mmol, 0.77 g) and the resulting mixture is stirred at room temperature for 15 mins. (E)-1-(5-Bromo-pyridin-3-yl)-4-hydroxy-4-methyl-pent-1-en-3-one (1 eq, 6.24 mmol, 1.687 g) is then added and the reaction stirred for 90 minutes. The reaction is quenched by addition of water and is then extracted with EtOAc. The organic extracts are concentrated in vacuo and the crude residue is purified by flash chromatography on silica (0-50% EtOAc in iso-hexane) to afford the title compound; [M+H]+ 370/372.

Step 3: 2-{5"-[4-(4-Isopropyl-piperazin-1-ylmethyl)-phenyl]-[2,2';4',3"]terpyridin-6'-yl}-propan-2-ol To a solution of 4-((4-isopropyl-piperazin-1-yl)methyl)-phenyl boronic acid (Intermediate B3) (1.2 eq, 0.324 mmol, 0.085 g) and 2M Na$_2$CO$_3$ (2.4 eq, 0.648 mmol, 0.32 ml) in DME (3 ml) is added 2-(5"-bromo-[2,2';4',3"]terpyridin-6'-yl)-propan-2-ol (1 eq, 0.27 mmol, 0.1 g) followed by [1,1'-bis(diphenylphosphino)-ferrocene]dichloropalladium (II), complex with DCM (0.1 eq, 0.027 mmol, 0.022 g). The reaction mixture is heated using microwave radiation at 95° C. for 90 minutes. The reaction mixture is dissolved in EtOAc and washed with water. The organic layer is washed with brine, dried over MgSO$_4$, filtered and the organic solvent is reduced in vacuo. The crude residue is purified by reverse phase column chromatography (Isolute™ C18, 0-20% acetonitrile in water—0.1% TFA). The appropriate fractions are combined and concentrated in vacuo. The resulting residue is dissolved in MeOH and loaded onto a SCX-2 cartridge eluting with MeOH followed by 2M NH$_3$ in MeOH. The methanolic ammonia fractions are combined, concentrated in vacuo and dried under vacuum to afford the title compound; [M+H]+ 508.

Example 2.81

2-[5"-(4-piperazin-1-ylmethyl-phenyl)-[2,2';4',3"]terpyridin-6'-yl]-propan-2-ol Step 1: 4-{4-[6'-(1-Hydroxy-1-methyl-ethyl)-[2,2';4',3"]terpyridin-5"-yl]-benzyl}piperazine-1-carboxylic acid tert-butyl ester is prepared analogously to 2-{5"-[4-(4-Isopropyl-piperazin-1-ylmethyl)-phenyl]-[2,2';4',3"]terpyridin-6'-yl}-propan-2-ol (Example 2.80) by replacing 4-(4-Isopropyl-piperazin-1-ylmethyl)-phenyl boronic acid with the appropriate boronic acid.

Step 2: 2-[5"-(4-piperazin-1-ylmethyl-phenyl)-[2,2';4',3"]terpyridin-6'-yl]-propan-2-ol To a solution of 4-{(4-[6'-(1-Hydroxy-1-methyl-ethyl)-[2,2';4',3"]terpyridin-5"-yl]-benzyl}piperazine-1-carboxylic acid tert-butyl ester (1 eq, 0.136 mmol, 76 mg) in DCM (3 ml) is added TFA (1 ml). After 1 h at room temperature, the solvent was evaporated. The crude residue is purified by reverse phase column chromatography (Isolute™ C18, 0-20% acetonitrile in water—0.1% TFA). The appropriate fractions by HPLC are combined and concentrated in vacuo. The resulting residue is dissolved in MeOH and loaded onto a SCX-2 cartridge eluting with MeOH followed by 2M NH$_3$ in MeOH. The methanolic ammonia fractions are combined, concentrated in vacuo and dried under vacuum to afford the title compound; [M+H]+ 466

Example 2.82 to 2.87

These compounds namely,
2-{5"-[4-(4-tert-Butyl-piperazin-1-ylmethyl)-phenyl]-[2,2';4',3"]terpyridin-6'-yl}-propan-2-ol (Example 2.82),
{4-[6'-(1-Hydroxy-1-methyl-ethyl)-[2,2';4',3"]terpyridin-5"-yl]-phenyl}-(4-methyl-d3-piperazin-1-yl)-methanone (Example 2.83),
2-{5"-[1-(Tetrahydro-pyran-4-yl)-1H-pyrazol-4-yl]-[2,2';4',3"]terpyridin-6'-yl}-propan-2-ol (Example 2.84),
2-{5"-[4-(4-Methyl-d3-piperazin-1-ylmethyl)-phenyl]-[2,2';4',3"]terpyridin-6'-yl}-propan-2-ol (Example 2.85),
2-[5"-(1-Methyl-1H-pyrazol-4-yl)-[2,2';4',3"]terpyridin-6'-yl]-propan-2-ol (Example 2.86), and
{4-[6'-(1-Hydroxy-1-methyl-ethyl)-[2,2';4',3"]terpyridin-5"-yl]-phenyl}-(3,4,5-trimethyl-piperazin-1-yl)-methanone (Example 2.87)
are prepared analogously to 2-(5"-[4-(4-Isopropyl-piperazin-1-ylmethyl)-phenyl]-[2,2';4',3"]terpyridin-6'-yl)-propan-2-ol (Example 2.80) by replacing 4-(4-Isopropyl-piperazin-1-ylmethyl)-phenyl boronic acid with the appropriate boronic acid.

Example 2.88

2-[5"-(1-Piperidin-4-yl-1H-pyrazol-4-yl)-[2,2';4',3"]terpyridin-6'-yl]-propan-2-ol is prepared analogously to Methyl-[5"-(1-piperidin-4-yl-1H-pyrazol-4-yl)-[2,2';4',3"]terpyridin-6'-yl]-amine (Example 2.183) by replacing (5"-Bromo-[2,2';4',3"]terpyridin-6'-yl)-methyl-amine (Example 2.1; step 1) with 2-(5"-Bromo-[2,2';4',3"]terpyridin-6'-yl)-propan-2-ol (Example 2.80; step2)

Example 2.89

2-{(5"-[1-(1-Isopropyl-piperidin-4-yl)-1H-pyrazol-4-yl]-[2,2';4',3"]terpyridin-6'-yl}-propan-2-ol is prepared analogously to (5"-[1-(1-Isopropyl-piperidin-4-yl)-1H-pyrazol-4-yl]-[2,2';4',3"]terpyridin-6'-yl)-methyl-amine (Example 2.175) by replacing (5"-Bromo-[2,2';4',3"]terpyridin-6'-yl)-methyl-amine (Example 2.1; step1) with 2-(5"-Bromo-[2,2';4',3"]terpyridin-6'-yl)-propan-2-ol (Example 2.80; step2)

Examples 2.90 to 2.93

These compounds namely,
2-{5"-[4-(4-Isopropyl-piperazin-1-ylmethyl)-2-methyl-phenyl]-[2,2';4',3"]terpyridin-6'-yl}-propan-2-ol (Example 2.90),
2-{5"-[4-((R)-3-Methyl-piperazin-1-ylmethyl)-phenyl]-[2,2';4',3"]terpyridin-6'-yl}-propan-2-ol (Example 2.91),
2{-5"-[4-(3,3-Dimethyl-piperazin-1-ylmethyl)-phenyl]-[2,2';4',3"]terpyridin-6'-yl}-propan-2-ol (Example 2.92), and
2-{5"-[4-(3,5-Dimethyl-piperazin-1-ylmethyl)-phenyl]-[2,2';4',3"]ter pyridin-6'-yl}-propan-2-ol (Example 2.93)
are prepared analogously to 2-{5"-[4-(4-Isopropyl-piperazin-1-ylmethyl)-phenyl]-[2,2';4',3"]terpyridin-6'-yl}-propan-2-ol (Example 2.80) by replacing 4-(4-Isopropyl-piperazin-1-ylmethyl)-phenyl boronic acid with the appropriate boronic acid.

Examples 2.94 to 2.95

These compounds namely,
6'-tert-Butyl-5"-(1-methyl-1H-pyrazol-4-yl)-[2,2';4',3"]terpyridine (Example 2.94) and
6'-tert-Butyl-5"-[4-(4-isopropyl-piperazin-1-ylmethyl)-phenyl]-[2,2';4',3"]terpyridine (Example 2.95)
are prepared analogously to 2-{5"-[4-(4-Isopropyl-piperazin-1-ylmethyl)-phenyl]-[2,2';4',3"]terpyridin-6'-yl}-propan-2-ol (Example 2.80) by replacing 4-(4-Isopropyl-piperazin-1-ylmethyl)-phenyl boronic acid with the appropriate boronic acid and by replacing (E)-1-(5-Bromo-pyridin-3-yl)-4-hydroxy-4-methyl-pent-1-en-3-one (Example 2.80; step2) with (E)-1-(5-Bromo-pyridin-3-yl)-4,4-dimethyl-pent-1-en-3-one (Intermediate A17).

Example 2.96

6'-(2,2-Dimethyl-propyl)-5"-[4-(4-isopropyl-piperazin-1-ylmethyl)-phenyl]-[2,2';4',3"]terpyridine is prepared analogously to 2-{5"-[4-(4-Isopropyl-piperazin-1-ylmethyl)-phenyl]-[2,2';4',3"]terpyridin-6'-yl}-propan-2-ol (Example 2.80) by replacing 4-(4-Isopropyl-piperazin-1-ylmethyl)-phenyl boronic acid with the appropriate boronic acid and by replacing (E)-1-(5-Bromo-pyridin-3-yl)-4-hydroxy-4-methyl-pent-1-en-3-one (Example 2.80; step2) with (E)-1-(5-Bromo-pyridin-3-yl)-5,5-dimethyl-hex-1-en-3-one (Intermediate A18)

Example 2.97

1-{5"-[4-(4-Isopropyl-piperazin-1-ylmethyl)-phenyl]-[2,2';4',3"]terpyridin-6'-yl}-1-methyl-ethylamine Step 1: N-[1-(5"-Bromo-[2,2';4',3"]terpyridin-6'-yl)-1-methyl-ethyl]-acetamide To a solution of 2-(5"-Bromo-[2,2';4',3"]terpyridin-6'-yl)-propan-2-ol (Example 2.80; step1) (1 eq, 0.135 mmol, 50 mg) in acetonitrile (2 ml) is added tetrafluoroboric acid diethyl ether complex (3.5 eq, 0.473 mmol, 0.06 ml) and the reaction mixture is heated at 85° C. overnight. The pH of the reaction mixture is adjusted to 8-9 by addition of sodium hydroxide (2M). The solution is dissolved in DCM and washed with water. The combined organic extracts are washed with brine, dried over $MgSO_4$ and concentrated in vacuo to afford the title compound; $[M+H]^+$ 411/413

Step 2: 1-(5"-Bromo-[2,2';4',3"]terpyridin-6'-yl)-1-methyl-ethylamine

N-[1-(5"-Bromo-[2,2';4',3"]terpyridin-6'-yl)-1-methyl-ethyl]-acetamide (Example 2.97; step1) (1 eq, 0.151 mmol, 62 mg) and 5M HCl (20 eq, 3.01 mmol, 0.602 ml) are heated together at 100° C. overnight. The pH of the reaction mixture is adjusted to 8-9 by addition of sodium hydroxide (2M). The solution is dissolved in DCM and washed with water. The combined organic extracts are washed with brine, dried over $MgSO_4$ and concentrated in vacuo to afford the title compound; $[M+H]^+$ 369/371

Step 3: 1-{5"-[4-(4-Isopropyl-piperazin-1-ylmethyl)-phenyl]-[2,2';4",3"]terpyridin-6'-yl}-1-methyl-ethylamine is prepared analogously to [4-(6'-Methylamino-[2,2';4',3"]terpyridin-5"-yl)-phenyl]-(4-methyl-piperazin-1-yl)-methanone (Example 2.1) by replacing (5"-Bromo-[2,2';4',3"]terpyridin-6'-yl)-methyl-amine (Example 2.1; step1) with 1-(5"-Bromo-[2,2';4',3"]terpyridin-6'-yl)-1-methyl-ethylamine (Example 2.97; step2) and (4-methyl-piperazin-1-yl)-[4-(4,4,5,5-tetramethyl-[1,3,2]dioxaborolan-2-yl)-phenyl]-methanone with 4-(4-Isopropyl-piperazin-1ylmethyl)-phenyl boronic acid (Intermediate B3)

Example 2.98 to 2.101

These compounds namely,
[4-(6'-Methyl-d3-amino-[2,2';4',3"]terpyridin-5"-yl)-phenyl]-(4-methyl-piperazin-1-yl)-methanone (Example 2.98),
Methyl-d3-{5"-[4-(4-methyl-d3-piperazin-1-ylmethyl)-phenyl]-[2,2';4',3"]terpyridin-6'-yl}-amine (Example 2.99),
{5"-[4-(4-Isopropyl-piperazin-1-ylmethyl)-phenyl]-[2,2';4',3"]terpyridin-6'-yl}-methyl-d3-amine (Example 2.100), and
{5"-[3-(4-Isopropyl-piperazin-1-ylmethyl)-phenyl]-[2,2';4',3"]terpyridin-6'-yl}-methyl-d3-amine (Example 2.101)
are prepared analogously to [4-(6'-Methylamino-[2,2';4',3"]terpyridin-5"-yl)-phenyl]-(4-methyl-piperazin-1-yl)-methanone (Example 2.1) by replacing (4-Methyl-piperazin-1-yl)-[4-(4,4,5,5-tetramethyl-[1,3,2]dioxaborolan-2-yl)-phenyl]-methanone with the appropriate boronic acid and by replacing (5"-Bromo-[2,2';4',3"]terpyridin-6'-yl)-methyl-amine (step1) with (5"-Bromo-[2,2';4',3"]terpyridin-6'-yl)-methyl-d3-amine (Example 1.29)

Example 2.102

Methyl-d3-[5"-(4-piperazin-1-ylmethyl-phenyl)-[2,2';4',3"]terpyridin-6'-yl]-amine is prepared analogously to 2-[5"-(4-piperazin-1-ylmethyl-phenyl)-[2,2';4',3"]terpyridin-6'-yl]-propan-2-ol (Example 2.81) by replacing 2-(5"-Bromo-[2,2';4',3"]terpyridin-6'-yl)-propan-2-ol (Example 2.80, step2) with (5"-Bromo-[2,2';4',3"]terpyridin-6'-yl)-methyl-d3-amine (Example 1.29)

Example 2.103

{5"-[1-(1-Isopropyl-piperidin-4-yl)-1H-pyrazol-4-yl]-[2,2';4',3"]terpyridin-6'-yl}-methyl-d3-amine is prepared analogously to {5"-[1-(1-Isopropyl-piperidin-4-yl)-1H-pyrazol-4-yl]-[2,2';4',3"]terpyridin-6'-yl}-methyl-amine (Example 2.175) by replacing (5"-Bromo-[2,2';4',3"]terpyridin-6'-yl)-methyl-amine (Example 2.1; step1) with (5"-Bromo-[2,2';4',3"]terpyridin-6'-yl)-methyl-d3-amine (Example 1.29).

Example 2.104 to 2.108

These compounds namely,
Methyl-d3-[5"-(1-methyl-1H-pyrazol-4-yl)-[2,2';4',3"]terpyridin-6'-yl]-amine (Example 2.104),
Methyl-d3-{5"-[1-(tetrahydro-pyran-4-yl)-1H-pyrazol-4-yl]-[2,2';4',3"]terpyridin-6'-yl}-amine (Example 2.105),
[4-(6'-Methyl-d3-amino-[2,2';4',3"]terpyridin-5"-yl)-phenyl]-(4-methyl-d3-piperazin-1-yl)-methanone (Example 2.106),
{5"-[4-(4-tert-Butyl-piperazin-1-ylmethyl)-phenyl]-[2,2';4',3"]terpyridin-6'-yl}-methyl-d3-amine (Example 2.107), and {5"-[4-((S)-3-Dimethylamino-pyrrolidin-1-ylmethyl)-phenyl]-[2,2';4',3"]terpyridin-6'-yl}-methyl-d3-amine (Example 2.108)

are prepared analogously to [4-(6'-Methylamino-[2,2';4',3"]terpyridin-5"-yl)-phenyl]-(4-methyl-piperazin-1-yl)-methanone (Example 2.1) by replacing (4-Methyl-piperazin-1-yl)-[4-(4,4,5,5-tetramethyl-[1,3,2]dioxaborolan-2-yl)-phenyl]-methanone with the appropriate boronic acid and by replacing (5"-Bromo-[2,2';4',3"]terpyridin-6'-yl)-methyl-amine (Example 2.1, step1) with (5"-Bromo-[2,2';4',3"]terpyridin-6'-yl)-methyl-d3-amine (Example 1.29).

Example 2.109

[4-(6'-Hydroxy-6-methyl-[2,2';4',3"]terpyridin-5"-yl)-phenyl]-(4-isopropyl-piperazin-1-yl)-methanone Step 1: 5"-Bromo-6-methyl-[2,2';4',3"]terpyridin-6'-ol (E)-3-(S-Bromo-pyridin-3-yl)-1-(6-methyl-pyridin-2-yl)-propenone (Intermediate A11) (1 eq, 1.65 mmol, 0.5 g), 1-(aminoformylmethyl)pyridium chloride (1.2 eq, 1.98 mmol, 0.34 g) are mixed together in EtOH (15 ml) and heated at 80° C. for 15 mins. Cesium carbonate (1.25 eq, 2.06 mmol, 0.67 g) is added and the reaction mixture heated at 0° C. for 30 mins. The reaction mixture is dissolved in DCM and washed with water. The combined organic extracts are washed with brine, dried over MgSO$_4$ and concentrated in vacuo. iso-Hexane (50 ml) is added to the residue resulting in the formation of a white precipitate. The solid is filtered, washed with iso-hexane and dried in vacuo to afford the title compound; [M+H]$^+$ 342/344.

Step 2: [4-(6'-Hydroxy-6-methyl-[2,2';4',3"]terpyridin-5"-yl)-phenyl]-(4-isopropyl-piperazin-1-yl)-methanone To a solution of (4-Isopropyl-piperazin-1-yl)-[4-(4,4,5,5-tetramethyl-[1,3,2]dioxaborolan-2-yl)-phenyl]-methanone (Intermediate B4) (1.1 eq, 0.161 mmol, 57 mg) and 2M Na$_2$CO$_3$ (2.0 eq, 0.292 mmol, 0.15 ml) in DME (1 ml) is added 5"-Bromo-6-methyl-[2,2';4',3"]terpyridin-6'-ol (Example 2.109; step1) (1 eq, 0.146 mmol, 50 mg) followed by [1,1'-Bis(diphenylphosphino)-ferrocene]dichloropalladium (II), complex with DCM (0.1 eq, 0.015 mmol, 12 mg). The reaction mixture is heated using microwave radiation at 90° C. for 90 mins. The reaction mixture is dissolved in DCM and washed with water. The organic layer is washed with brine, dried over drying agent MgSO$_4$, filtered and the organic solvent is reduced in vacuo. The crude residue is purified by reverse phase column chromatography (Isolute™ C18, 0-20% acetonitrile in water—0.1% TFA). The appropriate fractions by HPLC are combined and concentrated in vacuo. The resulting residue is dissolved in MeOH and loaded onto a SCX-2 cartridge eluting with MeOH followed by 2M NH$_3$ in MeOH. The methanolic ammonia fractions are combined, concentrated in vacuo and dried under vacuum to afford the title compound; [M+H]$^+$ 494

Example 2.110

5"-[4-(4-Isopropyl-piperazin-1-ylmethyl)-phenyl]-6-methyl-[2,2';4',3"]terpyridin-6'-ol is prepared analogously to [4-(6'-Hydroxy-6-methyl-[2,2';4', 3"]terpyridin-5"-yl)-phenyl]-(4-isopropyl-piperazin-1-yl)-methanone (Example 2.109) by replacing (4-isopropyl-piperazin-1-yl)-[4-(4,4,5,5-tetramethyl-[1,3,2]dioxaborolan-2-yl)-phenyl]-methanone with 4-(4-Isopropyl-piperazin-1-ylmethyl)-phenyl boronic acid (Intermediate B3).

Examples 2.111 to 2114

These compounds namely,

{5"-[3-(4-tert-Butyl-piperazin-1-ylmethyl)-phenyl]-[2,2';4', 3"]terpyridin-6'-yl}-ethyl-amine (Example 2.111), (4-tert-Butyl-piperazin-1-yl)-[4-(6'-ethylamino-[2,2';4',3"]terpyridin-5"-yl)-phenyl]-methanone (Example 2.112), Ethyl-{5"-[4-(4-isopropyl-piperazin-1-ylmethyl)-phenyl]-[2,2';4',3"]terpyridin-6'-yl}-amine (Example 2.113), and Ethyl-{5"-[3-(4-isopropyl-piperazin-1-ylmethyl)-phenyl]-[2,2';4',3"]terpyridin-6'-yl}-amine (Example 2.114)

are prepared analogously to [4-(6'-Methylamino-[2,2';4',3"]terpyridin-5"-yl)-phenyl]-(4-methyl-piperazin-1-yl)-methanone (Example 2.1) by replacing (5"-Bromo-[2,2';4',3"]terpyridin-6'-yl)-methyl-amine with (5"-Bromo-[2,2';4',3"]terpyridin-6'-yl)-ethyl-amine (Example 1.24) and by replacing (4-Methyl-piperazin-1-yl)-[4-(4,4,5,5-tetramethyl-[1,3,2]dioxaborolan-2-yl)-phenyl]-methanone with the appropriate boronic acid (preparations described hereinafter).

Examples 2.115

Ethyl-[5"-(1-piperidin-4-yl-1H-pyrazol-4-yl)-[2,2';4', 3"]terpyridin-6'-yl]-amine is prepared analogously to Methyl-[5"-(1-piperidin-4-yl-1H-pyrazol-4-yl)-[ 2,2';4',3"]terpyridin-6'-yl]-amine (Example 2.183) by replacing (5"-Bromo-[ 2,2';4',3"]terpyridin-6'-yl)-methyl-amine (Example 2.1; step1) with (5"-Bromo-[ 2,2';4', 3"]terpyridin-6'-yl)-ethyl-amine (Example 1.24).

Example 2.116

[5"-(3-Aminomethyl-5-methyl-phenyl)-[2,2';4',3"]terpyridin-6'-yl]-ethyl-amine

To a solution of 5"-(3-Aminomethyl-5-methyl-phenyl boronic acid (Intermediate B27) (2.0 eq, 0.303 mmol, 50 mg) and 2M Na$_2$CO$_3$ (2.0 eq, 0.303 mmol, 0.152 ml) in DME (1 ml) is added (5"-Bromo-[2,2';4',3"]terpyridin-6'-yl)-ethylamine (Ex. 1.24) (1 eq, 0.152 mmol, 54 mg) followed by [1,1'-Bis(diphenylphosphino)-ferrocene]dichloropalladium (II), complex with DCM (0.1 eq, 0.015 mmol, 12.3 mg). The reaction mixture is heated using microwave radiation at 90° C. for 90 minutes. The reaction mixture is dissolved in DCM and washed with water. The organic layer is washed with brine, dried over drying agent MgSO$_4$, filtered and the organic solvent is reduced in vacuo. The residue is purified by reverse phase chromatography (Isolute™ C18, 0-20% acetonitrile in water—0.1% TFA). The appropriate fractions by HPLC are combined and concentrated in vacuo. The resulting residue is dissolved in MeOH and loaded onto a SCX-2 cartridge eluting with MeOH and 2M NH$_3$ in MeOH. The methanolic ammonia fractions are combined, concentrated in vacuo and dried under vacuum to afford the title compound; [M+H]$^+$ 397.

Examples 2.117 to 2.123

These compounds namely,

Cyclopropyl-{5"-[4-(pyrrolidin-3-ylaminomethyl)-phenyl]-[2,2';4',3"]terpyridin-6'-yl}-amine (Example 2.117),

[4-(6'-Cyclopropylamino-[2,2';4',3"]terpyridin-5"-yl)-phenyl]-(3,4,5-trimethyl-piperazin-1-yl)-methanone (Example 2.118), {5"-[3-(4-tert-Butyl-piperazin-1-ylmethyl)-phenyl]-[2,2';4',3"]terpyridin-6'-yl}-cyclopropyl-amine (Example 2.119), {5"-[4-(4-tert-Butyl-piperazin-1-ylmethyl)-phenyl]-[2,2';4',3"]terpyridin-6'-yl}-cyclopropyl-amine (Example 2.120), (4-tert-Butyl-piperazin-1-yl)-[4-(6'-cyclopropylamino-[2,2';4',3"]terpyridin-5"-yl)-phenyl]-methanone (Example 2.121),

[5"-(4-Aminomethyl-phenyl)-[2,2';4',3"]terpyridin-6'-yl]-cyclopropyl-amine (Example 2.122), and Cyclopropyl-{5"-[3-(3-dimethylamino-pyrrolidin-1-yl)-phenyl]-[2,2';4',3"]terpyridin-6'-yl}-amine (Example 2.123), are prepared analogously to [4-(6'-Methylamino-[2,2';4',3"]terpyridin-5"-yl)-phenyl]-(4-methyl-piperazin-1-yl)-methanone (Example 2.1) by replacing (5"-Bromo-[2,2';4',3"]terpyridin-6'-yl)-methyl-amine with (5"-Bromo-[2,2';4',3"]terpyridin-6'-yl)-cyclopropyl-amine (Example 1.26) and by replacing (4-Methyl-piperazin-1-yl)-[4-(4,4,5,5-tetramethyl-[1,3,2]dioxaborolan-2-yl)-phenyl]-methanone with the appropriate boronic acid.

Examples 2.124 to 2.125

These compounds namely,

{4-[2'-Cyclopropylamino-6'-(5-methyl-furan-2-yl)-[3,4']bipyridinyl-5-yl]-phenyl}-(4-isopropyl-piperazin-1-yl)-methanone (Example 2.124) and Cyclopropyl-[5-[4-(4-isopropyl-piperazin-1-ylmethyl)-phenyl]-6'-(5-methyl-furan-2-yl)-[3,4']bipyridinyl-2'-yl]-amine (Example 2.125)

are prepared analogously to [4-(6'-Methylamino-[2,2';4',3"]terpyridin-5"-yl)-phenyl]-(4-methyl-piperazin-1-yl)-methanone (Example 2.1) by replacing (5"-Bromo-[2,2';4',3"]terpyridin-6'-yl)-methyl-amine with 5-Bromo-6'-(5-methyl-furan-2-yl)-[3,4']bipyridinyl-2'-yl]-cyclopropyl-amine (Example 1.30) and by replacing (4-Methyl-piperazin-1-yl)-[4-(4,4,5,5-tetramethyl-[1,3,2]dioxaborolan-2-yl)-phenyl]-methanone with the appropriate boronic acid.

Example 2.126

4-(6'-Cyclopropylamino-[2,2';4',3"]terpyridin-5"-ylethynyl)-1-methyl-piperidin-4-ol is prepared analogously to Methyl-[5"-(3-methyl-3H-imidazol-4-ylethynyl)-[2,2';4',3"]terpyridin-6'-yl]-amine (Example 2.182) by replacing (5"-Bromo-[2,2';4',3"]terpyridin-6'-yl)-methyl-amine (Example 2.1; step1) with (5"-Bromo-[2,2';4',3"]terpyridin-6'-yl)-cyclopropyl-amine (Example 1.26) and by replacing 1-methyl-5-((trimethylsilyl)ethynyl)-1H-imidazole with 4-ethynyl-1-methylpiperidin-4-ol.

Example 2.127

Cyclopropyl-{5"-[3-(4-isopropyl-piperazin-1-yl)-prop-1-ynyl]-[2,2';4',3"]terpyridin-6'-yl}-amine is prepared analogously to Methyl-[5"-(3-methyl-3H-imidazol-4-ylethynyl)-[2,2';4',3"]terpyridin-6'-yl]-amine (Example 2.182) by replacing (5"-Bromo-[2,2';4',3"]terpyridin-6'-yl)-methyl-amine (Example 2.1; step1) with (5"-Bromo-[2,2';4',3"]terpyridin-6'-yl)-cyclopropyl-amine (Example 1.26) and by replacing 1-methyl-5-((trimethylsilyl)ethynyl)-1H-imidazole with 1-isopropyl-4-(prop-2-ynyl)piperazine (Intermediate D1).

Example 2.128

Cyclopropyl-(5"-ethynyl-[2,2';4',3"]terpyridin-6'-yl)-amine

Step 1: Cyclopropyl-(5"-trimethylsilanylethynyl-[2,2';4',3"]terpyridin-6'-yl)-amine is prepared analogously to Methyl-[5"-(3-methyl-3H-imidazol-4-ylethynyl)-[2,2';4',3"]terpyridin-6'-yl]-amine (Example 2.182) by replacing (5"-Bromo-[2,2';4',3"]terpyridin-6'-yl)-methyl-amine (Example 2.1; step 1) with (5"-Bromo-[2,2';4',3"]terpyridin-6'-yl)-cyclopropyl-amine (Example 1.26) and by replacing 1-methyl-5-((trimethylsilyl)ethynyl)-1H-imidazole with ethynyl-trimethyl-silane to afford the title compound; $[M+H]^+$ 385.

Step 2: Cyclopropyl-(5"-ethynyl-[2,2';4',3"]terpyridin-6'-yl)-amine

Cyclopropyl-(5"-trimethylsilanylethynyl-[2,2';4',3"]terpyridin-6'-yl)-amine (Example 2.128, step1) (1 eq, 0.127 mmol, 49 mg) is dissolved in MeOH (2 ml) and potassium carbonate is added (2 eq, 0.255 mmol, 35 mg). The reaction mixture is dissolved in EtOAc and washed with water. The organic layer is washed with brine, dried over drying agent $MgSO_4$, filtered and the organic solvent is reduced in vacuo. The crude residue is purified by reverse phase column chromatography (Isolute™ C18, 0-20% acetonitrile in water—0.1% TFA). The appropriate fractions by HPLC are combined and concentrated in vacuo. The resulting residue is dissolved in MeOH and loaded onto a SCX-2 cartridge eluting with MeOH followed by 2M $NH_3$ in MeOH. The methanolic ammonia fractions are combined, concentrated in vacuo and dried under vacuum to afford the title compound; $[M+H]^+$ 313.

Example 2.129

Cyclopropyl-[5"-(1,2,3,4-tetrahydro-isoquinolin-6-yl)-[2,2';4',3"]terpyridin-6'-yl]-amine To a solution of 6-(4,4,5,5-Tetramethyl-[1,3,2]dioxaborolan-2-yl)-3,4-dihydro-1H-isoquinoline-2-carboxylic acid tert-butylester (Intermediate B26) (3 eq, 0.960 mmol, 0.344 g) in dry DME (1 ml) under an inert atmosphere of argon is added 2M $Na_2CO_3$ (2 eq, 0.640 mmol, 0.32 ml) followed by (5"-Bromo-[2,2';4',3"]terpyridin-6'-yl)-cyclopropyl-amine (Example 1.26) (1 eq, 0.320 mmol, 100 mg) and $PdCl_2dppf$ (0.1 eq, 0.032 mmol, 23 mg). The reaction mixture is heated using microwave radiation at 90° C. for 2 hours. The reaction mixture is dissolved in DCM and washed with water. The organic solvent is reduced in vacuo and the residue is purified by reverse phase column chromatography (Isolute™ C18, 0-40% acetonitrile in water—0.1% TFA). The appropriate fractions by HPLC are combined and concentrated in vacuo. The resulting residue is dissolved in MeOH and loaded onto a SCX-2 cartridge eluting with MeOH followed by 2M $NH_3$ in MeOH. The methanolic ammonia fractions are combined, concentrated in vacuo and dried under vacuum to afford the title compound; $[M+H]^+$ 420.

Example 2.130

Cyclopropyl-{5"-[1-(2-morpholin-4-yl-ethyl)-1H-pyrazol-4-yl]-[2,2';4',3"]terpyridin-6'-yl}-amine This compound is prepared analogously to [4-(6'-Cyclopropylamino-[2,2';4',3"]terpyridin-5"-yl)-phenyl]-piperazin-1-yl-methanone (Example 2.30) by replacing piperazin-1-yl-[4-(4,4,5,5-tetramethyl-[1,3,2]dioxaborolan-2-yl)-phenyl]-methanone with the appropriate boronate ester which is commercially available.

Example 2.131

Cyclopropyl-{5"-[3-(2-dimethylamino-ethoxy)-phenyl]-[2,2';4',3"]terpyridin-6'-yl}-amine Step 1:
[2-(3-Bromo-phenoxy)-ethyl]-dimethyl-amine 3-Bromophenol (1 eq, 1.156 mmol, 0.2 g), 2-chloro-N,N-dimethylethanamine (1.1 eq, 1.272 mmol, 0.137 g) and potassium carbonate (3 eq, 3.47 mmol, 0.479 g) are mixed together in NMP (5 ml). The reaction mixture is heated at 80° C. for 6 hrs. The reaction mixture is dissolved in EtOAC and washed with water. The organic layer is washed with brine, dried over drying agent MgSO$_4$, filtered and the organic solvent is reduced in vacuo to afford [2-(3-Bromo-phenoxy)-ethyl]-dimethyl-amine; [M+H]$^+$ 245/247

Step 2: Dimethyl-{2-[3-(4,4,5,5-tetramethyl-[1,3,2]dioxaborolan-2-yl)-phenoxy]-ethyl}-amine A suspension of [2-(3-Bromo-phenoxy)-ethyl]-dimethyl-amine (1 eq, 0.41 mmol, 100 mg) in DME (1 ml) under an atmosphere of N$_2$ is treated with dry potassium acetate (3 eq, 1.23 mmol, 121 mg). A mixture of bis-(pinacolato) diboron (1.2 eq, 0.492 mmol, 125 mg) and PdCl$_2$(dppf).DCM (0.1 eq, 0.041 mmol, 33 mg) are added to the suspension and the resulting mixture is heated using microwave radiation at 100° C. for 1 hour. The mixture is filtered through Celite® (filter material) and concentrated in vacuo to afford the title compound which is used without further purification; [M+H]$^+$ 292.

Step 3: Cyclopropyl-{5"-[3-(2-dimethylamino-ethoxy)-phenyl][2,2';4',3"]terpyridin-6'-yl}-amine To a solution of Dimethyl-(2-[3-(4,4,5,5-tetramethyl-[1,3,2]dioxaborolan-2-yl)-phenoxy]-ethyl)-amine (2 eq, 0.272 mmol, 0.079 g) in dry DME (1 ml) under an inert atmosphere of argon is added 2M Na$_2$CO$_3$ (3 eq, 0.408 mmol, 0.204 ml) followed by (5"-Bromo-[2,2';4',3"]terpyridin-6'-yl)-cyclopropyl-amine (Example 1.26) (1 eq, 0.136 mmol, 50 mg) and PdCl2dppf (0.1 eq, 0.014 mmol, 11 mg). The reaction mixture is heated using microwave radiation at 90° C. for 90 minutes. The reaction mixture is dissolved in EtOAc and washed with water. The organic solvent is reduced in vacuo and the residue is purified by reverse phase column chromatography (Isolute™ C18, 0-40% acetonitrile in water—0.1% TFA). The appropriate fractions by HPLC are combined and concentrated in vacuo. The resulting residue is dissolved in MeOH and loaded onto a SCX-2 cartridge eluting with MeOH followed by 2M NH$_3$ in MeOH. The methanolic ammonia fractions are combined, concentrated in vacuo and dried under vacuum to afford the title compound; [M+H]$^+$ 452.

Example 2.132

{5"-[4-((R)-3-Dimethylamino-pyrrolidin-1-ylmethyl)-phenyl]-[2,2';4',3"]terpyridin-6'-1}-isopropyl-amine This compound is prepared analogously to [4-(6'-Methylamino-[2,2';4',3"]terpyridin-5"-yl)-phenyl]-(4-methyl-piperazin-1-yl)-methanone (Example 2.1) by replacing (5"-Bromo-[2,2';4',3"]terpyridin-6'-yl)-methyl-amine with (5"-Bromo-[2,2';4',3"]terpyridin-6'-yl)-isopropyl-amine (Example 2.46, step1) and by replacing (4-isopropyl-piperazin-1-yl)-[4-(4,4,5,5-tetramethyl-[1,3,2]dioxaborolan-2-yl)-phenyl]-methanone with (R)-4-((3-(dimethylamino)pyrrolidin-1-yl)methyl)phenylboronic acid (Intermediate B8).

Example 2.133

{5"-[3-(4-tert-Butyl-piperazin-1-ylmethyl)-phenyl]-[2,2';4',3"]terpyridin-6'-yl}-isopropyl-amine To a solution of 3-(4-tert-Butyl-piperazin-1-ylmethyl)-phenyl boronic acid (Intermediate B11) (1.1 eq, 0.149 mmol, 41 mg) and 2M Na$_2$CO$_3$ (2.0 eq, 0.270 mmol, 0.14 ml) in DME (1 ml) are added (5"-Bromo-[2,2';4',3"]terpyridin-6'-yl)-isopropyl-amine (Example 2.46, step1) (1 eq, 0.135 mmol, 50 mg) and [1,1'-Bis(diphenylphosphino)-ferrocene] dichloropalladium (II), complex with DCM (0.1 eq, 0.0135 mmol, 9.9 mg). The reaction mixture is heated using microwave radiation at 90° C. for 3 hours. The reaction mixture is dissolved in DCM and washed with water. The organic layer is washed with brine, dried over drying agent MgSO$_4$, filtered and the organic solvent is reduced in vacuo. The residue is purified by reverse phase chromatography (Isolute™ C18, 0-20% acetonitrile in water—0.1% TFA). The appropriate fractions by HPLC are combined and concentrated in vacuo. The resulting residue is dissolved in MeOH and loaded onto a SCX-2 cartridge eluting with MeOH and 2M NH$_3$ in MeOH. The methanolic ammonia fractions are combined, concentrated in vacuo and dried under vacuum to afford the title compound; [M+H]$^+$ 521.

Examples 2.134 to 2.136

These compounds namely,
{5"-[4-(4-tert-Butyl-piperazin-1-ylmethyl)-phenyl]-[2,2';4',3"]terpyridin-6'-yl}-isopropyl-amine (Example 2.134),
Isopropyl-{5"-[4-(4-isopropyl-piperazin-1-ylmethyl)-phenyl]-[2,2';4',3"]terpyridin-6'-yl}-amine (Example 2.135) and
Isopropyl-[5'-(1-methyl-1H-pyrazol-4-yl)-[2,2';4',3"]terpyridin-6'-yl]-amine (Example 2.136)
are prepared analogously to {5"-[3-(4-tert-Butyl-piperazin-1-ylmethyl)-phenyl]-[2,2';4',3"]terpyridin-6'-yl}-isopropyl-amine (Example 2.133) by replacing 3-(4-tert-Butyl-piperazin-1-ylmethyl)-phenyl boronic acid (Intermediate B11) with the appropriate boronic acid.

Examples 2.137

{5"-[3-(4-tert-Butyl-piperazin-1-yl)-prop-1-ynyl]-[2,2';4',3"]terpyridin-6'-yl}-isopropyl-amine This compound is prepared analogously to Cyclopropyl-{5"-[3-(4-isopropyl-piperazin-1-yl)-prop-1-ynyl]-[2,2';4',3"]terpyridin-6'-yl}-amine (Example 2.127) by replacing (5"-Bromo-[2,2';4',3"]terpyridin-6'-yl)-cyclopropyl-amine (Example 1.26) with (5"-Bromo-[2,2';4',3"]terpyridin-6'-yl)-isopropyl-amine (Example 2.46, step1) and by replacing 1-isopropyl-4-(prop-2-ynyl)piperazine (Intermediate D1) with 1-tert-Butyl-4-prop-2-ynyl-piperazine (Intermediate D2).

Examples 2.138 to 2.139

These compounds namely,
Benzyl-{5"-[3-(4-tert-butyl-piperazin-1-yl)-prop-1-ynyl]-[2,2';4',3"]terpyridin-6'-yl}-amine (Example 2.138) and
Benzyl-{5"-[3-(4-isopropyl-piperazin-1-yl)-prop-1-ynyl]-[2,2';4',3"]terpyridin-6'-yl}-amine (Example 2.139)
are prepared analogously to {5"-[3-(4-tert-Butyl-piperazin-1-yl)-prop-1-ynyl]-[2,2';4',3"]terpyridin-6'-yl}-isopropyl-amine (Example 2.137) by replacing (5"-Bromo-[2,2';4',3"]terpyridin-6'-yl)-isopropyl-amine (Example 2.46, step1) with Benzyl-(5"-bromo-[2,2';4',3"]terpyridin-6'-yl)-amine (Example 1.25) and by replacing when necessary 1-tert-Butyl-4-prop-2-ynyl-piperazine (Intermediate D2) with 1-isopropyl-4-(prop-2-ynyl)piperazine (Intermediate D1).

Example 2.140

Benzyl-{5"-[3-(4-tert-butyl-piperazin-1-yl)-prop-1-ynyl]-6-methyl-[2,2';4',3"]terpyridin-6'-yl}-amine This compound is prepared analogously to Benzyl-{5"-[3-(4-tert-butyl-piperazin-1-yl)-prop-1-ynyl]-[2,2';4',3"]terpyridin-6'-yl}-amine (Example 2.138) by replacing Benzyl-(5"-bromo-[2,2';4',3"]terpyridin-6'-yl)-amine (Example 1.25) with Benzyl-(5"-bromo-6-methyl-[2,2';4',3"]terpyridin-6'-yl)-amine (Example 2.40, step1).

Example 2.140

Benzyl-{5"-[3-(4-isopropyl-piperazin-1-yl)-prop-1-ynyl]-6-methyl-[2,2';4',3"]terpyridin-6'-yl}-amine This compound is prepared analogously to Benzyl-{5"-[3-(4-isopropyl-piperazin-1-yl)-prop-1-ynyl]-[2,2';4',3"]terpyridin-6'-yl}-amine (Example 2.139) by replacing Benzyl-(5"-bromo-[2,2';4',3"]terpyridin-6'-yl)-amine (Example 1.25) with Benzyl-(5"-bromo-6-methyl-[2,2';4',3"]terpyridin-6'-yl)-amine (Example 2.40, step1).

Example 2.142

Benzyl-[5"-(1-piperidin-4-yl-1H-pyrazol-4-yl)-[2,2';4',3"]terpyridin-6'-yl]-amine This compound is prepared analogously to Methyl-[5"-(1-piperidin-4-yl-1H-pyrazol-4-yl)-[2,2';4',3"]terpyridin-6'-yl]-amine (Example 2.183) by replacing (5"-Bromo-[2,2';4',3"]terpyridin-6'-yl)-methyl-amine (Example 2.1; step1) with Benzyl-(5"-bromo-[2,2';4',3"]terpyridin-6'-yl)-amine (Example 1.25).

Example 2.143

3-(6'-Benzylamino-[2,2';4',3"]terpyridin-5"-yl)-phenol

This compound is prepared analogously to Benzyl-[5"-(3-methoxy-phenyl)-[2,2';4',3"]terpyridin-6'-yl]-amine (Example 2.43) by 3-methoxyphenylboronic acid with the appropriate boronic acid.

Example 2.144

Benzyl-{5"-[3-(2-dimethylamino-ethoxy)-phenyl]-[2,2';4',3"]terpyridin-6'-yl}-amine This compound is prepared analogously to Methyl-{5"-[3-(2-pyrrolidin-1-yl-ethoxy)-phenyl]-[2,2';4',3"]terpyridin-6'-yl}-amine (Example 2.189) by replacing methylamino-[2,2';4',3"]terpyridin-5"-yl)-phenol (example 2.189 step 1) with 3-(6'-Benzylamino-[2,2';4',3"]terpyridin-5"-yl)-phenol (Example 2.143) and by replacing 1-(2-Chloro-ethyl)-pyrrolidine with 2-Dimethyl-aminoethyl chloride.

Example 2.145

Benzyl-[6'-(1-methyl-1H-pyrazol-3-yl)-5-(1-piperidin-4-yl-1H-pyrazol-4-yl)-[3,4']bipyridinyl-2'-yl]-amine Step 1: Benzyl-[5-bromo-6'-(1-methyl-1H-pyrazol-3-yl)-[3,4']bipyridinyl-2'-yl]-amine (E)-3-(5-Bromo-pyridin-3-yl)-1-(1-methyl-1H-pyrazol-3-yl)-propenone (Intermediate A16) (1 eq, 0.856 mmol, 0.25 g), α-(benzotriazol-1-yl)-acetonitrile (1 eq, 0.856 mmol, 0.135 g) and benzylamine (1.5 eq, 1.284 mmol, 0.138 g) are mixed together in EtOH (3 ml) and heated using microwave radiation at 120° C. for 90 mins. The reaction mixture is dissolved in DCM and washed with water. The combined organic extracts are washed with brine, dried over MgSO$_4$ and concentrated in vacuo. The residue is purified by flash chromatography (0-50% EtOAc in iso-hexane) to afford the title compound; [M+H]$^+$ 420/422.

Step 2: Benzyl-[6'-(1-methyl-1H-pyrazol-3-yl)-5-(1-piperidin-4-yl-1H-pyrazol-4-yl)-[3,4']bipyridinyl-2'-yl]-amine This compound is prepared analogously to Methyl-[5"-(1-piperidin-4-yl-1H-pyrazol-4-yl)-[2,2';4',3"]terpyridin-6'-yl]-amine (Example 2.183) by replacing (5"-Bromo-[2,2';4',3"]terpyridin-6'-yl)-methyl-amine (Example 2.1; step 1) with Benzyl-[5-bromo-6'-(1-methyl-1H-pyrazol-3-yl)-[3,4']bipyridinyl-2'-yl]-amine (Example 2.145; step 1).

Example 2.146

{5"-[3-(4-tert-Butyl-piperazin-1-ylmethyl)-phenyl][2,2';4',3"]terpyridin-6'-yl}-cyclopentyl-amine Step 1: (5"-Bromo-[2,2';4',3"]terpyridin-6'-yl)-cyclopentyl-amine (E)-3-(5-Bromo-pyridin-3-yl)-1-pyridin-2-yl-propenone (Intermediate A10) (1 eq, 1.73 mmol, 500 mg), α-(benzotriazol-1-yl)-acetonitrile (1 eq, 1.73 mmol, 273 mg) and cyclopentylamine (1.5 eq, 0.26 ml, 2.60 mmol) are mixed together in EtOH (5 ml) and heated using microwave radiation at 120° C. for 90 mins. The reaction mixture is dissolved in DCM and washed with water. The combined organic extracts are washed with brine, dried over MgSO$_4$ and concentrated in vacuo. The residue is purified by flash chromatography (0-50% EtOAc in iso-hexane) to afford the title compound; [M+H]$^+$ 394/396.

Step 2: {5"-[3-(4-tert-Butyl-piperazin-1-ylmethyl)-phenyl]-[2,2';4',3"]terpyridin-6'-yl}-cyclopentyl-amine To a solution of 3-(4-tert-Butyl-piperazin-1-ylmethyl)-phenyl boronic acid (Intermediate B11) (1.1 eq, 0.195 mmol, 54 mg) and 2M $Na_2CO_3$ (2.0 eq, 0.354 mmol, 0.18 ml) in DME (1 ml) is added (5"-Bromo-[2,2';4',3"]terpyridin-6'-yl)-cyclopentylamine (1 eq, 0.177 mmol, 70 mg) followed by [1,1'-Bis(diphenylphosphino)-ferrocene]dichloropalladium (II), complex with DCM (0.1 eq, 0.0177 mmol, 13 mg). The reaction mixture is heated using microwave radiation at 90° C. for 90 mins. The reaction mixture is dissolved in DCM and washed with water. The organic layer is washed with brine, dried over drying agent $MgSO_4$, filtered and the organic solvent is reduced in vacuo. The crude residue is purified by reverse phase column chromatography (Isolute™ C18, 0-20% acetonitrile in water—0.1% TFA). The appropriate fractions by HPLC are combined and concentrated in vacuo. The resulting residue is dissolved in MeOH and loaded onto a SCX-2 cartridge eluting with MeOH followed by 2M $NH_3$ in MeOH. The methanolic ammonia fractions are combined, concentrated in vacuo and dried under vacuum to afford the title compound; $[M+H]^+$ 547.

Example 2.147 to 2.148

These compounds namely,
{5"-[4-(4-tert-Butyl-piperazin-1-ylmethyl)-phenyl]-[2,2';4',3"]terpyridin-6'-yl}-cyclopentyl-amine (Example 2.147) and
(4-tert-Butyl-piperazin-1-yl)-[4-(6'-cyclopentylamino-[2,2';4',3"]terpyridin-5"-yl)-phenyl]-methanone (Example 2.148)
are prepared analogously to {5"-[3-(4-tert-Butyl-piperazin-1-ylmethyl)-phenyl][2,2';4',3"]terpyridin-6'-yl}-cyclopentyl-amine (Example 2.146) by replacing 3-(4-tert-Butyl-piperazin-1-ylmethyl)-phenyl boronic acid (Intermediate B11) with the appropriate boronic acids.

Example 2.149

{5"-[3-(4-tert-Butyl-piperazin-1-ylmethyl)-phenyl]-[2,2';4',3"]terpyridin-6'-yl}-cyclopropylmethyl-amine

Step 1: (5"-Bromo-[2,2';4',3"]terpyridin-6'-yl)-cyclopropylmethyl-amine (E)-3-(5-Bromo-pyridin-3-yl)-1-pyridin-2-yl-propenone (Intermediate A10) (1 eq, 1.73 mmol, 0.500 g), α-(benzotriazol-1-yl)-acetonitrile (1 eq, 1.76 mmol, 0.273 g) and aminomethylcyclopropane (1.5 eq, 2.60 mmol, 0.22 ml) are mixed together in EtOH (5 ml) and heated using microwave radiation at 120° C. for 90 mins. The reaction mixture is dissolved in DCM and washed with water. The combined organic extracts are washed with brine, dried over $MgSO_4$ and concentrated in vacuo. The residue is purified by flash chromatography (0-50% EtOAc in iso-hexane) to afford the title compound; $[M+H]^+$ 382/384.

Step 2: {5"-[3-(4-tert-Butyl-piperazin-1-ylmethyl)-phenyl]-[2,2';4',3"]terpyridin-6'-yl}-cyclopropylmethyl-amine To a solution of 3-(4-tert-Butyl-piperazin-1-ylmethyl)-phenyl boronic acid (Intermediate B11) (1.5 eq, 0.197 mmol, 54 mg) and 2M $Na_2CO_3$ (2.0 eq, 0.262 mmol, 0.13 ml) in DME (1 ml) are added (5"-Bromo-[2,2';4',3"]terpyridin-6'-yl)-cyclopropylmethyl-amine (Example 2.149; step1) (1 eq, 0.131 mmol, 50 mg) and [1,1'-Bis(diphenylphosphino)-ferrocene]dichloropalladium (II), complex with DCM (0.1 eq, 0.0131 mmol, 9.6 mg). The reaction mixture is heated using microwave radiation at 90° C. for 3 hours. The reaction mixture is dissolved in DCM and washed with water. The organic layer is washed with brine, dried over drying agent $MgSO_4$, filtered and the organic solvent is reduced in vacuo. The residue is purified by reverse phase chromatography (Isolute™ C18, 0-20% acetonitrile in water—0.1% TFA). The appropriate fractions by HPLC are combined and concentrated in vacuo. The resulting residue is dissolved in MeOH and loaded onto a SCX-2 cartridge eluting with MeOH and 2M $NH_3$ in MeOH. The methanolic ammonia fractions are combined, concentrated in vacuo and dried under vacuum to afford the title compound; $[M+H]^+$ 533.

Example 2.150 to 2.151

These compounds namely,
{5"-[4-(4-tert-Butyl-piperazin-1-ylmethyl)-phenyl]-[2,2';4',3"]terpyridin-6'-yl}-cyclopropylmethyl-amine (Example 2.150) and
Cyclopropylmethyl-{5"-[4-(4-isopropyl-piperazin-1-ylmethyl)-phenyl]-[2,2';4',3"]terpyridin-6'-yl}-amine (Example 2.151)
are prepared analogously to {5"-[3-(4-tert-Butyl-piperazin-1-ylmethyl)-phenyl]-[2,2';4',3"]terpyridin-6'-yl}-cyclopropylmethyl-amine (Example 2.149) by replacing 3-(4-tert-Butyl-piperazin-1-ylmethyl)-phenyl boronic acid (Intermediate B11) with the appropriate boronic acid.

Example 2.152

{5"-[3-(4-tert-Butyl-piperazin-1-ylmethyl)-phenyl]-[2,2';4',3"]terpyridin-6'-yl}-cyclobutyl-amine

Step 1: (5"-Bromo-[2,2';4',3"]terpyridin-6'-yl)-cyclobutyl-amine (E)-3-(5-Bromo-pyridin-3-yl)-1-pyridin-2-yl-propenone (Intermediate A10) (1 eq, 1.73 mmol, 0.500 g), α-(benzotriazol-1-yl)-acetonitrile (1 eq, 1.76 mmol, 0.273 g) and cyclobutylamine (1.5 eq, 2.60 mmol, 0.22 ml) are mixed together in EtOH (5 ml) and heated using microwave radiation at 120° C. for 90 mins. The reaction mixture is dissolved in DCM and washed with water. The combined organic extracts are washed with brine, dried over $MgSO_4$ and concentrated in vacuo. The residue is purified by flash chromatography (0-50% EtOAc in iso-hexane) to afford the title compound; $[M+H]^+$ 382/384.

Step 2: {5"-[3-(4-tert-Butyl-piperazin-1-ylmethyl)-phenyl]-[2,2';4',3"]terpyridin-6'-yl}-cyclobutyl-amine To a solution of 3-(4-tert-Butyl-piperazin-1-ylmethyl)-phenyl boronic acid (Intermediate B11) (1.5 eq, 0.197 mmol, 54 mg) and 2M $Na_2CO_3$ (2.0 eq, 0.262 mmol, 0.13 ml) in DME (1 ml) are added (5"-Bromo-[2,2';4',3"]terpyridin-6'-yl)-cyclobutyl-amine (Example 2.152, step1) (1 eq, 0.131 mmol, 50 mg) and [1,1'-Bis(diphenylphosphino)-ferrocene]dichloropalladium (II), complex with DCM (0.1 eq, 0.0131 mmol, 9.6 mg). The reaction mixture is heated using microwave radiation at 90° C. for 3 hours. The reaction mixture is dissolved in DCM and washed with water. The organic layer is washed with brine, dried over drying agent MgSO$_4$, filtered and the organic solvent is reduced in vacuo. The residue is purified by reverse phase chromatography (Isolute™ C18, 0-20% acetonitrile in water—0.1% TFA). The appropriate fractions by HPLC are combined and concentrated in vacuo. The resulting residue is dissolved in MeOH and loaded onto a SCX-2 cartridge eluting with MeOH and 2M NH$_3$ in MeOH. The methanolic ammonia fractions are combined, concentrated in vacuo and dried under vacuum to afford the title compound; [M+H]$^+$ 533.

Example 2.153

{5"-[4-(4-Isopropyl-piperazin-1-ylmethyl)-phenyl]-[2,2';4',3"]terpyridin-6'-yl}-dimethyl-amine Step 1: (5"-Bromo-[2,2';4',3"]terpyridin-6'-yl)-dimethyl-amine This compound is prepared analogously to (6'-Furan-2-yl-[3,4']bipyridinyl-2'-yl)-[2-(1H-indol-3-yl)-ethyl]-amine (Example 1.1) by replacing (E)-1-furan-2-yl-3-pyridin-3-yl-propenone (Intermediate A1) with the appropriate chalcone intermediate (preparations described hereinafter) and by replacing tryptamine with the appropriate amine.

Step 2: {5"-[4-(4-Isopropyl-piperazin-1-ylmethyl)-phenyl]-[2,2';4',3"]terpyridin-6'-yl}-dimethyl-amine This compound is prepared analogously to [4-(6'-Methylamino-[2,2';4',3"]terpyridin-5"-yl)-phenyl]-(4-methyl-piperazin-1-yl)-methanone (Example 2.1) by replacing (5"-Bromo-[2,2';4',3"]terpyridin-6'-yl)-methyl-amine (Example 2.1 step1) with (5"-Bromo-[2,2';4',3"]terpyridin-6'-yl)-dimethyl-amine and by replacing (4-Methyl-piperazin-1-yl)-[4-(4,4,5,5-tetramethyl-[1,3,2]dioxaborolan-2-yl)-phenyl]-methanone with 4-(4-Isopropyl-piperazin-1-ylmethyl)-phenyl boronic acid (Intermediate B3).

Example 2.154

5"-[4-(4-Isopropyl-piperazin-1-ylmethyl)-phenyl]-6'-pyrrolidin-1-yl-[2,2';4',3"]terpyridine Step 1: 5"-Bromo-6'-pyrrolidin-1-yl-[2,2';4',3"]terpyridine This compound is prepared analogously to (6'-Furan-2-yl-[3,4']bipyridinyl-2'-yl)-[2-(1H-indol-3-yl)-ethyl]-amine (Example 1.1) by replacing (E)-1-furan-2-yl-3-pyridin-3-yl-propenone (Intermediate A1) with the appropriate chalcone intermediate (preparations described hereinafter) and by replacing tryptamine with the appropriate amine.

Step 2: 5"-[4-(4-Isopropyl-piperazin-1-ylmethyl)-phenyl]-6'-pyrrolidin-1-yl-[2,2';4',3"]terpyridine is prepared analogously to [4-(6'-Methylamino-[2,2';4',3"]terpyridin-5"-yl)-phenyl]-(4-methyl-piperazin-1-yl)-methanone (Example 2.1) by replacing (5"-Bromo-[2,2';4',3"]terpyridin-6'-yl)-methyl-amine (Example 2.1, step1) with 5"-Bromo-6'-pyrrolidin-1-yl-[2,2';4',3"]terpyridine and by replacing (4-Methyl-piperazin-1-yl)-[4-(4,4,5,5-tetramethyl-[1,3,2]dioxaborolan-2-yl)-phenyl]-methanone with 4-(4-Isopropyl-piperazin-1-ylmethyl)-phenyl boronic acid (Intermediate B3).

Example 2.155

5"-[3-(4-Isopropyl-piperazin-1-ylmethyl)-phenyl]-[2,2';4',3"]terpyridin-6'-ylamine This compound is prepared analogously to [4-(6'-Amino-[2,2';4',3"]terpyridin-5"-yl)-phenyl]-piperazin-1-yl-methanone (Example 2.50) by replacing piperazin-1-yl-[4-(4,4,5,5-tetramethyl-[1,3,2]dioxaborolan-2-yl)-phenyl]-methanone with 3-((4-isopropylpiperazin-1-yl)methyl)phenylboronic acid (Intermediate B14).

Example 2.156

5"-[1-(Tetrahydro-pyran-4-yl)-1H-pyrazol-4-yl]-[2,2';4',3"]terpyridin-6'-ylamine This compound is prepared analogously to [4-(6'-Methylamino-[2,2';4',3"]terpyridin-5"-yl)-phenyl]-(4-methyl-piperazin-1-yl)-methanone (Example 2.1) by replacing (4-methyl-piperazin-1-yl)-[4-(4,4,5,5-tetramethyl-[1,3,2]dioxaborolan-2-yl)-phenyl]-methanone with 1-(tetrahydro-pyran-4-yl)-4-(4,4,5,5-tetramethyl-[1,3,2]dioxaborolan-2-yl)-1H-pyrazole (Intermediate B18) and by replacing (5"-Bromo-[2,2';4',3"]terpyridin-6'-yl)-methyl-amine with 5"-Bromo-[2,2';4',3"]terpyridin-6'-ylamine (Example 1.31).

Example 2.157

5"-(3-Aminomethyl-5-methyl-phenyl)-[2,2';4',3"]terpyridin-6'-ylamine

This compound is prepared analogously to [4-(6'-Amino-[2,2';4',3"]terpyridin-5"-yl)-phenyl]-piperazin-1-yl-methanone (Example 2.50) by replacing piperazin-1-yl-[4-(4,4,5,5-tetramethyl-[1,3,2]dioxaborolan-2-yl)-phenyl]-methanone with 5"-(3-Aminomethyl-5-methyl-phenyl boronic acid (Intermediate B27).

Example 2.158

5"-[4-(4-tert-Butyl-piperazin-1-ylmethyl)-phenyl]-[2,2';4',3"]terpyridin-6'-ylamine This compound is prepared analogously to 5"-[1-(Tetrahydro-pyran-4-yl)-1H-pyrazol-4-yl]-[2,2';4',3"]terpyridin-6'-ylamine (Example 2.156) by replacing 1-(tetrahydro-pyran-4-yl)-4-(4,4,5,5-tetramethyl-[1,3,2]dioxaborolan-2-yl)-1H-pyrazole (Intermediate B18) with 4-((4-tert-butylpiperazin-1-yl)methyl)phenylboronic acid (Intermediate B10).

Example 2.159

5"-(4-piperazin-1-ylmethyl-phenyl)-[2,2';4',3"]terpyridin-6'-ylamine

Step 1: 4-[4-(6'-Amino-[2,2';4',3"]terpyridin-5"-yl)-benzyl]-piperazine-1-carboxylic acid tert-butyl ester This compound is prepared analogously to 5"-[1-(Tetrahydro-pyran-4-yl)-1H-pyrazol-4-yl]-[2,2';4',3"]terpyridin-6'-ylamine (Example 2.156) by replacing 1-(tetrahydro-pyran-4-yl)-4-(4,4,5,5-tetramethyl-[1,3,2]dioxaborolan-2-yl)-1H-pyrazole (Intermediate B18) with 4-[4-(4,4,5-trimethyl-[1,3,2]dioxaborolan-2-yl)-benzyl]-piperazine-1-carboxylic acid tert-butyl ester.

Step 2: 5"-(4-piperazin-1-ylmethyl-phenyl)-[2,2';4', 3"]terpyridin-6'-ylamine To a solution of 4-[4-(6'-Amino-[2,2';4',3"]terpyridin-5"-yl)-benzyl]-piperazine-1-carboxylic acid tert-butyl ester (1.0 eq, 0.105 mmol, 55.1 mg) in DCM (1.0 ml) is added TFA (24.0 eq, 2.60 mmol, 0.2 ml). The reaction mixture is allowed to stir at room temperature for 30 minutes. The organic solvent is reduced in vacuo. The residue is purified by reverse phase chromatography (Isolute™ C18, 0-20% acetonitrile in water—0.1% TFA). The appropriate fractions by HPLC are combined and concentrated in vacuo. The resulting residue is dissolved in MeOH and loaded onto a SCX-2 cartridge eluting with MeOH and 2M NH$_3$ in MeOH. The methanolic ammonia fractions are combined, concentrated in vacuo and dried under vacuum to afford the title compound; [M+H]$^+$ 423.

Example 2.160

5"-(1-Piperidin-4-yl-1H-pyrazol-4-yl)-[2,2';4',3"]terpyridin-6'-ylamine

This compound is prepared analogously to methyl-[5"-(1-piperidin-4-yl-1H-pyrazol-4-yl)-[2,2';4',3"]terpyridin-6'-yl]-amine (Example 2.183) by replacing (5"-Bromo-[2,2';4',3"]terpyridin-6'-yl)-methyl-amine (Example 2.1; step1) with 5"-Bromo-[2,2';4',3"]terpyridin-6'-ylamine (Example 1.31).

Example 2.161

5"-[1-(1-Isopropyl-piperidin-4-yl)-1H-pyrazol-4-yl]-[2,2';4',3"]terpyridin-6'-ylamine This compound is prepared analogously to {5"-[1-(1-Isopropyl-piperidin-4-yl)-1H-pyrazol-4-yl]-[2,2';4',3"]terpyridin-6'-yl}-methyl-amine (Example 2.175) by replacing (5"-Bromo-[2,2';4',3"]terpyridin-6'-yl)-methyl-amine (Example 2.1; step1) with 5"-Bromo-[2,2';4',3"]terpyridin-6'-ylamine (Example 1.31).

Example 2.162 to 2.164

These compounds namely
5"-[1-(2-Morpholin-4-yl-ethyl)-1H-pyrazol-4-yl]-[2,2';4', 3"]terpyridin-6'-ylamine (Example 2.162),
5"-(1-Methyl-1H-pyrazol-4-yl)-[2,2';4',3"]terpyridin-6'-ylamine (Example 2.163), and
5"-[4-((S)-3-Dimethylamino-pyrrolidin-1-ylmethyl)-phenyl]-[2,2';4',3"]terpyridin-6'-ylamine (Example 2.164)
are prepared analogously to 5"-[1-(Tetrahydro-pyran-4-yl)-1H-pyrazol-4-yl]-[2,2';4',3"]terpyridin-6'-ylamine (Example 2.156) by replacing 1-(tetrahydro-pyran-4-yl)-4-(4,4,5,5-tetramethyl-[1,3,2]dioxaborolan-2-yl)-1H-pyrazole (Intermediate B18) with the appropriate boronic acid.

Examples 2.165 to 2.174

{5"-[3-(4-tert-Butyl-piperazin-1-ylmethyl)-phenyl]-[2,2';4', 3"]terpyridin-6'-yl}-methyl-amine (Example 2.165),
{5"-[4-(4-tert-Butyl-piperazin-1-ylmethyl)-phenyl]-[2,2';4', 3"]terpyridin-6'-yl}-methyl-amine (Example 2.166),
Methyl-[5"-(1-methyl-1H-pyrazol-4-yl)-[2,2';4',3"]terpyridin-6'-yl]-amine (Example 2.167),
{5"-[4-((R)-3-Dimethylamino-pyrrolidin-1-ylmethyl)-phenyl]-[2,2';4',3"]terpyridin-6'-yl}-methyl-amine (Example 2.168),
{5"-[4-((S)-3-Dimethylamino-pyrrolidin-1-ylmethyl)-phenyl]-[2,2';4',3"]terpyridin-6'-yl}-methyl-amine (Example 2.169),
{5"-[3-(4-Isopropyl-piperazin-1-ylmethyl)-phenyl]-[2,2';4', 3"]terpyridin-6'-yl}-methyl-amine (Example 2.170),
(5"-Isoxazol-4-yl-[2,2';4',3"]terpyridin-6'-yl)-methyl-amine (Example 2.171),
Methyl-[5"-(4-piperazin-1-ylmethyl-phenyl)-[2,2';4',3"]terpyridin-6'-yl]-amine (Example 2.172),
Methyl-{5"-[1-(tetrahydro-pyran-4-yl)-1H-pyrazol-4-yl]-[2, 2';4',3"]terpyridin-6'-yl}-amine (Example 2.173), and
(5"-{1-[2-(4-Isopropyl-piperazin-1-yl)-ethyl]-1H-pyrazol-4-yl}-[2,2';4',3"]terpyridin-6'-yl)-methyl-amine (Example 2.174)
are prepared analogously to [4-(6'-Methylamino-[2,2';4',3"]terpyridin-5"-yl)-phenyl]-(4-methyl-piperazin-1-yl)-methanone (Example 2.1) by replacing (4-Methyl-piperazin-1-yl)-[4-(4,4,5,5-tetramethyl-[1,3,2]dioxaborolan-2-yl)-phenyl]-methanone with the appropriate boronic acid.

Example 2.175

{5"-[1-(1-Isopropyl-piperidin-4-yl)-1H-pyrazol-4-yl]-[2,2';4',3"]terpyridin-6'-yl}-methyl-amine To a solution of Methyl-[5"-(1-piperidin-4-yl-1H-pyrazol-4-yl)-[2,2';4',3"]terpyridin-6'-yl]-amine (Example 2.183) (1 eq, 0.122 mmol, 50 mg) in DMF (3 ml) cooled at 0° C. is added 2-iodopropane (7 eq, 0.854 mmol, 0.084 ml) and the reaction is stirred at room temperature for 5 hours. The reaction mixture is dissolved in EtOAc and washed with water. The combined organic extracts are washed with brine, dried over MgSO$_4$ and concentrated in vacuo. The residue is purified by reverse phase column chromatography (Isolute™ C18, 0-20% acetonitrile in water—0.1% TFA). The appropriate fractions by HPLC are combined and concentrated in vacuo. The resulting residue is dissolved in MeOH and loaded onto a SCX-2 cartridge eluting with MeOH followed by 2M NH$_3$ in MeOH. The methanolic ammonia fractions are combined, concentrated in vacuo and dried under vacuum to afford the title compound; [M+H]$^+$ 454.

Examples 2.176 to 2.177

Methyl-{6-methyl-5"-[3-(4-methyl-piperazin-1-ylmethyl)-phenyl]-[2,2';4',3"]terpyridin-6'-yl}-amine (Example 2.176) and
{5"-[4-((R)-3-Dimethylamino-pyrrolidin-1-ylmethyl)-phenyl]-6-methyl-[2,2';4',3"]terpyridin-6'-yl}-methyl-amine (Example 2.177)
are prepared analogously to [4-(6'-Methylamino-[2,2';4',3"]terpyridin-5"-yl)-phenyl]-(4-methyl-piperazin-1-yl)-methanone (Example 2.1) by replacing (5"-Bromo-[2,2';4',3"]terpyridin-6'-yl)-methyl-amine (Example 2.1, step1) with (5"-Bromo-6-methyl-[2,2';4',3"]terpyridin-6'-yl)-methyl-amine (Example 1.27) and by replacing (4-Methyl-piperazin-1-yl)-[4-(4,4,5,5-tetramethyl-[1,3,2]dioxaborolan-2-yl)-phenyl]-methanone with the appropriate boronic acid.

Example 2.178

[5-[4-(4-Isopropyl-piperazin-1-ylmethyl)-phenyl]-6'-(1-methyl-1H-pyrazol-3-yl)-[3,4']bipyridinyl-2'-yl]-methyl-amine Step 1: [5-Bromo-6'-(1-methyl-1H-pyrazol-3-yl)-[3, 4']bipyridinyl-2'-yl]-methyl-amine (E)-3-(5-Bromo-pyridin-3-yl)-1-(1-methyl-1H-pyrazol-3-yl)-propenone (Intermediate A16) (1 eq, 0.685 mmol, 0.2 g), α-(benzotriazol-1-yl)-acetonitrile (1 eq, 0.685 mmol, 0.108 g) and 33% methylamine solution in EtOH (1.5 eq, 1.03 mmol, 0.135 ml) are mixed together in EtOH (4 ml) and heated using microwave radiation at 120° C. for 90 mins. The reaction mixture is dissolved in DCM and washed with water. The combined organic extracts are washed with brine, dried over $MgSO_4$ and concentrated in vacuo. The residue is purified by flash chromatography (0-50% EtOAc in iso-hexane) to afford the title compound; $[M+H]^+$ 344/346.

Step 2: [5-[4-(4-Isopropyl-piperazin-1-ylmethyl)-phenyl]-6'-(1-methyl-1H-pyrazol-3-yl)-[3,4']bipyridinyl-2'-yl]-methyl-amine To a solution of 4-(4-Isopropyl-piperazin-1-ylmethyl)-phenyl boronic acid (Intermediate B3) (1.5 eq, 0.218 mmol, 0.057 g) and 2M $Na_2CO_3$ (3.0 eq, 0.436 mmol, 0.218 ml) in DME (1 ml) is added [5-Bromo-6'-(1-methyl-1H-pyrazol-3-yl)-[3,4']bipyridinyl-2'-yl]-methyl-amine (Example 2.178, step1) (1 eq, 0.145 mmol, 0.050 g) followed by [1,1'-Bis(diphenylphosphino)-ferrocene]dichloropalladium (II), complex with DCM (0.1 eq, 0.015 mmol, 0.012 g). The reaction mixture is heated using microwave radiation at 90° C. for 90 mins. The reaction mixture is dissolved in DCM and washed with water. The organic layer is washed with brine, dried over drying agent $MgSO_4$, filtered and the organic solvent is reduced in vacuo. The crude residue is purified by reverse phase column chromatography (Isolute™ C18, 0-50% acetonitrile in water—0.1% TFA). The appropriate fractions by HPLC are combined and concentrated in vacuo. The resulting residue is dissolved in MeOH and loaded onto a SCX-2 cartridge eluting with MeOH followed by 2M $NH_3$ in MeOH. The methanolic ammonia fractions are combined, concentrated in vacuo and dried under vacuum to afford the title compound; $[M+H]^+$ 482.

Example 2.179

Methyl-[6'-(1-methyl-1H-pyrazol-3-yl)-5-(1-piperidin-4-yl-1H-pyrazol-4-yl)-[3,4']bipyridinyl-2'-yl]-amine This compound is prepared analogously to Methyl-[5"-(1-piperidin-4-yl-1H-pyrazol-4-yl)-[2,2';4',3"]terpyridin-6'-yl]-amine (Example 2.183) by replacing (5"-Bromo-[2,2';4',3"]terpyridin-6'-yl)-methyl-amine (Example 2.1; step1) by [5-Bromo-6'-(1-methyl-1H-pyrazol-3-yl)-[3,4']bipyridinyl-2'-yl]-methyl-amine (Example 2.178, step 1).

Example 2.180

(4-tert-Butyl-piperazin-1-yl)-[4-(6'-methylamino-[2,2';4',3"]terpyridin-5-yl)-phenyl]-methanone This compound is prepared analogously to [4-(6'-Methylamino-[2,2';4',3"]terpyridin-5"-yl)-phenyl]-(4-methyl-piperazin-1-yl)-methanone (Example 2.1) by replacing (4-Methyl-piperazin-1-yl)-[4-(4,4,5,5-tetramethyl-[1,3,2]dioxaborolan-2-yl)-phenyl]-methanone with the appropriate boronic acid.

Examples 2.181

{5"-[3-(4-Isopropyl-piperazin-1-yl)-prop-1-ynyl]-[2,2';4',3"]terpyridin-6'-yl}-methyl-amine This compound is prepared analogously to Methyl-[5"-(3-methyl-3H-imidazol-4-ylethynyl)-[2,2';4',3"]terpyridin-6'-yl]-amine (Example 2.182) by replacing 1-methyl-5-((trimethylsilyl)ethynyl)-1H-imidazole with 1-isopropyl-4-(prop-2-ynyl)piperazine (Intermediate D1)

Example 2.182

Methyl-[5"-(3-methyl-3H-imidazol-4-ylethynyl)-[2,2';4',3"]terpyridin-6'-yl]-amine To a solution of (5"-Bromo-[2,2';4',3"]terpyridin-6'-yl)-methyl-amine (Example 2.1, step1) (1 eq, 0.147 mmol, 0.050 g) in DME (1 ml) is added potassium carbonate (1 eq, 0.147 mmol, 0.020 g), tetrakis(triphenylphosphine)palladium(0) (0.1 eq, 0.015 mmol, 17 mg), triethylamine (2 eq, 0.293 mmol, 0.041 ml) and 1-methyl-5-((trimethylsilyl)ethynyl)-1H-imidazole (1 eq, 0.147 mmol, 26.1 mg), followed by Copper (I) iodide (0.5 eq, 0.073 mmol, 14 mg). The reaction mixture is heated using microwave radiation at 70° C. for 2 hrs. The reaction mixture is dissolved in EtOAc and washed with water. The organic layer is washed with brine, dried over drying agent $MgSO_4$, filtered and the organic solvent is reduced in vacuo. The crude residue is purified by reverse phase column chromatography (Isolute™ C18, 0-50% acetonitrile in water—0.1% TFA). The appropriate fractions by HPLC are combined and concentrated in vacuo. The resulting residue is dissolved in MeOH and loaded onto a SCX-2 cartridge eluting with MeOH followed by 2M $NH_3$ in MeOH. The methanolic ammonia fractions are combined, concentrated in vacuo and dried under vacuum to afford the title compound; $[M+H]^+$ 367.

Example 2.183

Methyl-[5"-(1-piperidin-4-yl-1H-pyrazol-4-yl)-[2,2';4',3"]terpyridin-6'-yl]-amine Step 1: 4-[4-(6'-Methylamino-[2,2';4',3"]terpyridin-5"-yl)-pyrazol-1-yl]-piperidine-1-carboxylic acid tert-butyl ester To a solution of 4-[4-(4,4,5,5-Tetramethyl-[1,3,2]dioxaborolan-2-yl)-pyrazol-1-yl]-piperidine-1-carboxylic acid tert-butyl ester (Intermediate B20) (1.5 eq, 1.095 mmol, 0.413 g) and 2M $Na_2CO_3$ (2.0 eq, 1.460 mmol, 0.730 ml) in DME (5 ml) is added (5"-Bromo-[2,2';4',3"]terpyridin-6'-yl)-methyl-amine (Example 2.1, step1) (1 eq, 0.730 mmol, 0.249 g) followed by [1,1'-Bis(diphenylphosphino)-ferrocene] dichloropalladium (II), complex with DCM (0.1 eq, 0.073 mmol, 0.059 g). The reaction mixture is heated using microwave radiation at 90° C. for 3 hours. The reaction mixture is dissolved in DCM and washed with water. The organic layer is washed with brine, dried over drying agent $MgSO_4$, filtered and the organic solvent is reduced in vacuo. The crude residue is purified by flash chromatography (0-100% EtOAc in iso-hexane and up to 10% MeOH in EtOAc), to afford title compound.

Step 2: Methyl-[5'-(1-piperidin-4-yl-1H-pyrazol-4-yl)-[2,2';4',3"]terpyridin-6'-yl]-amine 4-[4-(6'-Methylamino-[2,2';4',3"]terpyridin-5"-yl)-pyrazol-1-yl]-piperidine-1-carboxylic acid tert-butyl ester is dissolved in DCM (3 ml) and TFA (1 ml) added. The reaction is stirred at room temperature for 30 mins. The solvent is evaporated and the residue is purified by reverse phase column chromatography (Isolute™ C18, 0-100% acetonitrile in water—0.1% TFA). The appropriate fractions by HPLC are combined and concentrated in vacuo. The resulting residue is dissolved in MeOH and loaded onto a SCX-2 cartridge eluting with MeOH followed by 2M NH₃ in MeOH. The methanolic ammonia fractions are combined, concentrated in vacuo and dried under vacuum to afford the title compound [M+H]⁺ 412.

Example 2.184 to 2.186

These compounds namely,
Methyl-(5"-thiophen-3-yl-[2,2';4',3"]terpyridin-6'-yl)-amine (Example 2.184),
Methyl-{5"-[1-(2-morpholin-4-yl-ethyl)-1H-pyrazol-4-yl]-[2,2';4',3"]terpyridin-6'-yl}-amine (Example 2.185) and
Methyl-[5"-(1-methyl-1H-pyrazol-3-yl)-[2,2';4',3"]terpyridin-6'-yl]-amine (Example 2.186)
are prepared analogously to [4-(6'-Methylamino-[2,2';4',3"]terpyridin-5"-yl)-phenyl]-(4-methyl-piperazin-1-yl)-methanone (Example 2.1) by replacing (4-Methyl-piperazin-1-yl)-[4-(4,4,5,5-tetramethyl-[1,3,2]dioxaborolan-2-yl)-phenyl]-methanone with the appropriate boronic acid.

Example 2.187

{5"-[4-(4-Isopropyl-piperazin-1-ylmethyl)-phenyl]-6-methyl-[2,2';4',3"]terpyridin-6'-yl}-methyl-amine This compound is prepared analogously to [4-(6'-Methylamino-[2,2';4',3"]terpyridin-5"-yl)-phenyl]-(4-methyl-piperazin-1-yl)-methanone (Example 2.1) by replacing (5"-Bromo-[2,2';4',3"]terpyridin-6'-yl)-methyl-amine (Example 2.1, step1) with (5"-Bromo-6-methyl-[2,2';4',3"]terpyridin-6'-yl)-methyl-amine (Example 1.27) and by replacing (4-Methyl-piperazin-1-yl)-[4-(4,4,5,5-tetramethyl-[1,3,2]dioxaborolan-2-yl)-phenyl]-methanone with the appropriate boronic acid.

Example 2.188

Methyl-[6-methyl-5"-(1-piperidin-4-yl-1H-pyrazol-4-yl)-[2,2';4',3"]terpyridin-6'-yl]-amine This compound is prepared analogously to Methyl-[5"-(1-piperidin-4-yl-1H-pyrazol-4-yl)-[2,2';4',3"]terpyridin-6'-yl]-amine (Example 2.183) by replacing (5"-Bromo-[2,2';4',3"]terpyridin-6'-yl)-methyl-amine (Example 2.1, step1) with (5"-Bromo-6-methyl-[2,2';4',3"]terpyridin-6'-yl)-methyl-amine (Example 1.27).

Example 2.189

Methyl-{5"-[3-(2-pyrrolidin-1-yl-ethoxy)-phenyl]-[2,2';4',3"]terpyridin-6'-yl}-amine Step 1: 3-(6'-Methylamino-[2,2';4',3"]terpyridin-5"-yl)-phenol To a solution 3-Hydroxphenolboronic acid, pinacol ester (2.0 eq, 1.172 mmol, 0.258 g) and 2M Na₂CO₃ (2.0 eq, 1.172 mmol, 0.586 ml) in DME (2.5 ml) is added (5"-Bromo-[2,2'; 4',3"]terpyridin-6'-yl)-methyl-amine (Example 2.1; step1) (1 eq, 0.586 mmol, 0.200 g) followed by [1,1'-Bis(diphenylphosphino)-ferrocene]dichloropalladium (II), complex with DCM (0.1 eq, 0.059 mmol, 0.048 g). The reaction mixture is heated using microwave radiation at 90° C. for 90 mins. The reaction mixture is dissolved in DCM and washed with water. The organic layer is washed with brine, dried over drying agent MgSO₄, filtered and the organic solvent is reduced in vacuo. The crude residue is purified by flash chromatography (0-100% EtOAc in iso-hexane and up to 10% MeOH in EtOAc), to yield intermediate to afford the title compound; [M+H]⁺ 355.

Step 2: Methyl-{5"-[3-(2-pyrrolidin-1-yl-ethoxy)-phenyl]-[2,2';4',3"]terpyridin-6'-yl}-amine Potassium carbonate (3.0 eq, 0.686 mmol, 95 mg) is added to a suspension of 3-(6'-Methylamino-[2,2';4',3"]terpyridin-5"-yl)-phenol (Example 2.189, step 1) (1.0 eq, 0.229 mmol, 81 mg) in dry acetonitrile (2.0 ml) under an inert atmosphere of nitrogen. 1-(2-Chloro-ethyl)-pyrrolidine (3 eq, 0.686 mmol, 92 mg) is added and the reaction is heated using microwave radiation at 150° C. for 2 hours. The reaction mixture is dissolved in DCM and washed with water. The organic layer is washed with brine, dried over drying agent MgSO₄, filtered and the organic solvent is reduced in vacuo. The residue is purified by reverse phase column chromatography (Isolute™ C18, 0-40% acetonitrile in water—0.1% TFA). The appropriate fractions by HPLC are combined and concentrated in vacuo. The resulting residue is dissolved in MeOH and loaded onto a SCX-2 cartridge eluting with MeOH followed by 2M NH₃ in MeOH. The methanolic ammonia fractions are combined, concentrated in vacuo and dried under vacuum to afford the title compound; [M+H]⁺ 453.

| Ex. | Physical data |
| --- | --- |
| 1.10 | ¹H NMR (500 MHz, DMSO-d6) δ 10.86 (1H, Br), 8.91 (1H, d, 2.5 Hz), 8.67 (1H, dd, 1.8 Hz), 8.66 (1H, dd, 1.7 Hz), 8.40 (1H, d, 8.4 Hz), 8.11 (1H, ddd, 8.0, 2.0, 2.0 Hz), 7.95 (1H, ddd, 7.7, 7.7, 1.9 Hz), 7.85 (1H, d, 1.5 Hz), 7.63 (1H, d, 7.8 Hz), 7.55 (1H, ddd, 7.9 Hz, 4.8 Hz), 7.43 (1H, ddd, 7.5, 4.6, <0.5 Hz), 7.37 (1H, d, 8.1 Hz), 7.25 (1H, d, 2.4 Hz), 7.09 (1H, ddd, 7.3, 7.0, <0.5 Hz), 7.0 (1H, dd, 7.3 Hz, 7.3 Hz), 6.94 (1H, br t, 7 Hz), 6.85 (1H, d, 1 Hz), 3.77 (2H, dt, 7.3, 7 Hz), 3.08 (2H, t, 7.3 Hz) |
| 2.1 | ¹H NMR (400 MHz, DMSO-d6) δ 8.99 (1H, d, 1.2 Hz), 8.93 (1H, d, 1.1 Hz), 8.66 (1H, dd, 4.7 Hz, 1.6 Hz), 8.40 (1H, dd, 7.9 Hz, 1.1 Hz), 8.37 (1H, dd, 1.2 Hz, 1.1 Hz), 7.95 (1H, m), 7.94 (2H, d, 8.1 Hz), 7.93 (1H, d, 1.5 Hz), 7.54 (2H, d, 8.1 Hz), 7.42 (1H, m), 6.91 (1H, d, 1.5 Hz), 6.75 (1H, q, 4.8 Hz), 3.64-3.40 (4H, broad humps), 2.97 (3H, d, 4.8 Hz), 2.33 (4H, broad hump), 2.23 (3H, s) |
| 2.2 | ¹H NMR (400 MHz, DMSO-d6) δ 8.91 (1H, d, 1.72 Hz), 8.8 (1H, s), 8.67 (1H, d, 4.56 Hz), 8.41 (1H, d, 7.96 Hz), 8.23 (1H, m), 7.94 (2H, m), 7.73 (2H, d, 8.64 Hz), 7.43 (1H, m), 7.07 (2H, d, 8.68 Hz), 6.88 (1H, s), 6.75 (1H, m), 3.3-3.2 (8H, broad hump), 2.97 (3H, d, 4.68 Hz), 2.26 (3H, s). |
| 2.12 | ¹H NMR (400 MHz, DMSO-d6) δ 8.93 (1H, d, 2.17 Hz), 8.88 (1H, d, 2.15 Hz), 8.68 (1H, dd, 7.9 Hz, 1.72 Hz), 8.4 (1H, dd, 1.2 Hz, 1.1 Hz), 8.27 (1H, m), 7.94 (1H, m), 7.9 (1H, d, 1.56 Hz), 7.43 (1H, m), 7.33 (1H, t), 7.0 (1H, d, 2.32 Hz), 6.88 (2H, m), 6.78 (1H, m), 6.64 (1H, dd, 8, 2.48 Hz), 3.34 (4H, broad hump), 2.97 (3H, d, 4.8 Hz), 1.99 (4H, broad). |
| 2.23 | ¹H NMR (400 MHz, DMSO-d6) δ 8.95 (1H, d, 2.16 Hz), 8.9 (1H, d, 2.12 Hz), 8.67 (1H, m), 8.41 (1H, d, 7.91 Hz), 8.31 (1H, m), 7.96 (1H, m), 7.92 (1H, m), 7.73 (2H, m), 7.48 (2H, m), 7.42 (1H, m), 6.9 (1H, d, 1.36 Hz), 6.75 (1H, m), 3.56 (2H, s), 2.97 (3H, d, 4.8 Hz), 2.55-2.20 (8H, br humps), 2.15 (3H, s) |

-continued

| Ex. | Physical data |
|---|---|
| 2.24 | ¹H NMR (500 MHz, DMSO-d6) δ 8.95 (1H, d, 1.8 Hz), 8.89 (1H, d, 1.8 Hz), 8.66 (1H, m), 8.39 (1H, d, 8.0 Hz), 8.31 (1H, m), 7.95 (1H, m), 7.91 (1H, m), 7.8 (2H, d, 8.0 Hz), 7.44 (2H, d, 8.0 Hz), 7.42 (1H, m), 6.9 (1H, d, 1.0 Hz), 6.74 (1H, q, 4.8 Hz), 3.51 (2H, s), 2.96 (3H, d, 4.7 Hz), 2.59 (1H, septet, 6.5 Hz), 2.55-2.20 (8H, br humps), 0.95 (6H, d, 6.5 Hz) |
| 2.26 | ¹H NMR (400 MHz, DMSO-d6) δ 8.96 (1H, d, 2.16 Hz), 8.89 (1H, d, 2.12 Hz), 8.67 (1H, m), 8.41 (1H, d, 7.93 Hz), 8.31 (1H, m), 7.96 (1H, m), 7.92 (1H, m), 7.8 (2H, m), 7.46 (2H, m), 7.42 (1H, m), 6.9 (1H, d, 1.32 Hz), 6.75 (1H, m), 3.53 (2H, s), 2.97 (3H, d, 4.8 Hz), 2.55-2.20 (8H, br humps), 2.17 (3H, s) |
| 2.28 | ¹H NMR (400 MHz, MeOD-d4) δ 8.94 (2H, dd), 8.48 (1H, t), 8.20 (1H, m), 7.91 (2H, m), 7.83 (2H, d, 1.32 Hz), 7.62 (2H, m), 7.31 (1H, d, 7.56 Hz), 6.88 (1H, d, 1.4 Hz), 3.82 (2H, br), 3.56 (2H, br), 3.06 (3H, s), 2.65 (3H, s), 2.36 (3H, s). |
| 2.30 | ¹H NMR (400 MHz, DMSO-d6) δ 9 (1H, d, 1.2 Hz), 8.95 (1H, d, 1.1 Hz), 8.66 (1H, dd, 4.7 Hz, 1.6 Hz), 8.40 (1H, dd, 7.9 Hz, 1.1 Hz), 8.37 (1H, dd, 1.2 Hz, 1.1 Hz), 7.95 (1H, m), 7.94 (2H, d, 8.1 Hz), 7.93 (1H, d, 1.5 Hz), 7.54 (2H, d, 8.1 Hz), 7.42 (1H, m), 7.08 (1H, d, 1.5 Hz), 7.02 (1H, q, 4.8 Hz), 5.76 (1H, s), 3.64-3.40 (4H, broad humps), 3.63 (1H, broad), 2.78 (4H, broad hump), 0.80 (2H, m), 0.54 (2H, m). |
| 2.31 | ¹H NMR (500 MHz, DMSO-d6) δ 8.96 (1H, d, 2.2 Hz), 8.91 (1H, d, 2.1 Hz), 8.67 (1h, dd, 5 Hz, 1.5 Hz), 8.36 (1H, dd, 7.9 Hz, <1 Hz), 8.37 (1h, m), 7.96 (1H, d, 1.5 Hz), 7.93 (1H, m), 7.80 (2h, d, 7.7 Hz), 7.45 (2H, d, 7.7 Hz), 7.45 (1H, m), 7.08 (1H, d, 2.5 Hz), 7.01 (1h, d, 1.5 Hz), 3.51 (2H, s), 2.73 (1H, m), 2.60 (1H, septet, 6.4 Hz), 2.50-2.30 (8H, broad hump), 0.95 (6H, d, 6.4 Hz), 0.79 (2H, m), 0.53 (2H, m). |
| 2.62 | ¹H NMR (500 MHz, DMSO-d6) δ 8.96 (1H, d, 1.79 Hz), 8.9 (1H, d, 1.79 Hz), 8.66 (1H, d, 3.4 Hz), 8.36 (1H, d, 7.9 Hz), 8.32 (1H, br s), 7.96 (1H, s), 7.93 (1H, t, 7.72 Hz), 7.8 (2H, d, 7.95 Hz), 7.45 (2H, d, 7.82 Hz), 7.42 (1H, br t, 6.0 Hz), 7.08 (1H, s), 7.00 (1H, s), 3.61 (2H, br m), 2.73 (1H, m), 2.72 (1H, m), 2.68-2.29 (2H, m), 2.59-2.46 (2H, m), 2.09 (6H, s), 1.85-1.62 (2H, m), 0.79-0.53 (4H, m). |
| 2.72 | ¹H NMR (400 MHz, DMSO-d6) δ 8.96 (1H, d, 3.0 Hz), 8.87 (1H, d, 2.0 Hz), 8.66 (1H, d, 4.0 Hz), 8.32 (1H, s), 8.29 (1H, d, 3.0 Hz), 7.92 (2H, m), 7.81 (2H, d, 1.3 Hz), 7.44 (3H, m), 6.91 (1H, d, 1.0 Hz), 6.23 (1H, s), 3.53 (2H, s), 3.31 (1H, m), 2.49 (8H, br), 0.98 (6H, s) |
| 2.80 | ¹H NMR (500 MHz, DMSO-d6) δ 8.99 (1H, d, 2.2 Hz), 8.98 (1H, d, 2.2 Hz), 8.71 (1H, m), 8.58 (1H, d, 1.7 Hz), 8.5 (1H, dd, 7.9 Hz), 8.42 (1H, dd, 2.2 Hz, 2.2 Hz), 8.1 (1H, d, 1.7 Hz), 7.99 (1H, ddd, 7.9, 7.9, 1.6 Hz), 7.82 (2H, d, 8.1 Hz), 7.48 (1H, m), 7.45 (2H, d, 8.1 Hz), 5.4 (1H, s), 3.5 (2H, s), 2.59 (1H, septet, 6.4 Hz), 2.48-2.28 (8H, broad humps), 1.6 (6H, s), 0.95 (6H, d, 6.4 Hz). |
| 2.81 | ¹H NMR (400 MHz, DMSO-d6) δ 9 (1H, d, 2.2 Hz), 8.99 (1H, d, 2.2 Hz), 8.73 (1H, m), 8.59(1H, d, 1.7 Hz), 8.51 (1H, dd, 7.9 Hz), 8.43 (1H, dd, 2.2 Hz, 2.2 Hz), 8.1 (1H, d, 1.7 Hz), 7.99 (1H, ddd, 7.9, 7.9, 1.6 Hz), 7.82 (2H, d, 8.1 Hz), 7.48 (1H, m), 7.45 (2H, d, 8.1 Hz), 5.4 (1H, s), 3.5 (2H, s), 2.71 (4H, m), 2.32 (4H, m), 1.6 (6H, s). |
| 2.82 | ¹H NMR (400 MHz, DMSO-d6) δ 9.00 (2H, q), 8.74 (1H, d, 4.58 Hz), 8.59 (1H, s), 8.51 (1H, d, 7.92 Hz), 8.45 (1H, s), 8.12 (1H, s), 8.00 (1H, t), 7.84 (2H, d, 8.04 Hz), 7.47 (3H, m), 5.41 (1H, s), 3.52 (2H, s), 2.39 (8H, br), 1.62 (6H, s), 1.00 (9H, s). |
| 2.83 | ¹H NMR (400 MHz, DMSO-d6) δ 9.06 (2H, q), 8.74 (1H, d, 4.26 Hz), 8.61 (1H, s), 8.52 (1H, s), 8.50 (1H, s), 8.12 (1H, d, 1.27 Hz), 7.98 (3H, m), 7.57 (2H, d, 8.12 Hz), 7.50 (1H, m), 5.42 (1H, s), 3.67 (4H, br), 2.37 (4H, br), 1.63 (6H, s). |
| 2.84 | ¹H NMR (400 MHz, DMSO-d6) δ 8.99 (1H, s), 8.81 (1H, d, 1.91 Hz), 8.74 (1H, m), 8.60 (1H, s), 8.55 (1H, s), 8.50 (1H, d, 7.93 Hz), 8.39 (1H, s), 8.17 (1H, s), 8.05 (1H, s), 8.00 (1H, t), 7.51 (1H, m), 4.45 (1H, m), 3.99 (2H, m), 3.51 (2H, m), 2.02 (4H, m), 1.62 (6H, s). |
| 2.85 | ¹H NMR (400 MHz, DMSO-d6) δ 9.01 (2H, q), 8.73 (1H, d, 4.29 Hz), 8.61 (1H, s), 8.52 (1H, d, 7.89 Hz), 8.44 (1H, s), 8.13 (1H, s), 8.00 (1H, t), 7.84 (2H, d), 7.47 (3H, m), 5.41 (1H, s), 3.56 (2H, s), 2.42 (8H, br), 1.62 (6H, s). |
| 2.86 | ¹H NMR (400 MHz, DMSO-d6) δ 8.95 (1H, d, 2.08 Hz), 8.8 (1H, d, 2.16 Hz), 8.74 (1H, m), 8.54 (1H, d, 1.64 Hz), 8.5 (1H, s), 8.44 (1H, m), 8.37 (1H, m), 8.13 (1H, d, 0.6 Hz), 8.05 (1H, d, 1.65 Hz), 7.98 (1H, m), 7.49 (1H, m), 5.4 (1H, s), 3.9 (1H, s), 1.6 (6H, s) |
| 2.87 | ¹H NMR (400 MHz, DMSO-d6) δ 9.06 (2H, q), 8.74 (1H, d, 3.96 Hz), 8.62 (1H, d, 1.57 Hz), 8.52 (2H, m), 8.13 (1H, d, 1.58), 7.99 (3H, m), 7.56 (2H, d, 8.19 Hz), 7.50 (1H, m), 5.42 (1H, s), 2.19 (4H, br), 1.63 (6H, s), 1.10 (6H, t), 0.94 (3H, br). |
| 2.88 | ¹H NMR (400 MHz, DMSO-d6) δ 8.98 (1H, d, 1.89 Hz), 8.80 (1H, d, 2.12 Hz), 8.75 (1H, m), 8.54 (3H, m), 8.50 (1H, d, 7.89 Hz), 8.40 (1H, s), 8.17 (1H, s), 8.06 (1H, s), 8.01 (1H, t), 7.50 (1H, m), 5.41 (1H, s), 4.25 (1H, br), 3.09 (2H, br), 2.64 (2H, br), 2.02 (2H, br), 1,86 (2H, br), 1.62 (6H, s). |
| 2.89 | ¹H NMR (400 MHz, DMSO-d6) δ 8.98 (1H, d, 2.01 Hz), 8.80 (1H, d, 2.12 Hz), 8.74 (1H, d, 3.95 Hz), 8.60 (1H, s), 8.55 (1H, s), 8.50 (1H, d, 1.55 Hz), 8.40 (1H, s), 8.16 (1H, s), 8.05 (1H, s), 8.01 (1H, t), 7.51 (1H, m), 5.41 (1H, s), 4.51 (1H, br m), 2.93 (2H, br d), 2.78 (1H, br m), 2.30 (2H, br t), 2.07 (2H, br), 1.94 (2H, br q), 1.61 (6H, s), 1.02 (6H, s). |
| 2.90 | ¹H NMR (400 MHz, DMSO-d6) δ 9.02 (1H, d, 2.08 Hz), 8.72 (1H, d, 4 Hz), 8.69 (1H, d, 1.92 Hz), 8.57 (1H, d, 1.42 Hz), 8.51 (1H, d, 7.93 Hz), 8.45 (1H, s), 8.09 (1H, s), 7.98 (1H, m), 7.49 (1H, m), 7.32 (3H, m), 5.38 (1H, s), 3.49 (2H, s), 2.60 (1H, septet), 2.43 (8H, br), 2.30 (3H, s), 1.62 (6H, s), 0.97 (6H, d, 6.52 Hz). |
| 2.91 | ¹H NMR (400 MHz, DMSO-d6) δ 9.01 (2H, dd), 8.74 (1H, d, 4.08), 8.60 (1H, d, 1.31 Hz), 8.52 (1H, d, 7.93 Hz), 8.45 (1H, s), 8.11 (1H, s), 8.01 (1H, t), 7.84 (2H, d, 8.08 Hz), 7.48 (4H, m), 5.43 (1H, s), 3.51 (3H, m), 2.69 (6H, m), 1.62 (6H, s), 0.91 (3H, s). |
| 2.92 | ¹H NMR (400 MHz, DMSO-d6) δ 9.00 (2H, dd), 8.75 (1H, d, 3.94 Hz), 8.60 (1H, d, 1.48 Hz), 8.51 (1H, d, 7.91 Hz), 8.46 (1H, m), 8.12 (1H, d, 1.42 Hz), 8.01 (1H, t), 7.85 (2H, d, 7.7 Hz), 7.47 (3H, m), 5.41 (1H, s), 3.48 (2H, s), 2.78 (2H, br), 2.28 (2H, br), 2.09 (2H, br), 1.63 (6H, s), 1.07 (6H, s). |
| 2.95 | ¹H NMR (400 MHz, DMSO-d6) δ 9.01 (1H, d, 2.2 Hz), 8.98 (1H, d, 2.2 Hz), 8.72 (1H, m), 8.54 (1H, d, 1.6 Hz), 8.50 (1H, dd, 7.9, 1.2, 1.2 Hz), 8.30 (1H, dd, 2.2, 2.2 Hz), 7.99 (1H, ddd, 7.9, 7.9, 1.9 Hz), 7.91 (1H, d, 1.6 Hz), 7.83 (2H, d, 7.8 Hz), 7.48 (1h, ddd, 7.9, 4.8, 1.2 Hz), 7.45 (2H, d, 7.8 Hz), 3.52 (2H, s), 2.59 (1H, m), 2.55-2.3 (8H, broad hump), 1.48 (9H, s), 0.95 (6H, d, 6.2 Hz). |
| 2.100 | ¹H NMR (400 MHz, DMSO-d6) δ 8.96 (1H, d, 1.8 Hz), 8.89 (1H, d, 1.8 Hz), 8.66 (1H, m), 8.39 (1H, d, 8.0 Hz), 8.31 (1H, m), 7.96 (1H, m), 7.91 (1H, m), 7.81 (2H, d, 8.0 Hz), 7.46 (2H, d, 8.0 Hz), 7.42 (1H, m), 6.9 (1H, d, 1.0 |

| Ex. | Physical data |
|---|---|
| | Hz), 6.72 (1H, q, 4.8 Hz), 3.51 (2H, s), 2.60 (1H, septet, 6.5 Hz), 2.55-2.20 (8H, br humps), 0.95 (6H, d, 6.5 Hz) |
| 2.102 | $^1$H NMR (400 MHz, DMSO-d6) δ 8.96 (1H, d, 1.8 Hz), 8.89 (1H, d, 1.8 Hz), 8.66 (1H, m), 8.39 (1H, d, 8.0 Hz), 8.31 (1H, m), 7.96 (1H, m), 7.91 (1H, m), 7.81 (2H, d, 8.0 Hz), 7.46 (2H, d, 8.0 Hz), 7.42 (1H, m), 6.9 (1H, d, 1.0 Hz), 6.72 (1H, q, 4.8 Hz), 3.51 (2H, s), 2.83 (4H, br humps), 2.41 (4h, broad hump). |
| 2.104 | $^1$H NMR (400 MHz, DMSO-d6) δ 8.91 (1H, d, 2.08 Hz), 8.7 (1H, s), 8.68 (1H, d, 3.96 Hz), 8.41 (1H, d, 8.3 Hz), 8.39 (1H, m), 8.25 (1H, m), 8.1 (1H, m), 7.94 (1H, t), 7.87 (1H, m), 7.43 (1H, m), 6.84 (1H, m), 6.74 (1H, q, 4.8 Hz), 3.9 (3H, s) |
| 2.106 | $^1$H NMR (400 MHz, DMSO-d6) δ 9.00 (1H, d, 1.9 Hz), 8.9 (1H, d, 1,84 Hz), 8.65 (1H, d, 4.01 Hz), 8.45 (2H, m), 7.95 (4H, m), 7.55 (2H, d, 7.95 Hz), 7.45 (1H, m), 6.9 (1H, s), 6.7 (1H, s), 3.65 (4H, br), 2.5 (4H, br). |
| 2.107 | $^1$H NMR (400 MHz, DMSO-d6) δ 8.5 (1H, d, 2.14 Hz), 8.0 (1H, d, 2.12 Hz), 8.65 (1H, d, 3.9 Hz), 8.4 (1H, d, 3.9 Hz), 8.3 (1H, d, 7.97 Hz), 7.95 (1H, m), 7.90 (1H, s), 7.80 (2H, d, 8.05 Hz), 7.45 (3H, m), 6.9 (1H, d, 1.36 Hz), 6.7 (1H, s), 3.5 (2H, br), 2.5 (4H, br), 2.4 (4H, br), 1.0 (9H, s). |
| 2.111 | $^1$H NMR (400 MHz, DMSO-d6 δ 8.99 (1H, m), 8.96 (1H, s), 8.90 (1H, d, 2 Hz), 8.81 (1H, m), 8.67 (1H, d, 8.51 Hz), 8.40 (1H, d, 7.93 Hz), 8.30 (1H, m), 7.95 (1H, t), 7.90 (1H, s), 7.78 (1H, br), 7.54 (1H, m), 7.43 (2H, m), 6.89 (1H, m), 6.80 (1H, t), 3.72 (2H, s), 3.45 (4H, br), 3.02 (2H, br), 2.40 (2H, br), 1.24 (12H, br) |
| 2.114 | $^1$H NMR (400 MHz, DMSO-d6) δ 8.95 (1H, d, 8.13 Hz), 8.90 (1H, d, 8.04), 8.66 (1H, d, 3.94 Hz), 8.39 (1H, d, 7.94 Hz), 8.29 (1H, s), 7.96 (1H, t), 7.89 (1H, s), 7.71 (2H, m), 7.51 (1H, t), 7.41 (2H, m), 6.90 (1H, s), 6.78 (1H, t), 5.76 (1H, s), 3.57 (2H, s), 3.47 (2H, t), 2.60 (2H, br), 2.43 (8H, br), 1.24 (3H, t), 0.95 (6H, d). |
| 2.116 | $^1$H NMR (400 MHz, DMSO-d6) δ 8.93 (1H, d, 2.16 Hz), 8.90 (1H, d, 2.12 Hz), 8.65 (1H, d, 5.61 Hz), 8.4 (1H, d, 7.93 Hz), 8.25 (1H, t), 7.95 (1H, t), 7.9 (1H, d, 1.36 Hz), 7.55 (2H, d, 5.75 Hz), 7.4 (1H, m), 7.25 (1H, s), 6.9 (1H, t), 6.75 (1H, t), 5.25 (2H, d, 5.67 Hz), 3.45 (2H, q), 2.4 (3H, s), 1.25 (3H, t). |
| 2.119 | $^1$H NMR (400 MHz, DMSO-d6) δ 8.95 (1H, m), 8.92 (1H, m), 8.68 (1H, m), 8.37 (1H, m), 8.32 (1H, s), 7.97 (2H, m), 7.75 (2H, m), 7.51 (1H, m), 7.40 (2H, m), 7.12 (1H, s), 7.02 (1H, s), 3.57 (2H, s), 2.75 (1H, s), 2.42 (8H, br), 0.98 (9H, s), 0.81 (2H, d, 4.88 Hz), 0.54 (2H, m). |
| 2.120 | $^1$H NMR (400 MHz, DMSO-d6) δ 8.97 (1H, s), 8.91 (1H. s), 8.67 (1H, m), 8.36 (1H, d, 7.8 Hz), 7.96 (2H, m), 7.82 (2H, d, 7.76 Hz), 7.44 (3H, m), 7.10 (1H, s), 7.04 (1H, s), 3.52 (2H, s), 2.75 (1H, s), 2.41 (8H, br), 1.00 (9H, s), 0.80 (2H, d, 4.96 Hz), 0.53 (2H, m). |
| 2.125 | $^1$H NMR (400 MHz, DMSO-d6) δ 8.95 (1H, d, 2 Hz), 8.91 (1H, d, 2 Hz), 8.34 (1H, m), 7.81 (2H, d, 8.08 Hz), 7.45 (2H, d, 8.04 Hz), 7.29 (1H, s), 7.04 (1H, s), 6.94 (1H, d, 3.12 Hz), 6.85 (1H, s), 6.24 (1H, d, 2.28 Hz), 3.54 (2H, s), 2.63 (1H, br), 2.46 (8H, br), 2.36 (3H, s), 0.97 (1H, m), 0.76 (2H, m), 0.49 (2H, m). |
| 2.133 | $^1$H NMR (400 MHz, DMSO-d6) δ 8.95 (1H, d, 2 Hz), 8.88 (1H, d, 2.3 Hz), 8.66 (1H, d, 4.04 Hz), 8.38 (1H, d, 8 Hz), 8.27 (1H, s), 7.94 (1H, t), 7.87 (1H, s), 7.73 (2H, m), 7.51 (1H, m), 7.42 (2H, m), 6.88 (1H, s), 6.63 (1H, d, 7.28 Hz), 4.24 (1H, m), 3.55 (2H, s), 2.41 (8H, br), 1.24 (6H, d, 6.44 Hz), 0.99 (9H, s). |
| 2.134 | $^1$H NMR (400 MHz, DMSO-d6) δ 8.96 (1H, d, 2.04 Hz), 8.88 (1H, d, 1.96), 8.66 (1H, d, 2.80 Hz), 8.37 (1H, d, 7.88 Hz), 8.29 (1H, s), 7.95 (1H, t), 7.89 (1H, s), 7.81 (1H, d, 8.04 Hz), 7.44 (4H, m), 6.89 (1H, s), 6.62 (1H, d, 7.44 Hz), 4.24 (1H, m), 3.51 (2H, s), 2.40 (8H, br), 1.26 (6H, d, 6.40 Hz), 1.00 (9H, s). |
| 2.158 | $^1$H NMR (400 MHz, DMSO-d6) δ 8.96 (1H, d, 2.0 Hz), 8.87 (1H, d, 1.88 Hz), δ 8.67 (1H, d, 4.12 Hz), 8.32 (1H, s), 8.30 (1H, d, 2.32 Hz), 7.95 (2H, m), 7.82 (2H, d, 7.96 Hz), 7.46 (3H, m), 6.91 (1H, s), 6.24 (2H, s), 3.51 (2H, s), 2.39 (8H, br), 1.0 (9H, s) |
| 2.159 | $^1$H NMR (400 MHz, DMSO-d6) δ 8.96 (1H, d, 2.12 Hz), 8.87 (1H, d, 2.12 Hz), 8.66 (1H, d, 3.89 Hz), 8.32 (1H, s), 8.30 (1H, d, 2.24 Hz), 7.95 (2H, m), 7.81 (2H, d, 8.24 Hz), 7.46 (3H, m), 6.91 (1H, d, 1.4 Hz), 6.24 (2H, s), 3.51 (2H, s), 2.75 (4H, br), 2.35 4H, br) |
| 2.172 | $^1$H NMR (400 MHz, DMSO-d6) δ 8.96 (1H, d, 1.2 Hz), 8.89 (1H, d, 1.1 Hz), 8.67 (1H, dd, 4.7 Hz, 1.6 Hz), 8.40 (1H, dd, 7.9 Hz, 1.1 Hz), 8.32 (1H, dd, 1.2 Hz, 1.1 Hz), 7.95 (2H, mult), 7.82 (2H, m), 7.45 (3H, multi), 6.91 (1H, d, 1.5 Hz), 6.74 (1H, q, 4.8 Hz), 3.5 (2H, s), 2.97 (3H, d, 4.76 Hz), 2.70 (4H, m), 2.32 (4H, m) |
| 2.179 | $^1$H NMR (400 MHz, DMSO-d6) δ 8.92 (1H, d, 1.92 Hz), 8.69 (1H, d, 2.04 Hz), 8.66 (1H, d, 3.93 Hz), 8.54 (1H, s), 8.40 (1H, d, 7.93 Hz), 8.29 (1H, m), 8.13 (1H, s), 7.95 (1H, m), 7.87 (1H, s), 7.42 (1H, m), 6.87 (1H, s), 6.78 (1H, m), 4.41 (1H, m), 2.96 (2H, d, 4.68 Hz), 3.31 (4H, m), 2.32 (2H, m), 2.16 (m, 2H) |

Preparation of Intermediates

Intermediate A1

(E)-1-Furan-2-yl-3-pyridin-3-yl-propenone

2-Acetylfuran (1 eq, 2.72 mmol, 0.3 g) is dissolved in dry THF (5 ml) under an inert atmosphere of argon. DBU (1 eq, 2.72 mmol, 0.411 ml) is then added followed by nicotinaldehyde (2 eq, 5.45 mmol, 0.512 ml) in THF (5 ml) and the reaction mixture is stirred at room temperature overnight. The solvent is removed in vacuo and the residue is dissolved in DCM. This organic portion is washed with water and brine, dried over MgSO$_4$, filtered and concentrated in vacuo. The crude residue is dry loaded onto silica and purification by flash chromatography eluting with DCM affords the title compound; [M+H]$^+$ 200.

Intermediate A2

(E)-1-(5-Methyl-furan-2-yl)-3-pyridin-3-yl-propenone

2-Acetyl-5-methylfuran (1 eq, 2.42 mmol, 0.281 ml) is dissolved in dry THF (10 ml) under an inert atmosphere of argon. DBU (1 eq, 2.42 mmol, 0.364 ml) and nicotinaldehyde (2 eq, 4.83 mmol, 0.454 ml) are added and the reaction mixture is stirred at room temperature overnight. The solvent is removed in vacuo and the crude residue is dry loaded onto silica. Purification by flash chromatography eluting with MeOH/DCM (0 to 2% MeOH in DCM) affords the title compound; [M+H]$^+$ 214.

Intermediates A3 to A7

These compounds namely,
(E)-3-(5-Methoxy-pyridin-3-yl)-1-pyridin-2-yl-propenone (Intermediate A3),
(E)-3-Pyridin-3-yl-1-pyridin-2-yl-propenone (Intermediate A4),
(E)-1-(6-Bromo-pyridin-2-yl)-3-pyridin-3-yl-propenone (Intermediate A5),
(E)-3-Pyridin-3-yl-1-(1H-pyrrol-2-yl)-propenone (Intermediate A6) and
(E)-3-Pyridin-2-yl-1-pyridin-3-yl-propenone (Intermediate A7)
are prepared analogously to (E)-1-(5-Methyl-furan-2-yl)-3-pyridin-3-yl-propenone (Intermediate A2) from the appropriate ketones and aldehydes.

Intermediate A8

(E)-1-(3,5-Dimethyl-1H-pyrrol-2-yl)-3-pyridin-3-yl-propenone 1-(3,5-Dimethyl-1H-pyrrol-2-yl)ethan-1-one (1 eq, 1.82 mmol, 0.25 g) is dissolved in dry THF (5 ml) under an inert atmosphere of argon. DBU (1 eq, 1.82 mmol, 0.275 ml) and nicotinaldehyde (2 eq, 3.65 mmol, 0.342 ml) are added and the reaction mixture is heated at reflux for 48 hours. On cooling to room temperature the solvent is removed in vacuo and the crude residue is purified by flash chromatography on silica eluting with MeOH/DCM (0 to 2% MeOH in DCM) resulting in the formation of a yellow solid. The solid is triturated with EtOAc/iso-hexane, filtered and dried under vacuum to afford the title compound; $[M+H]^+$ 227.

Intermediate A9

(E)-3-(5-Iodo-pyridin-3-yl)-1-pyridin-2-yl-propenone 2-acetylpyridine (1 eq, 0.83 mmol, 0.1 g) is dissolved in dry THF (3 ml) under an inert atmosphere of argon. DBU (1 eq, 0.83 mmol, 0.125 ml) is then added followed by 5-Iodo-pyridine-3-carbaldehyde (1.5 eq, 1.24 mmol, 0.288 g) and the reaction mixture is stirred at room temperature for 3 hours. The reaction mixture is then added dropwise to water (40 ml) resulting in the formation of a pale yellow precipitate. The solid is filtered, washed with water and dried under vacuum at 40° C. to afford the title compound; $[M+H]^+$ 337.

Intermediates A10

(E)-3-(5-Bromo-pyridin-3-yl)-1-pyridin-2-yl-propenone 2-acetylpyridine (1 eq, 10 mmol, 1.2 g) is dissolved in dry THF (15 ml) under an inert atmosphere of argon. DBU (1 eq, 10 mmol, 1.5 ml) is slowly added followed by 5-Bromo-pyridine-3-carbaldehyde (2 eq, 20 mmol, 3.7 g) and the reaction mixture is stirred at room temperature for 1 hour. The resulting suspension is filtered, washed with THF (60 ml) and dried under vacuum at 40° C. to afford the title compound; $[M+H]^+$ 289/291.

Intermediates A11

(E)-3-(5-Bromo-pyridin-3-yl)-1-(6-methyl-pyridin-2-yl)-propenone

2-Acetyl-6-methylpyridine (1 eq, 0.035 mol, 4.73 g) is dissolved in dry THF (40 ml) under an inert atmosphere of argon. DBU (1 eq, 0.035 mol, 5.27 ml) is slowly added followed by 5-Bromo-3-formylpyridine (1.5 eq, 0.0537 mol, 10 g) and the reaction mixture is stirred at room temperature for 2 hours 30 mins. The resulting suspension is filtered, washed with THF (15 ml) and dried under vacuum at 40° C. to afford the title compound; $[M+H]^+$ 303/305.

Intermediate A12

(E)-3-(3-Hydroxy-phenyl)-1-pyridin-2-yl-propenone

2-Acetylpyridine (1 eq, 2.47 mmol, 0.3 g) is dissolved in dry THF (5 ml) under an inert atmosphere of argon. DBU (1 eq, 2.47 mmol, 0.373 ml) and 3-hydroxy-benzaldehyde (2 eq, 4.95 mmol, 0.605 g) in THF (5 ml) are added and the reaction mixture is stirred at room temperature for 2 hours and then heated to 60° C. overnight. After cooling to room temperature, the solvent is removed in vacuo and the resulting crude residue is dry loaded onto silica. Purification is carried out by flash chromatography eluting with EtOAc/iso-hexane (0 to 20% EtOAc in iso-hexane) and the appropriate fractions are combined and concentrated in vacuo. The resulting residue is dissolved in MeOH and loaded onto a SCX-2 cartridge eluting with MeOH followed by 2M $NH_3$ in MeOH. The methanolic ammonia fractions are concentrated in vacuo and dried under vacuum to afford the title compound; $[M+H]^+$ 226.

Intermediate A13 to A14

These compounds namely,
(E)-1-(6-Methyl-pyridin-2-yl)-3-pyridin-3-yl-propenone (Intermediate A13) and
(E)-1-(6-Methoxy-pyridin-2-yl)-3-pyridin-3-yl-propenone (Intermediate A14)
are prepared analogously to (Intermediate A11) from the appropriate ketones and aldehydes.

Intermediate A15

3-((E)-3-Oxo-3-pyridin-2-yl-propenyl)-benzonitrile 3-((E)-3-Oxo-3-pyridin-2-yl-propenyl)-benzonitrile is prepared analogously to (Intermediate A2) from the appropriate ketone and aldehyde.

Intermediate A16

(E)-3-(5-Bromo-pyridin-3-yl)-1-(1-methyl-1H-pyrazol-3-yl)-propenone 1-(1-methyl-1H-pyrazol-3-yl)ethanone (1 eq, 2.42 mmol, 0.3 g) is dissolved in dry THF (10 ml) under an inert atmosphere of argon. DBU (1.1 eq, 2.66 mmol, 0.4 ml) is then added followed by 5-bromonicotinaldehyde (1.2 eq, 2.9 mmol, 0.539 g) and the reaction mixture is stirred at room temperature overnight. The resulting suspension is filtered, washed with ether and dried under vacuum at 40° C. to afford the title compound; $[M+H]^+$ 292/294.

Intermediates A17 to A18

These compounds namely,
(E)-1-(5-Bromo-pyridin-3-yl)-4,4-dimethyl-pent-1-en-3-one (Intermediate A17) and
(E)-1-(5-Bromo-pyridin-3-yl)-5,5-dimethyl-hex-1-en-3-one (Intermediate A18)

are prepared analogously to (E)-1-(5-Bromo-pyridin-3-yl)-4-hydroxy-4-methyl-pent-1-en-3-one (Example 2.80; step1) by replacing 3-Hydroxy-3-methyl-butan-2-one with the appropriate ketone.

Intermediate A19

(E)-3-(5-Bromo-pyridin-3-yl)-1-(5-methyl-furan-2-yl)-propenone
is prepared analogously to (E)-1-(5-Methyl-furan-2-yl)-3-pyridin-3-yl-propenone (Intermediate A2) from the appropriate ketones and aldehydes.

Intermediate B1

3-(4-Methyl-piperazin-1-ylmethyl)-phenyl boronic acid

A solution of 3-Formylphenylboronic acid (1 eq, 2 mmol, 0.3 g) in dry DCM (7 ml) under an inert atmosphere of argon is treated with 1-methyl-piperazine (1.2 eq, 2.4 mmol, 0.266 ml) followed by acetic acid (1.2 eq, 2.4 mmol, 0.14 ml) and NaBH(OAc)$_3$ (1.6 eq, 3.2 mmol, 0.678 mg) and the resulting mixture is stirred at room temperature for 3 hours. The reaction is quenched by addition of water and is then extracted with DCM. The organic extracts are concentrated in vacuo and the crude residue is purified by flash chromatography on silica eluting with MeOH/DCM (0 to 100% MeOH in DCM) followed by 2M NH$_3$ in MeOH. The appropriate fractions are combined and concentrated in vacuo to afford the title compound; [M+H]$^+$=235.

Intermediates B2 to B3

These compounds namely,
4-(4-Methyl-piperazin-1-ylmethyl)-phenyl boronic acid (Intermediate B2) and
4-(4-Isopropyl-piperazin-1-ylmethyl)-phenyl boronic acid (Intermediate B3)
are prepared analogously to (Intermediate B1) from the appropriate amines and boronic acids.

Intermediate B4

(4-Isopropyl-piperazin-1-yl)-[4-(4,4,5,5-tetramethyl-[1,3,2]dioxaborolan-2-yl)-phenyl]-methanone 4-Carboxyphenylboronic acid, pinacol ester (1.0 eq, 2.01 mmol, 500 mg) and HATU (2.0 eq, 4.02 mmol, 1.53 g) are mixed together in DMF peptide grade (10 mL). Triethylamine (1.2 eq, 2.41 mmol, 0.34 mL) is then added dropwise and the resulting reaction solution is allowed to stir at room temperature for 15 minutes. Isopropylpiperazine (1.2 eq, 2.41 mmol, 0.35 mL) is then added dropwise and the reaction mixture is stirred at room temperature overnight. The reaction mixture is dissolved in EtOAc and washed with water. The organic layer is dried over drying agent MgSO$_4$, filtered and the organic solvent is reduced in vacuo and dried under vacuum at 40° C. to afford the title compound; [M+H]$^+$=359.

Intermediates B5 to B7

These compounds namely,
(4-Ethyl-piperazin-1-yl)-[4-(4,4,5,5-tetramethyl-[1,3,2]dioxaborolan-2-yl)-phenyl]-methanone (Intermediate B5),
[4-(2-Methoxy-ethyl)-piperazin-1-yl]-[4-(4,4,5,5-tetramethyl-[1,3,2]dioxaborolan-2-yl)-phenyl]-methanone (Intermediate B6) and
2,6-Dimethyl-4-[4-(4,4,5,5-tetramethyl-[1,3,2]dioxaborolan-2-yl)-benzoyl]-piperazine-1-carboxylic acid tert-butyl ester (Intermediate B7)
are prepared analogously to (Intermediate B4) from the appropriate amines and boronic acids. Further boronic acids and boronate esters required to synthesise the Examples described herein can be prepared analogously to Intermediates B1 to B7 using the appropriate commercially available starting compounds.

Intermediates B8 to B16

These compounds namely,
(R)-4-((3-(dimethylamino)pyrrolidin-1-yl)methyl)phenylboronic acid (Intermediate B8)
4-((1-(tert-butoxycarbonyl)pyrrolidin-3-ylamino)methyl)phenylboronic acid (Intermediate B9)
4-((4-tert-butylpiperazin-1-yl)methyl)phenylboronic acid (Intermediate B10)
3-((4-tert-butylpiperazin-1-yl)methyl)phenylboronic acid (Intermediate B1)
4-((tert-butoxycarbonylamino)methyl)phenylboronic acid (Intermediate B12)
(S)-4-((3-(dimethylamino)pyrrolidin-1-yl)methyl)phenylboronic acid (Intermediate B13)
3-((4-isopropylpiperazin-1-yl)methyl)phenylboronic acid (Intermediate B14)
4-((4-Methyl-d3-piperazin-1-yl)methyl)phenylboronic acid (Intermediate B15)
4-(piperazin-1-ylmethyl)phenylboronic acid (Intermediate B16)
are prepared analogously to 3-(4-Methyl-piperazin-1-ylmethyl)-phenyl boronic acid (Intermediate B1) from the appropriate amine and boronic acid.

Intermediate B17

Isoxazol-4-ylboronic acid 4-bromoisoxazole (1 eq, 0.676 mmol, 0.1 g) is dissolved in dry THF (3 ml) under an inert atmosphere of argon. Triisopropylborate (1.2 eq, 0.811 mmol, 0.18 ml) is then added and the reaction mixture cooled to −78° C. After 10 mins, n-butyllithium (1.2 eq, 0.811 mmol, 0.324 ml) is added and the reaction mixture is stirred at room temperature overnight. The reaction mixture is quenched with HCl (1M) and the solvent evaporated to recover a yellow solid which is used without further purification.

Intermediate B18

1-(Tetrahydro-pyran-4-yl)-4-(4,4,5,5-tetramethyl-[1,3,2]dioxaborolan-2-yl)-1H-pyrazole Step 1: Methanesulfonic acid tetrahydro-pyran-4-yl ester Tetrahydro-pyran-4-ol (1 eq, 4.9 mmol, 0.5 g) is dissolved in dry DCM (10 ml) under an inert atmosphere of argon. NEt$_3$ (3 eq, 14.69 mmol, 2.047 ml) is then added at 0° C., followed by methanesulfonyl chloride (1.1 eq, 5.39 mmol, 0.417 ml) and the reaction mixture is stirred at room temperature overnight. The reaction mixture is quenched with NaHCO$_3$ (1M, 3 ml) and extracted with DCM. This organic portion is washed with water and brine, dried over MgSO$_4$, filtered and concentrated in vacuo to afford the title compound.

Step 2: 4-Bromo-1-(tetrahydro-pyran-4-yl)-1H-pyrazole 4-bromo-1H-pyrazole (1 eq, 3.92 mmol, 0.5 g) is dissolved in dry DMF (5 ml) under an inert atmosphere of nitrogen. The reaction mixture is cooled down to −10° C. and sodium hydride (1 eq, 3.92 mmol, 0.157 g) is added portionwise. After 15 mins at 0° C., the reaction was warmed to R.T and stirred for 30 mins at R.T. A solution of methane sulfonic acid tetrahydro-pyran-4-yl ester (Intermediate B18, step1) (1 eq, 3.92 mmol, 0.5 g) in DMF (5 ml) is added and the reaction mixture is stirred at 95° C. overnight. The reaction mixture is quenched at 0° C. with water and extracted with DCM. This organic portion is washed with water and brine, dried over MgSO$_4$, filtered and concentrated in vacuo. The resulting solid is triturated with MeOH and the solid filtered to afford the title compound; [M+H]$^+$ 231/233.

Step 3: 1-(Tetrahydro-pyran-4-yl)-4-(4,4,5,5-tetramethyl-[1,3,2]dioxaborolan-2-yl)-1H-pyrazole To a solution of 4,4,4',4',5,5,5',5'-octamethyl-2,2'-bi(1,3,2-dioxaborolane) (2 eq, 0.433 mmol, 110 mg) and potassium acetate (3 eq, 0.649 mmol, 63.7 mg) in dry DME (1 ml) under an inert atmosphere of nitrogen are added 4-Bromo-1-(tetrahydro-pyran-4-yl)-1H-pyrazole 3-Methoxy boronic acid (Intermediate B18, step 2) (1 eq, 0.216 mmol, 50 mg) and PdCl$_2$dppf (0.1 eq, 0.021 mmol, 17 mg). The reaction mixture is heated using microwave radiation at 90° C. for 1 hours. The reaction mixture is filtered through Celite® and washed with EtOAc. The organic solvent is reduced in vacuo to afford title compound which is used without further purification.

Intermediates B19 to B20

These compounds namely,
1-Isopropyl-4-{2-[4-(4,4,5,5-tetramethyl-[1,3,2]dioxaborolan-2-yl)-pyrazol-1-yl]-ethyl}-piperazine (Intermediate B19)
4-[4-(4,4,5,5-Tetramethyl-[1,3,2]dioxaborolan-2-yl)-pyrazol-1-yl]-piperidine-1-carboxylic acid tert-butyl ester (Intermediate B20)
are prepared analogously to 1-(Tetrahydro-pyran-4-yl)-4-(4,4,5,5-tetramethyl-[1,3,2]dioxaborolan-2-yl)-1H-pyrazole (Intermediate B18) from the appropriate alcohols.

Intermediate B21

[4-(4,4,5,5-Tetramethyl-[1,3,2]dioxaborolan-2-yl)-phenyl]-(3,4,5-trimethyl-piperazin-1-yl)-methanone

Step 1: 3,4,5-Trimethyl-piperazine-1-carboxylic acid benzyl ester

Benzyl 3,5-dimethylpiperazine-1-carboxylate (1 eq, 2.04 mmol, 0.5 g) and formaldehyde (37% in H$_2$O, 5 eq, 10.07 mmol, 0.277 ml) are dissolved in MeOH (10 ml). After 10 mins at room temperature, acetic acid (5 eq, 10.07 mmol, 0.576 ml) and sodium triacetoxyborohydride (5 eq, 10.07 mmol, 2.13 g) are added and the reaction mixture stirred overnight. The reaction is quenched with 5M HCl (15 ml) and the solvent evaporated under vacuo. The residue is taken to pH 13 by addition of sodium hydroxide (4M) and extracted with EtOAc. This organic portion is washed with water and brine, dried over MgSO$_4$, filtered and concentrated in vacuo to afford the title compound.

Step 2: 1,2,6-Trimethyl-piperazine

Under an inert atmosphere of nitrogen, 3,4,5-trimethyl-piperazine-1-carboxylic acid benzyl ester (1 eq, 1.87 mmol, 0.49 g) is dissolved in EtOH (20 ml) and palladium on carbon (0.1 eq, 0.187 mmol, 0.2 g) is added. The reaction is stirred at room temperature under an atmosphere of hydrogen for 4 hrs. The reaction mixture is filtered through Celite® and the solvent evaporated under vacuo to afford the title compound.

Step 3: [4-(4,4,5,5-Tetramethyl-[1,3,2]dioxaborolan-2-yl)-phenyl]-(3,4,5-trimethyl-piperazin-1-yl)-methanone is prepared analogously to (4-Isopropyl-piperazin-1-yl)-[4-(4,4,5,5-tetramethyl-[1,3,2]dioxaborolan-2-yl)-phenyl]-methanone (Intermediate B4) from the appropriate amine.

Intermediates B22 to B24

These compounds namely,
(4-tert-Butyl-piperazin-1-yl)-[4-(4,4,5,5-tetramethyl-[1,3,2]dioxaborolan-2-yl)-phenyl]-methanone (Intermediate B22)
(4-Methyl-d3-piperazin-1-yl)-[4-(4,4,5,5-tetramethyl-[1,3,2]dioxaborolan-2-yl)-phenyl]-methanone (Intermediate B23)
(4-Methyl-piperazin-1-yl)-[4-(4,4,5,5-tetramethyl-[1,3,2]dioxaborolan-2-yl)-phenyl]-methanone (Intermediate B24)
are prepared analogously to (4-Isopropyl-piperazin-1-yl)-[4-(4,4,5,5-tetramethyl-[1,3,2]dioxaborolan-2-yl)-phenyl]-methanone (Intermediate B4) from the appropriate amine.

Intermediate B25

Dimethyl-{1-[3-(4,4,5,5-tetramethyl-[1,3,2]dioxaborolan-2-yl)-phenyl]-pyrrolidin-3-yl}-amine

Step 1: [1-(3-Bromo-phenyl)-pyrrolidin-3-yl]-dimethyl-amine

1-Bromo-3-iodobenzene (1 eq, 3.53 mmol, 1 g), copper(I) iodide (0.05 eq, 0.177 mmol 0.034 g) and potassium phosphate tribasic carbonate (2 eq, 7.07 mmol, 1.51 g) are dissolved in 2-propanol (15 ml) under an inert atmosphere of nitrogen. Then, N,N-dimethylpyrrolidin-3-amine (2 eq, 7.07 mmol, 0.807 g) and ethylene glycol (2 eq, 7.07 mmol, 0.394 ml) are added and the reaction mixture heated at 80° C., overnight.

The reaction mixture is dissolved in EtOAc and washed with water. The organic solvent is reduced in vacuo and the residue purified by flash chromatography (0-20% EtOAc in iso-hexane) to afford the title compound; [M+H]$^+$ 270/272.

Step 2: Dimethyl-(1-[3-(4,4,5,5-tetramethyl-[1,3,2]dioxaborolan-2-yl)-phenyl]-pyrrolidin-3-yl)-amine To a solution of 4,4,4',4',5,5,5',5'-octamethyl-2,2'-bi(1,3,2-dioxaborolane) (1.2 eq, 0.535 mmol, 136 mg) and potassium acetate (3 eq, 1.337 mmol, 131 mg) in dry DME (2 ml) under an inert atmosphere of nitrogen are added [1-(3-Bromo-phenyl)-pyrrolidin-3-yl]-dimethyl-amine (Intermediate B25; step 2) (1 eq, 0.446 mmol, 120 mg) and PdCl$_2$dppf (0.1 eq, 0.021 mmol, 17 mg). The reaction mixture is heated using microwave radiation at 90° C. for 1 h 30. The reaction mixture is filtered through Celite® and washed with EtOAc. The organic solvent is reduced in vacuo to afford title compound which is used without further purification.

Intermediate B26

6-(4,4,5,5-Tetramethyl-[1,3,2]dioxaborolan-2-yl)-3, 4-dihydro-1H-isoquinoline-2-carboxylic acid tert-butylester A suspension of tert-butyl-6-bromo-3,4-dihydroisoquinoline-2(1H)-carboxylate (1 eq, 0.320 mmol, 100 mg) in DME (2 ml) under an atmosphere of $N_2$ is treated with dry potassium acetate (2 eq, 0.640 mmol, 63 mg). A mixture of bis-(pinacolato) diboron (1.2 eq, 0.384 mmol, 98 mg) and $PdCl_2$ (dppf).DCM (0.04 eq, 0.0128 mmol, 9.4 mg) is added to the suspension and the resulting mixture is heated using microwave radiation at 100° C. for 1 hour. The mixture is filtered through Celite® (filter material) and concentrated in vacuo to afford the title compound which is used without further purification; $[M+H]^+=360$.

Intermediate B27

5"-(3-Aminomethyl-5-methyl-phenyl boronic acid

A solution of 3-Formyl-5-methylphenylboronic acid (1 eq, 3.05 mmol, 0.5 g) in dry DCM (5 ml) under an inert atmosphere of argon is treated with ammonia solution 35% (1.1 eq, 3.35 mmol, 0.185 ml) followed by acetic acid (1.1 eq, 3.35 mmol, 0.192 ml) and $NaBH(OAc)_3$ (1.2 eq, 3.66 mmol, 0.776 mg) and the resulting mixture is stirred at room temperature overnight. The reaction is quenched by addition of acetonitrile and filtered under vacuum. The filtrate is concentrated in vacuo to afford the title compound which is used without further purification.

Intermediates B28 to B30

(R)-4-((3-methylpiperazin-1-yl)methyl)phenylboronic acid (Intermediate B28)
4-((3,3-dimethylpiperazin-1-yl)methyl)phenylboronic acid (Intermediate B29)
4-((4-(tert-butoxycarbonyl)-3,5-dimethylpiperazin-1-yl)methyl)phenylboronic acid (Intermediate B30)
are prepared analogously to 3-(4-Methyl-piperazin-1-ylmethyl)-phenyl boronic acid (Intermediate B1) from the appropriate amine and boronic acid.

Intermediate C1

(E,Z)-P,P-diphenyl-N-(1-(pyridin-2-yl)ethylidene) phosphinic amide

A solution of 1-pyridin-2-yl-ethanone oxime (1 eq, 5.88 mmol, 0.8 g) and triethylamine (1.2 eq, 7.05 mmol, 0.983 ml) in DCM/Ether (1:1, 16 ml) under an inert atmosphere of nitrogen is cooled at −40° C. and treated with a solution of chlorodiphenylphosphine (1 eq, 5.88 mmol, 1.27 g) in DCM (2 ml) over 2 minutes. After 1 h at −40° C., the reaction mixture is warmed at room temperature and stirred for 4 hours. The resulting suspension is filtered and washed with DCM (10 ml). The filtrate is evaporated to afford the title compound $[M+H]^+$ 321

Intermediate D1

1-Isopropyl-4-(prop-2-ynyl)piperazine

To a suspension of cesium carbonate (1 eq, 0.78 mmol, 0.254 g) in acetone (3 ml) is added 3-bromoprop-1-yne (80% in toluene) (1 eq, 0.78 mmol, 0.1 g) followed by 1-isopropylpiperazine (1 eq, 0.78 mmol, 0.073 ml). The reaction mixture is stirred for 4 hours at room temperature. The resulting suspension is filtered and the filtrate evaporated to afford the title compound; $[M+H]^+$ 167.

Intermediate D2

1-tert-Butyl-4-prop-2-ynyl-piperazine

This compound is prepared analogously to 1-Isopropyl-4-(prop-2-ynyl)piperazine (Intermediate D1) from the appropriate amine.

The invention claimed is:
1. A compound of Formula X:

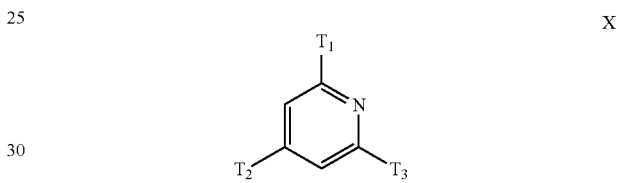

X which compound is selected from the group consisting of compounds 1.1-1.31 and 2.1-2.189 and is in free, salt or solvate form:

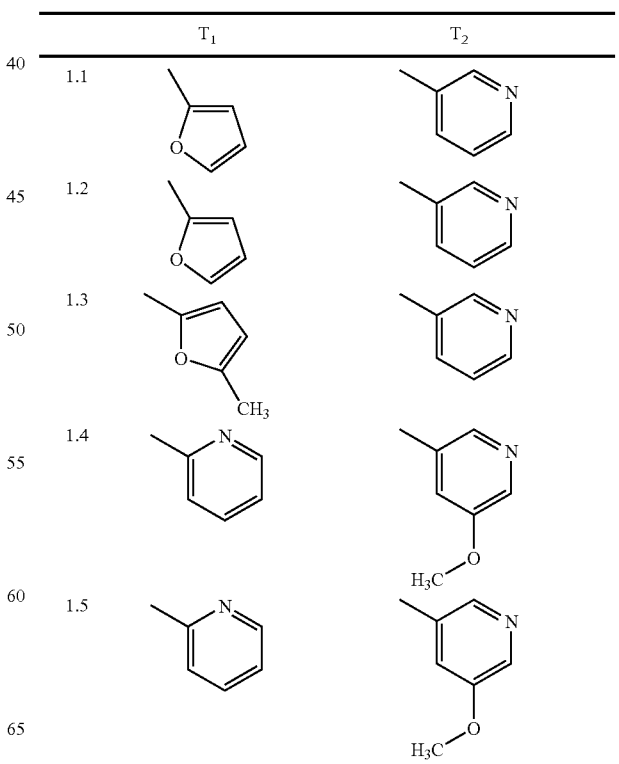

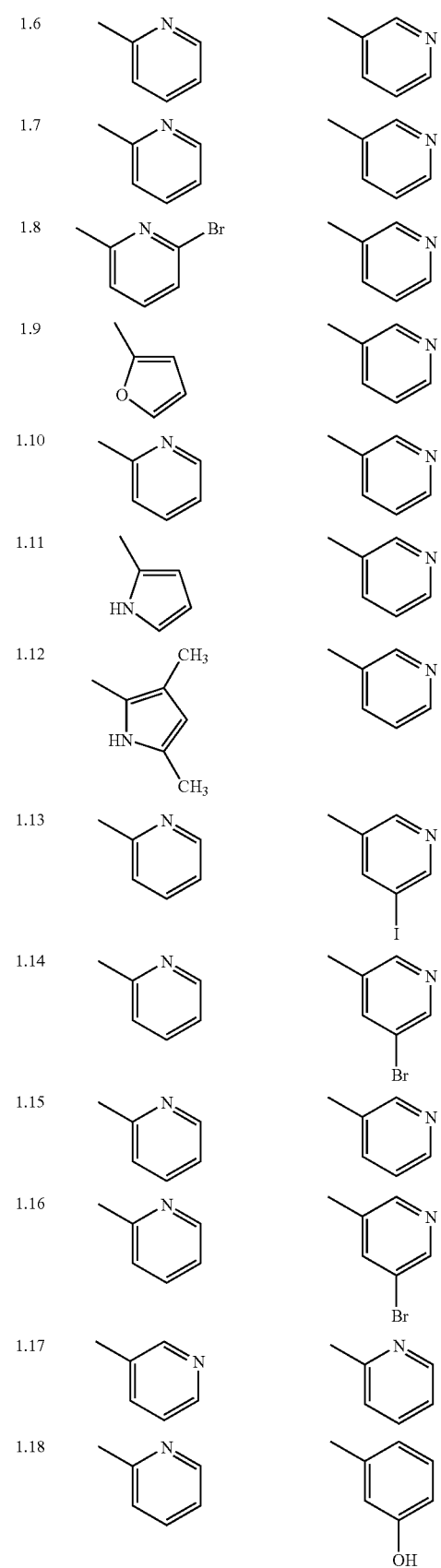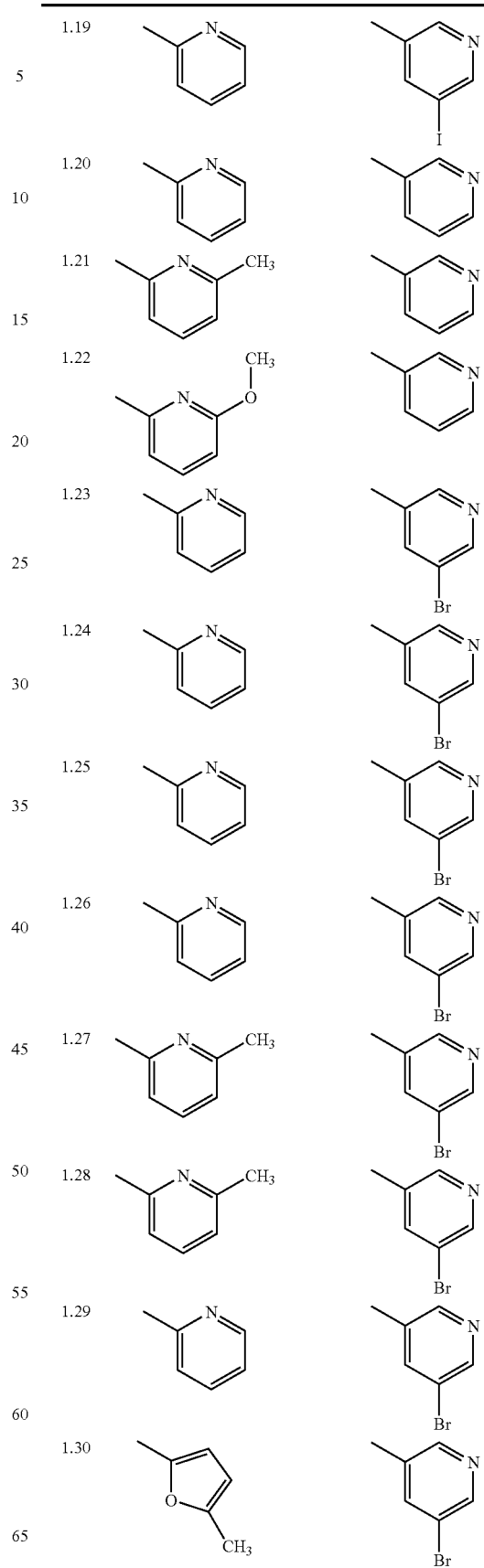

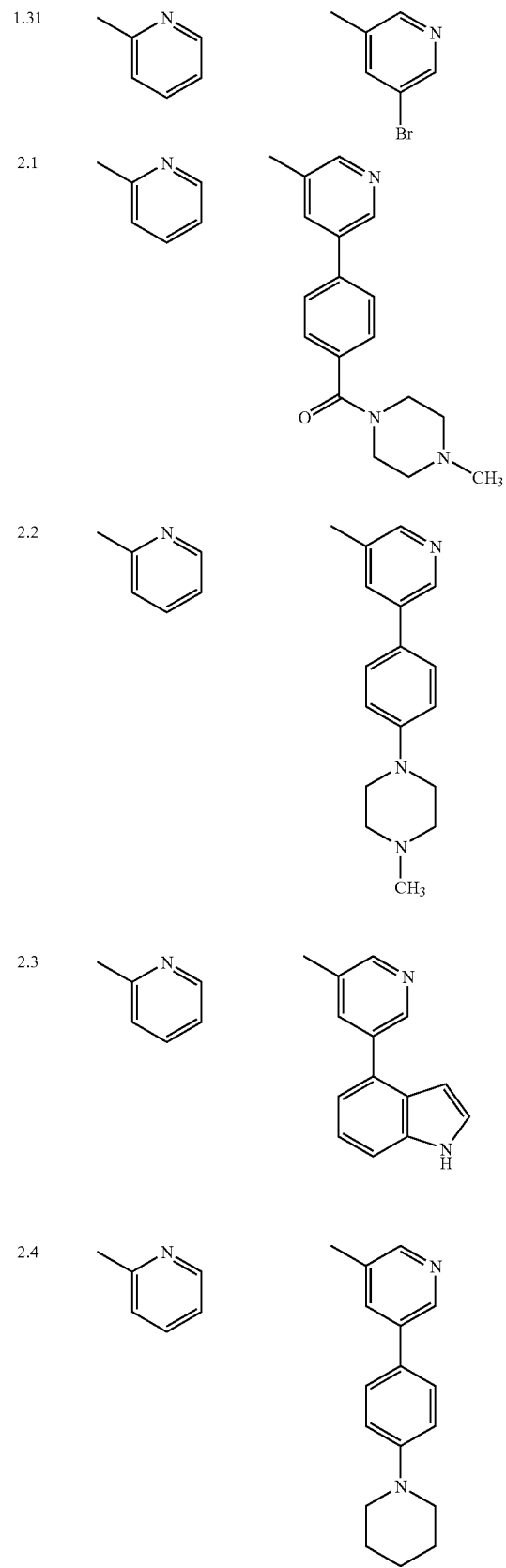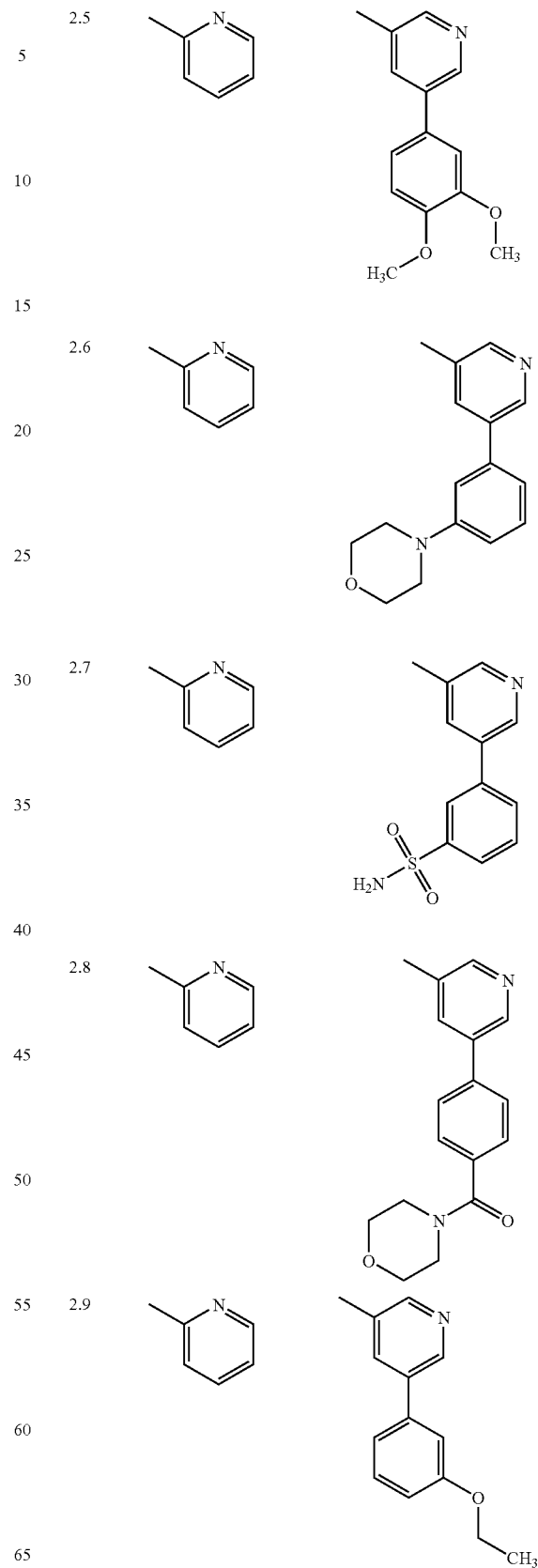

| | | | |
|---|---|---|---|
| 2.10 | 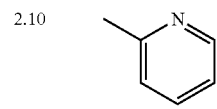 | 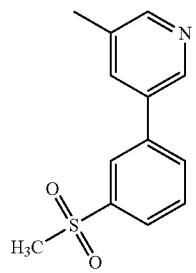 | |
| 2.11 | 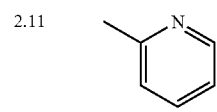 | 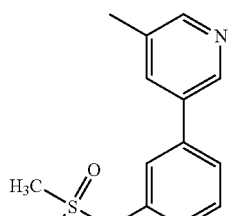 | |
| 2.12 | 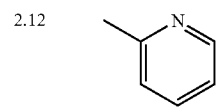 | 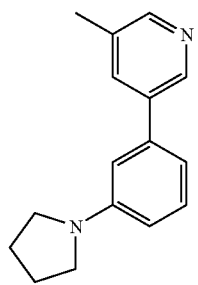 [SMILES: Cc1cncc(-c2cccc(N3CCCC3)c2)c1] | |
| 2.13 | 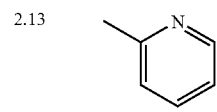 |  | |
| 2.14 | 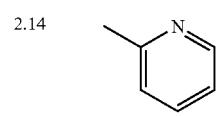 | 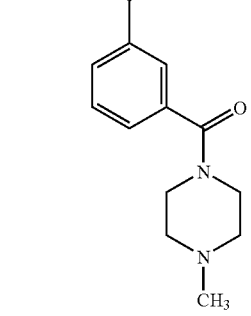 | |
| | | | |
|---|---|---|---|
| 2.15 | 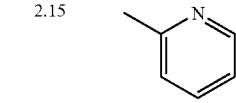 | 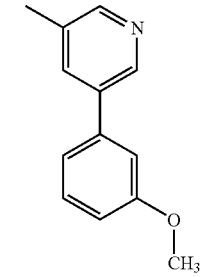 | |
| 2.16 | 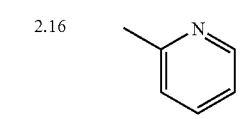 | 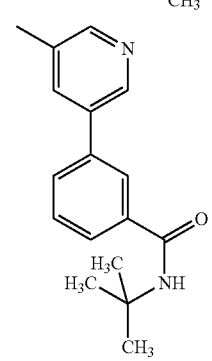 | |
| 2.17 | 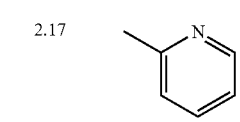 | 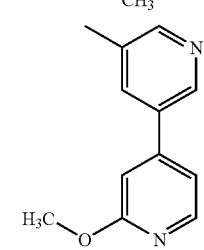 | |
| 2.18 | 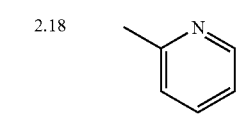 | 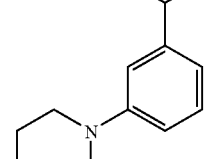 | |
| 2.19 | 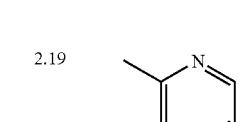 | 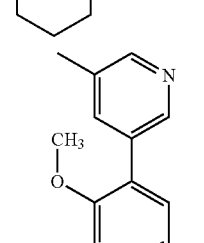 | |
| 2.20 | 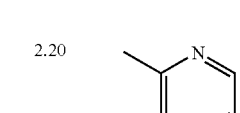 | 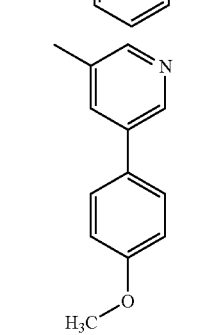 | |

| 177 -continued | 178 -continued |
|---|---|
| 2.21 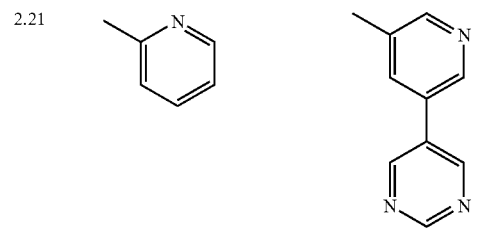 | 2.25 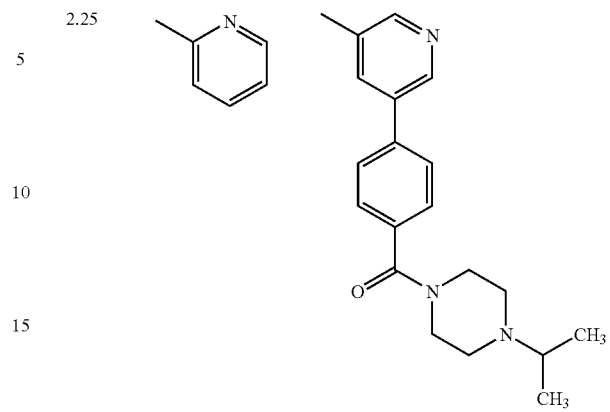 |
| 2.22 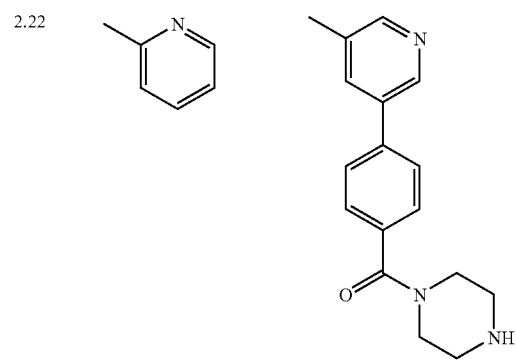 | |
| 2.23 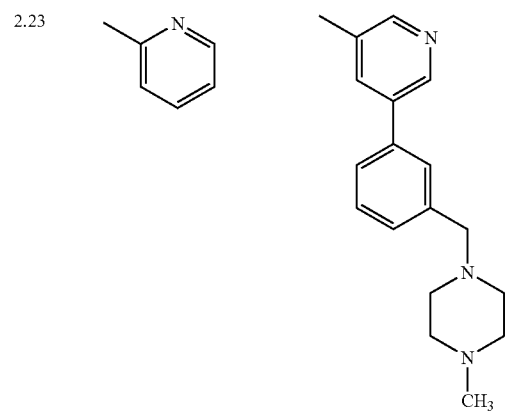 | |
| 2.24 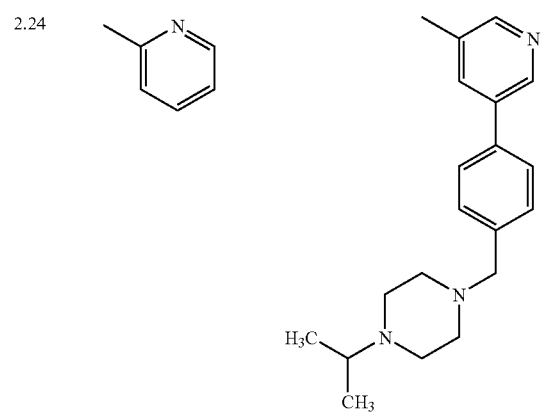 | |

| | | |
|---|---|---|
| 2.29 | 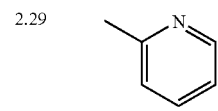 | 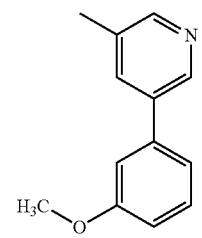 |
| 2.30 | 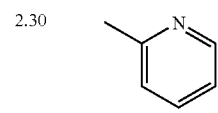 | 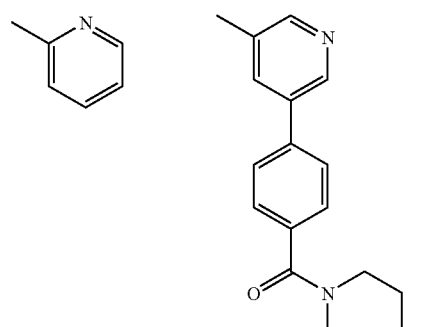 |
| 2.31 | 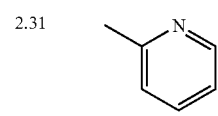 | 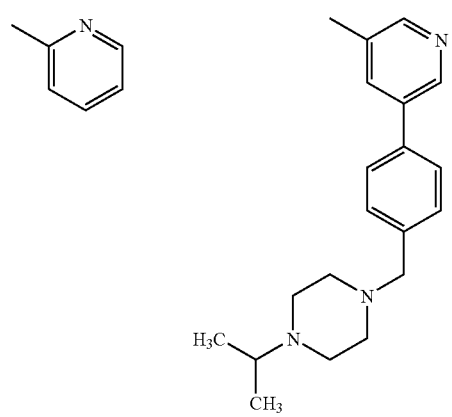 |
| 2.32 | 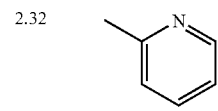 | 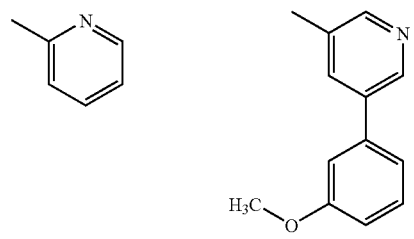 |
| 2.33 | 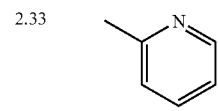 | |
| | | |
|---|---|---|
| 2.34 | 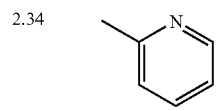 | 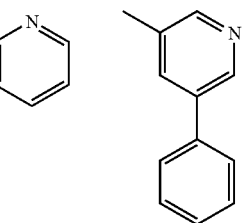 |
| 2.35 | | 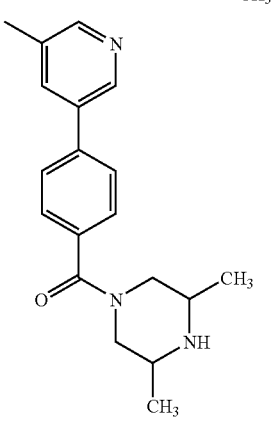 |
| 2.36 | 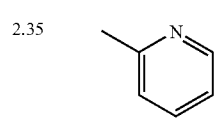 | 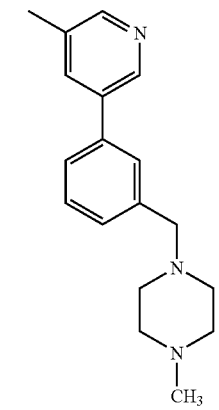 [SMILES: Cc1cncc(-c2cccc(CN3CCN(C)CC3)c2)c1] |
| 2.37 | | 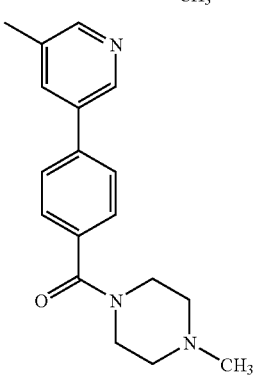 |

-continued
| | | | | | |
|---|---|---|---|---|---|
| 2.38 | 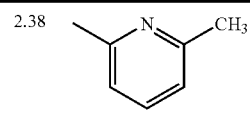 | 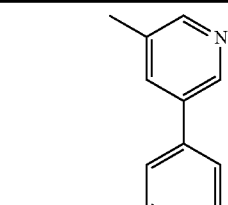 | 2.43 | 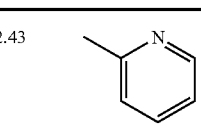 | 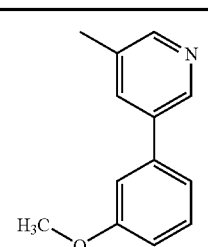 |
| 2.39 | 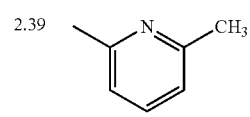 | 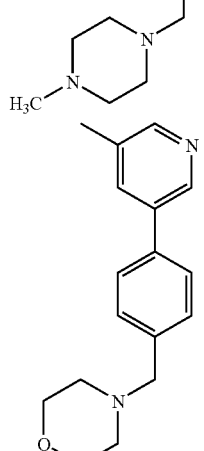 | 2.44 | 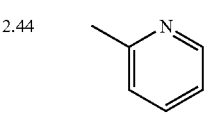 | 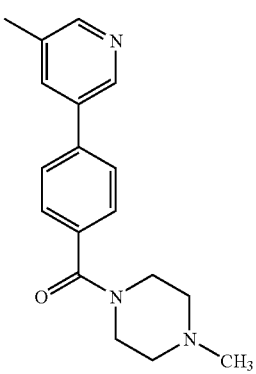 |
| 2.40 | 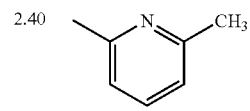 | 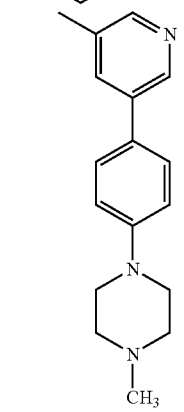 | 2.45 | 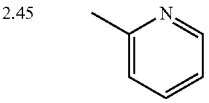 | 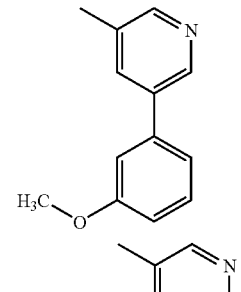 |
| 2.41 | 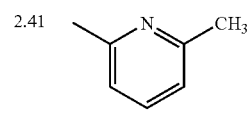 | 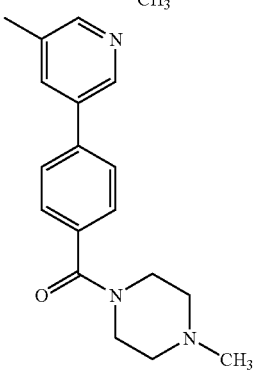 | 2.46 | 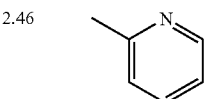 | 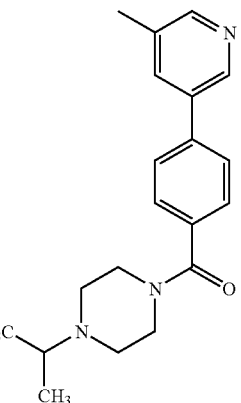 |
| 2.42 | 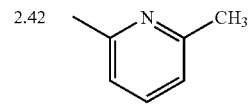 | 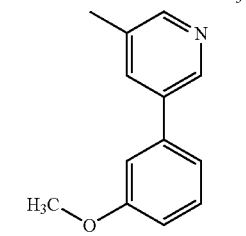 | 2.48 | 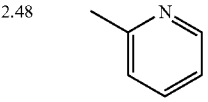 | 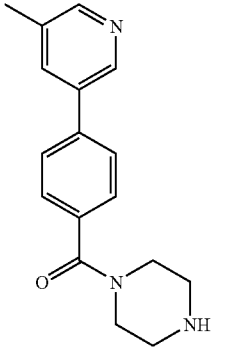 [SMILES: Cc1cncc(-c2ccc(C(=O)N3CCNCC3)cc2)c1] |

| | | |
|---|---|---|
| 2.49 | 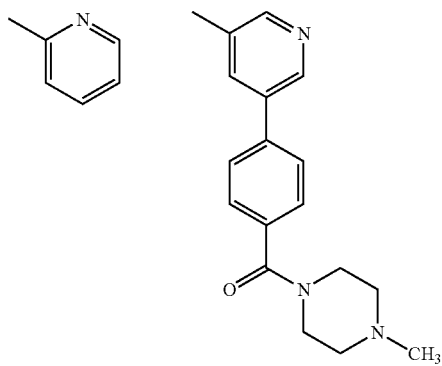 | |
| 2.50 | 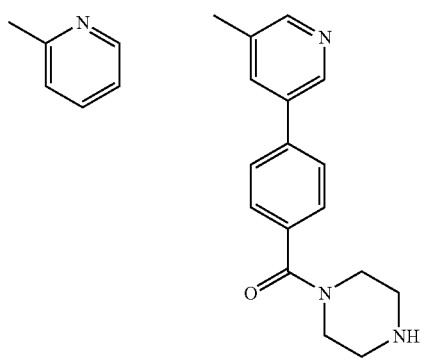 | |
| 2.51 | 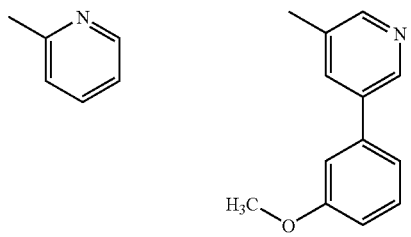 | |
| 2.52 | 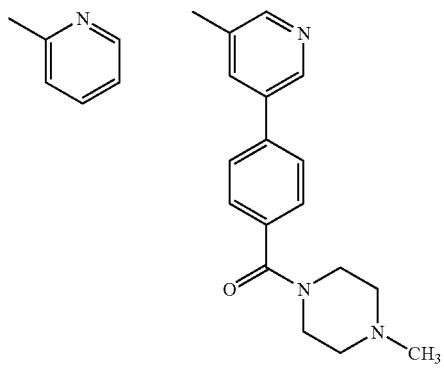 | |
| 2.53 | 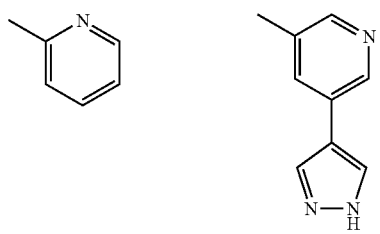 | |
| 2.54 | 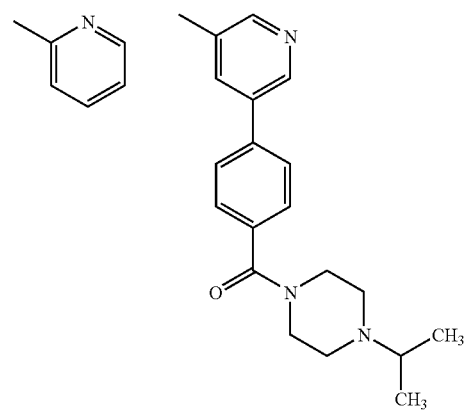 | |
| 2.55 | 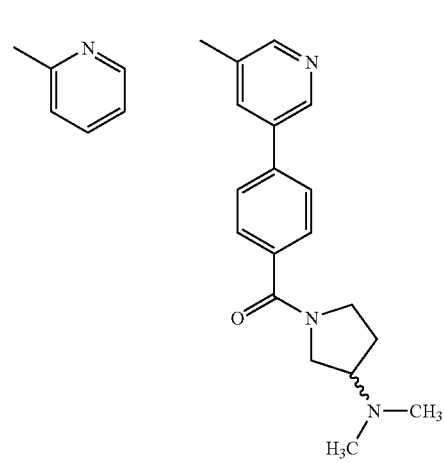 | |
| 2.56 | 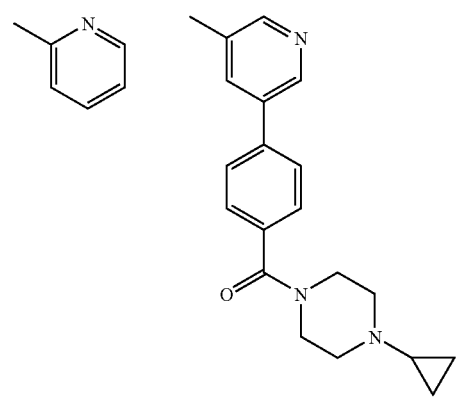 | |
| 2.57 | 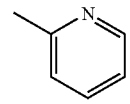 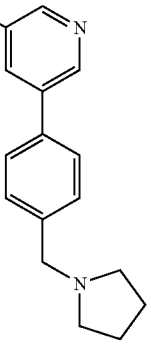 | |

| 2.58 | 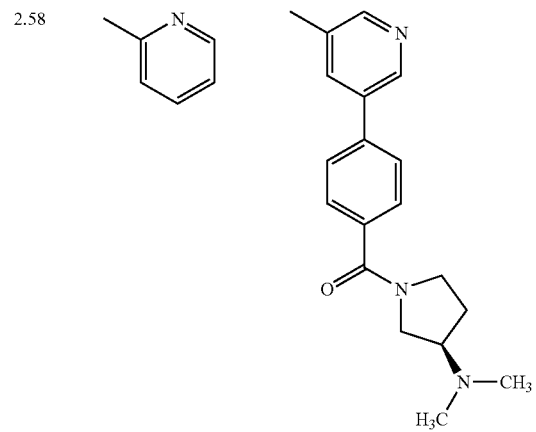 | 2.62 | 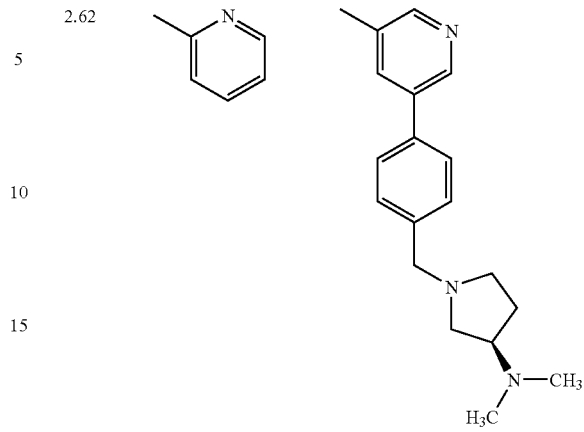 |
| 2.59 | 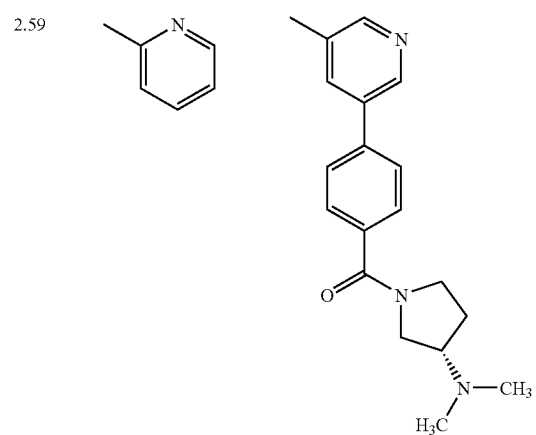 | 2.63 | 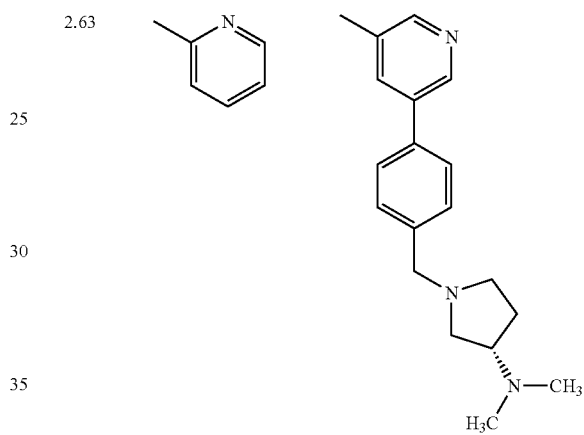 |
| 2.60 | 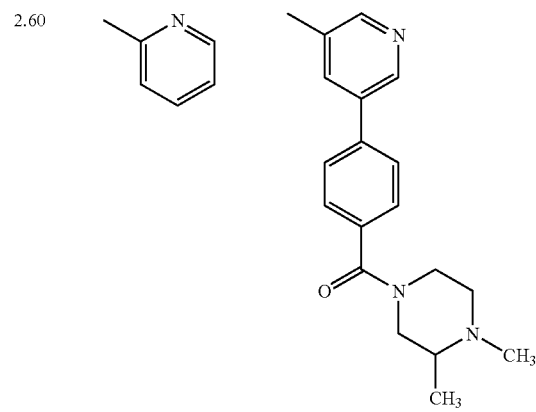 | 2.64 | 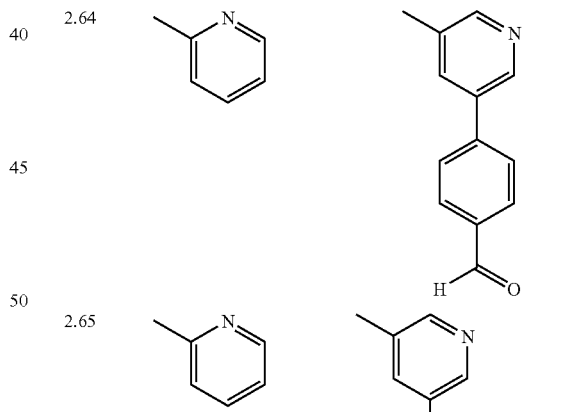 |
| 2.61 | 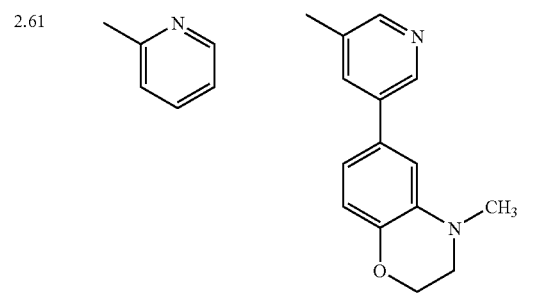 | 2.65 | 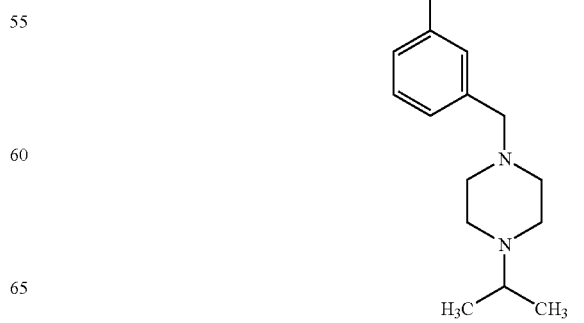 |

| | | |
|---|---|---|
| 2.66 | 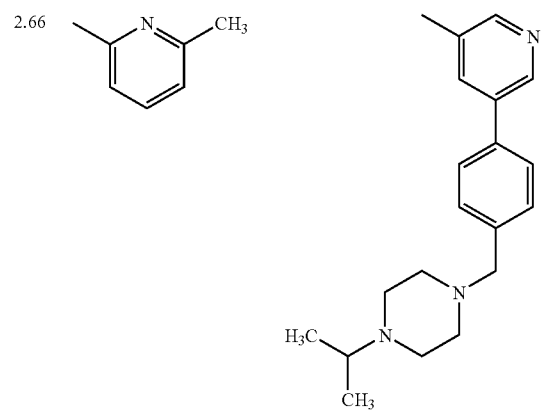 | |
| 2.67 | 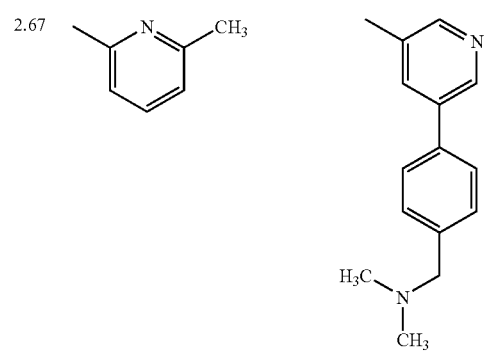 | |
| 2.68 | 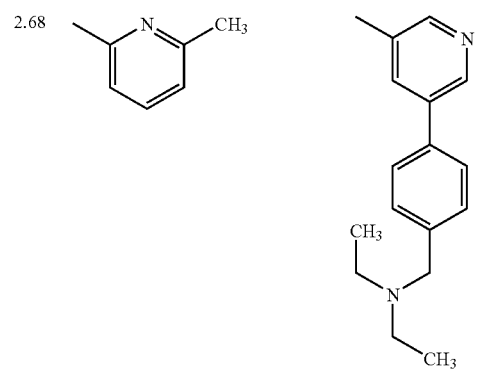 | |
| 2.69 | 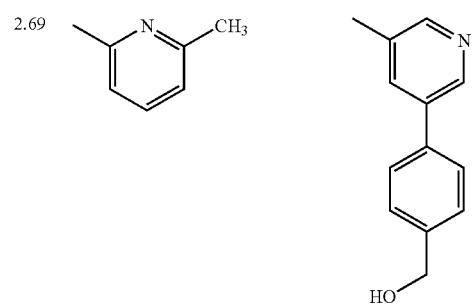 | |
| 2.70 | 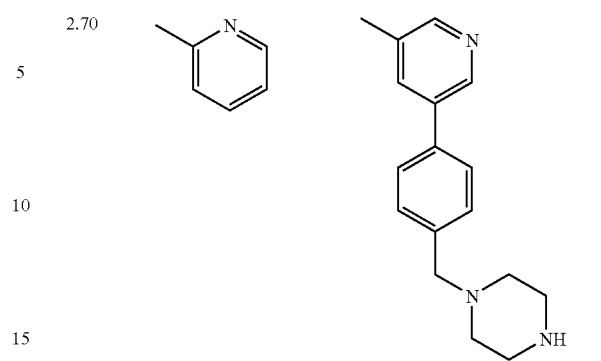 | |
| 2.71 | 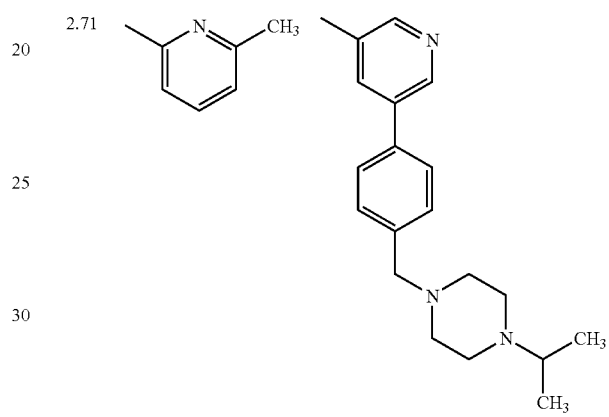 | |
| 2.72 | 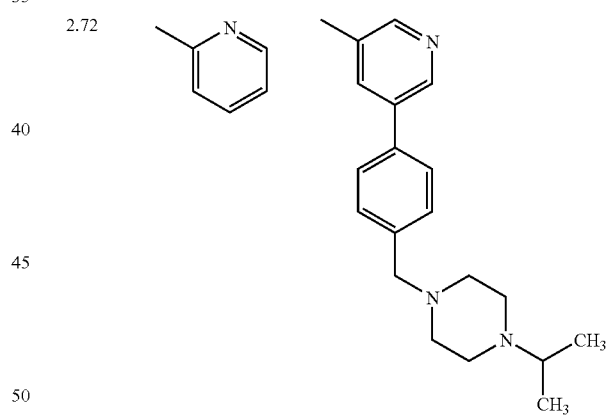 | |
| 2.73 | 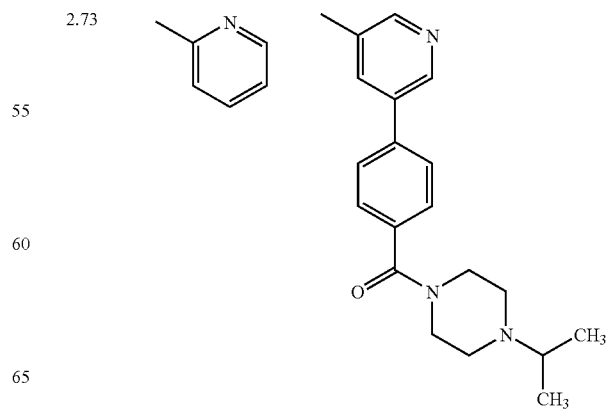 | |

| 189 -continued | | 190 -continued | |
|---|---|---|---|
| 2.74 | 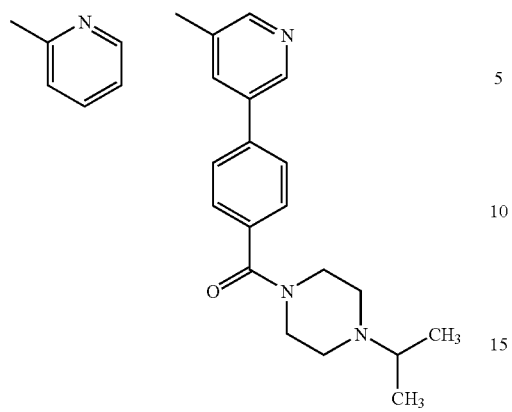 | 2.78 | 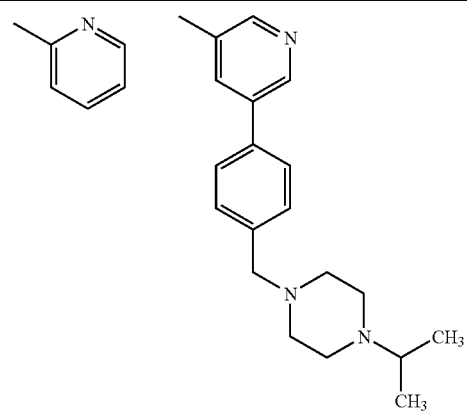 |
| 2.75 | 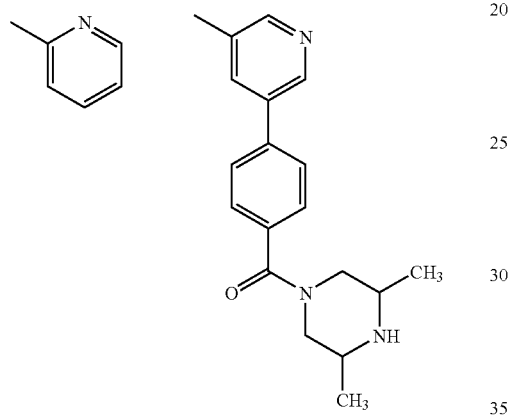 | 2.79 | 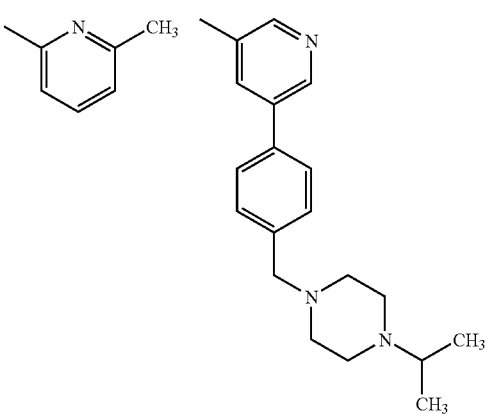 |
| 2.76 | 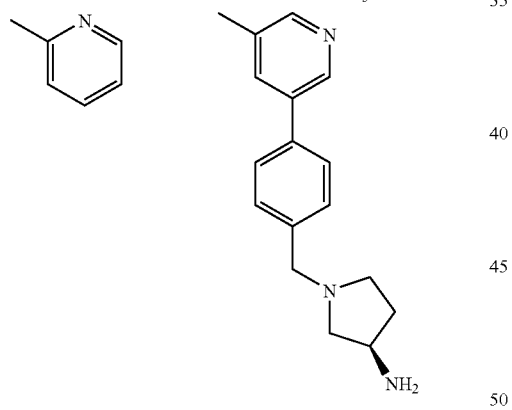 | 2.80 | 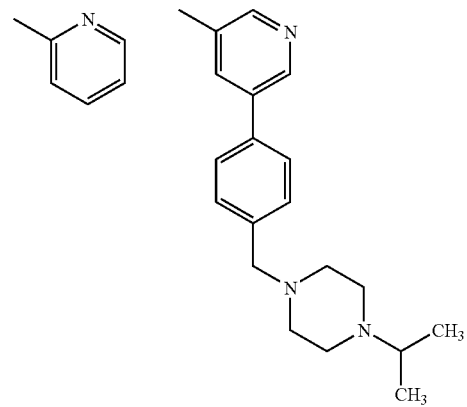 |
| 2.77 | 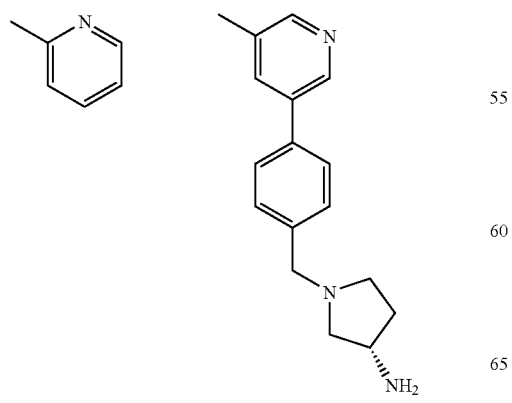 | 2.81 | 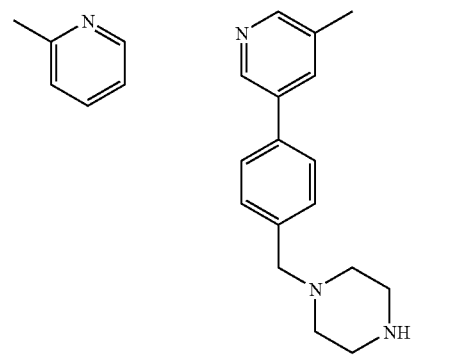 |

| | | |
|---|---|---|
| 2.82 | 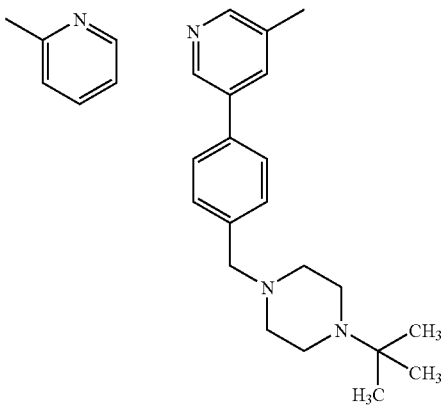 | |
| 2.83 | 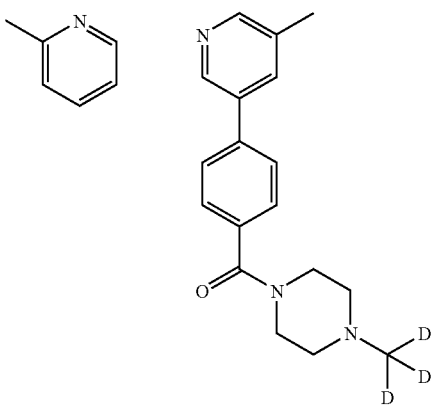 | |
| 2.84 | 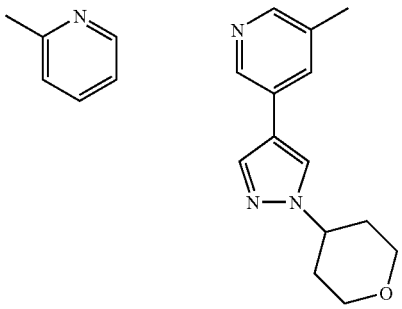 | |
| 2.85 | 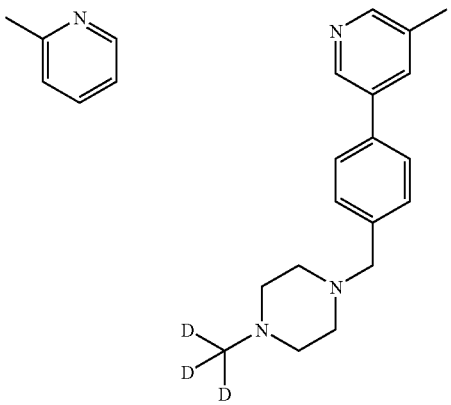 | |
| | | |
|---|---|---|
| 2.86 | 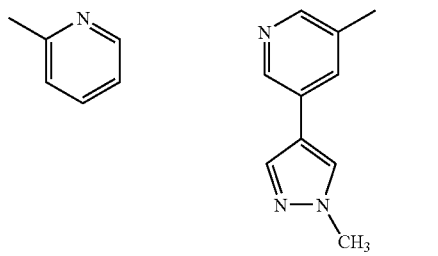 | |
| 2.87 | 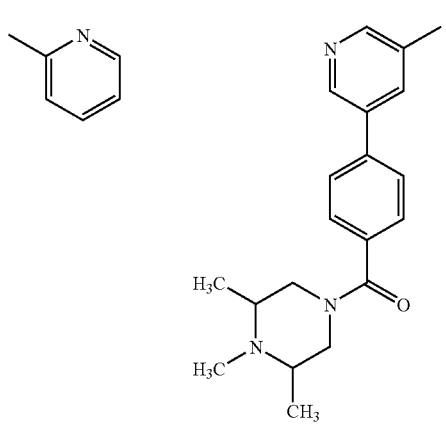 | |
| 2.88 | 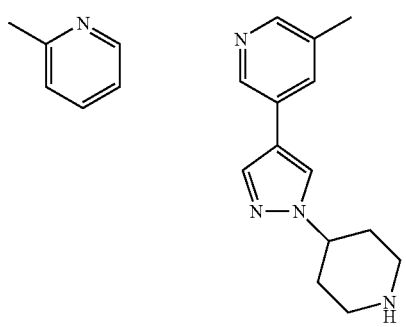 | |
| 2.89 | 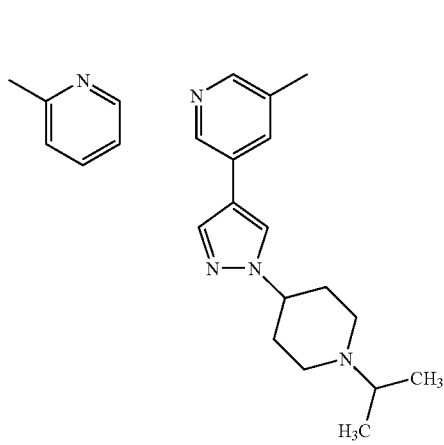 | |

| | | |
|---|---|---|
| 2.90 | 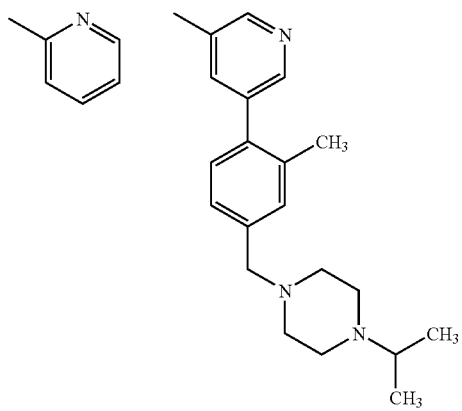 | |
| 2.91 | 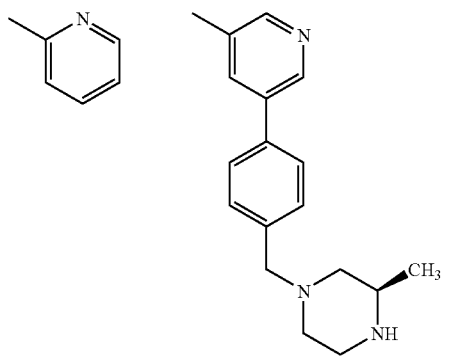 | |
| 2.92 | 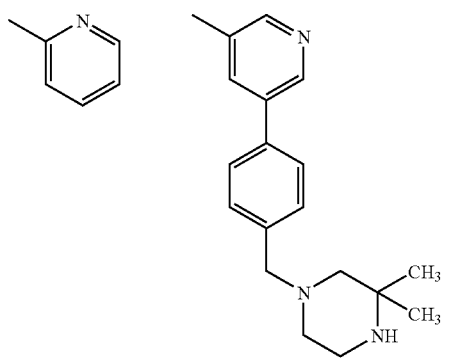 | |
| 2.93 | 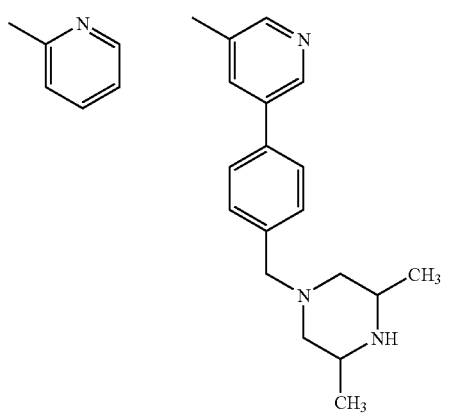 | |
| 2.94 | 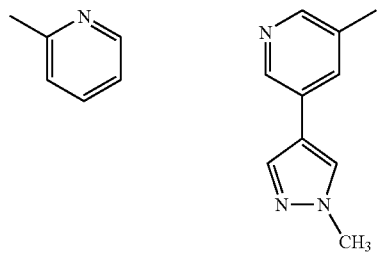 | |
| 2.95 | 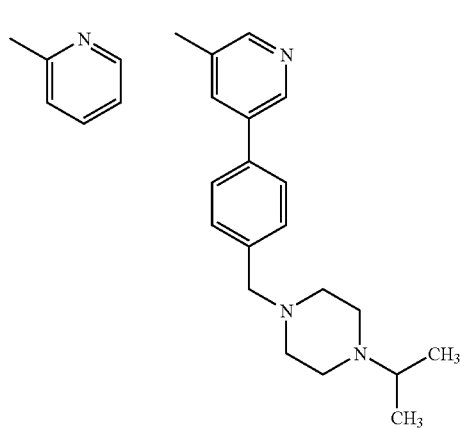 | |
| 2.96 | 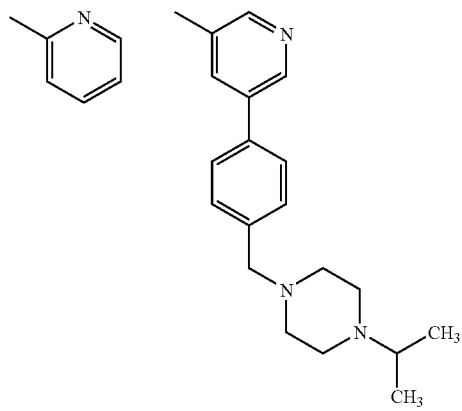 | |
| 2.97 | 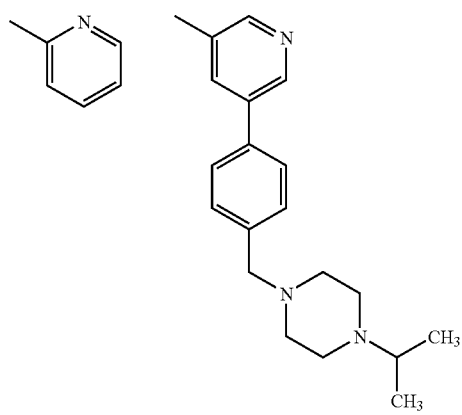 | |

| | | |
|---|---|---|
| 2.98 | 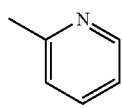 | 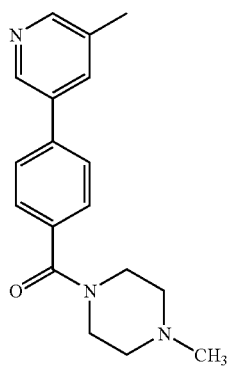 [SMILES: Cc1cncc(-c2ccc(C(=O)N3CCN(C)CC3)cc2)c1] |
| 2.99 | 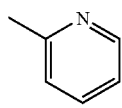 | 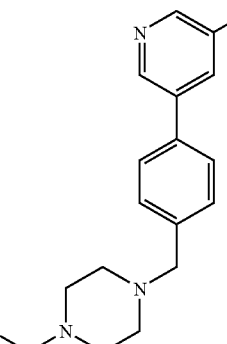 |
| 2.100 | 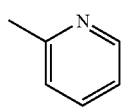 | 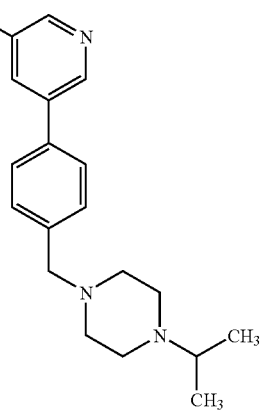 |
| 2.101 | 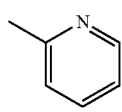 | 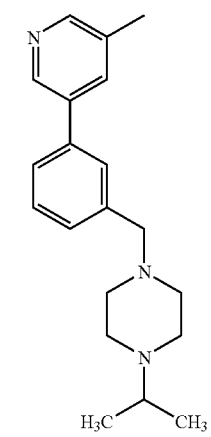 [SMILES: Cc1cncc(-c2cccc(CN3CCN(C(C)C)CC3)c2)c1] |
| 2.102 | 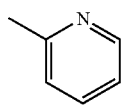 | 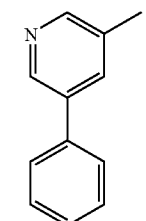 |
| 2.103 | 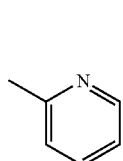 | 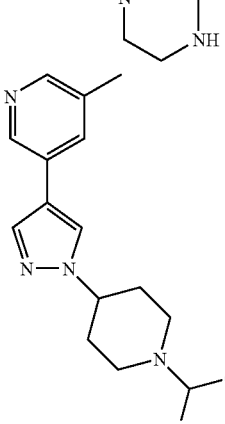 |
| 2.104 | 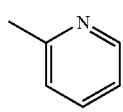 | 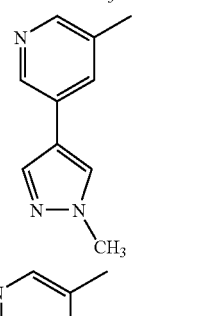 |
| 2.105 | 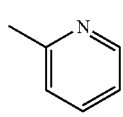 | 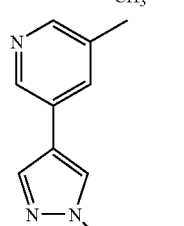 |
| 2.106 |  | 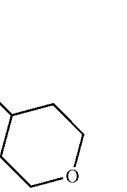 |

| | |
|---|---|
| 2.107 | 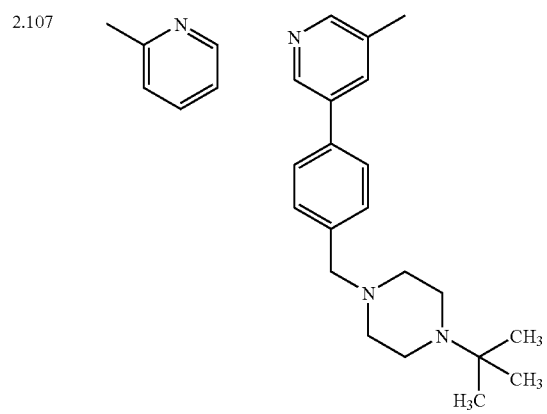 |
| 2.108 | 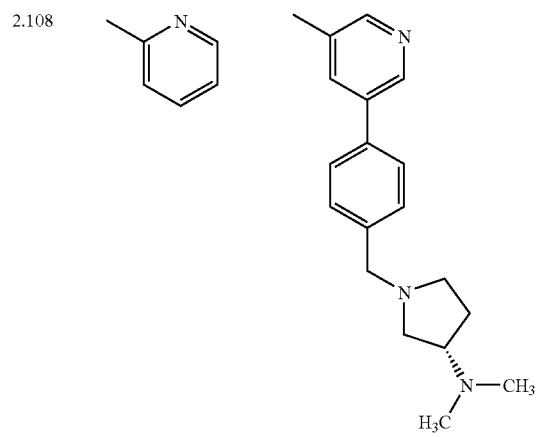 |
| 2.109 | 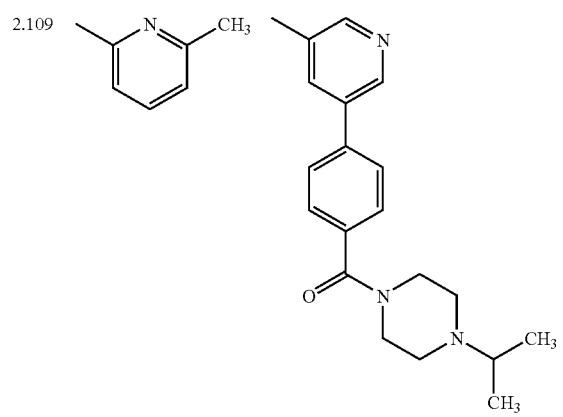 |
| 2.110 | 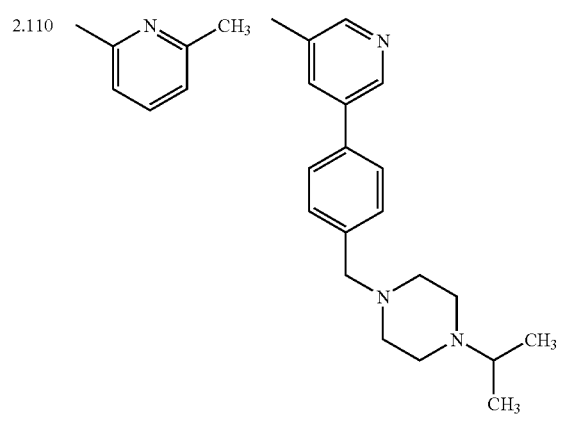 |
| | |
|---|---|
| 2.111 | |
| 2.112 | 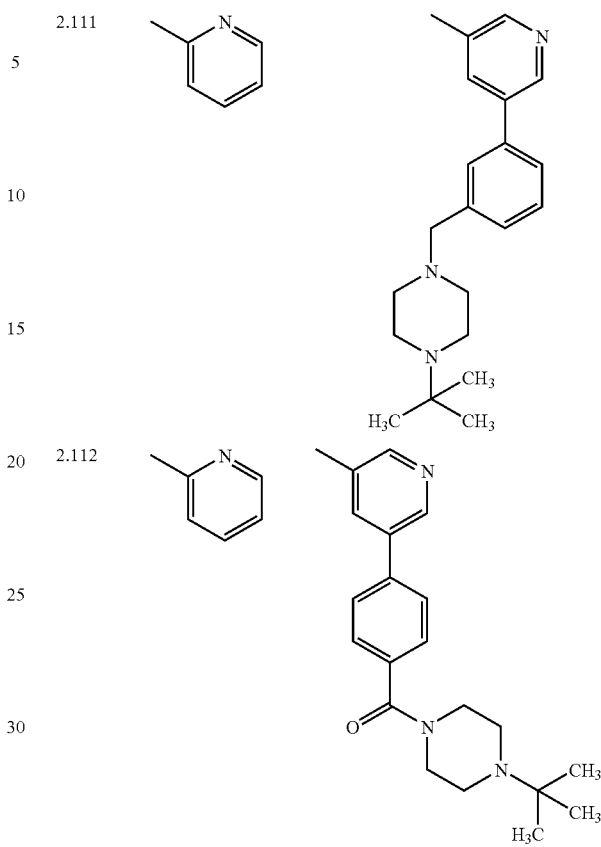 |
| 2.113 | |
| 2.114 | 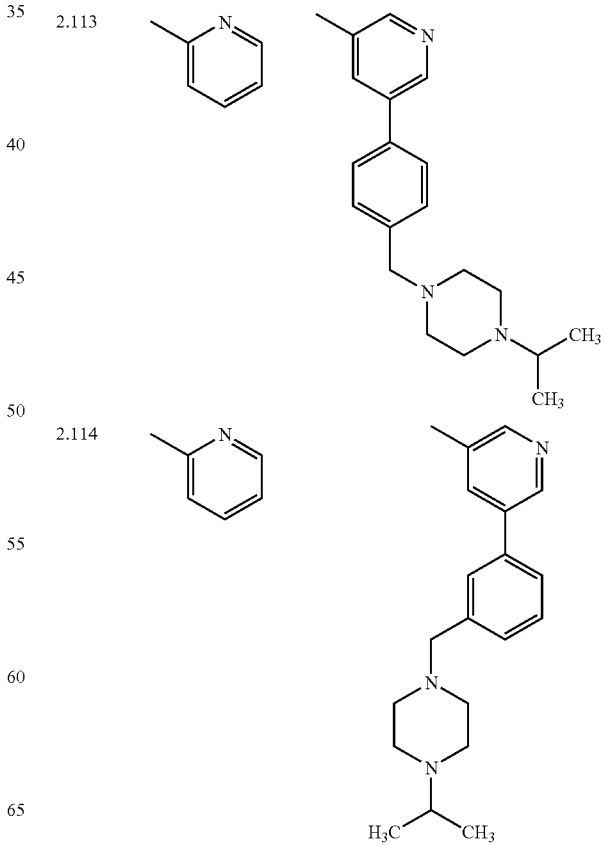 |

| | | | | | |
|---|---|---|---|---|---|
| 2.115 | 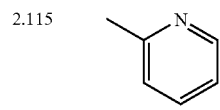 | 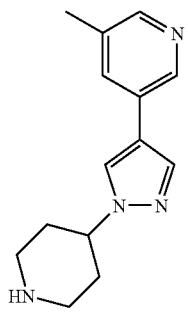 | 2.119 | 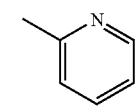 | 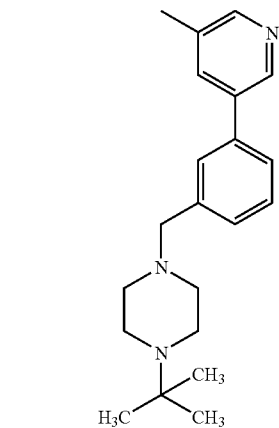 |
| 2.116 | 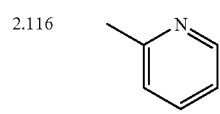 | 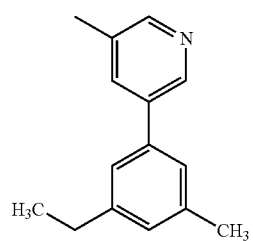 [SMILES: CCc1cc(C)cc(-c2cncc(C)c2)c1] | 2.120 | 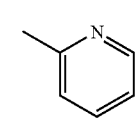 | 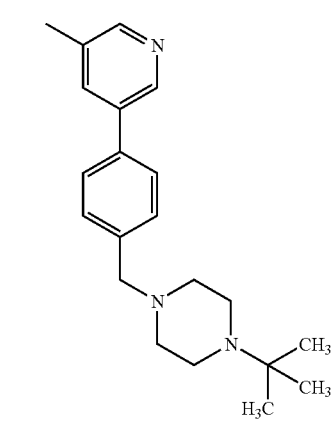 |
| 2.117 | 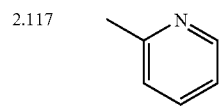 | 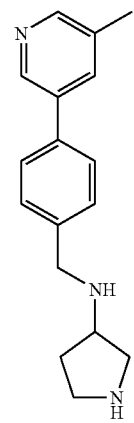 [SMILES: Cc1cncc(-c2ccc(CNC3CCNC3)cc2)c1] | 2.121 | 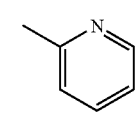 | 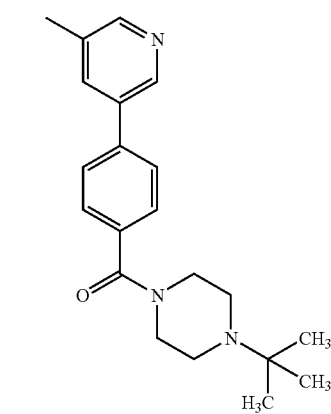 [SMILES: Cc1cncc(-c2ccc(C(=O)N3CCN(C(C)(C)C)CC3)cc2)c1] |
| 2.118 | 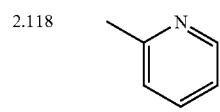 | 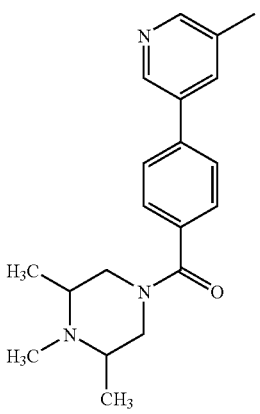 | 2.122 | 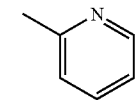 | 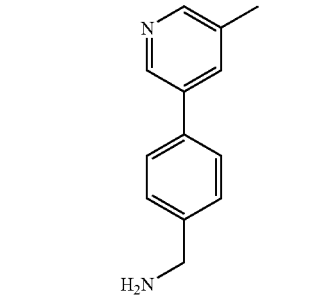 |

| | | | | | |
|---|---|---|---|---|---|
| 2.123 | 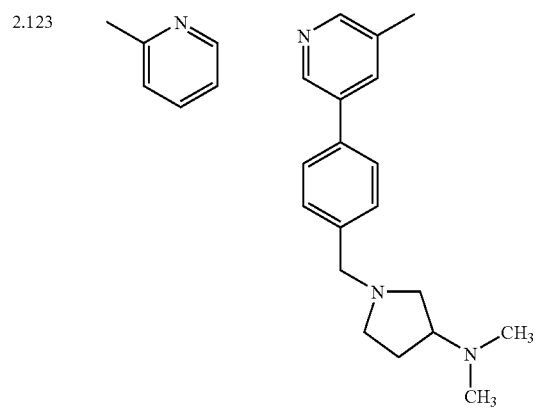 | | 2.127 | 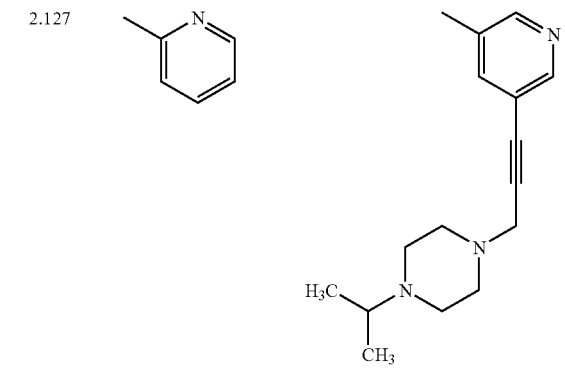 | |
| 2.124 | 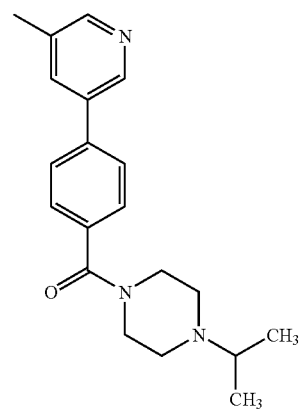 [SMILES: Cc1cncc(-c2ccc(C(=O)N3CCN(C(C)C)CC3)cc2)c1] | | 2.128 |  | |
| | | | | 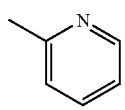 | |
| 2.125 | 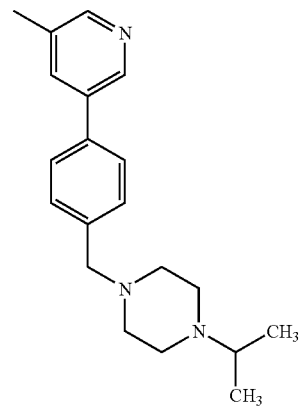 [SMILES: Cc1cncc(-c2ccc(CN3CCN(C(C)C)CC3)cc2)c1] | | 2.129 |  | |
| | | | | 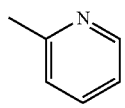 | |
| 2.126 | 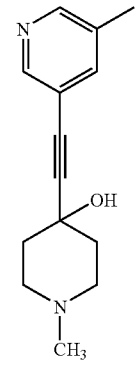 [SMILES: Cc1cncc(C#CC2(O)CCN(C)CC2)c1] | | 2.130 |  | |
| | | | 2.131 | 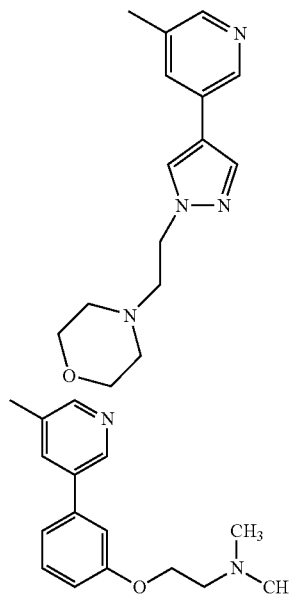 | |

-continued
| | | |
|---|---|---|
| 2.132 | 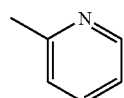 | 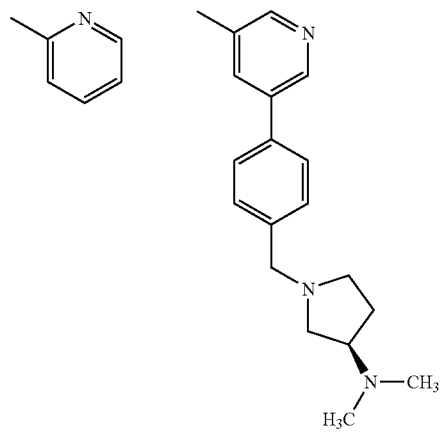 |
| 2.133 | 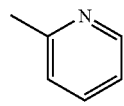 | 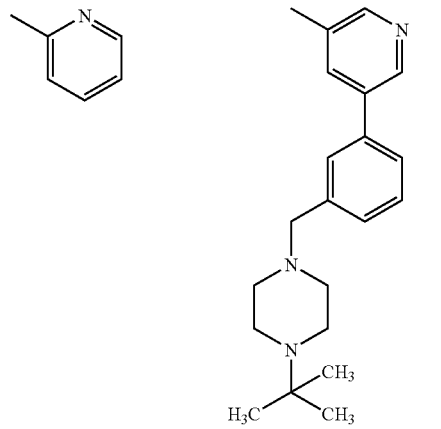 |
| 2.134 | 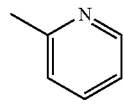 | 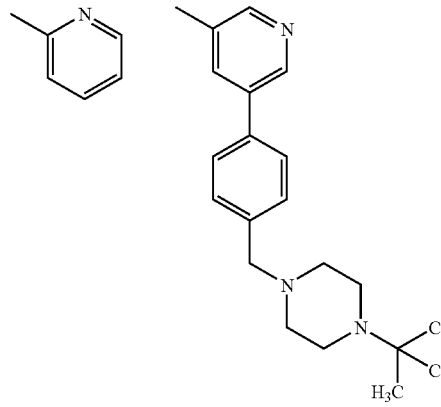 |
| 2.135 | 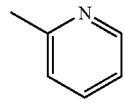 | 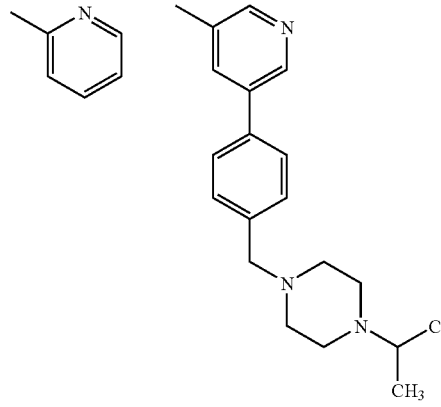 |
-continued
| | | |
|---|---|---|
| 2.136 | 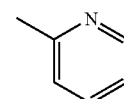 | 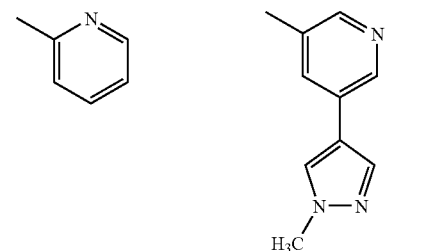 |
| 2.137 | 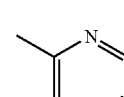 | 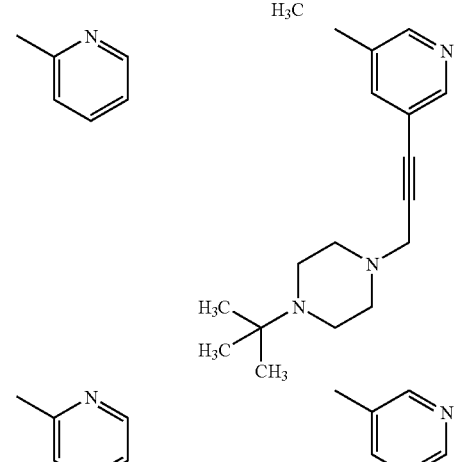 |
| 2.138 | 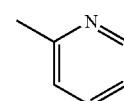 | 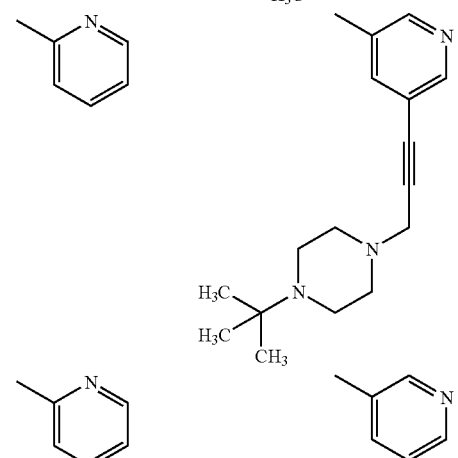 |
| 2.139 | 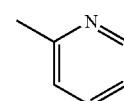 | 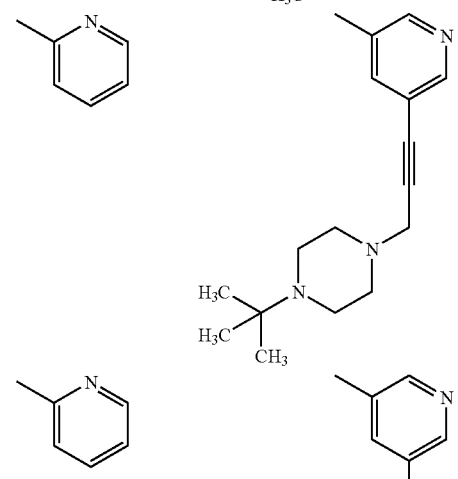 |
| 2.140 | 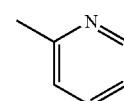 | 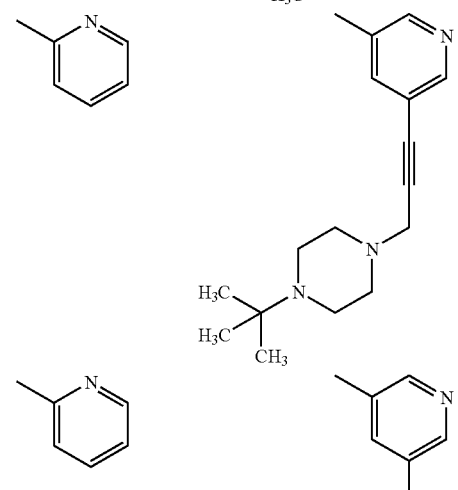 |

| | | |
|---|---|---|
| 2.141 | 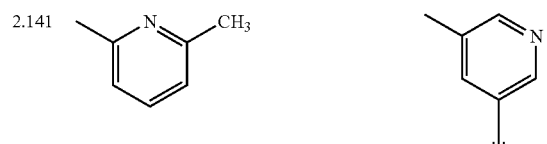 | |
| 2.142 | 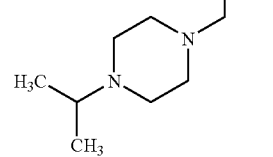 | 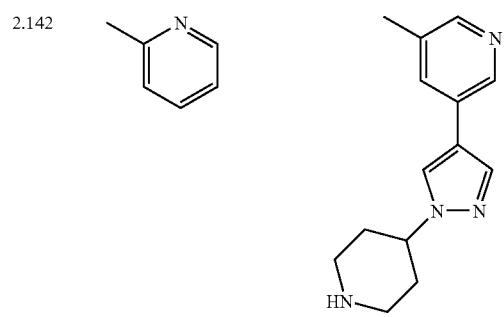 |
| 2.143 | | |
| 2.144 | 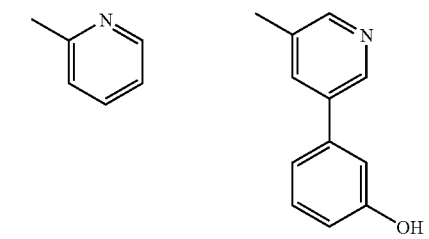 | |
| 2.145 | 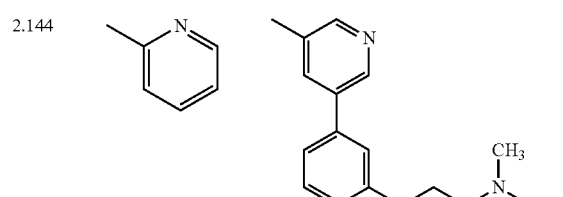 | |
| | 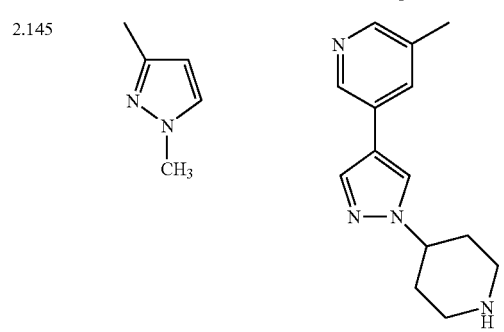 | |
| | | |
|---|---|---|
| 2.146 | 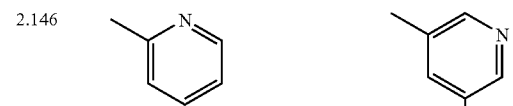 | 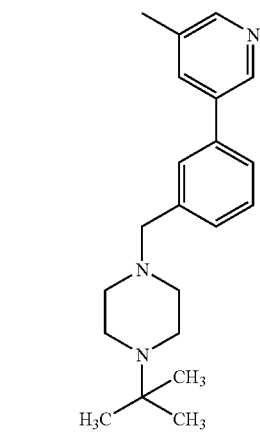 [SMILES: Cc1cncc(-c2cccc(CN3CCN(C(C)(C)C)CC3)c2)c1] |
| 2.147 | 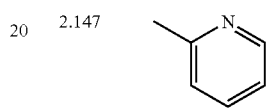 | 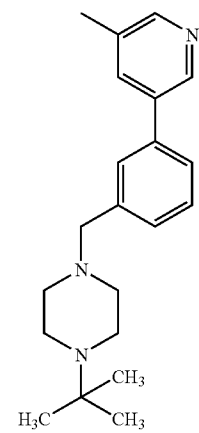 [SMILES: Cc1cncc(-c2cccc(CN3CCN(C(C)(C)C)CC3)c2)c1] |
| 2.148 | 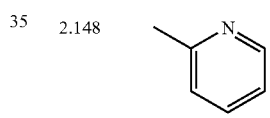 | 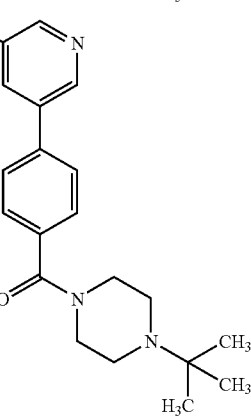 |
| 2.149 | 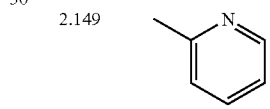 | 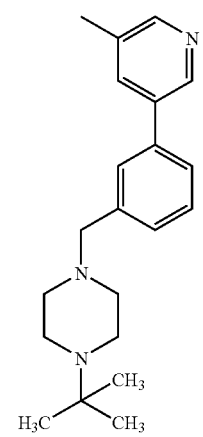 [SMILES: Cc1cncc(-c2cccc(CN3CCN(C(C)(C)C)CC3)c2)c1] |
| | 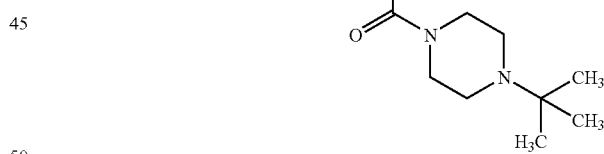 | |

| 207 -continued | | 208 -continued | |
|---|---|---|---|
| 2.150 | 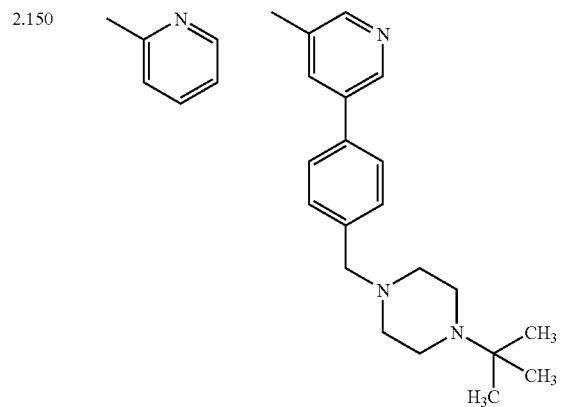 | 2.154 | 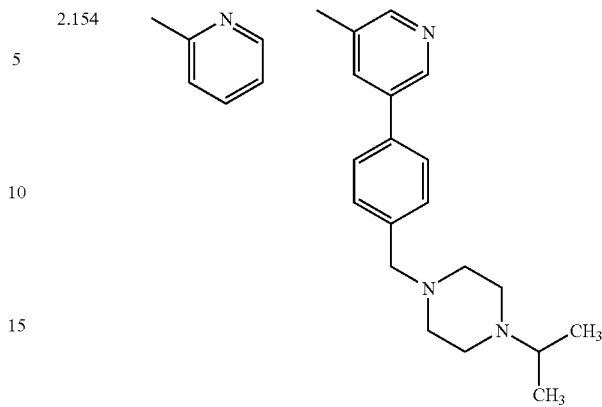 |
| 2.151 | 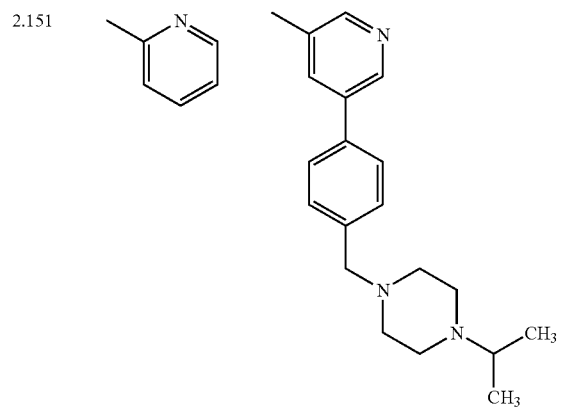 | 2.155 | 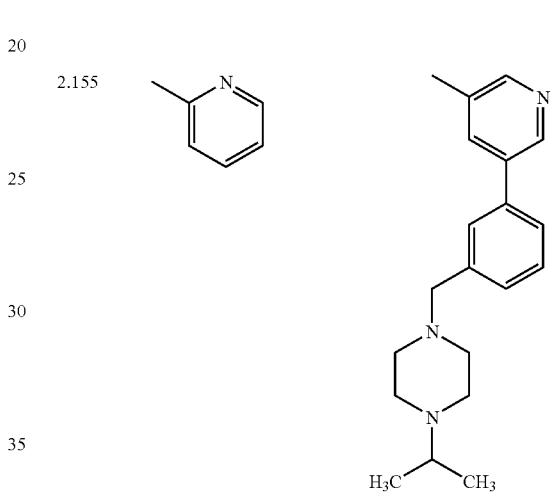 |
| 2.152 | 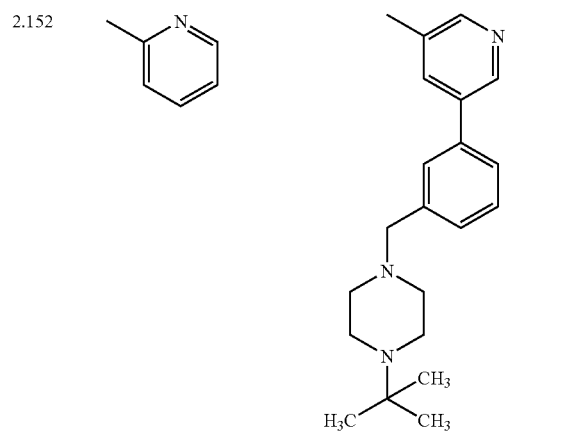 | 2.156 | 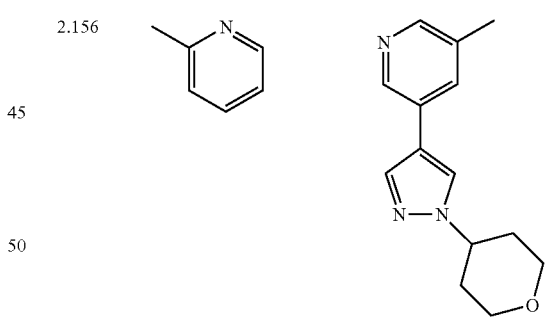 |
| 2.153 | 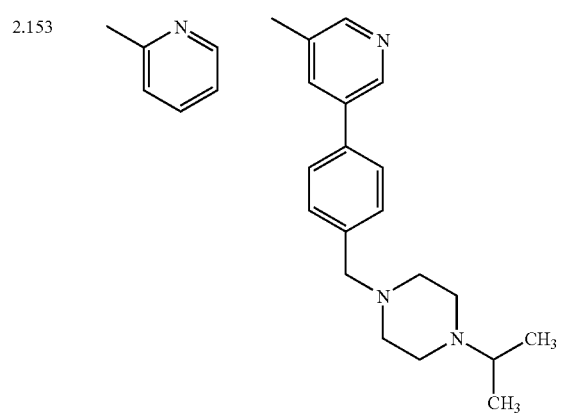 | 2.157 | 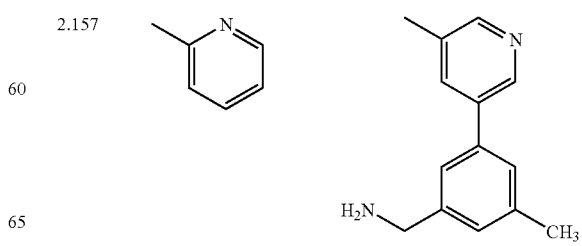 |

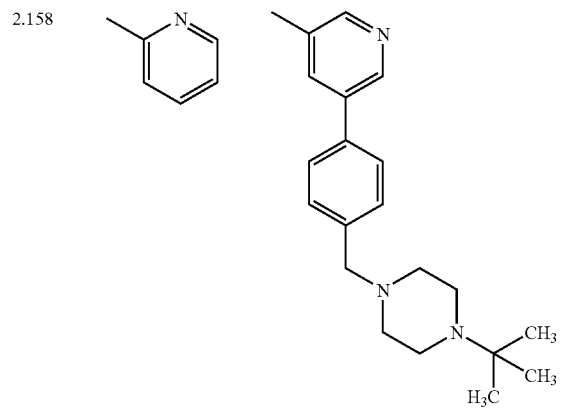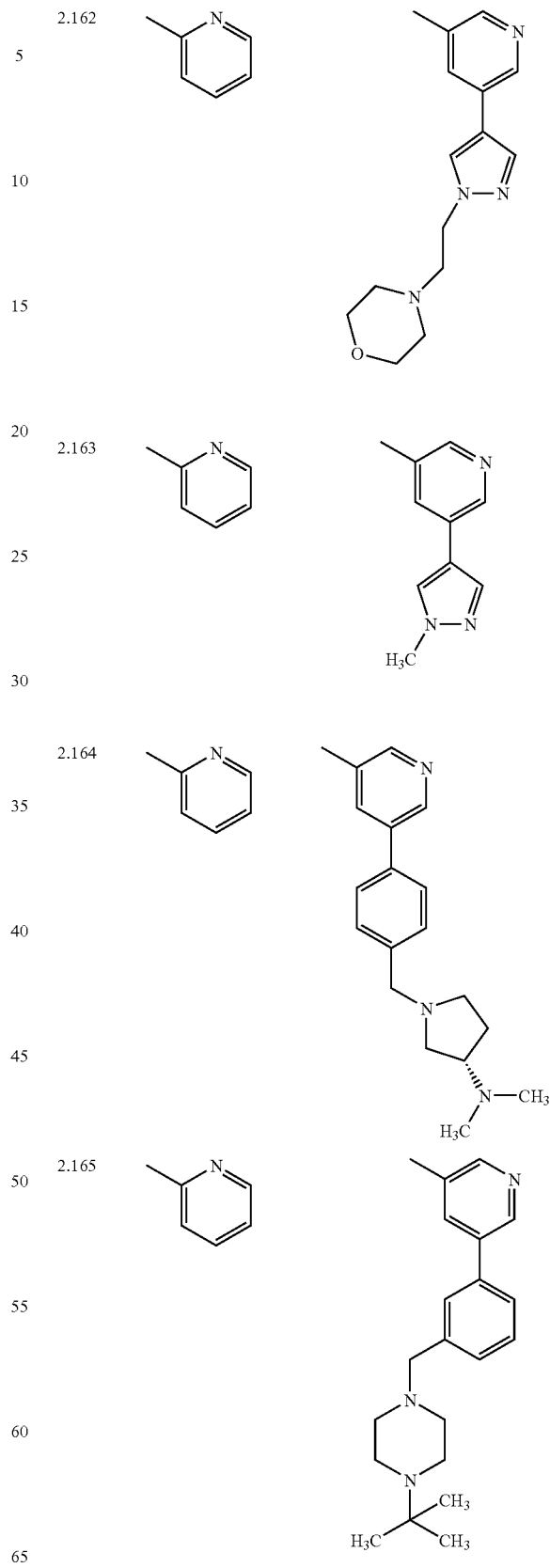

| 211 -continued | 212 -continued |
|---|---|
| 2.166 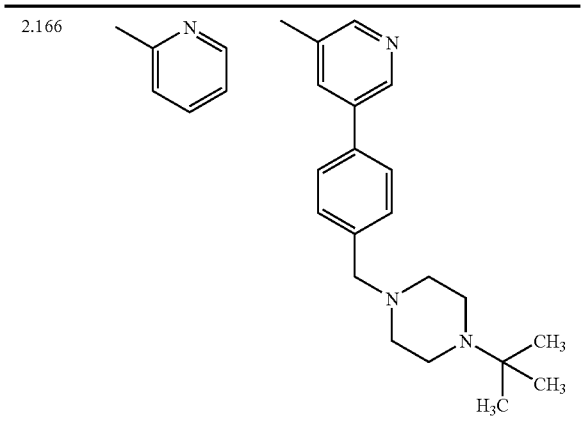 | 2.170 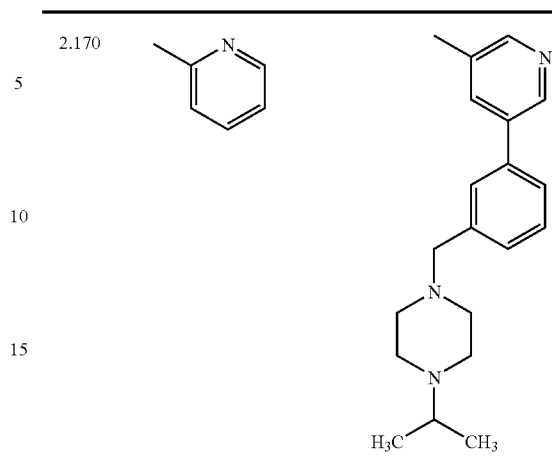 |
| 2.167 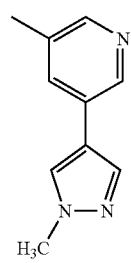 | 2.171 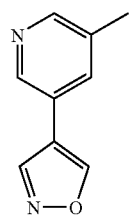 |
| 2.168 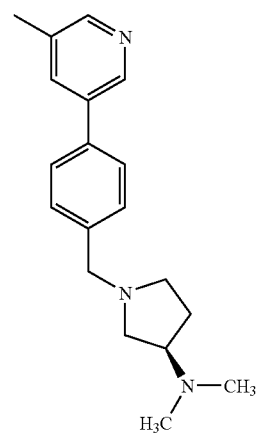 | 2.172 <br>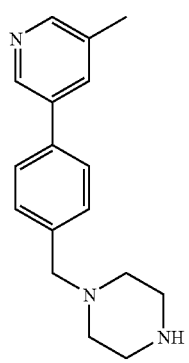 |
| 2.169 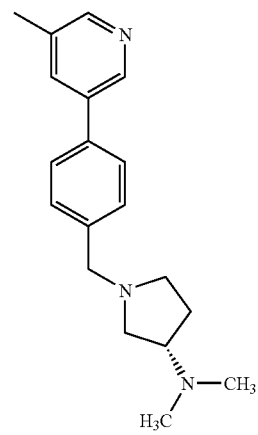 | 2.173 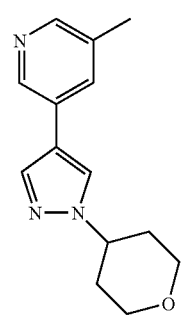 |

| | | | | | |
|---|---|---|---|---|---|
| 2.174 | 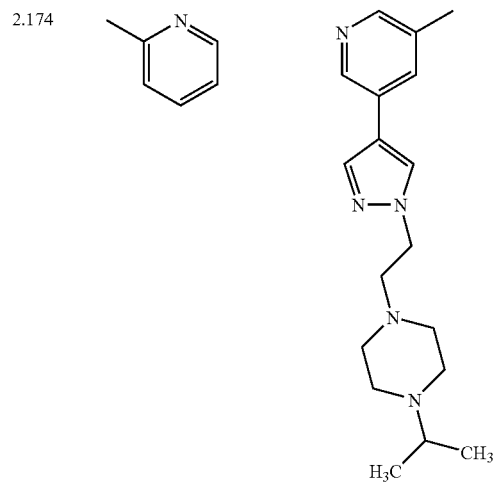 | | 2.178 | 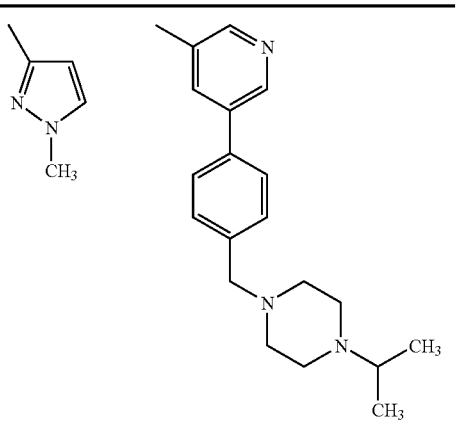 | |
| 2.175 | 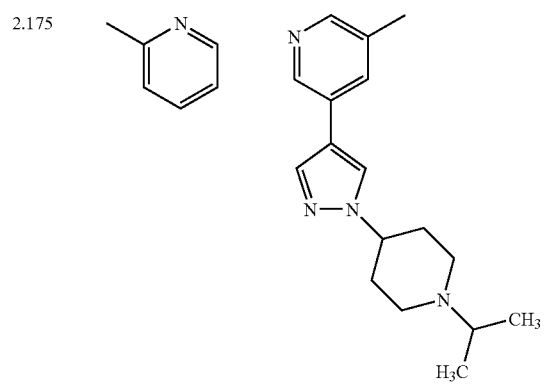 | | 2.179 | 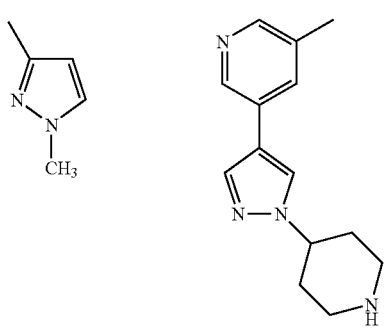 | |
| 2.176 | 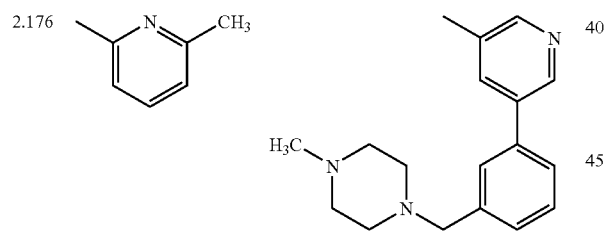 | | 2.180 | 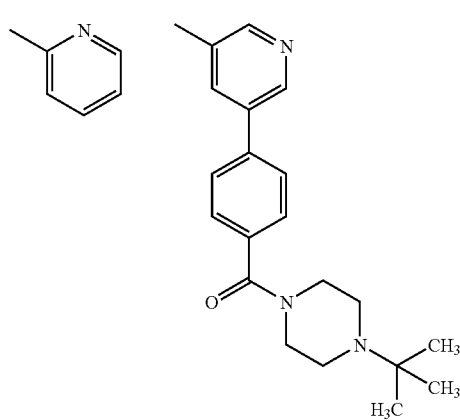 | |
| 2.177 | 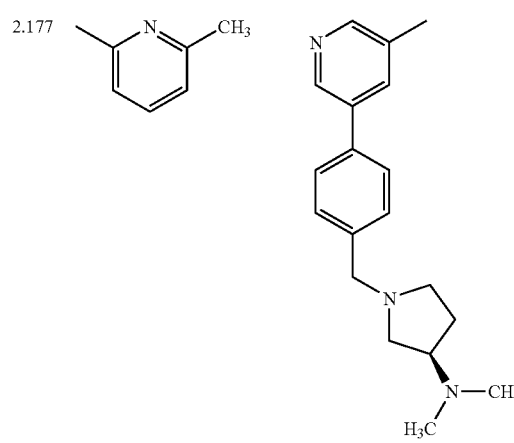 | | 2.181 | 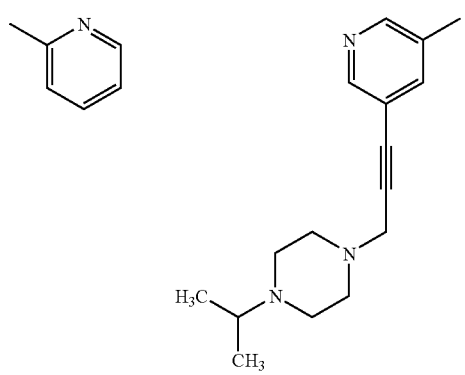 | |

| | 215 -continued | | | 216 -continued | |
|---|---|---|---|---|---|
| 2.182 | 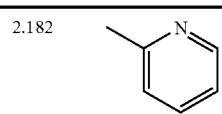 | 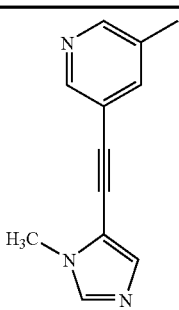 | 2.187 | 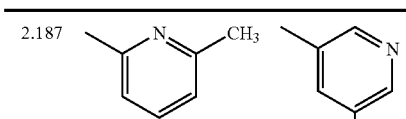 | 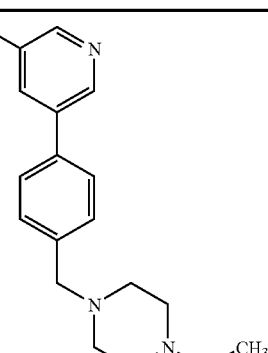 |
| 2.183 | 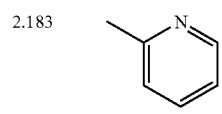 | 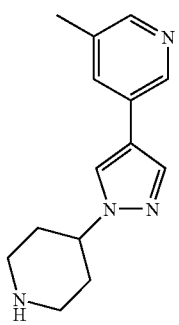 [SMILES: Cc1cncc(-c2cnn(C3CCNCC3)c2)c1] | 2.188 |  | 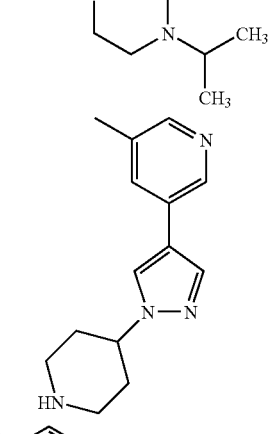 |
| 2.184 | 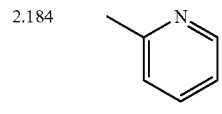 | 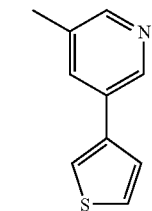 | 2.189 | 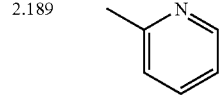 | 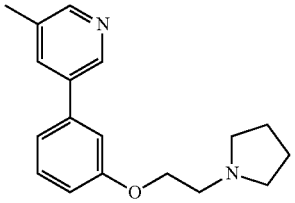 |
| 2.185 | 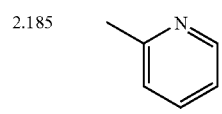 | 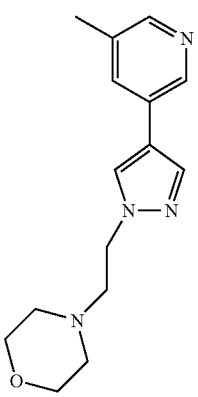 | | T₃ | |
| | | | 1.1 | | 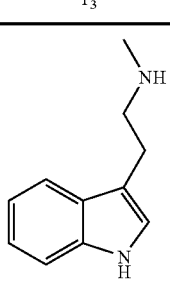 |
| 2.186 | 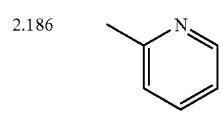 | 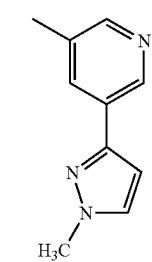 | 1.2 | | 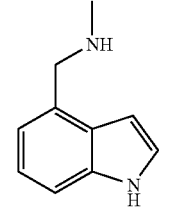 |
| | | | 1.3 | | 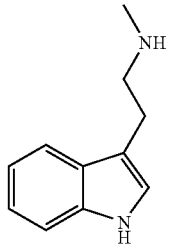 |

| 217 -continued | 218 -continued |
|---|---|
| 1.4 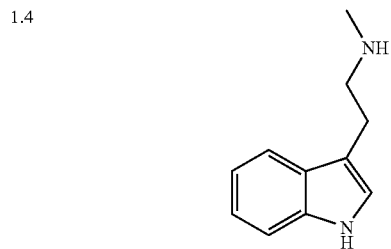 | 1.10 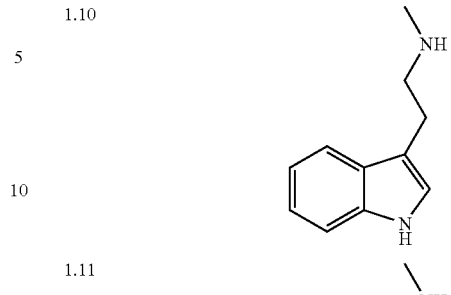 |
| 1.5 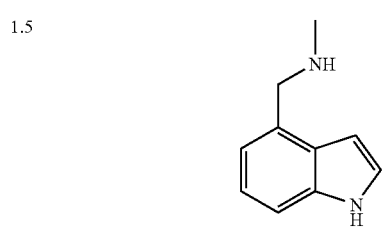 | 1.11 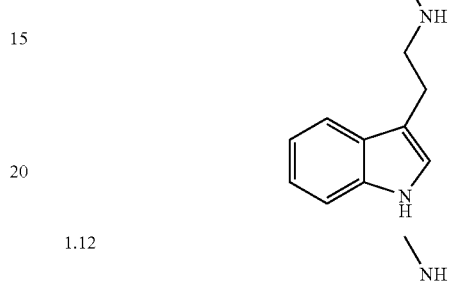 |
| 1.6 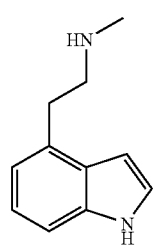 | 1.12 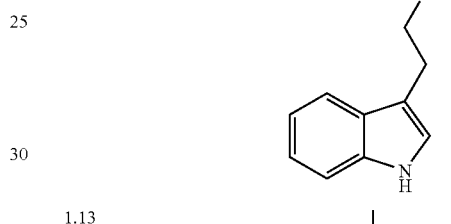 |
| 1.7 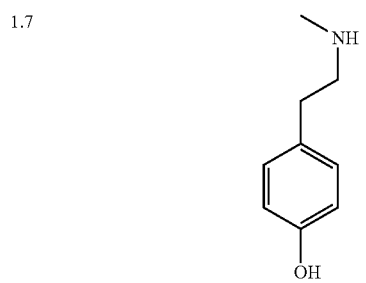 | 1.13 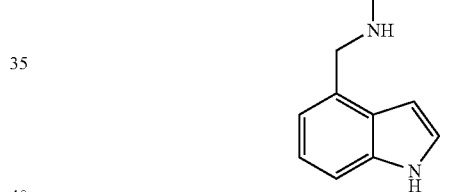 |
| 1.8 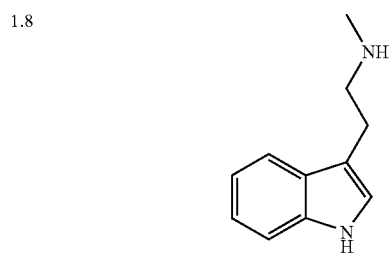 | 1.14 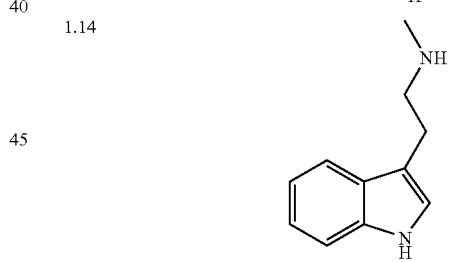 |
| 1.9 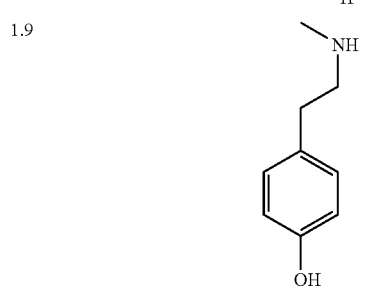 | 1.15 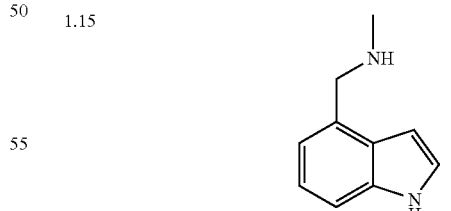 |
| | 1.16 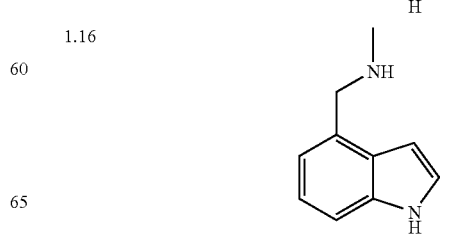 |

| | | | |
|---|---|---|---|
| 1.17 | 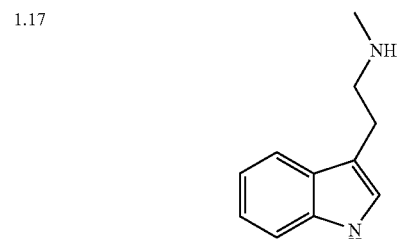 | 1.24 | |
| 1.18 | 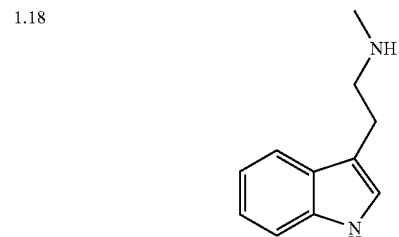 | | |
| 1.19 | 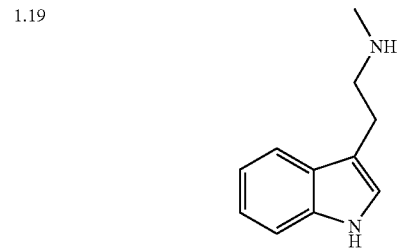 | | |
| 1.20 | 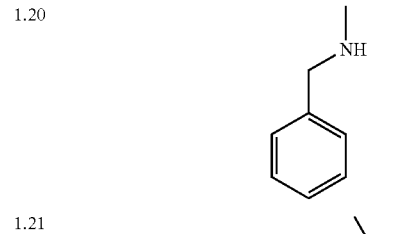 | | |
| 1.21 | 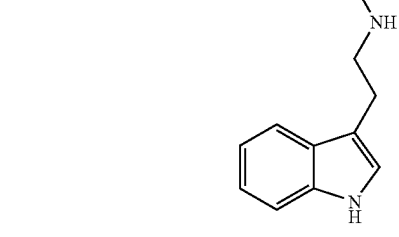 | | |
| 1.22 | 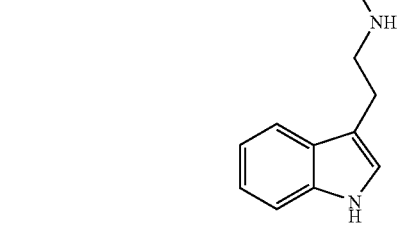 | | |
| 1.23 | 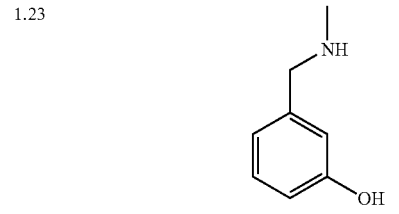 | | |
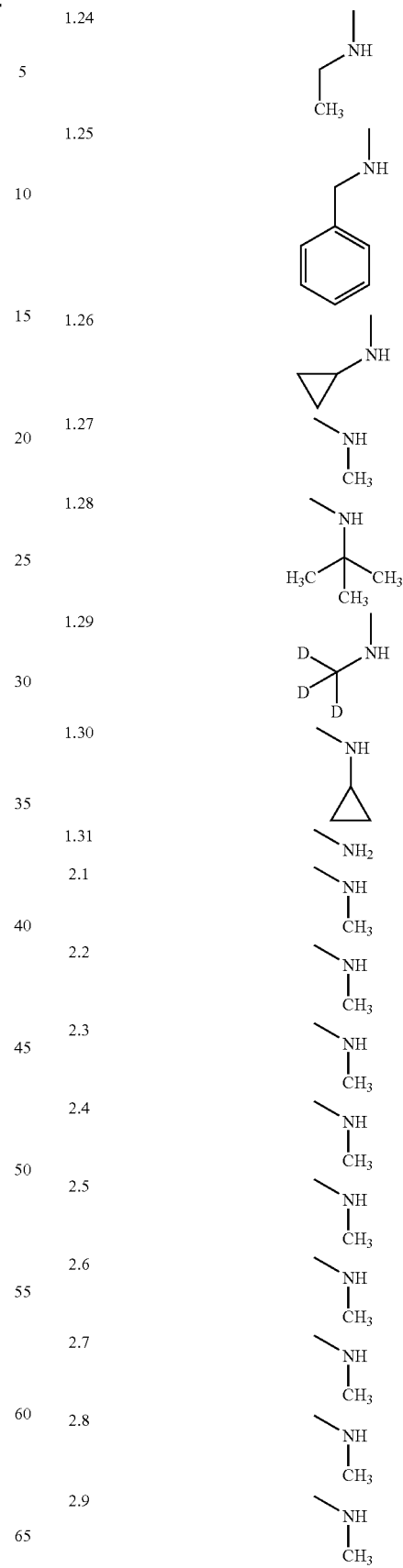

| | | | | |
|---|---|---|---|---|
| 2.10 | -NH-CH₃ | | 2.29 | -N(CH₃)-CH₂-CH₃ |
| 2.11 | -NH-CH₃ | | 2.30 | -N(CH₃)-cyclopropyl |
| 2.12 | -NH-CH₃ | | 2.31 | -N(CH₃)-cyclopropyl |
| 2.13 | -NH-CH₃ | | 2.32 | -N(CH₃)-cyclopropyl |
| 2.14 | -NH-CH₃ | | 2.33 | -N(CH₃)-cyclopropyl |
| 2.15 | -NH-CH₃ | | 2.34 | -N(CH₃)-cyclopropyl |
| 2.16 | -NH-CH₃ | | 2.35 | -N(CH₃)-cyclopropyl |
| 2.17 | -NH-CH₃ | | 2.36 | -N(CH₃)-cyclopropyl |
| 2.18 | -NH-CH₃ | | 2.37 | -N(CH₃)-cyclopropyl |
| 2.19 | -NH-CH₃ | | 2.38 | -N(CH₃)-cyclopropyl |
| 2.20 | -NH-CH₃ | | 2.39 | -N(CH₃)-cyclopropyl |
| 2.21 | -NH-CH₃ | | 2.40 | -N(CH₃)-CH₂-phenyl |
| 2.22 | -NH-CH₃ | | 2.41 | -N(CH₃)-CH₂-phenyl |
| 2.23 | -NH-CH₃ | | | |
| 2.24 | -NH-CH₃ | | | |
| 2.25 | -NH-CH₃ | | | |
| 2.26 | -NH-CH₃ | | | |
| 2.27 | -NH-CH₃ | | | |
| 2.28 | -NH-CH₃ | | | |

| 223 -continued | | | 224 -continued | |
|---|---|---|---|---|
| 2.42 | 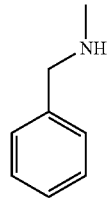 | 5 | 2.54 | 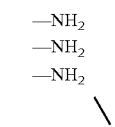 |
| 2.43 | 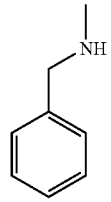 | 10 | 2.55 | 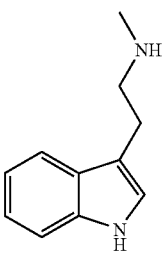 |
| 2.44 | 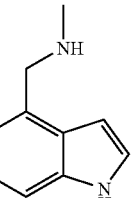 | 15 20 | 2.56 2.57 | 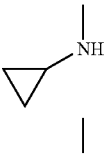 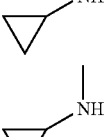 |
| 2.45 | 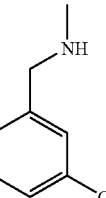 | 25 30 | 2.58 2.59 2.60 | 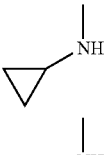 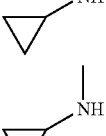 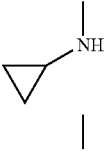 |
| 2.46 | 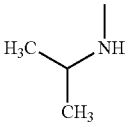 | 35 | 2.61 | 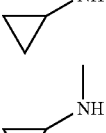 |
| 2.47 | 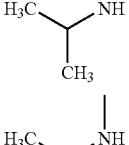 | 40 | 2.62 2.63 | 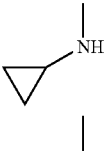 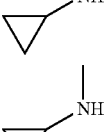 |
| 2.48 | 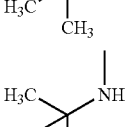 | 45 | 2.64 | 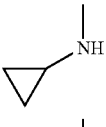 |
| 2.49 | 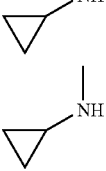 | 50 | 2.65 |  |
| 2.50 | —NH$_2$ | | 2.66 | |
| 2.51 | —NH$_2$ | 55 | | |
| 2.52 | —NH$_2$ | | 2.67 | |
| 2.53 |  | 60 65 | 2.68 | |

| # | Structure | | # | Structure |
|---|---|---|---|---|
| 2.69 | cyclopropyl-N(CH₃)H | | 2.87 | (CH₃)₂C(OH)- |
| 2.70 | cyclopropyl-N(CH₃)H | | 2.88 | (CH₃)₂C(OH)- |
| 2.71 | —NH₂ | | 2.89 | (CH₃)₂C(OH)- |
| 2.72 | —NH₂ | | | |
| 2.73 | (CH₃)₂C-N(CH₃)H, with extra CH₃ | | 2.90 | (CH₃)₂C(OH)- |
| 2.74 | —NH₂ | | 2.91 | (CH₃)₂C(OH)- |
| 2.75 | CH₃CH-N(CH₃)H | | 2.92 | (CH₃)₂C(OH)- |
| 2.76 | cyclopropyl-NH- | | 2.93 | (CH₃)₂C(OH)- |
| 2.77 | cyclopropyl-N(CH₃)H | | 2.94 | (CH₃)₃C- |
| 2.78 | (CH₃)₂C-N(CH₃)H with extra CH₃ | | 2.95 | (CH₃)₃C- |
| 2.79 | (CH₃)₂C-N(CH₃)H with extra CH₃ | | 2.96 | (CH₃)₃C-CH(CH₃)- type |
| 2.80 | (CH₃)₂C(OH)- | | 2.97 | (CH₃)₂C(NH₂)- |
| 2.81 | (CH₃)₂C(OH)- | | 2.98 | CD(D)(D)-N(CH₃)H |
| 2.82 | (CH₃)₂C(OH)- | | 2.99 | CD(D)(D)-N(CH₃)H |
| 2.83 | (CH₃)₂C(OH)- | | 2.100 | CD(D)(D)-N(CH₃)H |
| 2.84 | (CH₃)₂C(OH)- | | 2.101 | CD(D)(D)-N(CH₃)H |
| 2.85 | (CH₃)₂C(OH)- | | 2.102 | CD(D)(D)-N(CH₃)H |
| 2.86 | (CH₃)₂C(OH)- | | 2.103 | CD(D)(D)-N(CH₃)H |

-continued
| | | | |
|---|---|---|---|
| 2.104 | | 2.121 | |
| 2.105 | | 2.122 | |
| 2.106 | | 2.123 | |
| 2.107 | | 2.124 | |
| 2.108 | | 2.125 | |
| 2.109 | | 2.126 | |
| 2.110 | | 2.127 | |
| 2.111 | | 2.128 | |
| 2.112 | | 2.129 | |
| 2.113 | | 2.130 | |
| 2.114 | | 2.131 | |
| 2.115 | | 2.132 | |
| 2.116 | | 2.133 | |
| 2.117 | | 2.134 | |
| 2.118 | | 2.135 | |
| 2.119 | | | |
| 2.120 | | | |
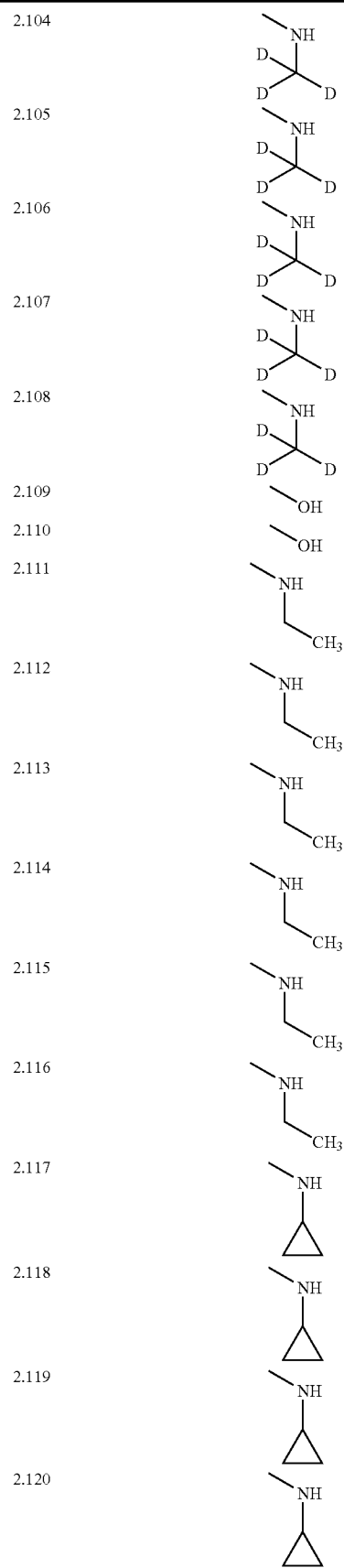
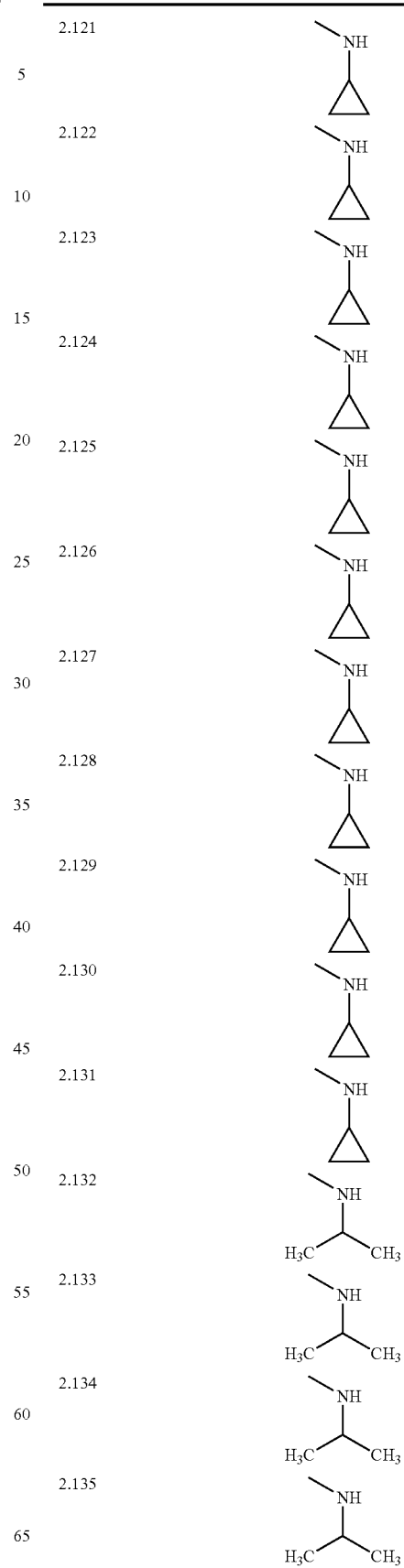

229
-continued

| | |
|---|---|
| 2.136 | CH₃-NH-CH(CH₃)₂ (isopropyl methylamine) |
| 2.137 | CH₃-NH-CH(CH₃)₂ (isopropyl methylamine) |
| 2.138 | N-methyl benzylamine |
| 2.139 | N-methyl benzylamine |
| 2.140 | N-methyl benzylamine |
| 2.141 | N-methyl benzylamine |
| 2.142 | N-methyl benzylamine |
| 2.143 | N-methyl benzylamine |
| 2.144 | N-methyl benzylamine |
| 2.145 | N-methyl benzylamine |
| 2.146 | cyclopentyl-NH |

230
-continued

| | |
|---|---|
| 2.147 | N-methyl cyclopentylamine |
| 2.148 | N-methyl cyclopentylamine |
| 2.149 | cyclopropylmethyl-N(CH₃)H |
| 2.150 | cyclopropylmethyl-N(CH₃)H |
| 2.151 | cyclopropylmethyl-N(CH₃)H |
| 2.152 | N-methyl cyclobutylamine |
| 2.153 | (CH₃)₂N-CH₂- (dimethylaminomethyl) |
| 2.154 | pyrrolidin-1-yl |
| 2.155 | —NH₂ |
| 2.156 | —NH₂ |
| 2.157 | —NH₂ |
| 2.158 | —NH₂ |
| 2.159 | —NH₂ |
| 2.160 | —NH₂ |
| 2.161 | —NH₂ |
| 2.162 | —NH₂ |
| 2.163 | —NH₂ |
| 2.164 | —NH₂ |
| 2.165 | —N(CH₃)H |
| 2.166 | —N(CH₃)H |
| 2.167 | —N(CH₃)H |
| 2.168 | —N(CH₃)H |
| 2.169 | —N(CH₃)H |
| 2.170 | —N(CH₃)H |
| 2.171 | —N(CH₃)H |
| 2.172 | —N(CH₃)H |

| | |
|---|---|
| 2.173 |  |
| 2.174 |  |
| 2.175 |  |
| 2.176 |  |
| 2.177 |  |
| 2.178 |  |
| 2.179 |  |
| 2.180 |  |
| 2.181 |  |
| 2.182 |  |
| 2.183 |  |
| 2.184 |  |
| 2.185 |  |
| 2.186 |  |
| 2.187 |  |
| 2.188 |  |
| 2.189 |  |
2. A pharmaceutical composition, comprising:
the compound according to claim 1 and
a pharmaceutically acceptable excipient.
* * * * *